US009133514B2

(12) United States Patent
Komatsu et al.

(10) Patent No.: US 9,133,514 B2
(45) Date of Patent: Sep. 15, 2015

(54) METHOD FOR IDENTIFYING OR DETECTING GENOMIC REARRANGEMENTS IN A BIOLOGICAL SAMPLE

(71) Applicants: Jun Komatsu, Bagneux (FR); Pierre Walrafen, Montrouge (FR); Maurizio Ceppi, Issy-les-Moulineaux (FR); Emmanuel Conseiller, Paris (FR)

(72) Inventors: Jun Komatsu, Bagneux (FR); Pierre Walrafen, Montrouge (FR); Maurizio Ceppi, Issy-les-Moulineaux (FR); Emmanuel Conseiller, Paris (FR)

(73) Assignee: GENOMIC VISION, Bagneux (FR)

( * ) Notice: Subject to any disclaimer, the term of this patent is extended or adjusted under 35 U.S.C. 154(b) by 92 days.

(21) Appl. No.: 13/665,440

(22) Filed: Oct. 31, 2012

(65) Prior Publication Data

US 2014/0011194 A1 Jan. 9, 2014

Related U.S. Application Data

(63) Continuation of application No. PCT/IB2012/002423, filed on Oct. 30, 2012.

(60) Provisional application No. 61/553,889, filed on Oct. 31, 2011.

(51) Int. Cl.
*C12Q 1/68* (2006.01)

(52) U.S. Cl.
CPC ............ *C12Q 1/6881* (2013.01); *C12Q 1/6827* (2013.01); *C12Q 1/6841* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS 7,985,542 B2 * 7/2011 Lebofsky et al. .............. 435/6.1

FOREIGN PATENT DOCUMENTS

WO WO 2008-028931 A1 * 3/2008

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Gad et al, Genes Chromosomes and Cancer 31: 75 (2001).*
Gad et al, J. Med. Genet. 39: 817 (2002).*

* cited by examiner

*Primary Examiner* — James Martinell
(74) *Attorney, Agent, or Firm* — Oblon, McClelland, Maier & Neustadt, L.L.P.

(57) ABSTRACT

A method for detection, visualization and/or comparison of polynucleotide sequences of interest using specially designed sets of long and short probes that enhance resolution and simplify visualization and detection. Probe compositions useful for practicing this method and procedures for identifying useful probes and probe combinations. These methods are useful for the detection of genomic rearrangements, especially those associated with various diseases, disorders and conditions including cancer or for assessment of genomic rearrangements associated with therapy. The probe compositions may be used in kits for detection of genetic rearrangements or in companion diagnostic products or kits, such as kits for the diagnosis or assessment of predisposition to cancer such as colorectal cancer.

35 Claims, 8 Drawing Sheets

Dot plot analysis of of MLH1 region. A) Dot-plot of MLH1 gene sequence on RP11-426N19 BAC clone. B) probe code v1 (without repetitive element) on RP11-426N19. C) probe code-v2 on RP11-426N19.

Designed code for MSH2 by exclusion of repetitive element. A) theoretical code (black and grey at bottom), and position of exon (black short segments with number of exon). B) actual hybridization image corresponding to MSH2-v1 code.

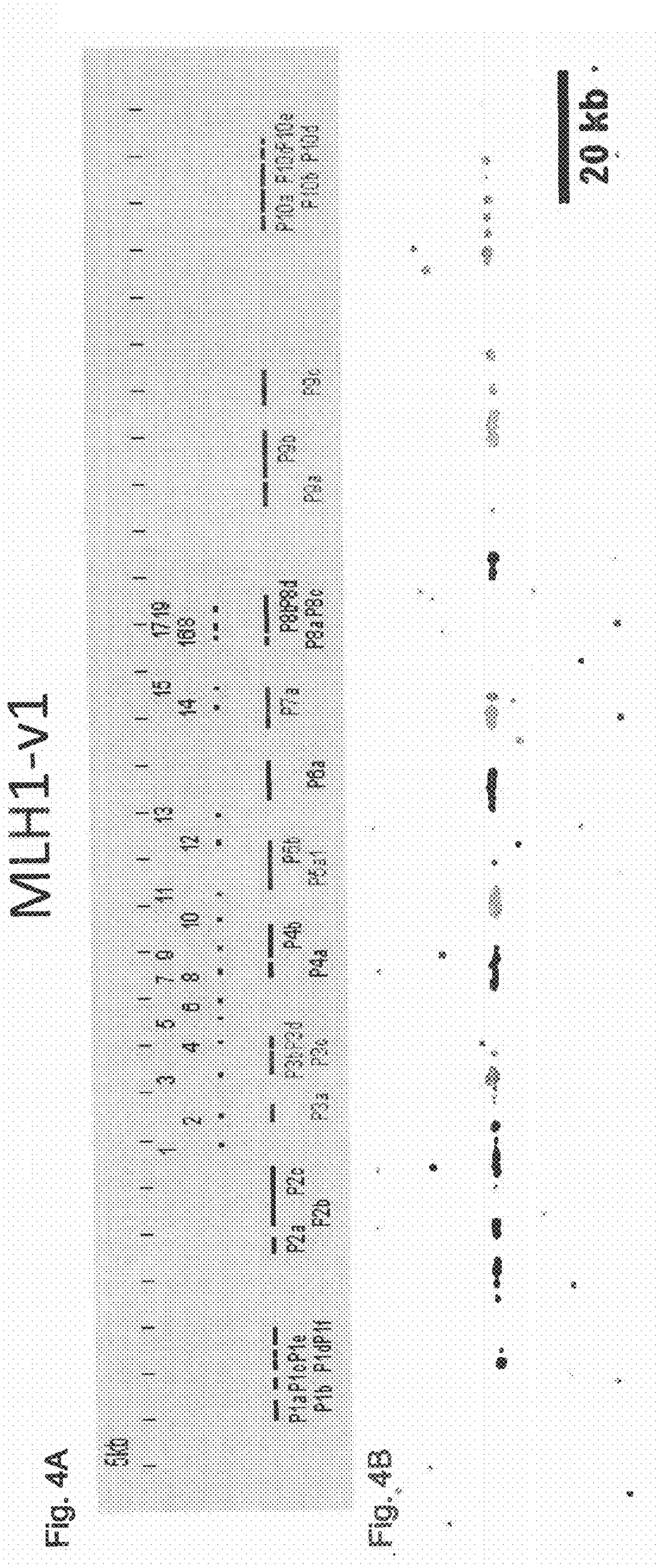
Designed code for MLH1 by exclusion of repetitive element. A) theoretical code (red and green), and position of exon (purple dot). B) actual hybridization image corresponding to MLH1-v1 code.

Fig. 8A
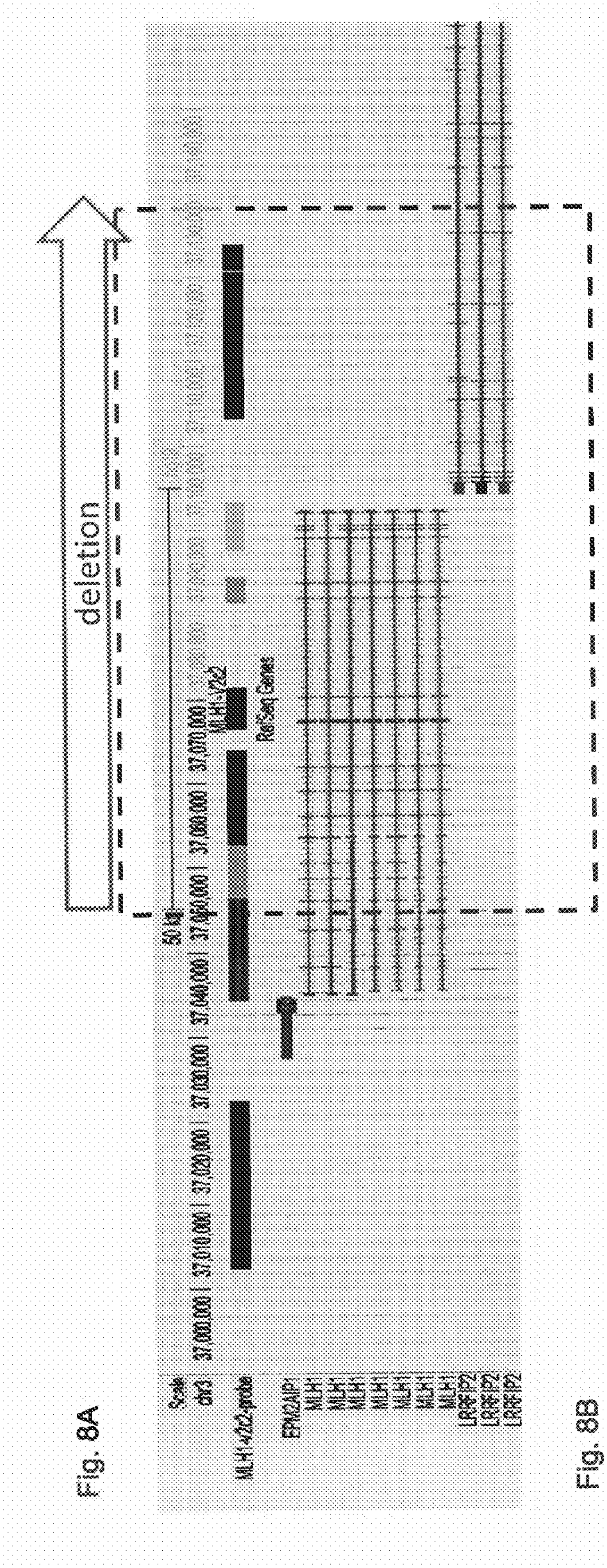
Fig. 8B
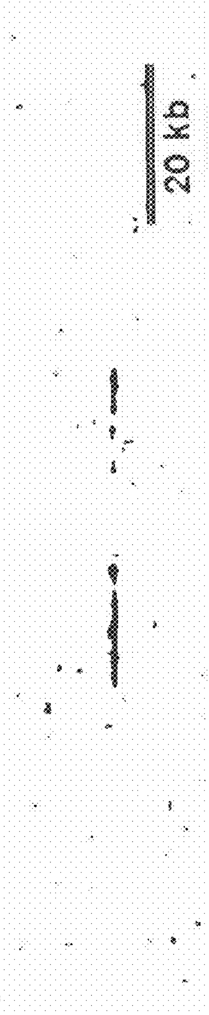
Fig. 8C
| measurement | MSH2 | MLH1 |
|---|---|---|
| 138 | 98 (2) | 4 (all first 3 signal) |

METHOD FOR IDENTIFYING OR DETECTING GENOMIC REARRANGEMENTS IN A BIOLOGICAL SAMPLE

CROSS-REFERENCE TO RELATED APPLICATIONS

The present application claims priority to U.S. Provisional Application No. 61/553,889, filed Oct. 31, 2011, the entire contents of which are incorporated herein by reference. On Oct. 30, 2012, an International Application (PCT/IB/12/02423; submission number 1000168921) was also filed with the same title, the entire contents of which are incorporated herein by reference.

BACKGROUND OF THE INVENTION

1. Field of the Invention

The invention relates to high-resolution, precise method for detecting genomic rearrangements in vitro using specially designed combinations of polynucleotide probes. The invention concerns accurate methods of detection and diagnosis of conditions, disorders and diseases associated with rearrangement of genomic DNA.

2. Description of the Related Art

The Multigenic Paradigm of Human Diseases

Advances in genetic analysis of human diseases have provided better insights into the molecular mechanisms contributing to disease initiation and progression. Previous associations were made between particular diseases and association and/or linkage disequilibrium to single base mutations in somatic genetic sequences or with particular single nucleotide polymorphisms ("SNPs") in genomic DNA. Newer technologies have provided evidence that larger genetic alterations and rearrangements are associated with, or can constitute major causes of diseases, disorders or conditions having a genetic origin or basis. Disease associations have now moved from a monogenic to a multigenic paradigm where a disease's origins and progression is mainly linked to more than one single genetic mutation or origin. While these new insights provide better avenues for disease detection and treatments, they also highlight the need for combinatorial genetic analysis that goes beyond detection of single mutational events or SNPs by assessing disease associations with larger genomic rearrangements. Such combinatorial genetic analysis would provide a better, more precise and accurate diagnosis of a particular condition, disorder, disease or pathology, but would also help establishing a more appropriate medical survey, more accurate therapeutic decisions and interventions, as well as help in assessing the efficacy of such therapies and interventions.

Multigenic Causes of Genetic Disease

Genetic disorders manifesting the same or similar clinical signs and consequences can arise from both single and exclusive, or combined, mutations in various genes. Such mutations can fall within either the single base alteration and/or the class of large genetic rearrangements. A few examples of such genetic disorders are Fragile X syndrome (mutations and expansions in the FMR1 gene), Ataxia Telangectasia (single base pair mutations in either intronic and exonic sequences as well as deletions and translocations of the ATM gene), Seckel syndrome (mutations as well as large rearrangements in SCKL1, SCKL2, SCKL3, PCTN and ATR), autism (mutations as well as large rearrangements in GLO 1, MTF 1 and SLC11A3), Spinal Muscular Atrophy (mutations, deletions, transconversions as well as cis-duplications involving the SMN1 and SMN2 genes) and myotonic dystrophy (trinucleotide/tetranucleotide expansions in DM1 and DM2).

Multigenic Causes of Cancer Predisposition

In the case of cancer predisposition, there are several examples of familial cancer predisposition syndromes for which one can nominate several causative genes for which both single base alterations and/or large rearrangements were identified.

Breast and Ovary Cancer. Causative genes: BRCA1, BRCA2, ATM . . .

mutation type: higher proportion of point mutations identified so far.

Hereditary nonpolyposis colorectal cancer (Lynch syndroma). Causative genes: MSH2, MLH1, MSH6, EPCAM, . . . mutation type: equivalent proportion of point mutations has also been identified.

Multigenic Causes of Cancer Progression

Cancer progression is surely the human disease domain where the monogenic causative hypothesis was definitely ruled out since several years. First, the disease's initiation is strictly dependent of two molecular events (immortalizing and transforming) due to genetic alterations in at least two independent genes classified at either oncogene or tumor suppressor genes. Second, the disease's progression is linked to additional genetic alterations independent from the causative ones. Not only do these additional alterations play a role in cancer progression, they also were demonstrated to be the basis for appearance of resistance to therapy during treatments. Strikingly, in the list of cancer related genes, if extremely rare examples are only subject to discrete single base mutations (e.g., KRas or BRaf), the large majority is either subject to only large rearrangements (e.g., HER2, ALK . . . ) or to both single base mutations and large rearrangements (p53, c-myc, c-Met, EGFR . . . ).

The identification and characterization of multigenic conditions, disorders and diseases, including cancer, cardiovascular disease, diabetes and other heritable genetic conditions has been made difficult in part due to the imprecision of existing methods of molecular diagnosis. Molecular Combing is probably the sole approach allowing detecting all type of large genetic rearrangements (deletion, amplification, expansions, inversions, translocations . . . ) even in a complex and heterogeneous population (such as tumors).

High resolution barcodes allowing multiplex analysis of patients could help diagnostic at different level such as for patient stratification/classification and/or prognosis.

Multiplex High Resolution Barcodes for Identifying the Right Genetic Alterations as a Key Driver for Therapeutic Intervention The Example of Myotonic Dystrophy Myotonic Dystrophy (DM1) and Myotonic Dystrophy 2 (DM2) are two muscular dystrophies characterized by trinucleotide/tetranucleotide expansions in two different genes. If severe forms of DM1 can be clinically differentiated from DM2, milder DM1 forms are displayed extremely similar clinical signs than DM2. There is currently no cure for or treatment specific to myotonic dystrophy. However, DM1 patients exhibit Complications of the disease (heart problems, cataracts . . . ) not existing in DM2 that could can be treated but not cured. Differentiating DM1 and DM2 by the use of a multiplex assay of high resolution barcodes could thus help preventing and treating secondary effects The Example of Hereditary Breast and Ovary Cancer In certain countries (U.S.) detecting constitutional alterations in BRCA1/2 drives to therapeutic intervention (surgery/reconstitution). Thus, there is a clear need for an accurate diagnostic comprising all the potentially involved genes.

Such a test could be made on the basis of a multiplex assay of high resolution barcodes comprising large chromosomal regions around genes known to be involved in this syndrome; BRCA1, BRCA2, ATM, ATR . . .

DNA Damage and Response Inhibitors Example

Synthetic lethality became a strong reality for therapeutic decision to include Cancer patients in specific protocols/regimens. One of the first examples was given with the demonstration that Breast cancer patients with BRCA deficiency exhibit a higher sensitivity to PARP inhibitors, a new category of drug acting on DNA Damage and Response pathway. More recently, this was extended to other type of inhibitors in this category such as ATM inhibitors but also to more traditional anti-cancer drugs including all types of DNA polymerase and replication inhibitors.

Not only does this concept extended to other inhibitors, but it was also demonstrated that it could be extended to other types of cancers such as lung and metastatic melanoma.

Here, a multiplex high resolution barcode will allow detection of genetic alteration in genes involved in DNA damage and response that could help predicting sensitivity to this class of inhibitors. A list of such genes could include BRCA1, BRCA2, ATM, ATR, MSH2, MLH1, MSH6, EPCAM . . .

The Lung Cancer Example

Numerous alterations involved in lung cancer could be multiplexed for a better patient classification such as:

LOH/Deletion (P53, STK11, LKB1, BRG1, KLF6);

Amplification (FGFR1, MET, EGFR, HER2 . . . );

Translocation: (ALK);

All these genetic alteration are associated to therapeutic treatments:

P53: Nutlin (low doses Actinomycin D produce similar effects)

FGFR1: Masitinib, PD173074, SU5402 TK1258 AZD4547 . . .

MET: GSK1363089, ARQ197, SGX523, XL184 . . .

EGFR: Tarceva, Erbitux, Vectibix . . .

HER2: Herceptin, Lapatinib . . .

ALK: Crizotinib

As at least 30% of NSCLCs were demonstrated to be dependent on at least one of these mutations, defining the genetic profile of the tumor could help driving therapeutic options. This could be made possible by designing multiplex assays combining high resolution barcodes covering this major genetic loci.

Localization of (Genetic) Sequences of Interest

Genetic sequence is the most fundamental information to synthesize functional protein. Alteration of genetic sequence sometimes results in loss of functional protein synthesis. In addition to alteration of genetic sequence, loss or gain of genetic sequence (copy number variation, CNV) also can be problematic for homeostasis of cellular activity. For example, loss of (functional) anti-tumor protein (p53) or gain of proto-oncogene (c-myc) results in cancer-prone cell. When such mutation happens (or exists) in germ cell, this mutation spreads whole cell in an individual who is either carrier or patient of genetic disease, or has a predisposition to cancer. The germline mutation can be heritable. These days CNV becomes more and more important to understand in the field of genetics (ref 1). However, copy number count alone is not always sufficient and it is often critical to establish the actual location of sequence elements. This is strikingly the case for e.g. balanced translocations. DNA sequencing and CNV detection methods such as array-based comparative genomic hybridization (aCGH) and quantitative PCR generally cannot detect these balanced mutations because these methods assess whether the sequence and the copy number are correct or not. FISH and its extended forms such as fiber-FISH or molecular combing can address these balanced mutations with different resolutions and precisions depending on methods.

Resolution and Precision

The use of BAC/PAC/cosmid probes on targeted regions was successfully conducted to detect large (a few kb to tens of kb) genomic rearrangements (ref 2). In these approaches, the minimum size of detectable events (e.g., the size of the deleted or amplified sequence), hereafter designated as the "resolution" of such an assay, is limited due to the large standard deviation involved in measuring probes or gaps of tens of kilobases. Indeed, in such assays the standard deviation of measurements increases with the length of the measured element. For example, a 40 kb-probe is measured with a standard deviation of ~5 kb. Thus, if 16 measurements of a given probe are made on a slide, the precision on the size of the probe obtained as the mean value of measurements is in the order of magnitude of 2.5 kb (Considering the distribution is gaussian, and the precision is the half-width of the confidence interval, i.e. $2.sd/\sqrt{n}$ where sd=standard deviation and n=number of measurements). For a 10 kb-probe, where the standard deviation is ~2 kb, the precision would be ~1 kb. This illustrates the fact that shorter probes allow for better (lower) resolution.

Besides, the location of such an event (the position of the extremities of the event) may be defined with a precision (hereafter the location precision) limited by the size of the probe or gap within which it occurs: e.g. if a 40 kb probe is estimated to measure 39 kb in a sample, one can conclude that a 1 kb deletion occurred somewhere within the probe, with no further precision—thus, somewhere in a 40 kb genomic region. If the same 1 kb deletion had occurred within a 10 kb probe, the location of that deletion would be known with a better precision, as the range would be reduced to a 10 kb genomic region. Therefore, the smaller the probes and gaps, the better the location precision.

There are limits to small probes: (i) below a certain size, they become difficult to detect; (ii) they involve more complex color schemes (as there are relatively more probes); (iii) there are more distinct probes to cover a given region, and the experiments are therefore more expensive and time-consuming; (iv) most importantly, fast and reliable identification of probes, whether by a human operator or a piece of software, is easier with longer probes, as they are more readily distinguished from background. Indeed, background is mainly constituted of roughly circular fluorescent spots. When large enough, the shape of these spots allows to one to easily distinguish them from probes. However, when their size is small enough, they appear difficult to distinguish from small probes.

In operating conditions according to the invention, probes shorter than ~3 kb are detected with a diminished efficiency. Within the 3-10 kb range, the standard deviation of measurements varies little, and there is therefore little benefit in resolution with the shorter probes within this range. Therefore, this range is usually considered to be a good compromise for probe size. However, in cases where probes are close enough (less than 10 kb gaps), smaller probes (within the 500-3000 bp range) are still useful, as they will be detected in at least a fraction of signals and the presence of the corresponding sequences may therefore be established with certainty. It was also found that detection of isolated probes longer than 12 kb (preferably longer than 14 kb) is more reliable, whether for a human operator or for automatic detection software.

Exclusion of Repeats

Eukaryotic genomic DNA contains various repetitive sequences, i.e., sequences that appear more than once (and more than statistically predicted based on their length and base content) in a normal haploid genome. Among these, some appear with very high frequency (tens of thousands to millions of copies). In human genomic DNA, the most abundant of these is the Alu family, which has ~1,000,000 copies constituting ~10% of the genome. In any hybridization procedure involving human genomic DNA, it is expected that probes carrying such repeats would hybridize on numerous targets, generating non-specific signal from regions throughout the genome. Other types of repetitive sequences exist, with lower frequency, and often more specific localization. The number of copies and repeat sequence length may vary widely, as well as the degree of homology. Beta-satellite sequences, for example, are present in multiple copies (hundreds to thousands), usually as tandem repeat arrays comprising hundreds of copies of the same 50-100 bp long sequence, specifically localized in a limited number of loci. Strategies to get rid of the non-specific signals depend on the type of procedure and probe. Schematically, when probes are very short sequences of DNA (oligonucleotides, typically less than 100 bp), as in aCGH procedures, the sequence of the oligonucleotides is chosen to be free of repetitive sequences, by comparison with repetitive sequences found in databases. This strategy is only practical for very short probes, as short sequences free of repetitive sequences are relatively abundant, but unpractical for longer probes, as long stretches completely devoid of repetitive elements are rare (although this has been adapted to longer FISH probes, in an approach that suffers multiple drawbacks, see below). Besides, even for short probes, it constrains the design of probes heavily and some genomic regions, rich in repetitive sequences, have lower density of coverage (and thus lower resolution of events) due to this constraint.

When probes are longer (typically PCR products or cloned DNA inserts—1 to 150 kb), in Southern Blot or in FISH procedures, non-labeled competitive DNA, enriched in repetitive elements such as Alu repeats (usually Cot-1 DNA), is added in large excess along with the labeled probe. Competition of unlabelled probes on the repetitive sequences minimizes the hybridization of labeled probes. This strategy is expensive and since the competitor DNA is not purely made of repetitive sequences, competition also occurs on the unique sequences for which the probes were designed, thus limiting the amount of competitor DNA that may be used. Therefore, the efficiency of this approach is limited.

An alternative approach for longer probes has been proposed by Knoll and collaborators (U.S. Pat. No. 7,014,997), resembling the strategy usually adopted for oligonucleotides: probes are chosen within sequence intervals devoid from repetitive elements. This strategy is based on bioinformatics analysis of the regions of interest and exclusion of known repetitive sequences by comparison with sequence databases. However, this approach has several limitations: prior knowledge of the repetitive sequences is required, which can be a problem e.g. in species where such knowledge is unavailable. More importantly, intervals longer than 2 kb devoid of repetitive sequences appear only once in 20-30 kb on average and are unevenly distributed (Considering the distribution is gaussian, and the precision is the half-width of the confidence interval, i.e. $2.sd/\sqrt{n}$ where sd=standard deviation and n=number o) so the design of probes would be highly constrained, impairing the possibility to design a high-resolution code. This would prove especially difficult in repeat-rich regions, and/or regions where pseudogenes are located next to homologous genes of interest—such low-copy repetitive sequences being also excluded with the strategy from Knoll and co (ref 3). Since regions targeted in rearrangement tests, e.g., for diagnostics purposes, often display these features, this approach is not suitable for the design of high-resolution barcodes and especially not if such a code is to be used for diagnostics purposes. Distinctions between this approach and the invention are disclosed in more detail below.

BRIEF SUMMARY OF THE INVENTION

The present invention concerns the field of the in vitro diagnosis and detection of genetic rearrangements and is related to a method to identify or detect genetic rearrangements in a biological sample to be tested which are already known or which are new and provide markers for example of diseases as cancers or metabolic or foetal genetic diseases. The invention is characterized by using compositions containing purified or synthesized nucleic acid molecules (polynucleotides) having nucleotide sequences selected as short sequences with a length of less than 10 Kb and associated in the said method with other different nucleic acid molecules (polynucleotides) having nucleotide sequences non-overlapping with the former ones and having a size longer than 12 Kb. The selected nucleotide sequences (polynucleotides) used as probes are partly deleted of their natural frequently repeated sequences. The present invention concerns also improvements brought to the design of set of probe sequences for the detection of genetic rearrangements by hybridization as with fiber-FISH-like technologies such as Molecular Combing. The improvements described herein allow for high precision/high-resolution detection of rearrangements in time- and cost-efficient assays. This invention also relates to the use of probe sequences for diagnostics applications and companion diagnostics tests, to a method of detection of presence or absence of alterations in sequences and to a kit for the above uses. This is illustrated hereinafter with sets of nucleotide sequences corresponding to parts of at least two genes: MSH2 and MLH1 or to the regions of MSH2 and MLH1, whose mutations increase the risk of occurrence of human colorectal cancer.

The invention is related to the sets of polynucleotides or probes labeled or not which are specific of said genes. Presently, the detection of genetic rearrangements using current technologies is often insufficiently reliable for diagnostics use. Unlike most technologies used to detect genetic alterations, which suffer strong intrinsic limitations towards some types of rearrangements, direct technologies such as FISH or Fiber-FISH can intrinsically detect any type of rearrangements. Their use is mainly limited by their resolution. Molecular Combing, on the other hand, may reach sufficient resolution, but probe designs currently used fail to allow cost- and time-efficient high resolution analysis of rearrangements.

These improvements involve the combination within the same sets of probes of—typically shorter—probes designed to optimize the sensitive detection and precise measurement of rearrangements and—typically longer—probes to allow for fast and reliable detection of signals of interest when analyzing results. Alternative designs where the longer probes are replace with a combination of shorter probes having equivalent functions and effects are also disclosed.

Specific aspects of the invention based on the concept of combining small probes for resolution and long probes for ease of detection for the detection on one or more genomic region(s) of interest as disclosed in more detail below.

The invention thus concerns a method for detecting mutated or rearranged genomic polynucleotide (target) sequence comprising:

(a1) hybridizing a target genomic polynucleotide comprising one or more genomic region(s) of interest, where mutations or rearrangements are sought, to a set of short probes that bind to each region of interest without long gaps between the portions of the target sequence bound by the set of short probes, where on each genomic region a subset of short probes are selected so that when taken together they form a long contiguous stretch inside or outside the region of interest, and wherein the probes may optionally have frequent repetitive sequences removed and thus more generally are optionally devoid of such repetitive sequences; or (a2) hybridizing a target genomic polynucleotide comprising one or more genomic region(s) of interest, where mutations or rearrangements are sought, to a set of short probes that bind to each region of interest without long gaps between the portions of the target sequence bound by the set of short probes and to one or more long (docking) probe(s) that bind to sequences near but outside of the region(s) of interest; wherein the sequence(s) of the long probe(s) does not overlap that of the short probes and wherein the short and/or long probes may optionally have frequent repetitive sequences removed and thus more generally are optionally devoid of such repetitive sequences;

(b) detecting the locations of hybridized probes on the genomic region(s) of interest; optionally, (c) comparing the location of the hybridized probes on the target genomic polynucleotide sequence with one or more motifs based on the hybridization of said probes to a reference, control, normal, not mutated, or not rearranged genomic polynucleotide sequence; and optionally, (d) correlating the presence of a mutated or rearranged genomic polynucleotide with a specific phenotype, disease, disorder, or condition.

The mutated or arranged genomic polynucleotide sequence can be obtained from a subject who has cancer or who is suspected to having cancer, for example, from a subject who has colorectal cancer or who is suspected of having colorectal cancer. In such a case, the short and long probes identify mutations or genomic rearrangements associated with colorectal cancer and a control or reference sample would not contain these mutations or rearrangements. The presence or risk of developing colorectal cancer is assessed by comparing a target genomic polynucleotide sequence with the reference and determining whether a mutation or rearrangement associated with colorectal cancer is present. This method can be practiced with specific probes corresponding to or derived from Probe sets 1, 2, 3 and 4. For colorectal cancer, a genomic region of interest can be selected from genes associated with this disease, such as MSH2, MLH1, MSH6, PMS2 or EPCAM.

Similarly, the method may be applied to samples obtained from subjects having or at risk of developing other kinds of cancer, such as breast cancer, ovary cancer, or lung cancer. The method may also be applied to samples obtained from subjects having or at risk of other kinds of diseases, disorders, or conditions, including cardiovascular disease, diabetes, neuromuscular disorders; such as myotonic dystrophy or spinal muscular atrophy or samples obtained from a subject who has, is suspected of having, or is suspected of being a carrier for a genetic or hereditary disease, disorder or condition, including known or unknown foetal genetic alterations. The sample can be obtained from a subject having a multigenic genetic or hereditary disease, disorder or condition or for a genetic or hereditary disease, disorder or condition associated with rearrangement of genomic DNA.

In some aspects of the invention, the sample will be obtained from a subject undergoing treatment for a disease, disorder or condition associated with a genomic or somatic genetic rearrangement and the results obtained are compared to results obtained at other time points before, during or after the termination of treatment. A companion test for evaluating the efficiency of a therapeutic drug on the mutated or rearranged nucleotide sequences of the gene or the region of the gene of interest can be performed using the short and long probes according to the invention.

Preferably, in the method described above, the hybridizing with the short and long probes in step a) will be performed simultaneously.

Preferably, the short probes range in length from 0.5 kb to 10 kb and the maximum size of the gaps between the short probes when they are bound to the target is 15 kb, preferably 12 kb and more preferably 10 kb.

The number of short probes employed in the method described above can range from 1, 2, 3 to 10, 15 or more.

The maximum size for the long probes is 150 kb and these probes preferably range from 12 kb to 40 kb in length. Preferably, in order to have "long probe(s) that bind to sequences near but outside of the region of interest", distance between the long probes and the region of interest is no longer than 150 kb, and more preferably no longer than 75 kb and even more preferably no longer than 25 kb from the region of interest. The minimum size for a genomic region to be tested or targeted is 50 kb. The minimum number of regions of interest is one for a singleplex test and two or more for a multiplex test. Examples of combinations of short and/or long probes include at least one short (less than 10 kb) sequence and at least one non-overlapping long sequence (more than 15 kb), or at least one group of at least two short sequences, less than 10 kb each, which total group length is longer than 14 kb and less than 150 kb, hybridizing contiguously on the mutated or rearranged polynucleotide sequence. The short probes can comprise a set of contiguous probes that span a stretch of the genomic polynucleotide sequences inside or outside the region of interest that is at least 15 kb.

The long probes may have repetitive DNA sequences excluded. These repetitive sequences to be excluded would ordinarily appear more than once and more often than statistically predicted based on their length and base content, for example, repetitive sequences between 50 and 400 bp can be excluded, though shorter or longer repetitive sequences that decrease sensitivity or specificity of the method can be identified and excluded. An example of such a sequence is the repetitive Alu family DNA sequences.

According to an embodiment of the invention, in order for the probes, either short probes or long probes, to have repetitive sequences excluded, these probes are designed to hybridize in regions of the genome which are free of such repetitive sequences, i.e. which have less than 10% preferably less than 2% of the selected type(s) of repetitive sequences to be excluded.

In the method described above, the short and long probes are preferably fluorescently tagged and different components of the probe sets may be tagged with different labels, such as labels with different colors. Tagging provides one means to identify motifs or submotifs characteristic of a mutated or rearranged sequence.

Compositions or kits comprising a set of short probes or a combination of short and long probes as described herein and optionally one or more components for binding said probes to a polynucleotide, for performing molecular combing, and/or for detecting whether hybridization has occurred are also contemplated. For example, a composition containing the short and long probe(s) described above, wherein at least two of said probe sequences detect a genetic rearrangement by using Molecular Combing, said composition comprising either at least one short (<12 kb) sequence and at least one non-overlapping long sequence (>14 kb), or at least one group of at least two short sequences, less than 10 kb each, which total length is longer than 14 kb and less than 150 kb, hybridizing contiguously on the genetic target. The short probe(s) in such a composition may preferably range from 0.5 kb to 12 kb and the long probe(s) range from 14 kb to 40 kb. Frequent repetitive sequences described above may be removed from the probes. Examples of probe sequences are those that hybridize specifically on the MSH2 gene or in the region of the MSH2 gene or on the MLH1 gene or in the region of the MLH1 gene. Specific kinds of short probe sequence(s) where repetitive sequences have been removed include those selected from the group consisting of or comprising the sequences obtained by PCR amplification on human genomic DNA using the primer pairs described in Table 1 in the lines:

MSH2-v1

P3 (primer pairs P3a_MSH2-v1 to P3c_MSH2-v1, SEQ ID NO:21-26)

P4 (primer pairs P4a_MSH2-v1 to P4b_MSH2-v1, SEQ ID NO:27-30)

P5 (primer pairs P5a_MSH2-v1 to P5c_MSH2-v1, SEQ ID NO:31-36) P6 (primer pairs P6a_MSH2-v1 to P6b_MSH2-v1, SEQ ID NO:37-40)

P7 (primer pairs P7a_MSH2-v1 to P7c_MSH2-v1, SEQ ID NO:41-46)

P8 (primer pairs P8a_MSH2-v1 to P8b_MSH2-v1, SEQ ID NO:47-50)

P9 (primer pairs P9a_MSH2-v1 to P9c_MSH2-v1, SEQ ID NO:51-56)

P10 (primer pairs P10a_MSH2-v1 to P10b_MSH2-v1, SEQ ID NO:57-60)

MLH1-v1

P3 (primer pairs P3a_MLH1-v1 to P3d_MLH1-v1, SEQ ID NO:95-102)

P4 (primer pairs P4a_MLH1-v1 to P4b_MLH1-v1, SEQ ID NO:103-106)

P5 (primer pairs P5a_MLH1-v1 to P5b_MLH1-v1, SEQ ID NO:107-110)

P6 (primer pair P6a_MLH1-v1, SEQ ID NO:111-112)

P7 (primer pair P7a_MLH1-v1, SEQ ID NO:113-114

P8 (primer pairs P8a_MLH1-v1 to P8d_MLH1-v1, SEQ ID NO:115-122)

and the short probes may be used in combination with the long probe sequence(s) selected from the group consisting of or comprising the sequences obtained by PCR amplification on human genomic DNA using the primer pairs described in Table 1 in the lines MSH2-v1

P11 (primer pairs P11a_MSH2-v1 to P11c_MSH2-v1, SEQ ID NO:61-66)

P12 (primer pairs P12a_MSH2-v1 to P12e_MSH2-v1, SEQ ID NO:67-76)

MLH1-v1

P9 (primer pairs P9a_MLH1-v1 to P9c_MLH1-v1, SEQ ID NO:123-128)

P10 (primer pairs P10a_MLH1-v1 to P10e_MLH1-v1, SEQ ID NO:129-138).

Specific kinds of contiguous short probe sequence(s) forming long stretches include those selected from the group consisting of or comprising the sequences obtained by PCR amplification on human genomic DNA using the primer pairs described in Table 1 in the lines:

MSH2-v2

PE1-2 (primer pairs PE1_MSH2-v2 to PE2_MSH2-v2, SEQ ID NO:163-166) and

PE3-6 (primer pairs PE3_MSH2-v2 to PE5-6_MSH2-v2, SEQ ID NO:167-172), together forming one stretch;

PE9 (primer pairs E9_MSH2-v2 and I9-10_MSH2-v2, SEQ ID NO:185-188),

PE10 (primer pair E10_MSH2-v2, SEQ ID NO:189-190),

PE11 (primer pairs E11_MSH2-v2 and I11-12_MSH2-v2, SEQ ID NO:191-194),

PE12-14 (primer pairs E12_MSH2-v2 and E13-14 MSH2-v2, SEQ ID NO:195-198) and

PE15-16 (primer pairs E15_MSH2-v2 and E16_MSH2-v2, SEQ ID NO:199-202), together forming one stretch;

MLH1-v2

PE1-2 (primer pairs E1_MLH1-v2 and E2_MLH1-v2, SEQ ID NO:227-230),

PE3-4 (primer pairs I23_MLH1-v2, E3_MLH1-v2 and E4_MLH1-v2, SEQ ID NO:231-236),

PE5-6 (primer pairs E5_MLH1-v2 and E6_MLH1-v2, SEQ ID NO:237-240),

PE7-9 (primer pairs E7-8_MLH1-v2 and E9_MLH1-v2, SEQ ID NO:241-244) and

PE10-11 (primer pairs E10_MLH1-v2 and E11_MLH1-v2, SEQ ID NO:245-248), together forming one stretch;

The primers designed for the purpose of preparing short probes of the invention may have a sequence of 20 to 40 nucleotides and comprise in their 3' end a sequence of at least 20 contiguous nucleotides that base pairs with the target. The primer sequence thus may also comprise additional nucleotides that do not base pair with the target in its 5' end. The nucleotides which do not base pair may be useful for the construction of the primers or for the cloning of the amplified sequence resulting from polymerization starting from the primers. In a particular embodiment the sequence of the primer that hybridizes to the target is longer than 20 nucleotides.

Molecular Combing is a powerful FISH-based technique for direct visualization of single DNA molecules that are attached, uniformly and irreversibly, to specially treated glass surfaces (Herrick and Bensimon, 2009); (Schurra and Bensimon, 2009). This technology considerably improves the structural and functional analysis of DNA across the genome and is capable of visualizing the entire genome at high resolution (in the kb range) in a single analysis.

Another embodiment of the invention is a method for designing a set of short probes or set of short and long probes as described above comprising:

identifying a polynucleotide containing a genomic region of interest, selecting long probe sequences outside of the genomic region of interest but within 100 kb of the closest probe in the region of interest, and preferably within 30 kb of the closest probe in the region of interest and optionally removing frequently repeated sequences from said long probe sequences, selecting a short probe sequences from within the genomic region of interest so that no gaps longer than 20 kb, and preferably no gaps longer than 12 kb appear between the short probes; or selecting a series of short probes that together form a long continuous stretch that covers the genomic region of interest;

hybridizing the probes to a genomic polynucleotide comprising the genomic region of interest, detecting the hybridized probes, and determining which sets of probes form motifs that specifically identify the genomic sequence of interest from a reference genomic sequence.

The comparison of the location of the hybridized probes on the target genomic polynucleotide sequence with one or more motifs based on the hybridization of said probes to a reference, control, normal, not mutated, or not rearranged genomic polynucleotide sequence, as disclosed in the databanks or experimentally obtained on samples.

The techniques disclosed herein may be applied to diagnosis of disease as well as for the identification of genetic rearrangements associated with a disease, disorder or condition. They may also be used as companion diagnostics to study the responses of a subject or group of subjects who have particular rearrangements to therapy, responses to environmental agents, or the effects of lifestyle choices. Specifically, the diagnostic products and methods of the invention are useful for diagnosis and assessments for subjects having or at risk of developing colorectal cancer. High resolution barcodes allow multiplex analysis of patients for extended or expanded diagnosis at the levels of patient stratification/classification and prognosis. Thus, the techniques disclosed herein can also be used to predict the course and probably outcome of a disease, disorder or condition as well as the likelihood of progression, stability, or recovery. Multiplex high resolution barcodes also permit the identification of key genetic alterations in a subject that would benefit from a particular kind of therapy as well as a way to assess the reaction of a subject to a particular kind of therapy or therapeutic intervention.

Specific embodiments of the invention include the following, which embodiments are especially carried out in vitro.

A method for detecting mutated or rearranged genomic polynucleotide sequence comprising: (a1) hybridizing a target genomic polynucleotide comprising one or more genomic region(s) of interest, where mutations or rearrangements are sought, to a set of short probes that bind to each region of interest without long gaps between the portions of the target sequence bound by the set of short probes said set of short probes optionally including or being in combination with a (sub)set of short probes selected so that on each genomic region some of the short probes when taken together form a long contiguous stretch inside or outside the region of interest and where the short probes may optionally have frequent repetitive sequences removed; or (a2) hybridizing a target genomic polynucleotide comprising one or more genomic region(s) of interest, where mutations or rearrangements are sought, to a set of short probes that bind to each region of interest without long gaps between the portions of the target sequence bound by the set of short probes and to one or more long (docking) probe(s) that bind to sequences near but outside of the region(s) of interest; wherein the sequence(s) of the long probe(s) does not overlap that of the short probes and wherein the short and/or long probes may optionally have some or all of the frequently repeating sequences removed; (b) detecting the locations of hybridized probes on the genomic region(s) of interest; optionally, (c) comparing the location of the hybridized probes on the target genomic polynucleotide sequence with one or more motifs based on the hybridization of said probes to a reference, control, normal, not mutated, or not rearranged genomic polynucleotide)sequence; and optionally, and/or (d) correlating the presence of a mutated or rearranged genomic polynucleotide with a specific phenotype, disease, disorder, or condition.

The invention relates in particular to the method herein described wherein the mutated or rearranged genomic polynucleotide sequence is obtained from a subject who has cancer or who is suspected of having cancer or who is susceptible to have a genetic predisposition to cancer.

The invention also relates in a particular embodiment to a method wherein the mutated or rearranged genomic polynucleotide sequence is obtained from a subject who has colorectal cancer or who is suspected of having colorectal cancer or who is susceptible to have a genetic predisposition to colorectal cancer, wherein said short and long probes identify mutations or genomic rearrangements associated with colorectal cancer, wherein said control, not mutated or normal genomic sequence is obtained from a subject not at risk for colorectal cancer and wherein the detection of a genomic rearrangement; and assessing presence of or risk of developing colorectal cancer when said genomic rearrangement is detected. In this method the probes can hybridize specifically on the MSH2 gene, in the region of the MSH2 gene, on the MLH1 gene, or in the region of the MLH1 gene.

The invention also relates in a particular embodiment to a method wherein the mutated or rearranged genomic polynucleotide sequence is obtained from a subject who has breast cancer or who is suspected to having breast cancer or who is susceptible to have a genetic predisposition to breast cancer.

The invention also relates in a particular embodiment to a method wherein the mutated or rearranged genomic polynucleotide sequence is obtained from a subject who has ovarian cancer or who is suspected to having ovarian cancer or who is susceptible to have a genetic predisposition to ovarian cancer.

The invention also relates in a particular embodiment to a method wherein the mutated or rearranged genomic polynucleotide sequence is obtained from a subject who has lung cancer or who is suspected to having lung cancer or who is susceptible to have a genetic predisposition to lung cancer.

The invention also relates in a particular embodiment to a method wherein the mutated or rearranged genomic polynucleotide sequence is obtained from a subject who has a cardiovascular disease, disorder or condition or who is suspected of having cardiovascular disease, disorder or condition or who is susceptible to have a genetic predisposition to cardiovascular disease, disorder or condition.

The invention also relates in a particular embodiment to a method wherein the mutated or rearranged genomic polynucleotide sequence is obtained from a subject who has a diabetes or who is suspected of having diabetes or who is susceptible to have a genetic predisposition to diabetes.

The invention also relates in a particular embodiment to a method wherein the mutated or rearranged genomic polynucleotide sequence is obtained from a subject who has a neuromuscular disorder or who is suspected of having a neuromuscular disorder.

The invention also relates in a particular embodiment to a method wherein the mutated or rearranged genomic polynucleotide sequence is obtained from a subject who has, is suspected of having, or is susceptible of being a carrier for a genetic or hereditary disease, disorder or condition.

The invention also relates in a particular embodiment to a method wherein the short and long probe sequences are specific to human genes or to human genomic regions associated with cancer, colorectal cancer or a foetal genetic alteration known or unknown when said region or gene is mutated or genetically rearranged.

The invention also relates in a particular embodiment to a method wherein the mutated or rearranged genomic polynucleotide sequence is obtained from a subject who has, is suspected of having, or is suspected of being a carrier for a multigenic genetic or hereditary disease, disorder or condition or for a genetic or hereditary disease, disorder or condition associated with rearrangement of genomic DNA.

The invention also relates in a particular embodiment to a method wherein the mutated or rearranged genomic polynucleotide sequence is obtained from a subject undergoing treatment for a disease, disorder or condition associated with a genomic inherited or acquired rearrangement and the results obtained are compared to results obtained at other time points before, during or after the termination of treatment.

The invention relates to method of any of the embodiments described herein, characterized by the following features taken individually or in any combination: the hybridizing with the short and long probes in (a2) is performed simultaneously; the short probes are 10 kb or less; and/or the short probe(s) comprise at least one short (less than 10 kb) sequence and at least one non-overlapping long sequence (more than 12 kb), or at least one group of at least two short sequences, less than 5, 6, 7, 8, 9 or 10 kb each, total group length is longer than 12 kb and less than 150 kb, hybridizing contiguously on the mutated or rearranged polynucleotide sequence. In these methods the short probes may comprise a set of contiguous probes that span a stretch of the genomic polynucleotide sequences inside or outside the region of interest that is at least 14 kb; and/or the long probe(s) may comprise one or more docking probes of more than 14 kb and less than 40 kb. The long probe(s) may have a length of at least 14 kb and bind to a polynucleotide sequence outside the region of interest.

Both the long and short probes may be designed to exclude frequently occurring repetitive DNA sequences. These repetitive DNA sequences, which may be excluded from the long and short probes, will generally appear more than once and more often than statistically predicted based on their length and base content. For example, a repetitive DNA sequence between 50 and 400 contiguous nucleotides in length, which appear more than once and more often than statistically predicted based on their length and base content, can be excluded from the short and/or long probe(s). One example of a repetitive sequence that can be excluded from the short and long probes is or are members of the repetitive Alu family DNA sequences.

In some embodiments of the invention the probes in (b) of the first embodiment are fluorescently tagged so that they can be detected fluorometrically. In other embodiments in b) each probe is tagged with one of two or more fluorescent tags.

According to other embodiments of the methods above, motifs or easily identifiable subsets of the probes are detected and compared instead of every probe sequence.

The methods described above may employ at least 3, 4, 5, 6, 7, 8, 9, 10, 11, 12 or more short probes. These short probes may each have a length of least 500, 600, 700, 800, 900 or more base pairs (bp). In some embodiments of the methods above, the probes will be selected so that the gaps between short probes in the genomic region of interest are no more than 12 kb each. In further embodiments the short probes will bind to a single contiguous genomic region of interest or the short probes can be selected to bind to more than one non-contiguous genomic region of interest. The long probes used in the method above may be selected so as to be no more than 20, 30 or 40 kb. The or each of the genomic region(s) of interest in the methods described above can be selected to be longer than 50 kb.

Another embodiment of the invention is a kit comprising a set of short probes or a set of short and a set of long probe(s); and optionally one or more components for binding said probes to a polynucleotide, for performing molecular combing, and/or for detecting whether hybridization has occurred; (i) wherein the short probes comprise a set of probes that taken together bind to a long continuous stretch of the genomic region of interest; or (ii) wherein the long probes bind to sequences outside the genomic region of interest, do not overlap the short probe sequences; and optionally, where the repetitive sequences have been removed from the long and/or short probes. A kit of the invention is suitable and/or is specific for use in a method of the invention as disclosed herein. In a particular embodiment its short and/or long probes are characterized by the features described herein in relation with the methods. Such a kit may be employed for or contain instructions for the detection of genomic rearrangements associated with colorectal cancer or genetic predisposition to colorectal cancer; for the detection of genomic rearrangements associated with breast cancer or genetic predisposition to breast cancer; for the detection of genomic rearrangements associated with ovarian cancer or genetic predisposition to ovarian cancer; for the detection of genomic rearrangements associated with lung cancer or genetic predisposition to lung cancer.

Another embodiment of the invention is a composition containing the short, or short and long probe(s) described by the first embodiment above, wherein at least two of said probe sequences detect a genetic rearrangement by using Molecular Combing, said composition comprising either (a) at least one short (less than 10 kb) sequence and at least one non-overlapping long sequence (more than 14 kb), or (b) at least one group of at least two short sequences, less than 10 kb each, which total length is longer than 14 kb and less than 150 kb, hybridizing contiguously on the genetic target. In this composition the short probe(s) can range from 0.5 kb to 9 kb and the long probe(s) can range from 14 kb to 40 kb. The size of the short probes may range from 0.5 to 9 kb and at least 90% of the frequent repetitive sequences can be been removed from the short probe sequences. This composition may contain probes sequences that hybridize specifically on the MSH2 gene or in the region of the MSH2 gene or on the MLH1 gene or in the region of the MLH1 gene.

In yet another embodiment the invention involves a method for designing short and long probes described herein in relation to methods comprising (a) identifying a polynucleotide containing a genomic region of interest, (b) selecting long probe sequences outside of the genomic region of interest but within 100 kb of the closest probe within the region of interest and optionally removing frequently repeated sequences from the long probe sequences, (c) selecting a set of short probe sequences from within the genomic region of interest so that no gaps longer than 15 kb appear between the short probes; or selecting a series of short probes that together form a long continuous stretch that covers the genomic region of interest; (d) hybridizing the probes to a genomic polynucleotide comprising the genomic region of interest, (e) detecting the hybridized probes, and (f) determining which sets of probes form motifs that distinguish the genomic sequence of interest from a reference genomic sequence.

probe code v1 (without repetitive element) on RP11-426N19. (C) probe code-v2 on RP11-426N19.

FIG. 3. Designed probe set for MSH2 by exclusion of repetitive element. A) theoretical probe set (labeled in red and green in microscopy experiments represented here in grey and black, respectively), and position of exon (small numbered dots). (B) actual hybridization image corresponding to MSH2-v1 probe set. Original microscopy images consist of three channel images where each channel is the signal from a given fluorophore—these are acquired separately in the microscopy procedure. These channels are represented here as different shades on a grayscale: green probes are shown in black and red probes in gray, while the background (absence of signal) is white. The aspect ratio was not preserved, signals have been "widened" (i.e. stretched perpendicularly to the direction of the DNA fiber) in order to improve the visibility of the probes.

FIG. 4. Designed probe set for MLH1 by exclusion of repetitive element. A) theoretical probe set (red and green), and position of exon (purple dot). (B) actual hybridization image corresponding to MLH1-v1 probe set. The same color conventions are used for diagrams and microscopy images as in panels A and B of FIG. 3.

FIG. 5. Designed probe set for MSH2 with docking probes (v2). (A) theoretical probe set). B) actual hybridization image corresponding to MSH2-v2 probe set. The color conventions in this and the other 3-color microscopy images (and corresponding diagrams) is as follows: blue probes are represented in black, green probes in dark gray, red probes in light gray and the background is white.

FIG. 6. Designed probe set for with docking probes (v2). (A) theoretical probe set). (B) actual hybridization image corresponding to MLH1-v1 probe set. The same color conventions are used for diagrams and microscopy images as in FIG. 5.

Figures 7A, 7B, 7C:
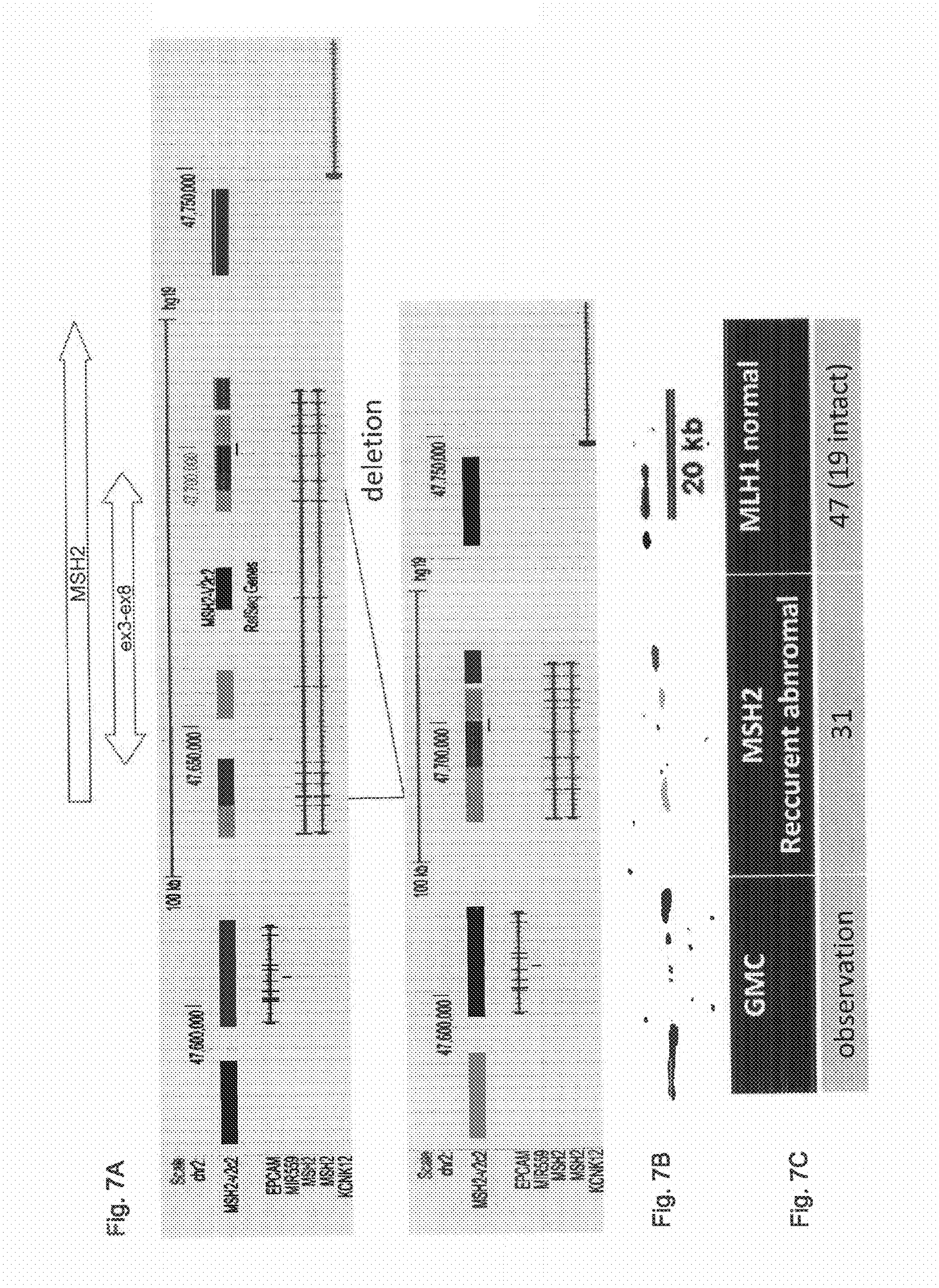

FIG. 7. Validation of genomic rearrangement in MSH2 in LoVo cell line with v2 probe set. Sketches of both theoretical probe set (FIG. 7A, top) and validated rearrangement (FIG. 7A, bottom) by molecular combing. The photo (FIG. 7B) is the recurrent abnormal signal set which corresponding to deletion from exon 3 to exon 8 of MSH2 (as in FIG. 7A, bottom). The same color conventions are used for diagrams and microscopy images as in FIG. 5. FIG. 7C provides the number of observations for each GMC.

FIG. 8. Validation of genomic rearrangement in MLH1 in SK-OV-3 cell line with v2 probe set. Sketches of both theoretical probe set (FIG. 8A, top) and validated rearrangement (FIG. 8A, bottom) by molecular combing. The photo (FIG. 8B) is the representative (but few cases) signal set corresponding to the upper stream of MLH1 probe set (left side of theoretical probe set). The difference of observation number between MSH2 probe signal (normal) and MLH1 (a part of left side) clearly demonstrates that deletion of exon 4 to 19 in MLH1 is homozygous, (consistent with reference 7 (FIG. 8C)). Molecular combing test also revealed that the breakpoint of deletion is larger than previously reported (downstream probes from exon 19 are all deleted). The same color conventions are used for diagrams and microscopy images as in FIG. 5

Table 1. describes primer sequences and coordinates on human genomic DNA used for hybridization fragment synthesis to design the probes of the invention. These primers or variant therefore obtained by adding nucleotides in the ends of the described sequences and having up to 40 nucleotides, are part of the invention.

Table 2. Analysis of sequence of probe sets and their covering region. These sequences and the sets of probes that are disclosed in particular, are part of the invention.

Sequence of each of probe sets or region was subjected to RepeatMasker test and some of representative values are shown in the table. Sum length: sum up of sequence of all probes in each set. For MLH1 and MSH2 regions, this is the total length of each region. Repeat length: sum of sequences recognized as sorts of repeat in human genome. This includes sequences other than SINE. Total repeat. % of repeat length in sum length. SINE: % of sequences categorized as SINE in sum length. ALUs: % of sequences categorized as Alu family sequences in sum length.

DETAILED DESCRIPTION OF THE INVENTION

The above described strategies, for the reasons mentioned, are unsuitable to design a high-resolution code for diagnostics applications using technologies such as molecular combing.

In the present invention, the probes are defined as follows: a short probe is a nucleic acid sequence complementary to a genomic sequence, which probe can be detected with a given marker (such as a fluorochrome) once hybridized on the genomic sequence. One probe may be either made of (i) one single fragment covering the whole sequence, or of (ii) several exactly contiguous fragments, and/or (iii) slightly overlapping fragments (with an overlap less than 250 bp) and/or (iv) fragments separated by a very short gap (less than 1000 bp). With such short overlaps or gaps, using Molecular combing in our current setup, the fragments appears almost contiguous. The distance may be adjusted depending on the specific technique and experimental conditions. For example, with less resolutive conditions, longer gaps (less than 2 kb) or overlaps may be tolerated, provided fragments separated by such a gap still appear contiguous. Under more resolutive conditions, gaps should be shorter (less than 200 bp) in order for the fragments to appear contiguous. Short probes range in size from 500 bp to 10 kb.

A long probe is a nucleic acid sequence complementary to a genomic sequence, which probe can be detected with a given marker (such as a fluorochrome) once hybridized on the genomic sequence. One probe may be either made of (i) one single fragment covering the whole sequence, or of (ii) several exactly contiguous fragments, and/or (iii) slightly overlapping fragments (with an overlap less than 250 bp) and/or (iv) fragments separated by a gap (less than 3.5 kb), provided that more than 70% of the target sequence stretch is covered by probes (i.e. provided the gaps represent less than 30% of the target sequence). With such overlaps or gaps, using Molecular combing in our current setup, the fragments are efficiently detected. The distance may be adjusted depending on the specific technique and experimental conditions. For example, with less resolutive conditions, longer gaps (less than 5 kb each, representing in total less than 50% of the sequence) or overlaps may be tolerated, provided fragments separated by such gaps are still detected efficiently. Also, under such conditions, longer probes should be used (more than 20 kb) to allow for efficient detection. Under more resolutive conditions, gaps should be shorter (less than 2 kb) in order for the fragments to be efficiently detected, and probes may still be efficiently detected with shorter size (more than 10 kb). Long probes range in size from 12 kb to 150 kb.

In the present invention, the size of probes reflects the length of the genomic sequence where the probe hybridizes, independently of the number of strands in the DNA molecules. Therefore, a probe may be described as 1 kb (1 kilobase=1000 bases) or, indifferently, as 1000 bp (base pairs): in both cases, the probe hybridizes over 1000 bases of one of the strands of the target DNA molecule (and, if the probe is double stranded, also on the 1000 complementary bases of the other strand of the target molecule).

In the present invention, a "barcode" designates a specific motif formed by a set of probes labeled with different markers, where the motif characteristics are the lengths of the probes in the set, the lengths of the gaps separating successive probes and the colors in which the probes are detected (or, more generally, the markers with which the probes are labeled).

If a high coverage barcode is to be designed for high resolution, probe and space lengths need to be roughly in the 0.5 kb to 10 kb range (see above). This makes it unpractical to design probes that completely exclude rearrangements, and yet are spaced closely enough for the code to allow high location precision. On the other hand, some non-specific hybridization (i.e. hybridization of [parts of] a probe on genomic regions that are not the designed target of that probe) of a probe is acceptable when using a code strategy for the reading of signals. Indeed, in applications such as Southern blot where the hybridization of a single probe is assessed or aCGH where hybridization of every probe is considered separately, the non-specific hybridization of probes on even a very limited number of regions may lead to completely unusable results. To a lesser extent, this is also the case with multiple-probe applications such as FISH, since the resolution of FISH is insufficient to distinguish genomic regions as far apart as several tens of megabases: a single non-specific hybridization would lead to unusable results if it were located close enough to the targeted region.

In molecular combing and other similar applications using a code strategy, the quantity of non-specifically hybridized probes is not in issue per se. If a probe (or fragments of a probe) hybridizes even multiple times outside the region of interest, it is unlikely it will recreate a motif sufficiently similar to the code to be confusing. Also, non-specific hybridization over short sequences (<<1 kb), even within the region of interest, would most likely not be detected, unless they are sufficiently clustered to generate a long (>1 kb) stretch of non-specific hybridization. For the above reasons, the inventors have developed an alternative approach for the design of probes when the main issue is the design of a (several) high resolution code(s) in a (several) given genomic region(s). The main step of this approach relies only on the knowledge of the sequence of the region(s) themselves. When designing such a code, the major issue is to avoid significant non-specific hybridization within the regions of interest(s). Non-specific hybridization becomes an issue only if several probes display non-specific hybridization on neighboring sequences outside the region of interest. In the latter case, there is a risk that the pattern of probes resembles the original code, or a rearranged version of it, and this would likely lead to false conclusions. Although the invention described herein does not allow excluding such occurrences, this is relatively easily done once the method described herein has been used to exclude other non-specific hybridizations (see below).

The basis for this approach is the detection and exclusion of sequences that are repetitive within the region(s) of interest. For this, only the corresponding sequence(s) (the target sequence(s)) have to be known. One easy way to detect such repeats is the search for local sequence alignments within the target sequence(s), which can be done with e.g. a dot-plot comparison of each target sequence with itself and the other target sequences. A dot-plot is a graph with the two (sets of) sequences that are being compared forming the two axis, while dots are printed at every point where the coordinates correspond to a local homology. For example, if nucleotide x from sequence A (horizontal axis) matches nucleotide y from sequence B (vertical axis), then a dot will appear at the point with (x; y) coordinates. Graphically, local alignments appear as diagonal lines. Some more elaborate tools inspired from dot-plots are available, that compare short sequences ("words", typically a few nucleotides/tens of nucleotides long) rather than single nucleotides, and display dots in various shades of gray depending on the extent of homology, thus allowing a direct visual reading of relaxed homologies (non-specific hybridization may well appear with incomplete homology). The comparison may also be done directly on both strands for one of the sequences, so homologies appear for both sense and reverse complement orientations. An example of such a tool is "Dotter" (ref. 4).

With these tools, very frequent repetitive sequences, such as Alu sequences in the Human genome, appear quite clearly, as they have local homologies with numerous other sequences within the target regions. Therefore, stretches with a high frequency of these sequences appear as a gray band (horizontal or vertical depending on whether the stretch is located on the vertical or horizontal axis). The exact appearance of these stretches with dot-plot display tools will depend on settings, and possibly word size. Settings were selected such that sequence stretches longer than 200 bp with more than 80% homology appear clearly and can be located with a roughly 10 bp precision.

A sequence of 200 bp or more that contains more than 10 significant homologous sequences (less than 1, 2, 3, 4, 5, 10, 15 or 20% nucleotide mismatch or insertion/deletion) within the regions of interest is a frequent repetitive sequence, prone to generate significant non-specific hybridization. It is generally possible to design probes in such a way that they are void of these frequent repetitive sequences, thus increasing the specificity and the high resolution of the present technology compared to the published previous methods.

"Docking" Probes

Although, as shown above, shorter probes make for more precise localization of breakpoints and measurement of deleted or amplified sequences, they are, generally speaking, more difficult to detect with fiber-fish techniques and molecular combing, as they appear as shorter stretches of signal, i.e., they are both smaller and less easy to distinguish from noise (fluorescent spots either unrelated to probes or to hybridization of probes). This is particularly true when considering automatic (computer-based) detection of signals.

It is therefore desirable to include longer probes in the code (for example, more than 12 kb and less than 150 kb, preferably more than 14 kb and less than 40 kb, in particular for the detection of genetic rearrangements in the regions of MSH2 or MLH1 genes). These probes would appear as actual lines (rather than spots), readily distinguishable from noise and easily detectable due to their size. Once the signals of interest are detected, the detection of other probes located on the same DNA fiber is easier.

This is especially true using technologies such as Molecular Combing where the linearity of the fibers implies the other probes, if any, are located in the alignment of the first probe. Therefore, the invention provides that the inclusion of longer (>12 kb, preferably >14 kb) probes in the set of probes is a step towards easier detection of signals of interest. Not all probes in the set need to be that long: in a fast and "rough" detection step, the long probes are sought, which allows the localization of signals of interest. These probes are called "docking probes" as they allow to "land" on the regions of interest efficiently. In a second step, the shorter probes are sought in the neighborhood of the docking probes (and more specifically in the case of Molecular Combing or related technologies, in the alignment of these probes). Although when performed by a human operator these steps can hardly be formally executed consecutively, if an operator may limit his search to longer probes, he can browse through images more rapidly, which would only allow him to detect these probes and spend more time on images where a docking probe is seen in order to look for other shorter probes. As the longer docking probes would locally diminish the location precision and the resolution of the code, it is preferable for them not to be located in the region where rearrangements are sought. This is possible if the probes are located near, but not in, the region of interest, e.g. at either end of this region.

If it is desirable to only consider complete signals in the analysis of a given region (i.e. signals covering the entire contiguous region), these longer probes may also be used to assess the integrity of the region: if there is a probe located at each end and both probes are present, no breakage of the fiber has occurred during the DNA preparation or stretching step. In cases where several non contiguous regions are analyzed in a single test, obviously each region has to have its "docking" probes in order to be correctly detected.

Continuous Stretch of Short Probes

An alternative to the "docking probes" approach above is to design the set of probes in such a way that at least some groups of shorter probes form a continuous stretch of signal. This is possible if probe sequences are adjacent. In that case, several probes, although short enough (less than 10 kb) to provide for sufficient resolution, may well combine to form a long enough (more than 14 kb) signal for fast and reliable detection. Indeed, if the operator may combine color channels to view images, this stretch would still appear as a long line rather than a spot, allowing its distinction from background noise. This is possible by using either common optical setups such as tri-color filters in fluorescence microscopy, or by using common image viewing software. In the case of automatic detection, it is also possible to use combined color information and therefore to make use of the very characteristic aspect of a multicolor line relatively to background spot-like noise.

Measurements

The probe designs described above likely lead to a large number of probes to be measured in a test. The usual approach for probe measurement is to measure all of the probes constituting a signal, as well as the gaps separating them. In a test with a large number of probes, the amount of work required for analyzing results is increased. In order to balance this, the invention relates to a more efficient designed approach for signal measurement. This approach consists in the measurement of subgroups of probes constituting easily recognizable motifs. The subgroups are two or several consecutive probes and the gaps between them, and possibly gaps at either end, chosen in order for their total length to remain within reasonably precise measurement range (10-30 kb).

There is likely to be a systematic bias in the measurement of digitalized images of fluorescent segments. Indeed, at the extremity of such a fragment, the intensity of the signal decreases gradually when moving away from the center, to reach the level of the background. Depending on where the operator/the software sets the threshold for the determination of the actual end there may be a systematic over- or under-estimation of the lengths. This bias is compensated for if the measured motifs have a probe at one end and a gap at the other. Therefore, it is preferable to design motifs in this way.

If a motif is found to have an abnormal length (different from the expected theoretical length) in a given sample, it remains possible to measure the probes and gaps within this motif in order to further precise the location of the rearrangement. With this approach, it is possible to measure in a fast and efficient way all of the signals for initial screening, while keeping the location precision allowed by small probes. The somewhat lower precision on measurements due to the larger size of the subgroups compared to the probes is essentially compensated for by the higher number of signals that can be measured within the same operator time.

Application to HNPCC—Rationale

Colorectal cancer is the 4th most frequent form of cancer in human and around 5% of the cancer is considered as a hereditary form. The most frequent form of hereditary colorectal cancer is known as Lynch syndrome, or HNPCC (hereditary non-polyposis colorectal cancer). HNPCC increases a lifetime risk of cancer development in up to 80% (lifetime risk is around 7% in normal population US). HNPCC also increases other cancers (endometrial, ovarian, stomach).

Genetic aspect of HNPCC is known as a result of mutation in some of Mismatch Repair (MMR) genes such as MSH2, MLH1, MSH6, PMS2, etc. MSH2 and MLH1 mutation accounts for more than 80% of all mutation of MMR genes in HNPCC. Both point mutation and large rearrangements are reported in mutation of those genes, and especially high % of large mutation in MSH2 is observed because of high level of small repetitive element in its genetic sequence. Today the molecular diagnosis is done after studies of familial cancer history, tumor characterization by microsatellite instability test.

Normally mutation one alleles of one of MMR genes is sufficient for molecular diagnosis of HNPCC. All HNPCC individuals have both wild and mutated genes. Point mutation of targeted MMR genes can be detected by sequencing of genes and current sequencing test investigates only the sequence of exons. In case of large rearrangements such as deletion and amplification (loss and gain of genetic elements, respectively), sequencing does not detect them because altered sequences do not exist, and frequently primer binding regions for sequencing are deleted. As a result, sequence information comes from only wild allele and gives false negative. Indeed, MSH2 and MLH1 genes are higher percentage of repetitive elements of SINE in their genetic sequence. To address this large rearrangement, the test should detect presence of deletion or amplification in the MMR genes. One approach is cartography of MMR genes with designed probes of hybridization. Causal large rearrangement has a wide range from sub-kb to loss of total gene (up to 100 kb). A given cartography has to be sensitive to this wide dynamic range of mutation. To cope with it specific probe design was done for MSH2 and MLH1 loci.

The present invention is also related to the detection of known or unknown genomic rearrangements. It is also related to kits containing probes according to the invention, for the detection of known or unknown genomic rearrangements and the associated pathologies, or associated predispositions to pathologies such as cancers or cardiovascular diseases for example.

EXAMPLES

Application to HNPCC—Materials and Method

Probe Design v1

Each probe (probe means continuous hybridization signal, can consist of multiple cloned DNA fragments, e.g., probe 1 of MSH2-v2 covers a 15 kb stretch and consists of five cloned DNA fragments of 3 kb. Since gap or overlap of each junction of these five fragments are smaller than resolution (<50 bp), they are considered and indeed look like continuous single probe of 15 kb) on a region of gene sequence itself has a length between 3-6 kb. In case of larger rearrangement than probe or gap size, obvious change of color pattern of designed probe will be observed. As well as large rearrangement in probe region, such rearrangement is also detectable in gap region, meaning any rearrangement larger than 1 kb at any position in the target genes are detectable. This is a uniqueness of cartography method with high resolution probe hybridization. Other techniques (MLPA, aCGH) can detect only such rearrangement involving probe sequence. For genes with high frequency of large rearrangement such as MSH2 and MLH1, presence of repetitive element in their genetic sequence limits a freedom of probe design for the other technology. Inclusion of repetitive element sequence in their probe design increases false detection a lot, their probe designing has to be free of repetitive element in principle.

Figures 1A, 1B, 1C:
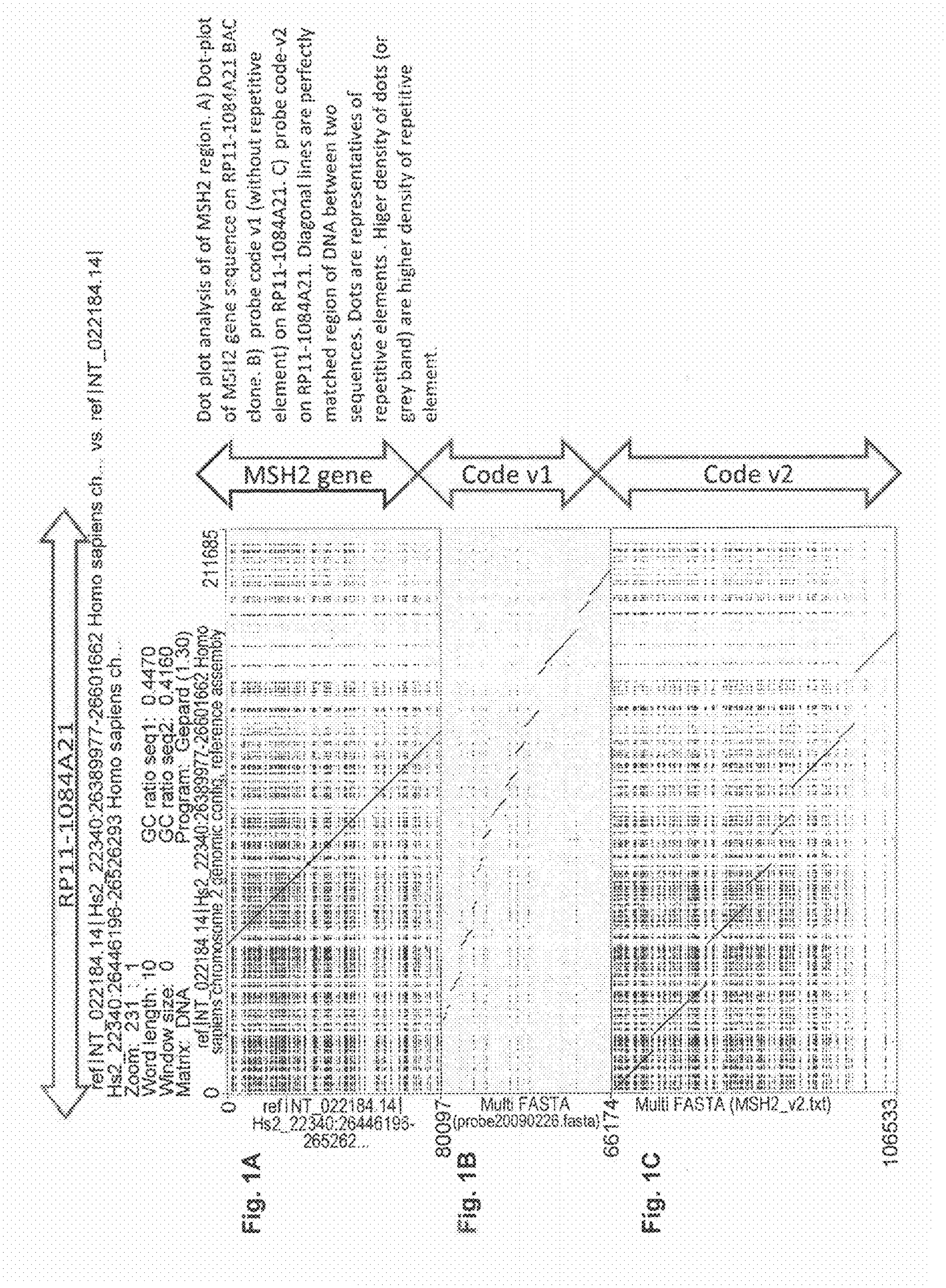
FIG. 1. (A) Dot-plot of MSH2 gene sequence on RP11-1084A21 BAC clone. (B) probe code v1 (without repetitive element) on RP11-1084A21. (C) probe code-v2 on RP11-1084A21. Diagonal lines are perfectly matched region of DNA between two sequences. Dots are representatives of repetitive elements. Higher density of dots (or grey band) are higher density of repetitive element.
Figures 2A, 2B, 2C:
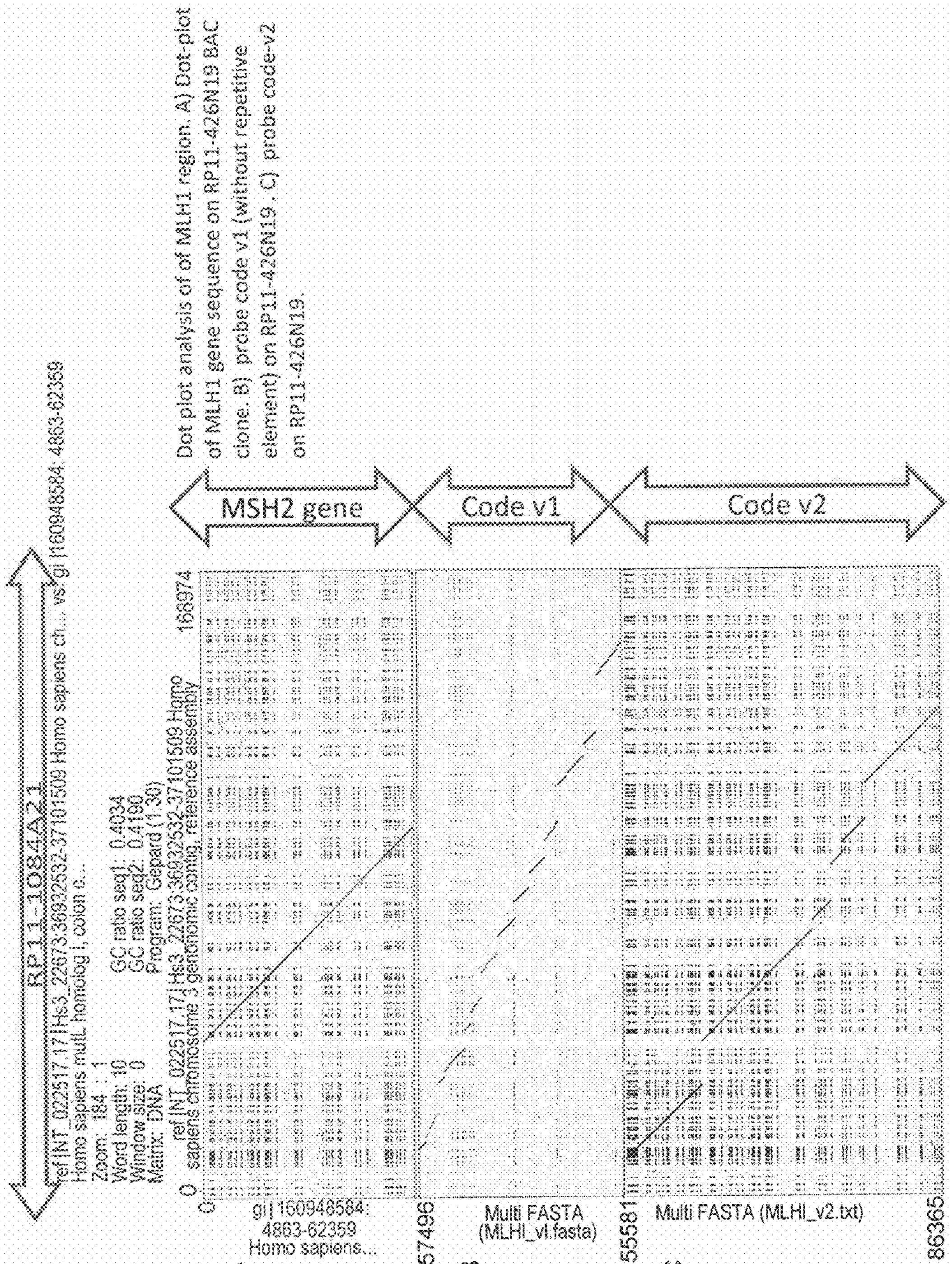
FIG. 2. Dot plot analysis of MLH1 region. (A) Dot-plot of MLH1 gene sequence on RP11-426N19 BAC clone. (B)

Probe sequence was chosen by a dot plot analysis. BAC clone sequence of each gene (RP11-1084A21 (Ch2:47,574,044-47,785,729 for MSH2, RP11-426N19 (Ch3: 36,992,516-37,161,490) for MLH1 was self-plotted and all grey bands region were excluded from the target region of PCR primer design. PCR primer set was designed in the target regions by Primer3plus PCR primer design tool (ref 6). A list of the primers' sequence is shown in table 1A and B. Exclusion of Alu repeat was verified by both dot-plot analysis and RepeatMasker (http://www._repeatmasker.org). FIG. 1B and FIG. 2B show a lot less grey band on dot-plot of probe fragment sequence on BAC clone than dot-plot of gene (containing Alu repeat) on BAC clone. This indicates that sequence of designed probes does not include recurrent repetitive sequence in this target regions. RepeatMasker analysis (with default setting of web server) also clearly shows a dramatic reduction of % of Alu sequence in designed probe sequence. (table 2).

Probe Design v2

To facilitate "recognition" of barcodes on hybridization images, an alternative design of probe set (called v2) was done as said in "Docking" probe section. Design process is same as v1 except no exclusion of repetitive elements based on dot-plot. For v2 probe design, each probe was designed to have more than 3 kb length, close to limit to be recognized as "line", and all exon sequences are covered by a probe stretch (no exons fall in gaps). Docking probes were designed on both extremities of each gene with 15-20 kb length. For MSH2-v2 code, specific probes covering EPCAM gene (see rationale part) was also included between two docking probes. DNA sequence of designed code v2 was subjected to dot-plot analysis to make sure that there is no segmental repeats inside of designed region (FIGS. 1C and 2C).

Cloning of Probe Fragments and Labeling for Hybridization Probe

Each fragment of probes was amplified by PCR, then the fragment was ligated into plasmid vector (pNEB193, pCR2.1-TOPO, pCRXL-TOPO). The ligation product was transformed into *E. coli* competent cells and end-sequences of cloned fragment were verified. Purified plasmid DNA set of each gene was separated into two (v1) or three (v2) gropes according to colors corresponding to theoretical barcodes (FIG. 3A and FIG. 4A for v1, FIG. 5 and FIG. 6 for v2 probe sets). Each group of plasmid DNA was labeled by random priming method. Either whole plasmids containing probe fragments' sequence or PCR amplified probe fragments were used as a template for random priming. There are three haptens to be used for three color detection, biotin (Biot), digoxigenin (Dig) and Alexa Fluor 488 (A488). Biot-labeling was done by BioPrime DNA labeling system (Invitrogen) with manufacture's instruction. For Dig and A488 labeling, dNTP mixture in the kit was replaced with home-blend dNTP mixtures (either 0.1 mM Digoxigenin-11-dUTP (Roche applied science) for Dig labeling or 0.1 mM ChromaTide® Alexa Fluor® 488-7-OBEA-dCTP (Invitrogen) for A488 labeling, 0.1 mM unmodified equivalent (dTTP or dCTP) and 0.2 mM each of other three deoxynucleotides in final labeling reaction solution.).

Sample DNA Preparation 3 cell human cell lines were used for validation for large rearrangement detection in either MSH2 or MLH1. Cell line GM17939 was used as non-mutated sample. Cell line LoVo was used for MSH2 rearrangement validation, which is homozygous for deletion of exon 3-exon8 in MSH2. Another cell line SK-OV-3 was used for rearrangement validation of MLH1, which was reported as homozygous deletion of exon 4-exon 19 in MLH1. For each cell line, cell culture was prepared according to cell bank's instruction. Cultured cells were harvested (for LoVo and SK-OV-3 when 50-70% confluency) or collected by centrifuge (for GM17939 when between 300,000-400,000 cells/ml of medium. Cell pellet was resuspended in 1×PBS/Trypsin mixture to have 1,000,000 cells in 45 μl the cell suspension was mixed with an equal volume of 1.2% (w/v) NuSieve GTG agarose solution in 1×PBS (melted and equilibrated at 50° C. in advance). The cell/agarose mixture as poured into a well of gel plug mold, followed by gelification at 4° C. for 30 min. the gelified agarose plug was immersed in a mixture of 2 mg/ml of Proteinase K, 1% (w/v) of sarcosyl in 0.5M EDTA (pH8.0, 2500 for each plug). The agarose plug was incubated at 50° C. overnight.

Next day the incubated plug was washed in 1×TE (10 mM Tris-HCl, 1 mM EDTA, pH8.0) 3 times for 1 hour each. The DNA plug can be stored in 0.5mEDTA at 4° C. The washed plug was stained in 1000 of 33 μM YOYO-1 (Invitrogen) in TE40.2 (40 mM Tris-HCl, 2 mM EDTA pH8.0) for 1 hour in the dark. The stained plug was heated at 68° C. in 1 ml of combing buffer (0.5M MES pH5.5) for 20 min, then cooled at 42° C. 10 min prior to add 1.5 unit of beta agarase I (NEB). Beta agarase treatment was carried overnight at 42° C. in the dark.

The following day the treated DNA solution was poured into a combing reservoir and a level of the solution in the reservoir was adjusted with additional combing buffer.

Molecular Combing

The DNA solution was set on a Molecular Combing Machine (MCS, Genomic Vision). Molecular combing was performed on a silanized coverslips (Combicoverslips, Genomic Vision). The combed coverslips was fixed at 68° C. for 4 hours, then used for hybridization (or stored at −20° C. until use).

Hybridization and Detection of Probe

For one hybridization, 5 μl of each of labeled probe solutions (of both MSH2 and MLH1) was combined together and with 10 μg of sonicated herring or salmon sperm DNA and 10 μg of human Cot1-DNA (only for V2 probe sets), then purified by standard ethanol precipitation. The precipitate was resuspended with 20 μlof hybridization buffer (50% formamide, 2×SSC, 1% SDS and BlockAid blocking solution (Invitrogen)). The resuspended probe solution was set on a clean glass slide and covered with a DNA combed coverslip. The slide was heated at 90° C. for 5 min for co-denaturation of both probe and combed DNA then incubated at 37° C. overnight with an humidity for hybridization between labeled probes and combed DNA.

The hybridized coverslips was washed in 50% Formamid/2×SSC solution 3 times for 5 min each, followed by another 3 times washing with 2×SSC for 5 min each. The washed coveslips was then developed with two or three layers of fluorescently labeled antibodies or streptavidin. For each layer, antibodies for all haptens were diluted 25 times in BlockAid blocking solution (200 in final volume) and incubated for 20 min at 37° C. For Biot, Streptavidin Alexa Fluor 594 (Invitrogen) was used for the 1st and the 3rd layer, biotin conjugated-goat anti-streptavidin antibody was used for the 2nd layer. Fr Dig, mouse anti-Digoxin AMCA conjugated (Jackson immunoresearch) was for the 1st layer, rat anti-mouse AMCA conjugated (Jackson immunoresearch) conjugated was for the 2nd, the goat anti-rat Alexa Fluore 350 conjugated (Invitrogen) was used for the 3rd layer. For A488, rabbit anti-Alexa Fluor 488 (Invitrogen) was used for the 1st layer, goat anti-rabbit Alexa Fluor 488 conjugated was used for the 2nd layer (no third antibody for A488). After 20 min incubation of each layer of antibody, the coverslip was washed in 2×SSC/1% Tween 20 washing solution 3 times for 5 min each at room temperature. After the washing of 3rd layer, the coverslip was rinsed in 1×PBS, followed by successive bath of 70, 90 and 100% ethanol for 1 min each. The coverslip was dried at room temperature prior to microscopy.

Signal Acquisition and Measurement

Fluorescent signal of developed antibody on the coverslip was obtained by standard epi-fluorescent microscope system or automated fluorescent microscope system (Image Xpress Micro, Molecular Devices) with custom scanning configuration for molecular combing signal. Every set of linearly aligned fluorescent signals and gaps was measured by ImageJ. Each measured set of signals (with color information) was subjected to pattern matching to determine position (if the set is a part of one of probe set) and orientation by comparison with the theoretical probe sets. All unclassified sets (did not match with any positions and orientations of theoretical probe sets) were subjected to similarity check between them to find whether recurrent abnormal pattern appears or not.

Application to HNPCC—Results

Figures 3A, 3B:
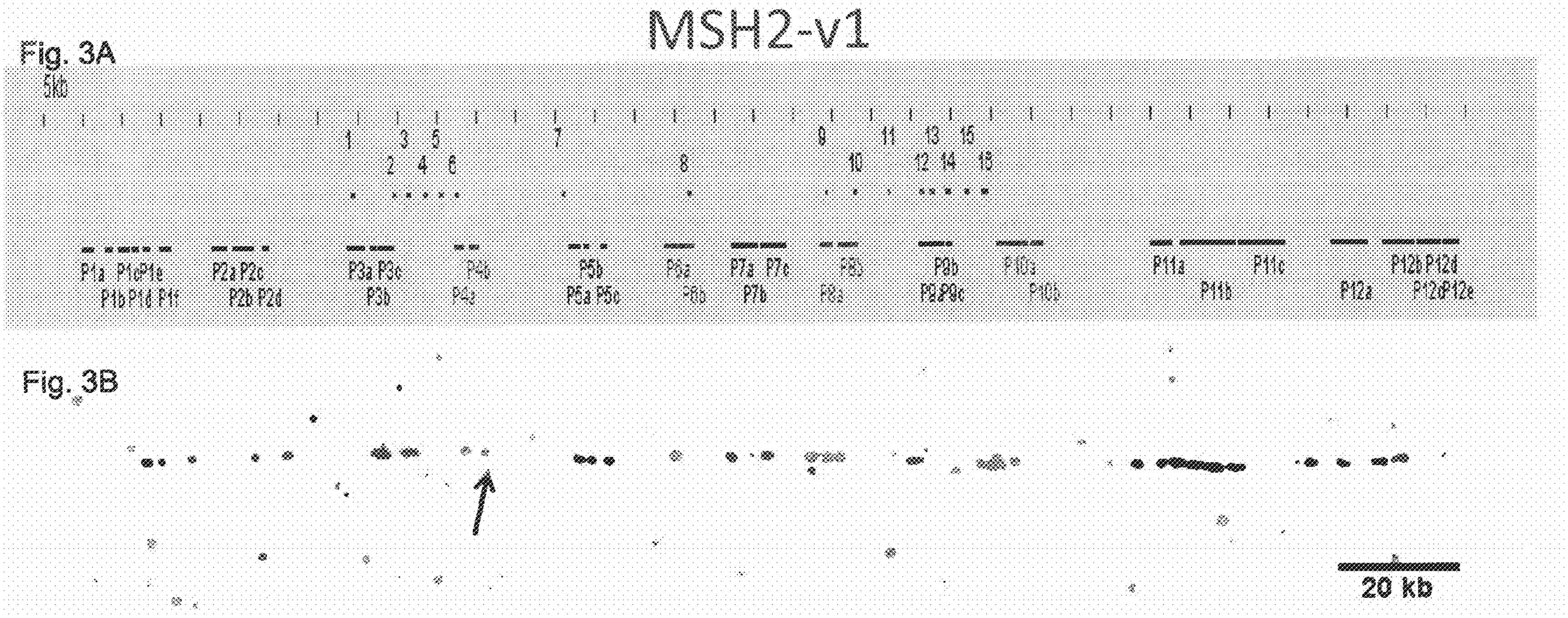
Figures 5A, 5B:
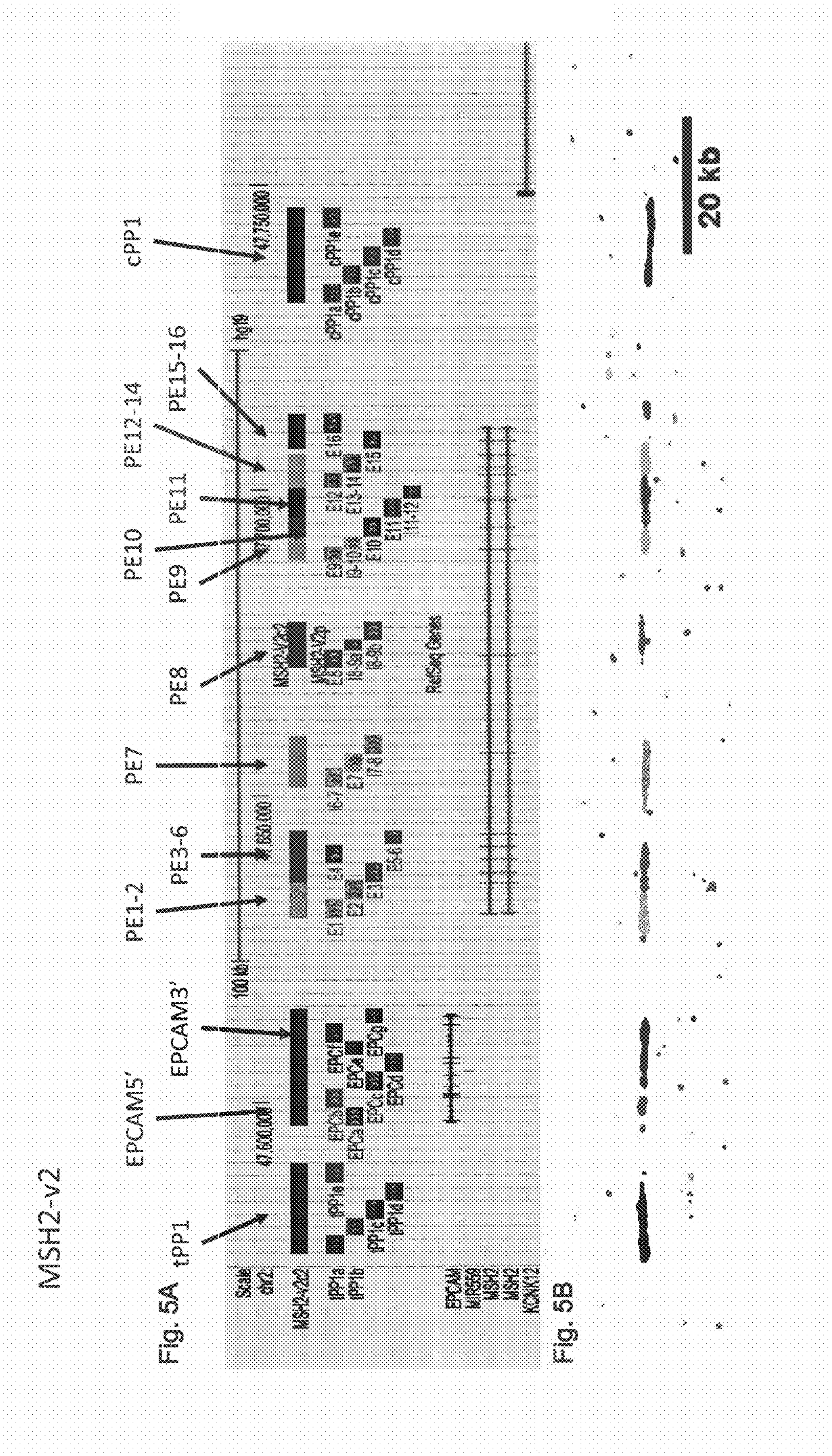
Figures 6A, 6B:
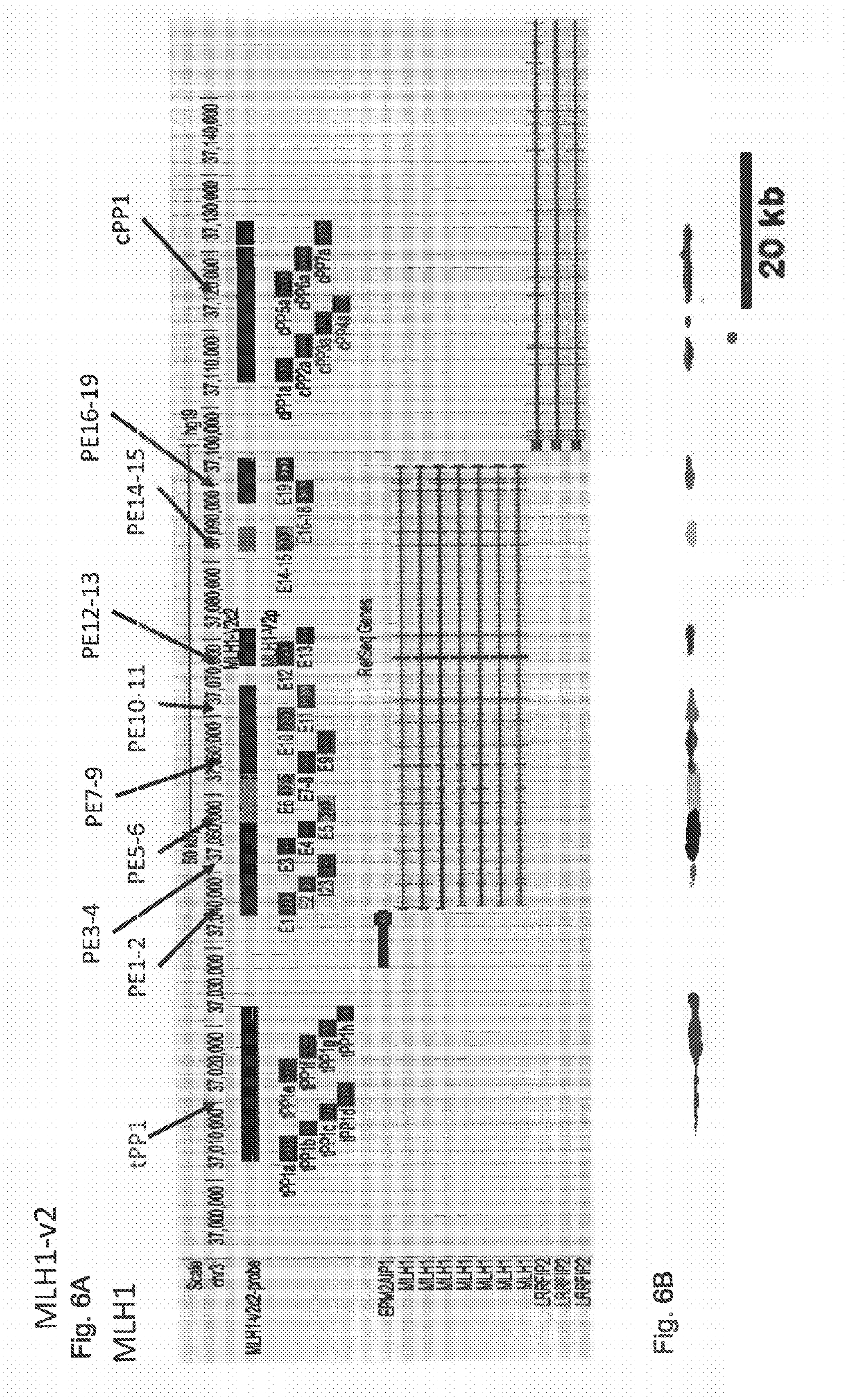

FIGS. 3B and 4B are representative images of signal from hybridized DNA. Some of probes look like "dot" rather than "line" as expected from their length. There are some "random" spots on images of hybridization, but these spots do not interfere recognition of designed code. Although signals of some small probes (arrowed in FIG. 3B, for example) is not evident to measure "length" of probe signals for size evaluation, measurement of "distance" between probe signals is possible and equivalent to measurement of the length of probe and gaps in normal probe set hybridization FIGS. 5B and 6B are the representative image of hybridization signal of barcodes-v2. Fluorescent signals are more continuous than the signals of barcodes-v1, and easier to find docking probes and measure the length of each probe and gap. These barcodes-v2 were used to visualize large genomic rearrangements of characterized cancer cell lines, LoVo and SK-OV-3 (ref. 5).

FIG. 7 is a result of hybridization of barcodes v2 on combed DNA from LoVo cell line; LoVo cell line is homozygous for deletion in MSH2 (from exon 3 to 8). Hybridization slide had many normal (identical to theoretical code) signal of MLH1 gene but none of normal MSH2 signals. Instead, there was a recurrent signal of truncated form of the normal MSH2 signal (FIG. 7B). By deduction from the truncated signals, this truncation results from loss of probes and gaps corresponding to ex3 to 8 of MSH2 gene.

FIG. 8 is a result of barcodes-v2 on SK-OV-3 cell line DNA, homozygous for deletion in MLH1 (from ex4 to 19). Among many normal MSH2 signals, only a few signals of part of MLH1 (from probe 1 to probe 3) were observed. This means a lack of following sequence of MLH1, which is consistent with reference. Moreover, a lack of the right (downstream of MLH1) docking probe indicates that this deletion affects beyond exon 19 of MLH1.

The sequences selected to detect predisposition to colorectal cancer linked to rearrangements in the MSH2 genomic region or the MLH1 genomic region are preferably chosen among the following nucleotide sequences and their corresponding complementary sequences and are described as:

The short probes covering the MSH2 gene region and constituting contiguous stretches (PE1-2 and PE3-6 (SEQ ID NO:354-358); PE9 to PE15-16 (SEQ ID NO:365-373) in table 1 under the header MSH2-v2) and the other short probes covering MSH2 gene region (PE7 and PE8, SEQ ID NO:359-364 in table 1 under the header MSH2-v2); the long probes neighboring the MSH2 gene (tPP1, EPCAM5', EPCAM3' (SEQ ID NO:342-353) and cPP1 (SEQ ID NO:374-378) in table 1 under the header MSH2-v2); the short probes covering the MLH1 gene region and constituting a contiguous stretch (PE1-2 to PE10-11, SEQ ID NO:386-396, in table 1 under the header MLH1-v2) and the other short probes covering MLH1 gene region (PE12-13, PE14-15 and PE16-19, SEQ ID NO:397-401, in table 1 under the header MLH1-v2); the long probes neighboring the MLH1 gene (tPP1 (SEQ ID NO:379-385) and cPP1 (SEQ ID NO:402-408) in table 1 under the header MLH1-v2). For example, these probes may be obtained by amplification of the fragments using the primers listed in Table 1 under the headers MSH2-v2 (SEQ ID NO:139-212) and MLH1-v2 (SEQ ID NO:213-272).

INCORPORATION BY REFERENCE

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of the cited documents is reserved.

TABLE 1

| Name of probe | Name of fragment | SEQ ID NO (fragment) | For/ Rev | SEQ ID NO (primer) | Sequence (5'-3') | start | end |
|---|---|---|---|---|---|---|---|
| | | | MSH2-v1 | | | | |
| P1 | P1a_MSH2-v1 | 273 | forward | 1 | TTCTTCCCAAGAGAGCCAAG | 47595911 | 47595930 |
| | | | reverse | 2 | CTGTTTTGGAACCCCAAGTC | 47597074 | 47597093 |
| | P1b_MSH2-v1 | 274 | forward | 3 | GGCTTCAATCTGGGACTACG | 47598716 | 47598735 |
| | | | reverse | 4 | GCTGTCACCGCCTCTTTTAC | 47599478 | 47599497 |
| | P1c_MSH2-v1 | 275 | forward | 5 | GCCAGGCACTTAGGCAGTAG | 47600433 | 47600452 |
| | | | reverse | 6 | TTGGTCCTGACATCCTTTCC | 47601671 | 47601690 |
| | P1d_MSH2-v1 | 276 | forward | 7 | TTAGTTGAACAGGGCATGACAC | 47602097 | 47602118 |
| | | | reverse | 8 | GGTAAAGGGGCCTGATGTC | 47602743 | 47602761 |

TABLE 1-continued

| Name of probe | Name of fragment | SEQ ID NO (fragment) | For/Rev | SEQ ID NO (primer) | Sequence (5'-3') | start | end |
|---|---|---|---|---|---|---|---|
| | P1e_MSH2-v1 | 277 | forward | 9 | GAGCCTTGATGTTCCCTCTTAAC | 47603695 | 47603717 |
| | | | reverse | 10 | ACCCAGATCCGAAACTGTTG | 47604324 | 47604343 |
| | P1f_MSH2-v1 | 278 | forward | 11 | CCGGCCTTACCTTTCATTTC | 47605735 | 47605754 |
| | | | reverse | 12 | CCAGGATCCAGATCCAGTTG | 47606965 | 47606984 |
| P2 | P2a_MSH2-v1 | 279 | forward | 13 | GAGTTCCATGGCAGATCACC | 47612521 | 47612540 |
| | | | reverse | 14 | GCAGCTTTCAATCACAAATCAG | 47614067 | 47614088 |
| | P2b_MSH2-v1 | 280 | forward | 15 | GAAGGGTTGGTCTTGCTGTC | 47615115 | 47615134 |
| | | | reverse | 16 | ACCCTTTGCACCTCTCTGTG | 47615632 | 47615651 |
| | P2c_MSH2-v1 | 281 | forward | 17 | CCCGGTGTTGAATCATTTG | 47616079 | 47616097 |
| | | | reverse | 18 | TTCAGCCCTGAAGGTAGAGG | 47617513 | 47617532 |
| | P2d_MSH2-v1 | 282 | forward | 19 | CTGGCCACTTTTTGGAAGAG | 47618884 | 47618903 |
| | | | reverse | 20 | TGGGACGCAGAGTGATACAG | 47619394 | 47619413 |
| P3 | P3a_MSH2-v1 | 283 | forward | 21 | TTACTGGCGATCCTCAGAGC | 47629651 | 47629670 |
| | | | reverse | 22 | AACGCCTCTTCCGTTGTATG | 47631623 | 47631642 |
| | P3b_MSH2-v1 | 284 | forward | 23 | GAAAGGACAGACCAAGTGCAG | 47632605 | 47632625 |
| | | | reverse | 24 | AGCCTGTGCAGGGAAACTC | 47633083 | 47633101 |
| | P3c_MSH2-v1 | 285 | forward | 25 | AGTGGGATGCAGCTGAAAAG | 47633591 | 47633610 |
| | | | reverse | 26 | CAACAGCATGGGAAAGATCC | 47635238 | 47635257 |
| P4 | P4a_MSH2-v1 | 286 | forward | 27 | TTGAAAGTTGGTCTTAGGAAGAGG | 47643286 | 47643309 |
| | | | reverse | 28 | CCCAACAAACCTGGCTTTAG | 47644179 | 47644198 |
| | P4b_MSH2-v1 | 287 | forward | 29 | AGACGCCCAAAATCAACAAC | 47645155 | 47645174 |
| | | | reverse | 30 | CCGCTTGCTGCTAAAAATTG | 47646042 | 47646061 |
| P5 | P5a_MSH2-v1 | 288 | forward | 31 | TGATTGCCAAGGAAGATTCAC | 47657647 | 47657667 |
| | | | reverse | 32 | TGGAAGTAAATGCAGGTGCTC | 47658763 | 47658783 |
| | P5b_MSH2-v1 | 289 | forward | 33 | TCATTCTTGGGTGTTTCTCG | 47659578 | 47659597 |
| | | | reverse | 34 | ATGGCGGTTTTGTGGAATAG | 47660015 | 47660034 |
| | P5c_MSH2-v1 | 290 | forward | 35 | GAGGGAGAGGGAACCTTTTG | 47661699 | 47661718 |
| | | | reverse | 36 | GGGGACTATACCGCATTCAC | 47662243 | 47662262 |
| P6 | P6a_MSH2-v1 | 291 | forward | 37 | TGTTGATTCATGGGCATTTG | 47669651 | 47669670 |
| | | | reverse | 38 | GCTGGGGAATCATGTATGAAG | 47671879 | 47671899 |
| | P6b_MSH2-v1 | 292 | forward | 39 | CATCAAGCACAGTTCCATTG | 47672243 | 47672262 |
| | | | reverse | 40 | TTCTCTTTCCGTTTCCAGTG | 47673113 | 47673132 |
| P7 | P7a_MSH2-v1 | 293 | forward | 41 | GGAGCTTGGGAATTCAACTG | 47678126 | 47678145 |
| | | | reverse | 42 | AGAAACGGGCATGTCATAGG | 47679330 | 47679349 |
| | P7b_MSH2-v1 | 294 | forward | 43 | CAGCCTACGTGCCCATTTC | 47679649 | 47679667 |
| | | | reverse | 44 | TCAAAAGATGGCCAAAATGC | 47681179 | 47681198 |
| | P7c_MSH2-v1 | 295 | forward | 45 | GTGTTGCACCCATTAACTCG | 47681915 | 47681934 |
| | | | reverse | 46 | AGCCTGGTGAGAGGTGACTG | 47684723 | 47684742 |
| P8 | P8a_MSH2-v1 | 296 | forward | 47 | CACGATGCCAGTCCAATTC | 47689478 | 47689496 |
| | | | reverse | 48 | AAGGTGGACTTTAATGCAAAGG | 47690835 | 47690856 |
| | P8b_MSH2-v1 | 297 | forward | 49 | GGAGTGAGAGCGACACCTTG | 47691634 | 47691653 |
| | | | reverse | 50 | CGACAGCTGACTGCTCTATGG | 47694068 | 47694088 |
| P9 | P9a_MSH2-v1 | 298 | forward | 51 | CACAATGGGAAAGGATGTAGC | 47701939 | 47701959 |
| | | | reverse | 52 | CAGAGAAAAACACCCATGACC | 47704112 | 47704132 |
| | P9b_MSH2-v1 | 299 | forward | 53 | CACCGTGATCCTCCTTATTTC | 47704395 | 47704415 |
| | | | reverse | 54 | GAACAAACAACGGATGAAAGG | 47704945 | 47704965 |
| | P9c_MSH2-v1 | 300 | forward | 55 | GTGGCATATCCTTCCCAATG | 47705311 | 47705330 |
| | | | reverse | 56 | CCCCCAGACTGTGAATTAAGG | 47705787 | 47705807 |
| P10 | P10a_MSH2-v1 | 301 | forward | 57 | GATGCAGATCAGGGAAATGC | 47711630 | 47711649 |
| | | | reverse | 58 | ATCTTGCTGGATGGACAAGG | 47715272 | 47715291 |
| | P10b_MSH2-v1 | 302 | forward | 59 | CTTAATCCTGAAAGGCAGGTG | 47715788 | 47715808 |
| | | | reverse | 60 | TGTTTCTCAGGCAACCACAG | 47717266 | 47717285 |
| P11 | P11a_MSH2-v1 | 303 | forward | 61 | GAAACCACAGAATCGCCTTC | 47731087 | 47731106 |
| | | | reverse | 62 | ACCTGGACAGTCCCACAGAC | 47733482 | 47733501 |
| | P11b_MSH2-v1 | 304 | forward | 63 | CAGTGCTTTTGCATCCTTCC | 47734903 | 47734922 |
| | | | reverse | 64 | ATTTAATCCCCTGGCCAATC | 47741649 | 47741668 |
| | P11c_MSH2-v1 | 305 | forward | 65 | CACCTGTGCCCATCACATAG | 47742239 | 47742258 |
| | | | reverse | 66 | GAGTCCCCTCTTGGAGAACC | 47747829 | 47747848 |
| P12 | P12a_MSH2-v1 | 306 | forward | 67 | AAAGCCATTTCCAGTGTCG | 47753989 | 47754007 |
| | | | reverse | 68 | ATTGTGCAGCCAGAATTGAG | 47758158 | 47758177 |
| | P12b_MSH2-v1 | 307 | forward | 69 | TTCACAGCAAAGTGGCTCAG | 47760593 | 47760612 |
| | | | reverse | 70 | GCTATTATGGGCTGCAAAGC | 47764302 | 47764321 |
| | P12c_MSH2-v1 | 308 | forward | 71 | TTCACTCCCAACAAGCACTG | 47764863 | 47764882 |
| | | | reverse | 72 | TGCCCAGTCCTTTTTCACT | 47765618 | 47765636 |
| | P12d_MSH2-v1 | 309 | forward | 73 | AATCCCTCCTGCACACTTTC | 47765925 | 47765944 |
| | | | reverse | 74 | AATGGATGCTTCCACTGTCC | 47767687 | 47767706 |
| | P12e_MSH2-v1 | 310 | forward | 75 | CCATCTGTGCAATTCCTTCC | 47768105 | 47768124 |
| | | | reverse | 76 | GTTCAAAGGCAGAAGCCATC | 47769886 | 47769905 |
| | | | | MLH1-v1 | | | |
| P1 | P1a_MLH1-v1 | 311 | forward | 77 | GTCTGGATTCTTTCACAATGTAGC | 37005551 | 37005576 |
| | | | reverse | 78 | TGCCAATCTTCTCCTCTGTTC | 37006562 | 37006582 |
| | P1b_MLH1-v1 | 312 | forward | 79 | AACCACCCAATGTGTTCACC | 37006815 | 37006836 |
| | | | reverse | 80 | GTTCATTCCTGCGAGTAGGC | 37007422 | 37007441 |
| | P1c_MLH1-v1 | 313 | forward | 81 | GCCAAAGGTGGAAAATGTTG | 37008987 | 37009008 |
| | | | reverse | 82 | GCCTTCTTCATGAAAGCACTG | 37009873 | 37009893 |

TABLE 1-continued

| Name of probe | Name of fragment | SEQ ID NO (fragment) | For/ Rev | SEQ ID NO (primer) | Sequence (5'-3') | start | end |
|---|---|---|---|---|---|---|---|
| | P1d_MLH1-v1 | 314 | forward | 83 | CCAGAAGGTGGAAGCTACAG | 37011079 | 37011100 |
| | | | reverse | 84 | TGGGGTCAATGAAGCAAG | 37011830 | 37011847 |
| | P1e_MLH1-v1 | 315 | forward | 85 | ACATCGACCCAGAAAGTTCC | 37012314 | 37012335 |
| | | | reverse | 86 | AATGTGCTTCGTACCACTGC | 37012867 | 37012886 |
| | P1f_MLH1-v1 | 316 | forward | 87 | AGCGTGCCATTGTACTCTCC | 37013822 | 37013843 |
| | | | reverse | 88 | TTTCTGAGCCCATGATTTCC | 37015267 | 37015286 |
| P2 | P2a_MLH1-v1 | 317 | forward | 89 | GTGCCCAGCTAGTTCCATTC | 37023623 | 37023644 |
| | | | reverse | 90 | TCAAGAGCGCTAATCCCATC | 37025002 | 37025021 |
| | P2b_MLH1-v1 | 318 | forward | 91 | TGCACATGCTCACTGAAAGAC | 37026505 | 37026527 |
| | | | reverse | 92 | TTTTGCCTGCAACTGACC | 37027818 | 37027836 |
| | P2c_MLH1-v1 | 319 | forward | 93 | CAGCAAGCACCAAATCACTG | 37028305 | 37028326 |
| | | | reverse | 94 | AGTACCAGCCGTCCAAACTG | 37032621 | 37032640 |
| P3 | P3a_MLH1-v1 | 320 | forward | 95 | CCTGGCCAGAAAATTCATTG | 37037607 | 37037628 |
| | | | reverse | 96 | ACCCTGCATTCCAAACTCAC | 37039199 | 37039218 |
| | P3b_MLH1-v1 | 321 | forward | 97 | GCAGTCCTTTGAGGATTTAGC | 37042493 | 37042515 |
| | | | reverse | 98 | GAAAGATATCCAACAGGAAGTGAG | 37043300 | 37043323 |
| | P3c_MLH1-v1 | 322 | forward | 99 | TGGCCTTGTTTAAGGTCCTG | 37043746 | 37043767 |
| | | | reverse | 100 | ATGGTCCTGCTGCTTCAGAG | 37044723 | 37044742 |
| | P3d_MLH1-v1 | 323 | forward | 101 | ACCCCGTCATAGCACAGTTC | 37045295 | 37045316 |
| | | | reverse | 102 | CAAAGGCCATTCATCAGTTTC | 37046439 | 37046459 |
| P4 | P4a_MLH1-v1 | 324 | forward | 103 | GTGGCGTGATATCCTTGATTC | 37053034 | 37053056 |
| | | | reverse | 104 | CTCTGGAATGACTGCTGCTG | 37054289 | 37054308 |
| | P4b_MLH1-v1 | 325 | forward | 105 | TGTGCTAGATGCCTCACTGG | 37055182 | 37055203 |
| | | | reverse | 106 | TTGCCAAGAAGCACAACAAG | 37058326 | 37058345 |
| P5 | P5a1_MLH1-v1 | 326 | forward | 107 | CGGAGGCTCTACTGTTGGAC | 37062345 | 37062366 |
| | | | reverse | 108 | TGCTGTCCACTCTGGAACTG | 37064753 | 37064772 |
| | P5b_MLH1-v1 | 327 | forward | 109 | ACATCAGAAGCCCTGGTTTG | 37064571 | 37064592 |
| | | | reverse | 110 | GCTGGGAGTTCAAGCATCTC | 37067377 | 37067396 |
| P6 | P6a_MLH1-v1 | 328 | forward | 111 | TCGGTCTCAGTCACCATTTG | 37072097 | 37072118 |
| | | | reverse | 112 | AACGCACCTGGCTGAAATAC | 37075920 | 37075939 |
| P7 | P7a_MLH1-v1 | 329 | forward | 113 | TGAACCTGCAATATCTCAGAGG | 37079607 | 37079630 |
| | | | reverse | 114 | CTTACCGATAACCTGAGAACACC | 37083805 | 37083827 |
| P8 | P8a_MLH1-v1 | 330 | forward | 115 | CCCAGCCCATATATTTTAAAGC | 37088387 | 37088410 |
| | | | reverse | 116 | CCAGCCACTCTCTGGACTATC | 37089049 | 37089069 |
| | P8b_MLH1-v1 | 331 | forward | 117 | GACATGGAGAGCCGAATCC | 37089669 | 37089689 |
| | | | reverse | 118 | CCATTAAAATCGGGTCTGAAAG | 37091446 | 37091467 |
| | P8c_MLH1-v1 | 332 | forward | 119 | TCCAGACCCAGTGCACATC | 37091887 | 37091907 |
| | | | reverse | 120 | CATGGTCAGTGCCATCAGAG | 37092412 | 37092431 |
| | P8d_MLH1-v1 | 333 | forward | 121 | AGCCTCCCAAAGTTAAGTGC | 37092788 | 37092809 |
| | | | reverse | 122 | CCCAGCTAAAACCAACACAC | 37093346 | 37093365 |
| P9 | P9a_MLH1-v1 | 334 | forward | 123 | TGCCCTCAGCTACTCACTCC | 37103285 | 37103306 |
| | | | reverse | 124 | AGGGCTCAGCCTTTAGGAAC | 37105620 | 37105639 |
| | P9b_MLH1-v1 | 335 | forward | 125 | GCCAGACTCTCGTTCCATTC | 37106390 | 37106411 |
| | | | reverse | 126 | ACTCCCCATTCAGTCCCTTC | 37111053 | 37111072 |
| | P9c_MLH1-v1 | 336 | forward | 127 | AGGCACAACGTCAGGTTTTC | 37114109 | 37114130 |
| | | | reverse | 128 | TTGGAATTTGTCCTGGTGTG | 37117519 | 37117538 |
| P10 | P10a_MLH1-v1 | 337 | forward | 129 | CACCATTGCCAACACTTCTG | 37132898 | 37132919 |
| | | | reverse | 130 | GCCATTGGTTTGAAGGTGAC | 37134201 | 37134220 |
| | P10b_MLH1-v1 | 338 | forward | 131 | CTTAGTCACCGCCTGTCCTC | 37134738 | 37134759 |
| | | | reverse | 132 | TAGCTGCATGTGGCTAATCG | 37136986 | 37137005 |
| | P10c_MLH1-v1 | 339 | forward | 133 | TGTGGCTCGCATTACATTTC | 37137579 | 37137600 |
| | | | reverse | 134 | CGCTGTCATTACCTGCTTTG | 37139742 | 37139761 |
| | P10d_MLH1-v1 | 340 | forward | 135 | TGACCTCCAAAATCATCCAG | 37140449 | 37140470 |
| | | | reverse | 136 | TTCTGAGCTAGGAGGTGCTG | 37141321 | 37141340 |
| | P10e_MLH1-v1 | 341 | forward | 137 | CCAGATTTGTAAATCCCTGTTC | 37142008 | 37142031 |
| | | | reverse | 138 | TGTGTGGTTCTTAAGCATTCC | 37142420 | 37142440 |
| | | | | MSH2-v2 | | | |
| tPP1 | tPP1a_MSH2-v2 | 342 | forward | 139 | CTCAGTCCATCAGCCTCCTC | 47574824 | 47577784 |
| | | | reverse | 140 | TGCTGTGCCCTGAGATTAAG | 47574823 | 47577783 |
| | tPP1b_MSH2-v2 | 343 | forward | 141 | AACTTAATCTCAGGGCACAGC | 47577763 | 47580677 |
| | | | reverse | 142 | TGCAGCTTCAGCCTCTTG | 47577762 | 47580676 |
| | tPP1c_MSH2-v2 | 344 | forward | 143 | GCGTGGTGTTTCGTACCAG | 47580604 | 47583785 |
| | | | reverse | 144 | GCTACTGGCCAGAAATCTTCC | 47580603 | 47583784 |
| | tPP1d_MSH2-v2 | 345 | forward | 145 | GCCCAGCCCTACTAAGGAAG | 47583750 | 47586723 |
| | | | reverse | 146 | CTGTGCTCCCCTGCTAGAAC | 47583749 | 47586722 |
| | tPP1e_MSH2-v2 | 346 | forward | 147 | GTCGTCCTCTTCGACCTAGC | 47586769 | 47589967 |
| | | | reverse | 148 | CAGCGCCTATTCTACAGCAG | 47586768 | 47589966 |
| EPCAM5' | EPCa_MSH2-v2 | 347 | forward | 149 | TTCTTCCCAAGAGAGCCAAG | 47595912 | 47598965 |
| | | | reverse | 150 | CCACCTTTAATCTGCCCAAC | 47595911 | 47598964 |
| | EPCb_MSH2-v2 | 348 | forward | 151 | GTGTTGGGCAGATTAAAGGTG | 47598944 | 47602122 |
| | | | reverse | 152 | GCAGTGTCATGCCCTGTTC | 47598943 | 47602121 |
| | EPCc_MSH2-v2 | 349 | forward | 153 | CTCTTTGTGCCCTTTCTTTTG | 47601745 | 47604931 |
| | | | reverse | 154 | AGTTCCTTAAAGCAGAGAAGATGG | 47601744 | 47604930 |
| EPCAM3' | EPCd_MSH2-v2 | 350 | forward | 155 | AACCTGTCCCTGTGGATGAG | 47604796 | 47607923 |
| | | | reverse | 156 | CCGAAGCATCCTTACATTCC | 47604795 | 47607922 |

TABLE 1-continued

| Name of probe | Name of fragment | SEQ ID NO (fragment) | For/ Rev | SEQ ID NO (primer) | Sequence (5'-3') | start | end |
|---|---|---|---|---|---|---|---|
| | EPCe_MSH2-v2 | 351 | forward | 157 | AATACCTGAACCCCCAAACC | 47607722 | 47609876 |
| | | | reverse | 158 | CTCAGGCTATTTTCCAGATTCAC | 47607721 | 47609875 |
| | EPCf_MSH2-v2 | 352 | forward | 159 | GCATGCCTGTCATTCTGG | 47609695 | 47612812 |
| | | | reverse | 160 | TCCAAGGGACTGAAACACAC | 47609694 | 47612811 |
| | EPCg_MSH2-v2 | 353 | forward | 161 | TTAGTGTGTTTCAGTCCCTTGG | 47612790 | 47615135 |
| | | | reverse | 162 | GACAGCAAGACCAACCCTTC | 47612789 | 47615134 |
| PE1-2 | E1_MSH2-v2 | 354 | forward | 163 | GCACATTACGAGCTCAGTGC | 47629942 | 47633045 |
| | | | reverse | 164 | CTACCAGGAGAACAGCACAGG | 47629941 | 47633044 |
| | E2_MSH2-v2 | 355 | forward | 165 | TGGGTTAGCATTGTGTTAGGTG | 47632899 | 47636029 |
| | | | reverse | 166 | CCACAGGTGTGTGCCAATAG | 47632898 | 47636028 |
| PE3-6 | E3_MSH2-v2 | 356 | forward | 167 | AAGTTGCAGTTTGGCTGGTC | 47635845 | 47638929 |
| | | | reverse | 168 | TTATCTCCAGCGGTGCTTATG | 47635844 | 47638928 |
| | E4_MSH2-v2 | 357 | forward | 169 | TACCATAAGCACCGCTGGAG | 47638906 | 47642053 |
| | | | reverse | 170 | ACTCCACCAAGCCCAGTCTC | 47638905 | 47642052 |
| | E5-6_MSH2-v2 | 358 | forward | 171 | TTTAGAGACTGGGCTTGGTG | 47642030 | 47644205 |
| | | | reverse | 172 | CTCTTCCCCAACAAACCTG | 47642029 | 47644204 |
| PE7 | I6-7_MSH2-v2 | 359 | forward | 173 | CCCAGTTTCAAGCGATTAAG | 47651443 | 47654570 |
| | | | reverse | 174 | AGGAAAAGCATGTTATCTCCAG | 47651442 | 47654569 |
| | E7_MSH2-v2 | 360 | forward | 175 | TTCCGTAGCAGTAGGCATCC | 47654026 | 47657170 |
| | | | reverse | 176 | TCACCACCACCAACTTTATGAG | 47654025 | 47657169 |
| | I7-8_MSH2-v2 | 361 | forward | 177 | TCCCAGATCTTAACCGACTTG | 47656956 | 47660035 |
| | | | reverse | 178 | ATGGCGGTTTTGTGGAATAG | 47656955 | 47660034 |
| PE8 | E8_MSH2-v2 | 362 | forward | 179 | CCCAAACAACAGCATTAGCC | 47670887 | 47673915 |
| | | | reverse | 180 | ACATCAGCCTCGGGACAAG | 47670886 | 47673914 |
| | I8-9a_MSH2-v2 | 363 | forward | 181 | TGAGCCCGTTGAATATAGTGG | 47673830 | 47675514 |
| | | | reverse | 182 | AGTTTTCCTAAACGGGATGATG | 47673829 | 47675513 |
| | I8-9b_MSH2-v2 | 364 | forward | 183 | ATGGGTGTGCACGTGTGTAG | 47675368 | 47678365 |
| | | | reverse | 184 | GCCATGTGCAATTGTGAGTC | 47675367 | 47678364 |
| PE9 | E9_MSH2-v2 | 365 | forward | 185 | CCTTGCATAGTTTGCTTCTGG | 47688375 | 47690450 |
| | | | reverse | 186 | ATCATACAAGGGCCTGTTGG | 47688374 | 47690449 |
| | I9-10_MSH2-v2 | 366 | forward | 187 | AAACAGAAATCGCCCAACAG | 47690418 | 47692377 |
| | | | reverse | 188 | TAGAGACCCACCCAGAAACG | 47690417 | 47692376 |
| PE10 | E10_MSH2-v2 | 367 | forward | 189 | CAGTCCGATTTCGTTTCTGG | 47692347 | 47695506 |
| | | | reverse | 190 | CACACCTAGATTTGGCAATGG | 47692346 | 47695505 |
| PE11 | E11_MSH2-v2 | 368 | forward | 191 | TTCCATTGCCAAATCTAGGTG | 47695484 | 47698468 |
| | | | reverse | 192 | GGCCCTAGTGTTTCCTTTCC | 47695483 | 47698467 |
| | I11-12_MSH2-v2 | 369 | forward | 193 | AAGGAAACACTAGGGCCTACAAC | 47698452 | 47700589 |
| | | | reverse | 194 | CCTGGCCTCAGTACACTTTTG | 47698451 | 47700588 |
| PE12-14 | E12_MSH2-v2 | 370 | forward | 195 | AGGGATTCTCCCCACTTAGC | 47700228 | 47702718 |
| | | | reverse | 196 | ATTGGAGGACTGGCTCAAAG | 47700227 | 47702718 |
| | E13-14_MSH2-v2 | 371 | forward | 197 | GCTTACCTTTGAGCCAGTCC | 47702694 | 47705819 |
| | | | reverse | 198 | ACATGTTCCTACCCCCAGAC | 47702693 | 47705818 |
| PE15-16 | E15_MSH2-v2 | 372 | forward | 199 | TTTCTGCATCAGTTGGTTGC | 47706613 | 47709532 |
| | | | reverse | 200 | GCCAAGTTATTGCTGCTTCAG | 47706612 | 47709531 |
| | E16_MSH2-v2 | 373 | forward | 201 | AGCCCTGTGAGGTTGGTAAC | 47709413 | 47712504 |
| | | | reverse | 202 | TCAACAACAGCTGGAACTGC | 47709412 | 47712503 |
| cPP1 | cPP1a_MSH2-v2 | 374 | forward | 203 | CCTCTCAGGTCAGGCTTCTG | 47730898 | 47733882 |
| | | | reverse | 204 | GCTCCCGCTAGAGAAACTCC | 47730897 | 47733881 |
| | cPP1b_MSH2-v2 | 375 | forward | 205 | GAGCGAAGCACCTAAAGCAC | 47733879 | 47736946 |
| | | | reverse | 206 | AATTGGAGGGGGTGGAGTAG | 47733878 | 47736945 |
| | cPP1c_MSH2-v2 | 376 | forward | 207 | TGTCACCCAGTCAGGTCATC | 47736760 | 47739876 |
| | | | reverse | 208 | TTGGAAGGAATCCAACAAGG | 47736759 | 47739875 |
| | cPP1d_MSH2-v2 | 377 | forward | 209 | TTCCCAGAACTCCTTGTTGG | 47739846 | 47742962 |
| | | | reverse | 210 | TGCAAACCCCTTCTTTTCAG | 47739845 | 47742961 |
| | cPP1e_MSH2-v2 | 378 | forward | 211 | ACCCCATGCAGAAGCAATAG | 47743027 | 47746218 |
| | | | reverse | 212 | AAATCCTGAAGGTGGGTTCC | 47743026 | 47746217 |
| | | | | MLH1v2 | | | |
| tPP1 | tPP1b_MLH1-v2 | 379 | forward | 213 | AGTTTCAGCCATGTTGCAG | 37005587 | 37005605 |
| | | | reverse | 214 | TTGGCAAAATTGTGACTGAG | 37007511 | 37007530 |
| | tPP1c_MLH1-v2 | 380 | forward | 215 | CAGTCACAATTTTGCCAAGG | 37007513 | 37007532 |
| | | | reverse | 216 | AGTTCGTGGCATCTAACTATCG | 37009688 | 37009709 |
| | tPP1d_MLH1-v2 | 381 | forward | 217 | GGTCCATGTGCTCCAAAAAG | 37009460 | 37009479 |
| | | | reverse | 218 | TCCAAAACTGGGAACAAACC | 37012624 | 37012643 |
| | tPP1e_MLH1-v2 | 382 | forward | 219 | TGGTTTGTTCCCAGTTTTGG | 37012623 | 37012642 |
| | | | reverse | 220 | TAGTGCACCACAGCCTCAAG | 37015706 | 37015725 |
| | tPP1f_MLH1-v2 | 383 | forward | 221 | GGATCACTTGAGGCTGTGGT | 37015700 | 37015719 |
| | | | reverse | 222 | TCCAACAACTGCTGTGAAGG | 37018677 | 37018696 |
| | tPP1g_MLH1-v2 | 384 | forward | 223 | CACCACTGACCTTCCCTTCC | 37018492 | 37018511 |
| | | | reverse | 224 | GCACAGAAAGACAAATATCACATGC | 37020534 | 37020558 |
| | tPP1h_MLH1-v2 | 385 | forward | 225 | CTCTTCCTCGTCTCCTCCTG | 37020430 | 37020449 |
| | | | reverse | 226 | CCAATTCAATGCAAAACCTG | 37022464 | 37022483 |
| PE1-2 | E1_MLH1-v2 | 386 | forward | 227 | CGAGCAGCTCTCTCTTCAGG | 37034273 | 37034292 |
| | | | reverse | 228 | AGCCTATAAGCACAGACCAACTG | 37037250 | 37037272 |
| | E2_MLH1-v2 | 387 | forward | 229 | TTCTCTAGCAGTTGGTCTGTGC | 37037242 | 37037263 |
| | | | reverse | 230 | ACCCTGCATTCCAAACTCAC | 37039199 | 37039218 |

TABLE 1-continued

| Name of probe | Name of fragment | SEQ ID NO (fragment) | For/Rev | SEQ ID NO (primer) | Sequence (5'-3') | start | end |
|---|---|---|---|---|---|---|---|
| PE3-4 | I23_MLH1-v2 | 388 | forward | 231 | GTTCATTTTGGGGCATGTTC | 37039148 | 37039167 |
| | | | reverse | 232 | CTGCAACCTCCTTTGAGACAG | 37042218 | 37042238 |
| | E3_MLH1-v2 | 389 | forward | 233 | TGTCTCAAAGGAGGTTGCAG | 37042219 | 37042238 |
| | | | reverse | 234 | CCAAAATGAAACTGCCTTCC | 37044367 | 37044386 |
| | E4_MLH1-v2 | 390 | forward | 235 | AGTTCCCTGGGTCATTTTCC | 37044393 | 37044412 |
| | | | reverse | 236 | TTGTGGGAAGGCAAACTAGC | 37046381 | 37046400 |
| PE5-6 | E5_MLH1-v2 | 391 | forward | 237 | CCTGTGCTAGTTTGCCTTCC | 37046376 | 37046395 |
| | | | reverse | 238 | GGTGGTCACCGTGGTAAAAG | 37049553 | 37049572 |
| | E6_MLH1-v2 | 392 | forward | 239 | GACCACCATGTGATTTCCAAG | 37049566 | 37049586 |
| | | | reverse | 240 | TTGGTTGGCGGTTATTTCTC | 37052510 | 37052529 |
| PE7-9 | E7-8_MLH1-v2 | 393 | forward | 241 | TAACCGCCAACCAAGAAAAG | 37052516 | 37052535 |
| | | | reverse | 242 | TGTCTGGAGACCTTCCCAAG | 37055360 | 37055379 |
| | E9_MLH1-v2 | 394 | forward | 243 | TGTGCTAGATGCCTCACTGG | 37055182 | 37055201 |
| | | | reverse | 244 | ACTTGCCTACATTGCCCATC | 37058175 | 37058194 |
| PE10-11 | E10_MLH1-v2 | 395 | forward | 245 | ATGGGCAATGTAGGCAAGTC | 37058176 | 37058195 |
| | | | reverse | 246 | TCTGCAGCCATGAATAAGTCC | 37061070 | 37061090 |
| | E11_MLH1-v2 | 396 | forward | 247 | CAGAGCTGAGGCGATAAATTG | 37060960 | 37060980 |
| | | | reverse | 248 | TGCTCCTCTCCAATCCATTC | 37063973 | 37063992 |
| PE12-13 | E12_MLH1-v2 | 397 | forward | 249 | ATACTTTCCCAGCCCAAACC | 37066434 | 37066453 |
| | | | reverse | 250 | TGATGGGGAAATGAGAGGAG | 37069438 | 37069457 |
| | E13_MLH1-v2 | 398 | forward | 251 | AGTGGCCTTTGTCCATTGAG | 37069405 | 37069424 |
| | | | reverse | 252 | GACAGAGGTGAGAGCCTAGGAG | 37071540 | 37071561 |
| PE14-15 | E14-15_MLH1-v2 | 399 | forward | 253 | AATGTGTTGGGGAAGTGGTC | 37081262 | 37081281 |
| | | | reverse | 254 | TTTGGACCACGGCTTTAGAC | 37084405 | 37084424 |
| PE16-19 | E16-18_MLH1-v2 | 400 | forward | 255 | AAGCTGAGGTCACGGATTTG | 37087522 | 37087541 |
| | | | reverse | 256 | GATGGGCAAGTTTCATCTCC | 37090568 | 37090587 |
| | E19_MLH1-v2 | 401 | forward | 257 | TGGGACGAAGAAAAGGAATG | 37090401 | 37090420 |
| | | | reverse | 258 | CACCGTGCCTCAGCCTATAC | 37093446 | 37093465 |
| cPP1 | cPP1a_MLH1-v2 | 402 | forward | 259 | GGACTAACCCACCTCCCTTC | 37103239 | 37103258 |
| | | | reverse | 260 | GCTATAGGCAGCCCAGAGTG | 37106372 | 37106391 |
| | cPP2a_MLH1-v2 | 403 | forward | 261 | GCCAGACTCTCGTTCCATTC | 37106390 | 37106409 |
| | | | reverse | 262 | AGGATTTGCCGTATGGACTC | 37109450 | 37109469 |
| | cPP3a_MLH1-v2 | 404 | forward | 263 | TCGCCCAAAGTCACAGTAAG | 37109303 | 37109322 |
| | | | reverse | 264 | GATCTGTAGGCCCAGGATTTC | 37112356 | 37112376 |
| | cPP4a_MLH1-v2 | 405 | forward | 265 | AGGGGTTTCTATGGCTGGTC | 37112314 | 37112333 |
| | | | reverse | 266 | CCTCCCTCAAACCTCCTCTC | 37114423 | 37114442 |
| | cPP5a_MLH1-v2 | 406 | forward | 267 | TTCTCCTGCAGAGGAAGAGG | 37114369 | 37114388 |
| | | | reverse | 268 | TTGGAATTTGTCCTGGTGTG | 37117519 | 37117538 |
| | cPP6a_MLH1-v2 | 407 | forward | 269 | AAAGCCAGGGAGTGAATGG | 37117566 | 37117584 |
| | | | reverse | 270 | ATGTGCATCTCCCTGGTGAC | 37120703 | 37120722 |
| | cPP7a_MLH1-v2 | 408 | forward | 271 | TGTGGGGAAATCAAAACCTG | 37120784 | 37120803 |
| | | | reverse | 272 | GGGTAGACTGTGCGTGTGTG | 37123930 | 37123949 |

TABLE 2

| | MLH1-v2 probe | MLH1-v1 probe | MLH1 region | MSH2-V2 probe | MSH2-V1 probe | MSH2 region | |
|---|---|---|---|---|---|---|---|
| sum length | 86366 | 55582 | 121536 | 106534 | 73609 | 171394 | bp |
| repeat length | 44684 | 18525 | 64712 | 53243 | 22133 | 94584 | bp |
| total repeat | 51.74 | 33.33 | 53.25 | 49.98 | 30.07 | 55.19 | % |
| SINE | 24.93 | 2.58 | 23.85 | 34.68 | 5.03 | 35.95 | % |
| ALUs | 22.38 | 0.09 | 21.85 | 32.85 | 0.76 | 34.15 | % |

REFERENCES

1. "Gene copy number variation and common human disease", Fanciulli, et. al. *Clinical Genetics,* 2010 77, 201-213
2. "Dynamic molecular combing: stretching the whole human genome for high-resolution studies" Michalet, et al., *Science* 1997 277, 1518-1523 and "Bar code screening on combed DNA for large rearrangemens of the BRCA1 and BRCA2 gene in French breast cancer families", Gad, et. al., *J. Medical Genetics,* 2002, 39, 817-821
3. "Sequence-based design of single-copy genomic DNA probes for fluorescence in situ hybridization" Rogan, et. al., Genome Res. 200111, 1086-94.
4. "A dot-matrix program with dynamic threshold control suited for genomic DNA and protein sequence analysis". Erik L. L. Sonnhammer and Richard Durbin. Gene 1995, 167:GC1-10
5. "Microsatellite instability, mismatch repair deficiency and genetic defects in human cancer cell lines", Boyer J. C., et al. *Cancer Research* 1995 55, 6063-6070,
6. "Primer3Plus, an enhanced web interface to Primer3", Untergasser A., et al. *Nucleic Acids Research* 2007 35, W71-W74

The invention claimed is:

1. A method of in vitro detecting mutated or rearranged genomic polynucleotide (target) sequence comprising:

(a1) hybridizing a target genomic polynucleotide comprising one or more genomic region(s) of interest, where mutations or rearrangements are sought, to a set consisting of short probes, of 0.5 to 10 kb, that bind to each region of interest without gaps longer than 15 kb between the portions of the target sequence bound by the set of short probes said set of short probes optionally including or being in combination with a set of short probes, of 0.5 to 10 kb, selected so that on each genomic region some of the short probes when taken together form a long contiguous stretch inside or outside the region of interest and wherein the short probes may optionally have sequences of more than 200 by of which more than 10 copies with less than 20% mismatch are found within the regions of interest removed; or (a2) hybridizing a target genomic polynucleotide comprising one or more genomic region(s) of interest, where mutations or rearrangements are sought, to a set of short probes of 0.5 to 10 kb that bind to each region of interest without gaps longer than 15 kb between the portions of the target sequence bound by the set of short probes and to one or more long probe(s), of 12 to 150 kb, that bind to sequences near but outside of the region(s) of interest; wherein the sequence(s) of the long probe(s) does not overlap that of the short probes and wherein the short and/or long probes may optionally have sequences of more than 200 by of which more than 10 copies with less than 20% mismatch are found within the regions of interest removed;

(b) detecting the locations of hybridized probes on the genomic region(s) of interest; optionally, (c) comparing the location of the hybridized probes on the target genomic polynucleotide sequence with one or more motifs based on the hybridization of said probes to a reference, control, normal, not mutated, or not rearranged genomic polynucleotide sequence; and optionally, (d) correlating the presence of a mutated or rearranged genomic polynucleotide with a specific phenotype, disease, disorder, or condition.

2. The method of claim 1, wherein the mutated or rearranged genomic polynucleotide sequence is obtained from a subject who has cancer or who is suspected to having cancer or who is susceptible to have a genetic predisposition to cancer.

3. The method of claim 1, wherein the mutated or rearranged genomic polynucleotide sequence is obtained from a subject who has colorectal cancer or who is suspected of having colorectal cancer or who is susceptible to have a genetic predisposition to colorectal cancer, wherein said short and long probes identify mutations or genomic rearrangements associated with colorectal cancer, wherein said control, not mutated or normal genomic sequence is obtained from a subject not at risk for colorectal cancer and wherein the detection of a genomic rearrangement; and assessing presence of or risk of developing colorectal cancer when said genomic rearrangement is detected.

4. The method of claim 3, wherein the probes hybridize specifically on the MSH2 gene, in the region of the MSH2 gene, or on the MLH1 gene, or in the region of the MLH1 gene.

5. The method of claim 1, wherein the mutated or rearranged genomic polynucleotide sequence is obtained from a subject who has breast cancer or who is suspected to having breast cancer or who is susceptible to have a genetic predisposition to breast cancer.

6. The method of claim 1, wherein the mutated or rearranged genomic polynucleotide sequence is obtained from a subject who has ovarian cancer or who is suspected to having ovarian cancer or who is susceptible to have a genetic predisposition to ovarian cancer.

7. The method of claim 1, wherein the mutated or rearranged genomic polynucleotide sequence is obtained from a subject who has lung cancer or who is suspected to having lung cancer or who is susceptible to have a genetic predisposition to lung cancer.

8. The method of claim 1, wherein the mutated or rearranged genomic polynucleotide sequence is obtained from a subject who has a cardiovascular disease, disorder or condition or who is suspected of having cardiovascular disease, disorder or condition or who is susceptible to have a genetic predisposition to cardiovascular disease, disorder or condition.

9. The method of claim 1, wherein the mutated or rearranged genomic polynucleotide sequence is obtained from a subject who has a diabetes or who is suspected of having diabetes or who is susceptible to have a genetic predisposition to diabetes.

10. The method of claim 1, wherein the mutated or rearranged genomic polynucleotide sequence is obtained from a subject who has a neuromuscular disorder or who is suspected of having a neuromuscular disorder.

11. The method of claim 1, wherein the mutated or rearranged genomic polynucleotide sequence is obtained from a subject who has, is suspected of having, or is susceptible of being a carrier for a genetic or hereditary disease, disorder or condition.

12. The method of claim 1, wherein the short and long probe sequences are specific to human genes or to human genomic regions associated with cancer, colorectal cancer or a foetal genetic alteration known or unknown when said region or gene is mutated or genetically rearranged.

13. The method of claim 1, wherein the mutated or rearranged genomic polynucleotide sequence is obtained from a subject who has, is suspected of having, or is suspected of being a carrier for a multigenic genetic or hereditary disease, disorder or condition or for a genetic or hereditary disease, disorder or condition associated with rearrangement of genomic DNA.

14. The method of claim 1, wherein the mutated or rearranged genomic polynucleotide sequence is obtained from a subject undergoing treatment for a disease, disorder or condition associated with a genomic inherited or acquired rearrangement and the results obtained are compared to results obtained at other time points before, during or after the termination of treatment.

15. The method of claim 1, wherein the hybridizing with the short and long probes in (a2) is performed simultaneously.

16. The method of claim 1, wherein the probe comprises at least one short sequence of less than 10 kb and at least one long sequence of more than 12 kb which does not overlap with said short sequence, or at least one group of at least two short sequences, less than 10 kb each, which total group length is longer than 12 kb and less than 150 kb, hybridizing contiguously on the mutated or rearranged polynucleotide sequence.

17. The method of claim 1, wherein the short probes comprise a set of contiguous probes that span a stretch of the genomic polynucleotide sequences inside or outside the region of interest that is at least 14 kb.

18. The method of claim 1, wherein the long probe(s) comprise one or more docking probes of more than 14 kb and less than 40 kb.

19. The method of claim 1, wherein the long probe(s) is at least 14 kb and binds to a polynucleotide sequence outside the region of interest.

20. The method of claim 1, wherein sequences of more than 200 by of which more than 10 copies with less than 20% mismatch are found within the regions of interest have been excluded from the short and/or long probes.

21. The method of claim 1, wherein repetitive DNA sequences, which appear more than once and more often than statistically predicted based on their length and base content, have been excluded from the short and/or long probes.

22. The method of claim 1, wherein repetitive DNA sequences between 50 and 400 contiguous nucleotides in length, which appear more than once and more often than statistically predicted based on their length and base content, have been excluded from the short and/or long probe(s).

23. The method of claim 1, wherein most of repetitive Alu family DNA sequences, have been excluded from the short and/or long probes.

24. The method of claim 1, wherein in b) the probes are fluorescently tagged are detected fluorometrically.

25. The method of claim 1, wherein in b) each probe is tagged with one of two or more fluorescent tags.

26. The method of claim 1, wherein subgroups of two or more consecutive probes optionally including gaps, chosen so their total length is 10 to 30 kb are detected and compared instead of every probe sequence.

27. The method of claim 1, wherein at least 3 short probes are employed.

28. The method of claim 1, wherein at least 10 short probes are employed.

29. The method of claim 1, wherein the gaps between short probes in the genomic region of interest are no more than 12 kb each.

30. The method of claim 1, wherein the long probes are no more than 40 kb each.

31. The method of claim 1, wherein each of the genomic region(s) of interest is (are) longer than 50 kb.

32. The method of claim 1, wherein the short probes bind to a single contiguous genomic region of interest.

33. The method of claim 1, wherein the short probes bind to more than one non-contiguous genomic region of interest.

34. A method for designing short probes of 0.5 kb to 10 kb and long probes of 12 kb to 150 kb comprising:

identifying a polynucleotide containing a genomic region of interest, selecting long probe sequences outside of the genomic region of interest but within 100 kb of at least one probe within the region of interest and optionally removing sequences of more than 200 bp of which more than 10 copies with less than 20% mismatch are found within the regions of interest from the long probe sequences, selecting short probe sequences from within the genomic region of interest so that no gaps longer than 20 kb appear between the short probes; or selecting a series of short probes that together form a long continuous stretch that covers the genomic region of interest;

hybridizing the probes to a genomic polynucleotide comprising the genomic region of interest, detecting the hybridized probes, and determining which subgroups of probes form motifs which have a length different from the expected theoretical length.

35. A method of claim 34, wherein the long probe(s) range from 14 kb to 40 kb.

* * * * *

UNITED STATES PATENT AND TRADEMARK OFFICE

CERTIFICATE OF CORRECTION

PATENT NO. : 9,133,514 B2
APPLICATION NO. : 13/665440
DATED : September 15, 2015
INVENTOR(S) : Jun Komatsu et al.

It is certified that error appears in the above-identified patent and that said Letters Patent is hereby corrected as shown below:

Column 395, delete line 52, in its entirety and replace with the following:

--optionally have sequences of more than 200 bp of which--

Column 395, delete line 65, in its entirety and replace with the following:

--more than 200 bp of which more than 10 copies with less--

Column 398, delete line 14, in its entirety and replace with the following:

--200 bp of which more than 10 copies with less than 20%--

Signed and Sealed this
Sixteenth Day of August, 2016

Michelle K. Lee
*Director of the United States Patent and Trademark Office*

SEQUENCE LISTING

<160> NUMBER OF SEQ ID NOS: 408

<210> SEQ ID NO 1
<211> LENGTH: 20
<212> TYPE: DNA
<213> ORGANISM: Homo sapiens

<400> SEQUENCE: 1
ttcttcccaa gagagccaag 20

<210> SEQ ID NO 2
<211> LENGTH: 20
<212> TYPE: DNA
<213> ORGANISM: Homo sapiens

<400> SEQUENCE: 2
ctgttttgga accccaagtc 20

<210> SEQ ID NO 3
<211> LENGTH: 20
<212> TYPE: DNA
<213> ORGANISM: Homo sapiens

<400> SEQUENCE: 3
ggcttcaatc tgggactacg 20

<210> SEQ ID NO 4
<211> LENGTH: 20
<212> TYPE: DNA
<213> ORGANISM: Homo sapiens

<400> SEQUENCE: 4
gctgtcaccg cctcttttac 20

<210> SEQ ID NO 5
<211> LENGTH: 20
<212> TYPE: DNA
<213> ORGANISM: Homo sapiens

<400> SEQUENCE: 5
gccaggcact taggcagtag 20

<210> SEQ ID NO 6
<211> LENGTH: 20
<212> TYPE: DNA
<213> ORGANISM: Homo sapiens

<400> SEQUENCE: 6
ttggtcctga catcctttcc 20

<210> SEQ ID NO 7
<211> LENGTH: 22
<212> TYPE: DNA
<213> ORGANISM: Homo sapiens

<400> SEQUENCE: 7
ttagttgaac agggcatgac ac 22

<210> SEQ ID NO 8
<211> LENGTH: 19
<212> TYPE: DNA
<213> ORGANISM: Homo sapiens

<400> SEQUENCE: 8
ggtaaagggg cctgatgtc 19

<210> SEQ ID NO 9
<211> LENGTH: 23
<212> TYPE: DNA
<213> ORGANISM: Homo sapiens

<400> SEQUENCE: 9
gagccttgat gttccctctt aac 23

<210> SEQ ID NO 10
<211> LENGTH: 20
<212> TYPE: DNA
<213> ORGANISM: Homo sapiens

<400> SEQUENCE: 10
acccagatcc gaaactgttg 20

<210> SEQ ID NO 11
<211> LENGTH: 20
<212> TYPE: DNA
<213> ORGANISM: Homo sapiens

<400> SEQUENCE: 11
ccggccttac ctttcatttc 20

<210> SEQ ID NO 12
<211> LENGTH: 20
<212> TYPE: DNA
<213> ORGANISM: Homo sapiens

<400> SEQUENCE: 12
ccaggatcca gatccagttg 20

<210> SEQ ID NO 13
<211> LENGTH: 20
<212> TYPE: DNA
<213> ORGANISM: Homo sapiens

<400> SEQUENCE: 13
gagttccatg gcagatcacc 20

<210> SEQ ID NO 14
<211> LENGTH: 22
<212> TYPE: DNA
<213> ORGANISM: Homo sapiens

<400> SEQUENCE: 14
gcagctttca atcacaaatc ag 22

<210> SEQ ID NO 15
<211> LENGTH: 20
<212> TYPE: DNA
<213> ORGANISM: Homo sapiens

<400> SEQUENCE: 15
gaagggttgg tcttgctgtc 20

<210> SEQ ID NO 16
<211> LENGTH: 20
<212> TYPE: DNA
<213> ORGANISM: Homo sapiens

<400> SEQUENCE: 16 acccttttgca cctctctgtg 20

<210> SEQ ID NO 17
<211> LENGTH: 19
<212> TYPE: DNA
<213> ORGANISM: Homo sapiens

<400> SEQUENCE: 17
cccggtgttg aatcatttg 19

<210> SEQ ID NO 18
<211> LENGTH: 20
<212> TYPE: DNA
<213> ORGANISM: Homo sapiens

<400> SEQUENCE: 18
ttcagccctg aaggtagagg 20

<210> SEQ ID NO 19
<211> LENGTH: 20
<212> TYPE: DNA
<213> ORGANISM: Homo sapiens

<400> SEQUENCE: 19
ctggccactt tttggaagag 20

<210> SEQ ID NO 20
<211> LENGTH: 20
<212> TYPE: DNA
<213> ORGANISM: Homo sapiens

<400> SEQUENCE: 20
tgggacgcag agtgatacag 20

<210> SEQ ID NO 21
<211> LENGTH: 20
<212> TYPE: DNA
<213> ORGANISM: Homo sapiens

<400> SEQUENCE: 21
ttactggcga tcctcagagc 20

<210> SEQ ID NO 22
<211> LENGTH: 20
<212> TYPE: DNA
<213> ORGANISM: Homo sapiens

<400> SEQUENCE: 22
aacgcctctt ccgttgtatg 20

<210> SEQ ID NO 23
<211> LENGTH: 21
<212> TYPE: DNA
<213> ORGANISM: Homo sapiens

<400> SEQUENCE: 23
gaaaggacag accaagtgca g 21

<210> SEQ ID NO 24
<211> LENGTH: 19
<212> TYPE: DNA
<213> ORGANISM: Homo sapiens

<400> SEQUENCE: 24
agcctgtgca gggaaactc 19

<210> SEQ ID NO 25
<211> LENGTH: 20
<212> TYPE: DNA
<213> ORGANISM: Homo sapiens

<400> SEQUENCE: 25
agtgggatgc agctgaaaag 20

<210> SEQ ID NO 26
<211> LENGTH: 20
<212> TYPE: DNA
<213> ORGANISM: Homo sapiens

<400> SEQUENCE: 26
caacagcatg ggaaagatcc 20

<210> SEQ ID NO 27
<211> LENGTH: 24
<212> TYPE: DNA
<213> ORGANISM: Homo sapiens

<400> SEQUENCE: 27
ttgaaagttg gtcttaggaa gagg 24

<210> SEQ ID NO 28
<211> LENGTH: 20
<212> TYPE: DNA
<213> ORGANISM: Homo sapiens

<400> SEQUENCE: 28
cccaacaaac ctggctttag 20

<210> SEQ ID NO 29
<211> LENGTH: 20
<212> TYPE: DNA
<213> ORGANISM: Homo sapiens

<400> SEQUENCE: 29
agacgcccaa aatcaacaac 20

<210> SEQ ID NO 30
<211> LENGTH: 20
<212> TYPE: DNA
<213> ORGANISM: Homo sapiens

<400> SEQUENCE: 30
ccgcttgctg ctaaaaattg 20

<210> SEQ ID NO 31
<211> LENGTH: 21
<212> TYPE: DNA
<213> ORGANISM: Homo sapiens

<400> SEQUENCE: 31
tgattgccaa ggaagattca c 21

<210> SEQ ID NO 32
<211> LENGTH: 21
<212> TYPE: DNA

<213> ORGANISM: Homo sapiens

<400> SEQUENCE: 32
tggaagtaaa tgcaggtgct c 21

<210> SEQ ID NO 33
<211> LENGTH: 20
<212> TYPE: DNA
<213> ORGANISM: Homo sapiens

<400> SEQUENCE: 33
tcattcttgg gtgtttctcg 20

<210> SEQ ID NO 34
<211> LENGTH: 20
<212> TYPE: DNA
<213> ORGANISM: Homo sapiens

<400> SEQUENCE: 34
atggcggttt tgtggaatag 20

<210> SEQ ID NO 35
<211> LENGTH: 20
<212> TYPE: DNA
<213> ORGANISM: Homo sapiens

<400> SEQUENCE: 35
gagggagagg gaaccttttg 20

<210> SEQ ID NO 36
<211> LENGTH: 20
<212> TYPE: DNA
<213> ORGANISM: Homo sapiens

<400> SEQUENCE: 36
ggggactata ccgcattcac 20

<210> SEQ ID NO 37
<211> LENGTH: 20
<212> TYPE: DNA
<213> ORGANISM: Homo sapiens

<400> SEQUENCE: 37
tgttgattca tgggcatttg 20

<210> SEQ ID NO 38
<211> LENGTH: 21
<212> TYPE: DNA
<213> ORGANISM: Homo sapiens

<400> SEQUENCE: 38
gctggggaat catgtatgaa g 21

<210> SEQ ID NO 39
<211> LENGTH: 20
<212> TYPE: DNA
<213> ORGANISM: Homo sapiens

<400> SEQUENCE: 39
catcaagcac agttccattg 20

<210> SEQ ID NO 40
<211> LENGTH: 20

<212> TYPE: DNA
<213> ORGANISM: Homo sapiens

<400> SEQUENCE: 40
ttctctttcc gtttccagtg 20

<210> SEQ ID NO 41
<211> LENGTH: 20
<212> TYPE: DNA
<213> ORGANISM: Homo sapiens

<400> SEQUENCE: 41
ggagcttggg aattcaactg 20

<210> SEQ ID NO 42
<211> LENGTH: 20
<212> TYPE: DNA
<213> ORGANISM: Homo sapiens

<400> SEQUENCE: 42
agaaacgggc atgtcatagg 20

<210> SEQ ID NO 43
<211> LENGTH: 19
<212> TYPE: DNA
<213> ORGANISM: Homo sapiens

<400> SEQUENCE: 43
cagcctacgt gcccatttc 19

<210> SEQ ID NO 44
<211> LENGTH: 20
<212> TYPE: DNA
<213> ORGANISM: Homo sapiens

<400> SEQUENCE: 44
tcaaaagatg gccaaaatgc 20

<210> SEQ ID NO 45
<211> LENGTH: 20
<212> TYPE: DNA
<213> ORGANISM: Homo sapiens

<400> SEQUENCE: 45
gtgttgcacc cattaactcg 20

<210> SEQ ID NO 46
<211> LENGTH: 20
<212> TYPE: DNA
<213> ORGANISM: Homo sapiens

<400> SEQUENCE: 46
agcctggtga gaggtgactg 20

<210> SEQ ID NO 47
<211> LENGTH: 19
<212> TYPE: DNA
<213> ORGANISM: Homo sapiens

<400> SEQUENCE: 47
cacgatgcca gtccaattc 19

<210> SEQ ID NO 48

<211> LENGTH: 22
<212> TYPE: DNA
<213> ORGANISM: Homo sapiens

<400> SEQUENCE: 48
aaggtggact ttaatgcaaa gg 22

<210> SEQ ID NO 49
<211> LENGTH: 20
<212> TYPE: DNA
<213> ORGANISM: Homo sapiens

<400> SEQUENCE: 49
ggagtgagag cgacaccttg 20

<210> SEQ ID NO 50
<211> LENGTH: 21
<212> TYPE: DNA
<213> ORGANISM: Homo sapiens

<400> SEQUENCE: 50
cgacagctga ctgctctatg g 21

<210> SEQ ID NO 51
<211> LENGTH: 21
<212> TYPE: DNA
<213> ORGANISM: Homo sapiens

<400> SEQUENCE: 51
cacaatggga aaggatgtag c 21

<210> SEQ ID NO 52
<211> LENGTH: 21
<212> TYPE: DNA
<213> ORGANISM: Homo sapiens

<400> SEQUENCE: 52
cagagaaaaa cacccatgac c 21

<210> SEQ ID NO 53
<211> LENGTH: 21
<212> TYPE: DNA
<213> ORGANISM: Homo sapiens

<400> SEQUENCE: 53
caccgtgatc ctccttattt c 21

<210> SEQ ID NO 54
<211> LENGTH: 21
<212> TYPE: DNA
<213> ORGANISM: Homo sapiens

<400> SEQUENCE: 54
gaacaaacaa cggatgaaag g 21

<210> SEQ ID NO 55
<211> LENGTH: 20
<212> TYPE: DNA
<213> ORGANISM: Homo sapiens

<400> SEQUENCE: 55
gtggcatatc cttcccaatg 20

-continued

<210> SEQ ID NO 56
<211> LENGTH: 21
<212> TYPE: DNA
<213> ORGANISM: Homo sapiens

<400> SEQUENCE: 56
cccccagact gtgaattaag g 21

<210> SEQ ID NO 57
<211> LENGTH: 20
<212> TYPE: DNA
<213> ORGANISM: Homo sapiens

<400> SEQUENCE: 57
gatgcagatc agggaaatgc 20

<210> SEQ ID NO 58
<211> LENGTH: 20
<212> TYPE: DNA
<213> ORGANISM: Homo sapiens

<400> SEQUENCE: 58
atcttgctgg atggacaagg 20

<210> SEQ ID NO 59
<211> LENGTH: 21
<212> TYPE: DNA
<213> ORGANISM: Homo sapiens

<400> SEQUENCE: 59
cttaatcctg aaaggcaggt g 21

<210> SEQ ID NO 60
<211> LENGTH: 20
<212> TYPE: DNA
<213> ORGANISM: Homo sapiens

<400> SEQUENCE: 60
tgtttctcag gcaaccacag 20

<210> SEQ ID NO 61
<211> LENGTH: 20
<212> TYPE: DNA
<213> ORGANISM: Homo sapiens

<400> SEQUENCE: 61
gaaaccacag aatcgccttc 20

<210> SEQ ID NO 62
<211> LENGTH: 20
<212> TYPE: DNA
<213> ORGANISM: Homo sapiens

<400> SEQUENCE: 62
acctggacag tcccacagac 20

<210> SEQ ID NO 63
<211> LENGTH: 20
<212> TYPE: DNA
<213> ORGANISM: Homo sapiens

<400> SEQUENCE: 63
cagtgctttt gcatccttcc 20

-continued

<210> SEQ ID NO 64
<211> LENGTH: 20
<212> TYPE: DNA
<213> ORGANISM: Homo sapiens

<400> SEQUENCE: 64
atttaatccc ctggccaatc 20

<210> SEQ ID NO 65
<211> LENGTH: 20
<212> TYPE: DNA
<213> ORGANISM: Homo sapiens

<400> SEQUENCE: 65
cacctgtgcc catcacatag 20

<210> SEQ ID NO 66
<211> LENGTH: 20
<212> TYPE: DNA
<213> ORGANISM: Homo sapiens

<400> SEQUENCE: 66
gagtcccctc ttggagaacc 20

<210> SEQ ID NO 67
<211> LENGTH: 19
<212> TYPE: DNA
<213> ORGANISM: Homo sapiens

<400> SEQUENCE: 67
aaagccattt ccagtgtcg 19

<210> SEQ ID NO 68
<211> LENGTH: 20
<212> TYPE: DNA
<213> ORGANISM: Homo sapiens

<400> SEQUENCE: 68
attgtgcagc cagaattgag 20

<210> SEQ ID NO 69
<211> LENGTH: 20
<212> TYPE: DNA
<213> ORGANISM: Homo sapiens

<400> SEQUENCE: 69
ttcacagcaa agtggctcag 20

<210> SEQ ID NO 70
<211> LENGTH: 20
<212> TYPE: DNA
<213> ORGANISM: Homo sapiens

<400> SEQUENCE: 70
gctattatgg gctgcaaagc 20

<210> SEQ ID NO 71
<211> LENGTH: 20
<212> TYPE: DNA
<213> ORGANISM: Homo sapiens

<400> SEQUENCE: 71
ttcactccca acaagcactg 20

<210> SEQ ID NO 72
<211> LENGTH: 19
<212> TYPE: DNA
<213> ORGANISM: Homo sapiens

<400> SEQUENCE: 72
tgcccagtcc tttttcact 19

<210> SEQ ID NO 73
<211> LENGTH: 20
<212> TYPE: DNA
<213> ORGANISM: Homo sapiens

<400> SEQUENCE: 73
aatccctcct gcacactttc 20

<210> SEQ ID NO 74
<211> LENGTH: 20
<212> TYPE: DNA
<213> ORGANISM: Homo sapiens

<400> SEQUENCE: 74
aatggatgct tccactgtcc 20

<210> SEQ ID NO 75
<211> LENGTH: 20
<212> TYPE: DNA
<213> ORGANISM: Homo sapiens

<400> SEQUENCE: 75
ccatctgtgc aattccttcc 20

<210> SEQ ID NO 76
<211> LENGTH: 20
<212> TYPE: DNA
<213> ORGANISM: Homo sapiens

<400> SEQUENCE: 76
gttcaaaggc agaagccatc 20

<210> SEQ ID NO 77
<211> LENGTH: 24
<212> TYPE: DNA
<213> ORGANISM: Homo sapiens

<400> SEQUENCE: 77
gtctggattc tttcacaatg tagc 24

<210> SEQ ID NO 78
<211> LENGTH: 21
<212> TYPE: DNA
<213> ORGANISM: Homo sapiens

<400> SEQUENCE: 78
tgccaatctt ctcctctgtt c 21

<210> SEQ ID NO 79
<211> LENGTH: 20
<212> TYPE: DNA
<213> ORGANISM: Homo sapiens

<400> SEQUENCE: 79

-continued aaccacccaa tgtgttcacc 20

<210> SEQ ID NO 80
<211> LENGTH: 20
<212> TYPE: DNA
<213> ORGANISM: Homo sapiens

<400> SEQUENCE: 80
gttcattcct gcgagtaggc 20

<210> SEQ ID NO 81
<211> LENGTH: 20
<212> TYPE: DNA
<213> ORGANISM: Homo sapiens

<400> SEQUENCE: 81
gccaaaggtg gaaaatgttg 20

<210> SEQ ID NO 82
<211> LENGTH: 21
<212> TYPE: DNA
<213> ORGANISM: Homo sapiens

<400> SEQUENCE: 82
gccttcttca tgaaagcact g 21

<210> SEQ ID NO 83
<211> LENGTH: 20
<212> TYPE: DNA
<213> ORGANISM: Homo sapiens

<400> SEQUENCE: 83
ccagaaggtg gaagctacag 20

<210> SEQ ID NO 84
<211> LENGTH: 18
<212> TYPE: DNA
<213> ORGANISM: Homo sapiens

<400> SEQUENCE: 84
tggggtcaat gaagcaag 18

<210> SEQ ID NO 85
<211> LENGTH: 20
<212> TYPE: DNA
<213> ORGANISM: Homo sapiens

<400> SEQUENCE: 85
acatcgaccc agaaagttcc 20

<210> SEQ ID NO 86
<211> LENGTH: 20
<212> TYPE: DNA
<213> ORGANISM: Homo sapiens

<400> SEQUENCE: 86
aatgtgcttc gtaccactgc 20

<210> SEQ ID NO 87
<211> LENGTH: 20
<212> TYPE: DNA
<213> ORGANISM: Homo sapiens

<400> SEQUENCE: 87
agcgtgccat tgtactctcc 20

<210> SEQ ID NO 88
<211> LENGTH: 20
<212> TYPE: DNA
<213> ORGANISM: Homo sapiens

<400> SEQUENCE: 88
tttctgagcc catgatttcc 20

<210> SEQ ID NO 89
<211> LENGTH: 20
<212> TYPE: DNA
<213> ORGANISM: Homo sapiens

<400> SEQUENCE: 89
gtgcccagct agttccattc 20

<210> SEQ ID NO 90
<211> LENGTH: 20
<212> TYPE: DNA
<213> ORGANISM: Homo sapiens

<400> SEQUENCE: 90
tcaagagcgc taatcccatc 20

<210> SEQ ID NO 91
<211> LENGTH: 21
<212> TYPE: DNA
<213> ORGANISM: Homo sapiens

<400> SEQUENCE: 91
tgcacatgct cactgaaaga c 21

<210> SEQ ID NO 92
<211> LENGTH: 19
<212> TYPE: DNA
<213> ORGANISM: Homo sapiens

<400> SEQUENCE: 92
ttttgcctgc aaactgacc 19

<210> SEQ ID NO 93
<211> LENGTH: 20
<212> TYPE: DNA
<213> ORGANISM: Homo sapiens

<400> SEQUENCE: 93
cagcaagcac caaatcactg 20

<210> SEQ ID NO 94
<211> LENGTH: 20
<212> TYPE: DNA
<213> ORGANISM: Homo sapiens

<400> SEQUENCE: 94
agtaccagcc gtccaaactg 20

<210> SEQ ID NO 95
<211> LENGTH: 20
<212> TYPE: DNA
<213> ORGANISM: Homo sapiens

<400> SEQUENCE: 95
cctggccaga aaattcattg 20

<210> SEQ ID NO 96
<211> LENGTH: 20
<212> TYPE: DNA
<213> ORGANISM: Homo sapiens

<400> SEQUENCE: 96
accctgcatt ccaaactcac 20

<210> SEQ ID NO 97
<211> LENGTH: 21
<212> TYPE: DNA
<213> ORGANISM: Homo sapiens

<400> SEQUENCE: 97
gcagtccttt gaggatttag c 21

<210> SEQ ID NO 98
<211> LENGTH: 24
<212> TYPE: DNA
<213> ORGANISM: Homo sapiens

<400> SEQUENCE: 98
gaaagatatc caacaggaag tgag 24

<210> SEQ ID NO 99
<211> LENGTH: 20
<212> TYPE: DNA
<213> ORGANISM: Homo sapiens

<400> SEQUENCE: 99
tggccttgtt taaggtcctg 20

<210> SEQ ID NO 100
<211> LENGTH: 20
<212> TYPE: DNA
<213> ORGANISM: Homo sapiens

<400> SEQUENCE: 100
atggtcctgc tgcttcagag 20

<210> SEQ ID NO 101
<211> LENGTH: 20
<212> TYPE: DNA
<213> ORGANISM: Homo sapiens

<400> SEQUENCE: 101
accccgtcat agcacagttc 20

<210> SEQ ID NO 102
<211> LENGTH: 21
<212> TYPE: DNA
<213> ORGANISM: Homo sapiens

<400> SEQUENCE: 102
caaaggccat tcatcagttt c 21

<210> SEQ ID NO 103
<211> LENGTH: 21
<212> TYPE: DNA
<213> ORGANISM: Homo sapiens

<400> SEQUENCE: 103
gtggcgtgat atccttgatt c 21

<210> SEQ ID NO 104
<211> LENGTH: 20
<212> TYPE: DNA
<213> ORGANISM: Homo sapiens

<400> SEQUENCE: 104
ctctggaatg actgctgctg 20

<210> SEQ ID NO 105
<211> LENGTH: 20
<212> TYPE: DNA
<213> ORGANISM: Homo sapiens

<400> SEQUENCE: 105
tgtgctagat gcctcactgg 20

<210> SEQ ID NO 106
<211> LENGTH: 20
<212> TYPE: DNA
<213> ORGANISM: Homo sapiens

<400> SEQUENCE: 106
ttgccaagaa gcacaacaag 20

<210> SEQ ID NO 107
<211> LENGTH: 20
<212> TYPE: DNA
<213> ORGANISM: Homo sapiens

<400> SEQUENCE: 107
cggaggctct actgttggac 20

<210> SEQ ID NO 108
<211> LENGTH: 20
<212> TYPE: DNA
<213> ORGANISM: Homo sapiens

<400> SEQUENCE: 108
tgctgtccac tctggaactg 20

<210> SEQ ID NO 109
<211> LENGTH: 20
<212> TYPE: DNA
<213> ORGANISM: Homo sapiens

<400> SEQUENCE: 109
acatcagaag ccctggtttg 20

<210> SEQ ID NO 110
<211> LENGTH: 20
<212> TYPE: DNA
<213> ORGANISM: Homo sapiens

<400> SEQUENCE: 110
gctgggagtt caagcatctc 20

<210> SEQ ID NO 111
<211> LENGTH: 20
<212> TYPE: DNA

<213> ORGANISM: Homo sapiens

<400> SEQUENCE: 111
tcggtctcag tcaccatttg 20

<210> SEQ ID NO 112
<211> LENGTH: 20
<212> TYPE: DNA
<213> ORGANISM: Homo sapiens

<400> SEQUENCE: 112
aacgcacctg gctgaaatac 20

<210> SEQ ID NO 113
<211> LENGTH: 22
<212> TYPE: DNA
<213> ORGANISM: Homo sapiens

<400> SEQUENCE: 113
tgaacctgca atatctcaga gg 22

<210> SEQ ID NO 114
<211> LENGTH: 23
<212> TYPE: DNA
<213> ORGANISM: Homo sapiens

<400> SEQUENCE: 114
cttaccgata acctgagaac acc 23

<210> SEQ ID NO 115
<211> LENGTH: 22
<212> TYPE: DNA
<213> ORGANISM: Homo sapiens

<400> SEQUENCE: 115
cccagcccat atattttaaa gc 22

<210> SEQ ID NO 116
<211> LENGTH: 21
<212> TYPE: DNA
<213> ORGANISM: Homo sapiens

<400> SEQUENCE: 116
ccagccactc tctggactat c 21

<210> SEQ ID NO 117
<211> LENGTH: 19
<212> TYPE: DNA
<213> ORGANISM: Homo sapiens

<400> SEQUENCE: 117
gacatggaga gccgaatcc 19

<210> SEQ ID NO 118
<211> LENGTH: 22
<212> TYPE: DNA
<213> ORGANISM: Homo sapiens

<400> SEQUENCE: 118
ccattaaaat cgggtctgaa ag 22

<210> SEQ ID NO 119
<211> LENGTH: 19

<212> TYPE: DNA
<213> ORGANISM: Homo sapiens

<400> SEQUENCE: 119
tccagaccca gtgcacatc 19

<210> SEQ ID NO 120
<211> LENGTH: 20
<212> TYPE: DNA
<213> ORGANISM: Homo sapiens

<400> SEQUENCE: 120
catggtcagt gccatcagag 20

<210> SEQ ID NO 121
<211> LENGTH: 20
<212> TYPE: DNA
<213> ORGANISM: Homo sapiens

<400> SEQUENCE: 121
agcctcccaa agttaagtgc 20

<210> SEQ ID NO 122
<211> LENGTH: 20
<212> TYPE: DNA
<213> ORGANISM: Homo sapiens

<400> SEQUENCE: 122
cccagctaaa accaacacac 20

<210> SEQ ID NO 123
<211> LENGTH: 20
<212> TYPE: DNA
<213> ORGANISM: Homo sapiens

<400> SEQUENCE: 123
tgccctcagc tactcactcc 20

<210> SEQ ID NO 124
<211> LENGTH: 20
<212> TYPE: DNA
<213> ORGANISM: Homo sapiens

<400> SEQUENCE: 124
agggctcagc ctttaggaac 20

<210> SEQ ID NO 125
<211> LENGTH: 20
<212> TYPE: DNA
<213> ORGANISM: Homo sapiens

<400> SEQUENCE: 125
gccagactct cgttccattc 20

<210> SEQ ID NO 126
<211> LENGTH: 20
<212> TYPE: DNA
<213> ORGANISM: Homo sapiens

<400> SEQUENCE: 126
actccccatt cagtcccttc 20

<210> SEQ ID NO 127

<211> LENGTH: 20
<212> TYPE: DNA
<213> ORGANISM: Homo sapiens

<400> SEQUENCE: 127
aggcacaacg tcaggttttc 20

<210> SEQ ID NO 128
<211> LENGTH: 20
<212> TYPE: DNA
<213> ORGANISM: Homo sapiens

<400> SEQUENCE: 128
ttggaatttg tcctggtgtg 20

<210> SEQ ID NO 129
<211> LENGTH: 20
<212> TYPE: DNA
<213> ORGANISM: Homo sapiens

<400> SEQUENCE: 129
caccattgcc aacacttctg 20

<210> SEQ ID NO 130
<211> LENGTH: 20
<212> TYPE: DNA
<213> ORGANISM: Homo sapiens

<400> SEQUENCE: 130
gccattggtt tgaaggtgac 20

<210> SEQ ID NO 131
<211> LENGTH: 20
<212> TYPE: DNA
<213> ORGANISM: Homo sapiens

<400> SEQUENCE: 131
cttagtcacc gcctgtcctc 20

<210> SEQ ID NO 132
<211> LENGTH: 20
<212> TYPE: DNA
<213> ORGANISM: Homo sapiens

<400> SEQUENCE: 132
tagctgcatg tggctaatcg 20

<210> SEQ ID NO 133
<211> LENGTH: 20
<212> TYPE: DNA
<213> ORGANISM: Homo sapiens

<400> SEQUENCE: 133
tgtggctcgc attacatttc 20

<210> SEQ ID NO 134
<211> LENGTH: 20
<212> TYPE: DNA
<213> ORGANISM: Homo sapiens

<400> SEQUENCE: 134
cgctgtcatt acctgctttg 20

<210> SEQ ID NO 135
<211> LENGTH: 20
<212> TYPE: DNA
<213> ORGANISM: Homo sapiens

<400> SEQUENCE: 135
tgacctccaa aatcatccag 20

<210> SEQ ID NO 136
<211> LENGTH: 20
<212> TYPE: DNA
<213> ORGANISM: Homo sapiens

<400> SEQUENCE: 136
ttctgagcta ggaggtgctg 20

<210> SEQ ID NO 137
<211> LENGTH: 22
<212> TYPE: DNA
<213> ORGANISM: Homo sapiens

<400> SEQUENCE: 137
ccagatttgt aaatccctgt tc 22

<210> SEQ ID NO 138
<211> LENGTH: 21
<212> TYPE: DNA
<213> ORGANISM: Homo sapiens

<400> SEQUENCE: 138
tgtgtggttc ttaagcattc c 21

<210> SEQ ID NO 139
<211> LENGTH: 20
<212> TYPE: DNA
<213> ORGANISM: Homo sapiens

<400> SEQUENCE: 139
ctcagtccat cagcctcctc 20

<210> SEQ ID NO 140
<211> LENGTH: 20
<212> TYPE: DNA
<213> ORGANISM: Homo sapiens

<400> SEQUENCE: 140
tgctgtgccc tgagattaag 20

<210> SEQ ID NO 141
<211> LENGTH: 21
<212> TYPE: DNA
<213> ORGANISM: Homo sapiens

<400> SEQUENCE: 141
aacttaatct cagggcacag c 21

<210> SEQ ID NO 142
<211> LENGTH: 18
<212> TYPE: DNA
<213> ORGANISM: Homo sapiens

<400> SEQUENCE: 142
tgcagcttca gcctcttg 18

-continued

<210> SEQ ID NO 143
<211> LENGTH: 19
<212> TYPE: DNA
<213> ORGANISM: Homo sapiens

<400> SEQUENCE: 143
gcgtggtgtt tcgtaccag 19

<210> SEQ ID NO 144
<211> LENGTH: 21
<212> TYPE: DNA
<213> ORGANISM: Homo sapiens

<400> SEQUENCE: 144
gctactggcc agaaatcttc c 21

<210> SEQ ID NO 145
<211> LENGTH: 20
<212> TYPE: DNA
<213> ORGANISM: Homo sapiens

<400> SEQUENCE: 145
gcccagccct actaaggaag 20

<210> SEQ ID NO 146
<211> LENGTH: 20
<212> TYPE: DNA
<213> ORGANISM: Homo sapiens

<400> SEQUENCE: 146
ctgtgctccc ctgctagaac 20

<210> SEQ ID NO 147
<211> LENGTH: 20
<212> TYPE: DNA
<213> ORGANISM: Homo sapiens

<400> SEQUENCE: 147
gtcgtcctct tcgacctagc 20

<210> SEQ ID NO 148
<211> LENGTH: 20
<212> TYPE: DNA
<213> ORGANISM: Homo sapiens

<400> SEQUENCE: 148
cagcgcctat tctacagcag 20

<210> SEQ ID NO 149
<211> LENGTH: 20
<212> TYPE: DNA
<213> ORGANISM: Homo sapiens

<400> SEQUENCE: 149
ttcttcccaa gagagccaag 20

<210> SEQ ID NO 150
<211> LENGTH: 20
<212> TYPE: DNA
<213> ORGANISM: Homo sapiens

<400> SEQUENCE: 150
ccacctttaa tctgcccaac 20

<210> SEQ ID NO 151
<211> LENGTH: 21
<212> TYPE: DNA
<213> ORGANISM: Homo sapiens

<400> SEQUENCE: 151
gtgttgggca gattaaaggt g 21

<210> SEQ ID NO 152
<211> LENGTH: 19
<212> TYPE: DNA
<213> ORGANISM: Homo sapiens

<400> SEQUENCE: 152
gcagtgtcat gccctgttc 19

<210> SEQ ID NO 153
<211> LENGTH: 21
<212> TYPE: DNA
<213> ORGANISM: Homo sapiens

<400> SEQUENCE: 153
ctctttgtgc cctttctttt g 21

<210> SEQ ID NO 154
<211> LENGTH: 24
<212> TYPE: DNA
<213> ORGANISM: Homo sapiens

<400> SEQUENCE: 154
agttccttaa agcagagaag atgg 24

<210> SEQ ID NO 155
<211> LENGTH: 20
<212> TYPE: DNA
<213> ORGANISM: Homo sapiens

<400> SEQUENCE: 155
aacctgtccc tgtggatgag 20

<210> SEQ ID NO 156
<211> LENGTH: 20
<212> TYPE: DNA
<213> ORGANISM: Homo sapiens

<400> SEQUENCE: 156
ccgaagcatc cttacattcc 20

<210> SEQ ID NO 157
<211> LENGTH: 20
<212> TYPE: DNA
<213> ORGANISM: Homo sapiens

<400> SEQUENCE: 157
aatacctgaa cccccaaacc 20

<210> SEQ ID NO 158
<211> LENGTH: 23
<212> TYPE: DNA
<213> ORGANISM: Homo sapiens

<400> SEQUENCE: 158
ctcaggctat tttccagatt cac 23

<210> SEQ ID NO 159
<211> LENGTH: 18
<212> TYPE: DNA
<213> ORGANISM: Homo sapiens

<400> SEQUENCE: 159
gcatgcctgt cattctgg 18

<210> SEQ ID NO 160
<211> LENGTH: 20
<212> TYPE: DNA
<213> ORGANISM: Homo sapiens

<400> SEQUENCE: 160
tccaagggac tgaaacacac 20

<210> SEQ ID NO 161
<211> LENGTH: 22
<212> TYPE: DNA
<213> ORGANISM: Homo sapiens

<400> SEQUENCE: 161
ttagtgtgtt tcagtccctt gg 22

<210> SEQ ID NO 162
<211> LENGTH: 20
<212> TYPE: DNA
<213> ORGANISM: Homo sapiens

<400> SEQUENCE: 162
gacagcaaga ccaacccttc 20

<210> SEQ ID NO 163
<211> LENGTH: 20
<212> TYPE: DNA
<213> ORGANISM: Homo sapiens

<400> SEQUENCE: 163
gcacattacg agctcagtgc 20

<210> SEQ ID NO 164
<211> LENGTH: 21
<212> TYPE: DNA
<213> ORGANISM: Homo sapiens

<400> SEQUENCE: 164
ctaccaggag aacagcacag g 21

<210> SEQ ID NO 165
<211> LENGTH: 22
<212> TYPE: DNA
<213> ORGANISM: Homo sapiens

<400> SEQUENCE: 165
tgggttagca ttgtgttagg tg 22

<210> SEQ ID NO 166
<211> LENGTH: 20
<212> TYPE: DNA
<213> ORGANISM: Homo sapiens

<400> SEQUENCE: 166
ccacaggtgt gtgccaatag 20

<210> SEQ ID NO 167
<211> LENGTH: 20
<212> TYPE: DNA
<213> ORGANISM: Homo sapiens

<400> SEQUENCE: 167
aagttgcagt ttggctggtc 20

<210> SEQ ID NO 168
<211> LENGTH: 21
<212> TYPE: DNA
<213> ORGANISM: Homo sapiens

<400> SEQUENCE: 168
ttatctccag cggtgcttat g 21

<210> SEQ ID NO 169
<211> LENGTH: 20
<212> TYPE: DNA
<213> ORGANISM: Homo sapiens

<400> SEQUENCE: 169
taccataagc accgctggag 20

<210> SEQ ID NO 170
<211> LENGTH: 20
<212> TYPE: DNA
<213> ORGANISM: Homo sapiens

<400> SEQUENCE: 170
actccaccaa gcccagtctc 20

<210> SEQ ID NO 171
<211> LENGTH: 20
<212> TYPE: DNA
<213> ORGANISM: Homo sapiens

<400> SEQUENCE: 171
tttagagact gggcttggtg 20

<210> SEQ ID NO 172
<211> LENGTH: 19
<212> TYPE: DNA
<213> ORGANISM: Homo sapiens

<400> SEQUENCE: 172
ctcttcccca acaaacctg 19

<210> SEQ ID NO 173
<211> LENGTH: 20
<212> TYPE: DNA
<213> ORGANISM: Homo sapiens

<400> SEQUENCE: 173
cccagtttca agcgattaag 20

<210> SEQ ID NO 174
<211> LENGTH: 22
<212> TYPE: DNA
<213> ORGANISM: Homo sapiens

<400> SEQUENCE: 174
aggaaaagca tgttatctcc ag 22

<210> SEQ ID NO 175
<211> LENGTH: 20
<212> TYPE: DNA
<213> ORGANISM: Homo sapiens

<400> SEQUENCE: 175
ttccgtagca gtaggcatcc 20

<210> SEQ ID NO 176
<211> LENGTH: 22
<212> TYPE: DNA
<213> ORGANISM: Homo sapiens

<400> SEQUENCE: 176
tcaccaccac caactttatg ag 22

<210> SEQ ID NO 177
<211> LENGTH: 21
<212> TYPE: DNA
<213> ORGANISM: Homo sapiens

<400> SEQUENCE: 177
tcccagatct taaccgactt g 21

<210> SEQ ID NO 178
<211> LENGTH: 20
<212> TYPE: DNA
<213> ORGANISM: Homo sapiens

<400> SEQUENCE: 178
atggcggttt tgtggaatag 20

<210> SEQ ID NO 179
<211> LENGTH: 20
<212> TYPE: DNA
<213> ORGANISM: Homo sapiens

<400> SEQUENCE: 179
cccaaacaac agcattagcc 20

<210> SEQ ID NO 180
<211> LENGTH: 19
<212> TYPE: DNA
<213> ORGANISM: Homo sapiens

<400> SEQUENCE: 180
acatcagcct cgggacaag 19

<210> SEQ ID NO 181
<211> LENGTH: 21
<212> TYPE: DNA
<213> ORGANISM: Homo sapiens

<400> SEQUENCE: 181
tgagcccgtt gaatatagtg g 21

<210> SEQ ID NO 182
<211> LENGTH: 22
<212> TYPE: DNA
<213> ORGANISM: Homo sapiens

<400> SEQUENCE: 182
agttttccta aacgggatga tg 22

<210> SEQ ID NO 183
<211> LENGTH: 20
<212> TYPE: DNA
<213> ORGANISM: Homo sapiens

<400> SEQUENCE: 183
atgggtgtgc acgtgtgtag 20

<210> SEQ ID NO 184
<211> LENGTH: 20
<212> TYPE: DNA
<213> ORGANISM: Homo sapiens

<400> SEQUENCE: 184
gccatgtgca attgtgagtc 20

<210> SEQ ID NO 185
<211> LENGTH: 21
<212> TYPE: DNA
<213> ORGANISM: Homo sapiens

<400> SEQUENCE: 185
ccttgcatag tttgcttctg g 21

<210> SEQ ID NO 186
<211> LENGTH: 20
<212> TYPE: DNA
<213> ORGANISM: Homo sapiens

<400> SEQUENCE: 186
atcatacaag ggcctgttgg 20

<210> SEQ ID NO 187
<211> LENGTH: 20
<212> TYPE: DNA
<213> ORGANISM: Homo sapiens

<400> SEQUENCE: 187
aaacagaaat cgcccaacag 20

<210> SEQ ID NO 188
<211> LENGTH: 20
<212> TYPE: DNA
<213> ORGANISM: Homo sapiens

<400> SEQUENCE: 188
tagagaccca cccagaaacg 20

<210> SEQ ID NO 189
<211> LENGTH: 20
<212> TYPE: DNA
<213> ORGANISM: Homo sapiens

<400> SEQUENCE: 189
cagtccgatt tcgtttctgg 20

<210> SEQ ID NO 190
<211> LENGTH: 21
<212> TYPE: DNA

<213> ORGANISM: Homo sapiens

<400> SEQUENCE: 190
cacacctaga tttggcaatg g 21

<210> SEQ ID NO 191
<211> LENGTH: 21
<212> TYPE: DNA
<213> ORGANISM: Homo sapiens

<400> SEQUENCE: 191
ttccattgcc aaatctaggt g 21

<210> SEQ ID NO 192
<211> LENGTH: 20
<212> TYPE: DNA
<213> ORGANISM: Homo sapiens

<400> SEQUENCE: 192
ggccctagtg tttcctttcc 20

<210> SEQ ID NO 193
<211> LENGTH: 23
<212> TYPE: DNA
<213> ORGANISM: Homo sapiens

<400> SEQUENCE: 193
aaggaaacac tagggcctac aac 23

<210> SEQ ID NO 194
<211> LENGTH: 21
<212> TYPE: DNA
<213> ORGANISM: Homo sapiens

<400> SEQUENCE: 194
cctggcctca gtacactttt g 21

<210> SEQ ID NO 195
<211> LENGTH: 20
<212> TYPE: DNA
<213> ORGANISM: Homo sapiens

<400> SEQUENCE: 195
agggattctc cccacttagc 20

<210> SEQ ID NO 196
<211> LENGTH: 20
<212> TYPE: DNA
<213> ORGANISM: Homo sapiens

<400> SEQUENCE: 196
attggaggac tggctcaaag 20

<210> SEQ ID NO 197
<211> LENGTH: 20
<212> TYPE: DNA
<213> ORGANISM: Homo sapiens

<400> SEQUENCE: 197
gcttaccttt gagccagtcc 20

<210> SEQ ID NO 198
<211> LENGTH: 20

-continued

<212> TYPE: DNA
<213> ORGANISM: Homo sapiens

<400> SEQUENCE: 198
acatgttcct acccccagac 20

<210> SEQ ID NO 199
<211> LENGTH: 20
<212> TYPE: DNA
<213> ORGANISM: Homo sapiens

<400> SEQUENCE: 199
tttctgcatc agttggttgc 20

<210> SEQ ID NO 200
<211> LENGTH: 21
<212> TYPE: DNA
<213> ORGANISM: Homo sapiens

<400> SEQUENCE: 200
gccaagttat tgctgcttca g 21

<210> SEQ ID NO 201
<211> LENGTH: 20
<212> TYPE: DNA
<213> ORGANISM: Homo sapiens

<400> SEQUENCE: 201
agccctgtga ggttggtaac 20

<210> SEQ ID NO 202
<211> LENGTH: 20
<212> TYPE: DNA
<213> ORGANISM: Homo sapiens

<400> SEQUENCE: 202
tcaacaacag ctggaactgc 20

<210> SEQ ID NO 203
<211> LENGTH: 20
<212> TYPE: DNA
<213> ORGANISM: Homo sapiens

<400> SEQUENCE: 203
cctctcaggt caggcttctg 20

<210> SEQ ID NO 204
<211> LENGTH: 20
<212> TYPE: DNA
<213> ORGANISM: Homo sapiens

<400> SEQUENCE: 204
gctcccgcta gagaaactcc 20

<210> SEQ ID NO 205
<211> LENGTH: 20
<212> TYPE: DNA
<213> ORGANISM: Homo sapiens

<400> SEQUENCE: 205
gagcgaagca cctaaagcac 20

<210> SEQ ID NO 206

-continued

<211> LENGTH: 20
<212> TYPE: DNA
<213> ORGANISM: Homo sapiens

<400> SEQUENCE: 206
aattggaggg ggtggagtag 20

<210> SEQ ID NO 207
<211> LENGTH: 20
<212> TYPE: DNA
<213> ORGANISM: Homo sapiens

<400> SEQUENCE: 207
tgtcacccag tcaggtcatc 20

<210> SEQ ID NO 208
<211> LENGTH: 20
<212> TYPE: DNA
<213> ORGANISM: Homo sapiens

<400> SEQUENCE: 208
ttggaaggaa tccaacaagg 20

<210> SEQ ID NO 209
<211> LENGTH: 20
<212> TYPE: DNA
<213> ORGANISM: Homo sapiens

<400> SEQUENCE: 209
ttcccagaac tccttgttgg 20

<210> SEQ ID NO 210
<211> LENGTH: 20
<212> TYPE: DNA
<213> ORGANISM: Homo sapiens

<400> SEQUENCE: 210
tgcaaacccc ttcttttcag 20

<210> SEQ ID NO 211
<211> LENGTH: 20
<212> TYPE: DNA
<213> ORGANISM: Homo sapiens

<400> SEQUENCE: 211
accccatgca gaagcaatag 20

<210> SEQ ID NO 212
<211> LENGTH: 20
<212> TYPE: DNA
<213> ORGANISM: Homo sapiens

<400> SEQUENCE: 212
aaatcctgaa ggtgggttcc 20

<210> SEQ ID NO 213
<211> LENGTH: 19
<212> TYPE: DNA
<213> ORGANISM: Homo sapiens

<400> SEQUENCE: 213
agtttcagcc atgttgcag 19

-continued

<210> SEQ ID NO 214
<211> LENGTH: 20
<212> TYPE: DNA
<213> ORGANISM: Homo sapiens

<400> SEQUENCE: 214
ttggcaaaat tgtgactgag 20

<210> SEQ ID NO 215
<211> LENGTH: 20
<212> TYPE: DNA
<213> ORGANISM: Homo sapiens

<400> SEQUENCE: 215
cagtcacaat tttgccaagg 20

<210> SEQ ID NO 216
<211> LENGTH: 22
<212> TYPE: DNA
<213> ORGANISM: Homo sapiens

<400> SEQUENCE: 216
agttcgtggc atctaactat cg 22

<210> SEQ ID NO 217
<211> LENGTH: 20
<212> TYPE: DNA
<213> ORGANISM: Homo sapiens

<400> SEQUENCE: 217
ggtccatgtg ctccaaaaag 20

<210> SEQ ID NO 218
<211> LENGTH: 20
<212> TYPE: DNA
<213> ORGANISM: Homo sapiens

<400> SEQUENCE: 218
tccaaaactg ggaacaaacc 20

<210> SEQ ID NO 219
<211> LENGTH: 20
<212> TYPE: DNA
<213> ORGANISM: Homo sapiens

<400> SEQUENCE: 219
tggtttgttc ccagttttgg 20

<210> SEQ ID NO 220
<211> LENGTH: 20
<212> TYPE: DNA
<213> ORGANISM: Homo sapiens

<400> SEQUENCE: 220
tagtgcacca cagcctcaag 20

<210> SEQ ID NO 221
<211> LENGTH: 20
<212> TYPE: DNA
<213> ORGANISM: Homo sapiens

<400> SEQUENCE: 221
ggatcacttg aggctgtggt 20

<210> SEQ ID NO 222
<211> LENGTH: 20
<212> TYPE: DNA
<213> ORGANISM: Homo sapiens

<400> SEQUENCE: 222
tccaacaact gctgtgaagg 20

<210> SEQ ID NO 223
<211> LENGTH: 20
<212> TYPE: DNA
<213> ORGANISM: Homo sapiens

<400> SEQUENCE: 223
caccactgac cttcccttcc 20

<210> SEQ ID NO 224
<211> LENGTH: 25
<212> TYPE: DNA
<213> ORGANISM: Homo sapiens

<400> SEQUENCE: 224
gcacagaaag acaaatatca catgc 25

<210> SEQ ID NO 225
<211> LENGTH: 20
<212> TYPE: DNA
<213> ORGANISM: Homo sapiens

<400> SEQUENCE: 225
ctcttcctcg tctcctcctg 20

<210> SEQ ID NO 226
<211> LENGTH: 20
<212> TYPE: DNA
<213> ORGANISM: Homo sapiens

<400> SEQUENCE: 226
ccaattcaat gcaaaacctg 20

<210> SEQ ID NO 227
<211> LENGTH: 20
<212> TYPE: DNA
<213> ORGANISM: Homo sapiens

<400> SEQUENCE: 227
cgagcagctc tctcttcagg 20

<210> SEQ ID NO 228
<211> LENGTH: 23
<212> TYPE: DNA
<213> ORGANISM: Homo sapiens

<400> SEQUENCE: 228
agcctataag cacagaccaa ctg 23

<210> SEQ ID NO 229
<211> LENGTH: 22
<212> TYPE: DNA
<213> ORGANISM: Homo sapiens

<400> SEQUENCE: 229
ttctctagca gttggtctgt gc 22

<210> SEQ ID NO 230
<211> LENGTH: 20
<212> TYPE: DNA
<213> ORGANISM: Homo sapiens

<400> SEQUENCE: 230
accctgcatt ccaaactcac 20

<210> SEQ ID NO 231
<211> LENGTH: 20
<212> TYPE: DNA
<213> ORGANISM: Homo sapiens

<400> SEQUENCE: 231
gttcattttg gggcatgttc 20

<210> SEQ ID NO 232
<211> LENGTH: 21
<212> TYPE: DNA
<213> ORGANISM: Homo sapiens

<400> SEQUENCE: 232
ctgcaacctc ctttgagaca g 21

<210> SEQ ID NO 233
<211> LENGTH: 20
<212> TYPE: DNA
<213> ORGANISM: Homo sapiens

<400> SEQUENCE: 233
tgtctcaaag gaggttgcag 20

<210> SEQ ID NO 234
<211> LENGTH: 20
<212> TYPE: DNA
<213> ORGANISM: Homo sapiens

<400> SEQUENCE: 234
ccaaaatgaa actgccttcc 20

<210> SEQ ID NO 235
<211> LENGTH: 20
<212> TYPE: DNA
<213> ORGANISM: Homo sapiens

<400> SEQUENCE: 235
agttccctgg gtcattttcc 20

<210> SEQ ID NO 236
<211> LENGTH: 20
<212> TYPE: DNA
<213> ORGANISM: Homo sapiens

<400> SEQUENCE: 236
ttgtgggaag gcaaactagc 20

<210> SEQ ID NO 237
<211> LENGTH: 20
<212> TYPE: DNA
<213> ORGANISM: Homo sapiens

<400> SEQUENCE: 237
cctgtgctag tttgccttcc 20

<210> SEQ ID NO 238
<211> LENGTH: 20
<212> TYPE: DNA
<213> ORGANISM: Homo sapiens

<400> SEQUENCE: 238
ggtggtcacc gtggtaaaag 20

<210> SEQ ID NO 239
<211> LENGTH: 21
<212> TYPE: DNA
<213> ORGANISM: Homo sapiens

<400> SEQUENCE: 239
gaccaccatg tgatttccaa g 21

<210> SEQ ID NO 240
<211> LENGTH: 20
<212> TYPE: DNA
<213> ORGANISM: Homo sapiens

<400> SEQUENCE: 240
ttggttggcg gttatttctc 20

<210> SEQ ID NO 241
<211> LENGTH: 20
<212> TYPE: DNA
<213> ORGANISM: Homo sapiens

<400> SEQUENCE: 241
taaccgccaa ccaagaaaag 20

<210> SEQ ID NO 242
<211> LENGTH: 20
<212> TYPE: DNA
<213> ORGANISM: Homo sapiens

<400> SEQUENCE: 242
tgtctggaga ccttcccaag 20

<210> SEQ ID NO 243
<211> LENGTH: 20
<212> TYPE: DNA
<213> ORGANISM: Homo sapiens

<400> SEQUENCE: 243
tgtgctagat gcctcactgg 20

<210> SEQ ID NO 244
<211> LENGTH: 20
<212> TYPE: DNA
<213> ORGANISM: Homo sapiens

<400> SEQUENCE: 244
acttgcctac attgcccatc 20

<210> SEQ ID NO 245
<211> LENGTH: 20
<212> TYPE: DNA
<213> ORGANISM: Homo sapiens

<400> SEQUENCE: 245

-continued atgggcaatg taggcaagtc 20

<210> SEQ ID NO 246
<211> LENGTH: 21
<212> TYPE: DNA
<213> ORGANISM: Homo sapiens

<400> SEQUENCE: 246
tctgcagcca tgaataagtc c 21

<210> SEQ ID NO 247
<211> LENGTH: 21
<212> TYPE: DNA
<213> ORGANISM: Homo sapiens

<400> SEQUENCE: 247
cagagctgag gcgataaatt g 21

<210> SEQ ID NO 248
<211> LENGTH: 20
<212> TYPE: DNA
<213> ORGANISM: Homo sapiens

<400> SEQUENCE: 248
tgctcctctc caatccattc 20

<210> SEQ ID NO 249
<211> LENGTH: 20
<212> TYPE: DNA
<213> ORGANISM: Homo sapiens

<400> SEQUENCE: 249
atactttccc agcccaaacc 20

<210> SEQ ID NO 250
<211> LENGTH: 20
<212> TYPE: DNA
<213> ORGANISM: Homo sapiens

<400> SEQUENCE: 250
tgatggggaa atgagaggag 20

<210> SEQ ID NO 251
<211> LENGTH: 20
<212> TYPE: DNA
<213> ORGANISM: Homo sapiens

<400> SEQUENCE: 251
agtggccttt gtccattgag 20

<210> SEQ ID NO 252
<211> LENGTH: 22
<212> TYPE: DNA
<213> ORGANISM: Homo sapiens

<400> SEQUENCE: 252
gacagaggtg agagcctagg ag 22

<210> SEQ ID NO 253
<211> LENGTH: 20
<212> TYPE: DNA
<213> ORGANISM: Homo sapiens -continued

<400> SEQUENCE: 253
aatgtgttgg ggaagtggtc 20

<210> SEQ ID NO 254
<211> LENGTH: 20
<212> TYPE: DNA
<213> ORGANISM: Homo sapiens

<400> SEQUENCE: 254
tttggaccac ggctttagac 20

<210> SEQ ID NO 255
<211> LENGTH: 20
<212> TYPE: DNA
<213> ORGANISM: Homo sapiens

<400> SEQUENCE: 255
aagctgaggt cacggatttg 20

<210> SEQ ID NO 256
<211> LENGTH: 20
<212> TYPE: DNA
<213> ORGANISM: Homo sapiens

<400> SEQUENCE: 256
gatgggcaag tttcatctcc 20

<210> SEQ ID NO 257
<211> LENGTH: 20
<212> TYPE: DNA
<213> ORGANISM: Homo sapiens

<400> SEQUENCE: 257
tgggacgaag aaaaggaatg 20

<210> SEQ ID NO 258
<211> LENGTH: 20
<212> TYPE: DNA
<213> ORGANISM: Homo sapiens

<400> SEQUENCE: 258
caccgtgcct cagcctatac 20

<210> SEQ ID NO 259
<211> LENGTH: 20
<212> TYPE: DNA
<213> ORGANISM: Homo sapiens

<400> SEQUENCE: 259
ggactaaccc acctcccttc 20

<210> SEQ ID NO 260
<211> LENGTH: 20
<212> TYPE: DNA
<213> ORGANISM: Homo sapiens

<400> SEQUENCE: 260
gctataggca gcccagagtg 20

<210> SEQ ID NO 261
<211> LENGTH: 20
<212> TYPE: DNA
<213> ORGANISM: Homo sapiens

<400> SEQUENCE: 261
gccagactct cgttccattc 20

<210> SEQ ID NO 262
<211> LENGTH: 20
<212> TYPE: DNA
<213> ORGANISM: Homo sapiens

<400> SEQUENCE: 262
aggatttgcc gtatggactc 20

<210> SEQ ID NO 263
<211> LENGTH: 20
<212> TYPE: DNA
<213> ORGANISM: Homo sapiens

<400> SEQUENCE: 263
tcgcccaaag tcacagtaag 20

<210> SEQ ID NO 264
<211> LENGTH: 21
<212> TYPE: DNA
<213> ORGANISM: Homo sapiens

<400> SEQUENCE: 264
gatctgtagg cccaggattt c 21

<210> SEQ ID NO 265
<211> LENGTH: 20
<212> TYPE: DNA
<213> ORGANISM: Homo sapiens

<400> SEQUENCE: 265
aggggtttct atggctggtc 20

<210> SEQ ID NO 266
<211> LENGTH: 20
<212> TYPE: DNA
<213> ORGANISM: Homo sapiens

<400> SEQUENCE: 266
cctccctcaa acctcctctc 20

<210> SEQ ID NO 267
<211> LENGTH: 20
<212> TYPE: DNA
<213> ORGANISM: Homo sapiens

<400> SEQUENCE: 267
ttctcctgca gaggaagagg 20

<210> SEQ ID NO 268
<211> LENGTH: 20
<212> TYPE: DNA
<213> ORGANISM: Homo sapiens

<400> SEQUENCE: 268
ttggaatttg tcctggtgtg 20

<210> SEQ ID NO 269
<211> LENGTH: 19
<212> TYPE: DNA

<213> ORGANISM: Homo sapiens

<400> SEQUENCE: 269
aaagccaggg agtgaatgg 19

<210> SEQ ID NO 270
<211> LENGTH: 20
<212> TYPE: DNA
<213> ORGANISM: Homo sapiens

<400> SEQUENCE: 270
atgtgcatct ccctggtgac 20

<210> SEQ ID NO 271
<211> LENGTH: 20
<212> TYPE: DNA
<213> ORGANISM: Homo sapiens

<400> SEQUENCE: 271
tgtggggaaa tcaaaacctg 20

<210> SEQ ID NO 272
<211> LENGTH: 20
<212> TYPE: DNA
<213> ORGANISM: Homo sapiens

<400> SEQUENCE: 272
gggtagactg tgcgtgtgtg 20

<210> SEQ ID NO 273
<211> LENGTH: 1133
<212> TYPE: DNA
<213> ORGANISM: Homo sapiens

<400> SEQUENCE: 273
ttcttcccaa gagagccaag atttcttctt tcctcttctt tctttttttt ttctttctaa 60
tttcaaagga gtataattaa attgccaggt aaaagctcaa aggtcttttt tatagtgttc 120
tggaaggttc tctgcctgtg tttgtatttc ctttagcctc cacgttcctc tatccagttc 180
ccgcaccctt ccccccaggc cccattcttc aaggcttcag agcagcgctc ctccggttaa 240
aaggaagtct cagcacagaa tcttcaaacc tcctcggagg ccaccaaaga tccctaacgc 300
cgccatggag acgaagcacc tggggcgggg cggagcgggg cgcgcgggcc cacacctgtg 360
gagagggccg cgccccaact gcagcgccgg ggctggggga ggggagccta ctcactcccc 420
caactcccgg gcggtgactc atcaacgagc accagcggcc agaggtgagc agtcccggga 480
aggggccgag aggcggggcc gccaggtcgg gcaggtgtgc gctccgcccc gccgcgcgca 540
cagagcgcta gtccttcggc gagcgagcac cttcgacgcg gtccggggac cccctcgtcg 600
ctgtcctccc gacgcggacc cgcgtgcccc aggcctcgcg ctgcccggcc ggctcctcgt 660
gtcccactcc cggcgcacgc cctcccgcga gtcccgggcc cctcccgcgc ccctcttctc 720
ggcgcgcgcg cagcatggcg cccccgcagg tcctcgcgtt cgggcttctg cttgccgcgg 780
cgacggcgac ttttgccgca gctcaggaag gtgaggcgcg gattggagca gagttgtgga 840
gctgggctgg gctgggggc agcggccccc ggccctcggc ccccgaaacg ggcataatag 900
ggaggggacc aagaggccgc gctttccagc gtggagaccg gacggtgcgg ccgtgctccg 960
gctcaggccc tccgcgcggt aggaaacggc gagggccgtc ccggggagca gcctcacttc 1020
gcagctttgc tcgccttggt agggaaatgg ccttgggcgg aggcggggga caggcaggga 1080
acggagtggc cacgtccagg tttcctgcgg ccaccgaacc ggtgcctcgc gcc 1133

<210> SEQ ID NO 274
<211> LENGTH: 782
<212> TYPE: DNA
<213> ORGANISM: Homo sapiens

<400> SEQUENCE: 274
ggcttcaatc tgggactacg tacttaatgt taaattgctt taaagtggtc atagctgcta 60
caggtttgtg ctcagaaagt ctgcacctga ctggtctgat ttaaatttta cgccccttag 120
gtatgaacag tgtgttttaa acaagtacag gatggggctg cagaagattt aaacgcttga 180
gaacaagtgc tgtattttcc ccttttgtga ccccagtatt gagtttagtg ttgggcagat 240
taaaggtggt tcatatcgac tataacttga acagggaaaa attgaaatca acttagggta 300
cttgggatac gaaggatcaa tataaaaact ctggtttgtc atgctagctt tttctttttt 360
ttcctcttca gttgaactga ggagatagtt tttgttttta atgattgtgc tcttttaact 420
agacaaaagg aattagatag tcttgcctat tcgaagttaa atgaactttt gaggttgtta 480
aggacaaaac tattaaactg acatcaataa tacagaatgg gctgcttagt atcactttcc 540
ttatcaggta ctaggattta atttagttag gaaactcact taaagggagg actataactg 600
cagttgaaag tgtaattttt ccaagatata aaattgttta aagattgaat atattcctgt 660
taagccccaa aggaaacatc cctcatttaa gaaaatgggg tgggagagca agagaaggtg 720
aggattcaca gatcctagaa ttggaatagt tgattttttt ttgtaaaaga ggcggtgaca 780
gc 782

<210> SEQ ID NO 275
<211> LENGTH: 1258
<212> TYPE: DNA
<213> ORGANISM: Homo sapiens

<400> SEQUENCE: 275
gccaggcact taggcagtag tctatagctg aaaaataaaa cattcagaac cactttttaa 60
ggttttgtgt ccttgtaact ttaggcatta ttattacaat ataacttagc tgggacatga 120
gagttaatag atccacattt taaagtagat ttttttttta attttctaga atgtgtctgt 180
gaaaactaca agctggccgt aaactgcttt gtgaataata atcgtcaatg ccagtgtact 240
tcagttggtg cacaaaatac tgtcatttgc tcaaagcgtg agtaaaatat cctaattacc 300
tgtaagcttt attttgactt aatacttctt taattgatgt gccttgagtt ggaaagagtt 360
ttattggctt aaatctgaat catgttacaa agtaagtgtg ggaacacata aatttcaaat 420
aatctttgac cctggaactt tagagttaat tttttttttc ccgtaatcat gaaatcagtt 480
atttttcagt ttggcattaa ggtttctttt tcagtggctg ccaaatgttt ggtgatgaag 540
gcagaaatga atggctcaaa acttgggaga agagcaaaac ctgaaggggc cctccagaac 600
aatgatgggc tttatgatcc tgactgcgat gagagcgggc tctttaaggc caagcagtgc 660
aacggcacct ccatgtgctg gtgtgtgaac actgctgggg tcagaagaac agacaaggac 720
actgaaataa cctgctctga gcgagtgaga acctagtgag tggggctgcc tatactactt 780
gttttcatgc tgttcagatt catttaatta aatttatttt tgattatgta atatgatttc 840
atggtttaga attcagaaga tatgagtgtc cagtgaaaag cttccttctc attccagtcc 900
ccctcgctac ccattggacc tccacagaat tgatgttatt gattattcta taaccttcca 960

-continued gagatagttg atgaatttgt tatatatctg ttttattatt tttacataaa tgatagcata 1020
ctaggtataa tttttctttt atatctttac ttaacattat tcagtatttc attgttgcat 1080
tagtagtaaa tgtatgtaat ttaacctatg tatttgctta ttgattgtgt tttaaaagtg 1140
agatatgctt gttttaggga ttgtttaatg aaaaggcaca gaaacccact caagctagct 1200
taagcaaaaa aagacttcat tggaagggac tagaaactgg aaaggatgtc aggaccaa 1258

<210> SEQ ID NO 276
<211> LENGTH: 665
<212> TYPE: DNA
<213> ORGANISM: Homo sapiens

<400> SEQUENCE: 276
ttagttgaac agggcatgac actgccagct aaactttgac ttaatgtgac tttatgtatt 60
gtgtccagag aacagagggt caatattaga aaaggtgttc cctcctgggt gtgtccttta 120
tgaaggatgt gtaagggaag aaattatagg aatagctact gcataaattt tttttctctt 180
agtccttata attcgagaat tttaggatta gcttattagg aaaatagtat ggaagactga 240
gttatagtca actgacattg tctttttact ttatagctgg atcatcattg aactaaaaca 300
caaagcaaga gaaaaacctt atgatagtaa aagtttgcgg acgtaagtgc aattaaatgc 360
atcatattct tgcacagttg gtggctcaaa tcttccatcc tacaccatta gaaaaagcaa 420
gtctaaatgc tttttatat ttctgaaaaa taaagttact tgaaatagag ttgcaagaat 480
agcacagaga ttctgggaat acacttcact cagattcacc aattaacatt ttggcacatt 540
tgctttttat atgtgtatgt gtggatgaat atgtgtgtgt gctttacatc agtgtatcta 600
tgcatgtata aatatttttc ccagaagcac atgagagcaa gttgtagaca tcaggcccct 660
ttacc 665

<210> SEQ ID NO 277
<211> LENGTH: 649
<212> TYPE: DNA
<213> ORGANISM: Homo sapiens

<400> SEQUENCE: 277
gagccttgat gttccctctt aactaaaagc aggttatgca tttttgacag gaaaactact 60
taagcgatct tgtgtccttt ataatacttc acattaggag ttgcatgatg tcagcttgtc 120
cctttactag taaagtaaac tttggttaaa gtggtatcca ccaggttttt ccactgtgaa 180
gttaccattc tccctttgta atccataaat aatctatggg cagatacttg gatactaagt 240
aaatgttctt tttctaatta aactggtacc cagcagtttg aatatcaatg gatgattcca 300
gcctgaatca attattatta tgatagttgc aaaatggcag aaaaatttta actttaatga 360
cagttttaga ccctgagctg tctgcttaaa gagtagtgct tcttactgtt gtgtggtaca 420
aacatttttt tttaatacag attttaaatt ctttacagtg cacttcagaa ggagatcaca 480
acgcgttatc aactggatcc aaaatttatc acgagtattt tggtatgatt ttttaataag 540
tgagctttag cagacagttg gtgagacagt atgttttgag tataaggaca gccagtgatt 600
taagtggtgg ttaaatgcac ttactggagc aacagtttcg gatctgggt 649

<210> SEQ ID NO 278
<211> LENGTH: 1250
<212> TYPE: DNA
<213> ORGANISM: Homo sapiens

<400> SEQUENCE: 278

-continued

```
ccggccttac ctttcatttc tttagtaatt tagttttaaa gtagttctaa tccaaataaa     60
atactttcat atcttattta aaaatctttt caatataaga aaatcctctt aggaaaaatt    120
gtacattgta attatgtttg gttgcatggc tgtcttattt ccctttgata gatttagaga    180
cctcccaaag atttcttgat tagtgataaa cttagttatc cactaatgga aaggaacagt    240
gatgcatgta gattatagaa aatcaaacac tgaatattct gattctcaat taatgttatt    300
ttcaaatgat tttgattata ttagtattaa tttgtattat tcaatttttt tccccagtat    360
gagaataatg ttatcactat tgatctggtt caaaattctt ctcaaaaaac tcagaatgat    420
gtggacatag ctgatgtggc ttattatttt gaaaaagatg tgagtatcat cttctttatt    480
cctgtgttca ggaatgtagt ctatcatgcc tcaatgaatt aaatatattt catcaccttt    540
ttatccactt acagatcaac caaatggttc gctgctgccg ttaattttgt cctccctgtc    600
actcacatgc atcttgcttg tttgtatatt tatgcctctt atcaaattgt tctgcctaaa    660
atatctcccc tctttcttat aattcttatt tattatctac ttggtggtta cttagtttgt    720
gcatatatgc tcccctatga tatttataat ttacacaaat aaaagtctgt taaaaaagac    780
tgtaactgat atgattaaaa tattttgttg aaactttaat atattatagt gaggtatttt    840
ctgctgaaat atgaggtttg cttcaaaata atctgggcgg gggtgaaagg atgaaaggaa    900
gaaaagatga agtaagagag gctatgtgtt gttggccttg catctgggtg ataggtacat    960
gggcatcatt gcactactct ttctactttc gtgtatgttg aaaggttcct gtaataaaca   1020
gtttttaaa gttccaataa attagattgt tatcactaaa accataaaga ttcttggcag    1080
cggttctttt ggcatacaat ttgtatgtaa ttatatgtgg ccatggttgg tttccttaaa   1140
tatttttaat tccttttctc cttttcaata caggttaaag gtgaatcctt gtttcattct   1200
aagaaaatgg acctgacagt aaatggggaa caactggatc tggatcctgg               1250
```

<210> SEQ ID NO 279
<211> LENGTH: 1568
<212> TYPE: DNA
<213> ORGANISM: Homo sapiens

<400> SEQUENCE: 279

```
gagttccatg gcagatcacc atctgttttc tgcctcatag aagagtggaa tgggaagcct     60
atggttttta ttctacaaag agtcaacatc taacagaatc ttctgaaggc atactccagt    120
ggattcacct tggagaaact cattgtgact gatgatctga tttattatct ctatgccagt    180
gaaataatca tttaatatga acttaatttg tcataatcta ttgtgtacta actagtctat    240
actagtgtga catcaaagtg tcagattgtt agtgtgtttc agtcccttgg aattgaatat    300
gaacacttat ccttgaaccc tatcaataac atttttcaca tatctcaatt tttgtgtgtc    360
tttgtagttg tatgtgggcc acttactaat attttagcaa gtaataaaaa tagaaacgta    420
aaggaatatt ggaaaaagtc taatggaacc agaaagttct agcatttttt tcccattctg    480
tagtaggtca tctggtttat ttggtttggt gaccgcaagt ctagaagact aaccctgaat    540
tgaatggtaa cagacaggca gaatgacaat gtagtgttgc agtgcagagc agtacagacc    600
tgggtttggc tgggcaaaat tatataactt ctttaagcct ccatgtttcc tcatctgtaa    660
aatgaggata atagatagta tggacctgtt gcaaggatta aacataatca gtgtaaagtg    720
ttggtcccat gcttgccaca taagaaaata tttgtcaaca gagtggtagt tgtcattatc    780
attgtctcag tttgcctgta actagttgtg tgatctgaga caaacactaa ttttgaactt    840
```

-continued

```
gagtttcccc acatgtaaaa tgaaagattg ataatagaaa gtaaatcaat tttttctagc    900

attaaaaata gtatgcattt aataaaaatc ttattcttaa tgatctagct tacctccaac    960

ttgccctagt cactttggcg atcttgtctc taaatagaac cttgaaaaca cttaaatgtg   1020

tgtttccttg caatataact ttttcttttt ttatttaaat aagtcttata aatgtgggaa   1080

aaaattatct tgtgttcctt taatttcatt tttatttaat actattttca gaatgaacaa   1140

aagattgaaa aattatttag aattttttttc tgtgcttttt cctgtttcag ataaaggaga   1200

tgggtgagat gcatagggaa ctcaatgcat aactatataa tttgaagatt atagaagaag   1260

ggaaatagca aatggacaca aattacaaat gtgtgtgcgt gggacgaaga catctttgaa   1320

ggtcatgagt ttgttagttt aacatcatat atttgtaata gtgaaacctg tactcaaaat   1380

ataagcagct tgaaactggc tttaccaatc ttgaaatttg accacaagtg tcttatatat   1440

gcagatctaa tgtaaaatcc agaacttgga ctccatcgtt aaaattattt atgtgtaaca   1500

ttcaaatgtg tgcattaaat atgcttccac agtaaaatct gaaaaactga tttgtgattg   1560

aaagctgc                                                             1568
```

<210> SEQ ID NO 280
<211> LENGTH: 537
<212> TYPE: DNA
<213> ORGANISM: Homo sapiens

<400> SEQUENCE: 280

```
gaagggttgg tcttgctgtc tctgggtcgc agaggcagaa gaggtggagg aggtagaagg     60

gaggcaggtg cacactgggt gtaactttta ttgaaaaaaa atgtgttcaa atatacccgc    120

acaattcaaa cccatgttca gggtcaattg tagttgtgac agacccaatg acccacagag    180

tctaaaatgt ttattggaaa tgtttgctga cccctgctct aggatgctgg gggaaagcta    240

ttcctaggta ggtgtctcag cagacatgga aagcagccta taatattgcc ccagcaggtg    300

gggtatggaa cagatgctca gggaggctgc tggctgctgt ccactgcagg cccagaagcg    360

tcctggagaa gccaccccat gctgcaagag ccagatcatg gagcagccct ggatgctgca    420

ggagcctgtc aagccaggac accagagcta ggaaacaaaa ccttcctttt cagtgcctct    480

ctagcaccct ctgctgacag agcttcagat ccattttcac agagaggtgc aaagggt       537
```

<210> SEQ ID NO 281
<211> LENGTH: 1454
<212> TYPE: DNA
<213> ORGANISM: Homo sapiens

<400> SEQUENCE: 281

```
cccggtgttg aatcatttgc tttctctgca gcctgtcacc aggatgactt ccccattctc     60

taccccactg tgttttcttt tttttccttt ggcttcactg gtatgaatct ctcctgattt    120

tttccctctt ctactgattg tgtaatactg atgttcccag gatttgtcct tagttctatt    180

tttcctccct ttttcttcct ggaggatttc atccactttc ttgcctttat taccttctgt    240

gaggctcaat gagaacagaa gcaccatctc catttctgtt ctttttttcct gagatctata    300

gtaaagtatg tatatttcac ataactagtt tttaatgatt tgatcatctt catccacaaa    360

catattttat ggcttgtatt ctcagaatca attgatggca ttgccatgaa ccaagtccca    420

aattccttct cttttacttc ctccattgtt ttagtcacca gagcctgtga tcctccccga    480

gaaacaaatg ctcctctaat ctgccttctc ttacacactt tccctggtct ctttataaac    540

aatctactcc ctctccagcc caaacctcat attgctccca ggattatttg cctaaagttg    600
```

atcacagcac ttttttacaa cataagatgt accccttcc cctgccagag gggcatatat 660
aaagcctttc agtgtggccc tgtagtgtga accttttctc cttttgtctg tctggcatcc 720
catttcctct gcaatttggg aagaattgtc tgcatgtttt gtaagagcca ggtctctacc 780
tccctcttta gaagtttaag ggcagagatc ctctcatggc tctcagcatc cagggcacag 840
gcacccccac atagtacttg gaatcttgtg atggaaagaa gtaagaacag ttgagaaaac 900
acccatgggc agtggtggca tgtgaccaat ggcagttata ggcatgttgc agtggtggca 960
tcccagccct tggtcatctc tgccctacat gaccctgtgg ccatccagct gtggttgctc 1020
tgcttggcct cccttggctg ctgattcctc tcccctccca ttgccaatac cctgctccag 1080
agctttatca catgcctgga ttaatttaat ttccgacttt cccaatacca aattctcccc 1140
actctcaatc ctttcccaac gtcattccca gaataactaa aatctagtca cagtctacct 1200
tatttctcac tgtacctcca atacatcaaa ttttcctgca tttaagattt cccttcccat 1260
tcctccaatg ttccttcttt ccttgcttcc ttccttcctt ccttccttcc tccctccctc 1320
cctccctccc tccctatctt cctttcttcc cttctttttt tctttttttc cctggacagg 1380
tcttggtctc ttgcccagtc tggagtgcag tggcacaaac acagctcact gcaacctcta 1440
ccttcagggc tgaa 1454

<210> SEQ ID NO 282
<211> LENGTH: 530
<212> TYPE: DNA
<213> ORGANISM: Homo sapiens

<400> SEQUENCE: 282
ctggccactt tttggaagag gaaatgtgtg agcaagcagt gtgggaacca gagtgagcga 60
atgctggaac tggttggtcg gtcctctctg gcaggagcag gctctgtaca gccctggcag 120
cagcatccaa gcccctgccc tcttggcacc cgggttcttg tctggcatcc aggaagaatc 180
aggacaaatg aatggattga aggggtagtg tatgtggagg attttactgg gtgatggaaa 240
tggccctcag tgggatggca gctagaatgg ggatggtgca ggaggtaccc tccgaagtta 300
gctgcgtctg cagtctctga cactcagtag cttctctgct cgctgcccag gcgcttatgt 360
tgctctgcca gctgaagtca ttatgggcac aggatagggg catggcaggc caaaaaggta 420
acattgggca gaaaaatggg gtcagctgtt ttcacttagg gccatggttc caggccttag 480
gggtggggtt tggccagtag cccagccatt ctgtatcact ctgcgtccca 530

<210> SEQ ID NO 283
<211> LENGTH: 1992
<212> TYPE: DNA
<213> ORGANISM: Homo sapiens

<400> SEQUENCE: 283
ttactggcga tcctcagagc caagaagagt ctgggacata gcaggccata taaatgtttt 60
cgaatgagtg aatcatcaac gagtggatga aacgataatg tggctaacag gcagcagtaa 120
ggaggctgtg tagaataaac ccgtaatccc gatgttggca gtttgcttag aaagaaaaag 180
ggaggcagtc ggagaggggc acacgtttta acaaaatact gggaggagga ggaaggctag 240 ttttttttt gttttcaagt ttccttctga tgttactccc atgcttccgg gcacattacg 300
agctcagtgc ctgccggaaa tctcccacct ggtggcaacc tacccttgca tacaccccac 360
ccaggggctt caagccttgc agctgagtaa acacagaaag gagctctact aaggatgcgc 420

```
gtctgcgggt ttccgcgcga cctaggcgca ggcatgcgca gtagctaaag tcaccagcgt    480

gcgcgggaag ctgggccgcg tctgcttatg attggttgcc gcggcagact cccacccacc    540

gaaacgcagc cctggaagct gattgggtgt ggtcgccgtg gccggacgcc gctcggggga    600

cgtgggaggg gaggcgggaa acagcttagt gggtgtgggg tcgcgcattt tcttcaacca    660

ggaggtgagg aggtttcgac atggcggtgc agccgaagga gacgctgcag ttggagagcg    720

cggccgaggt cggcttcgtg cgcttctttc agggcatgcc ggagaagccg accaccacag    780

tgcgcctttt cgaccggggc gacttctata cggcgcacgg cgaggacgcg ctgctggccg    840

cccgggaggt gttcaagacc cagggggtga tcaagtacat ggggccggca ggtgagggcc    900

gggacggcgc gtgctgggga gggacccggg gccttgtggc gcggctcctt tcccgcctca    960

gagagtgggc ggtgagcagc ctctccagtg cggaggcacg gggcggaac gttggtgctt   1020

gtgcggattc cgccgtcccc aggttctgct tggctccgga gggacgcccc cctcagccct   1080

gaaacccgtg cctctccagc cgccccggat ctgaacttgt gatcacggag tgtttacgtc   1140

gtgccaggca ttttaatgca ttgttctagt tcattttcca gcagtcgcat tcctcgcctt   1200

ggccctacat gtagcgctca ttacaaacac ggccagaatc tcttattaac aaacagcagc   1260

caggagtgag atttaaaata gactggggt ttaggagacc cttttatgac acgtaattct   1320

gctcccacga cgctcccatt tataccgccg gtccagctaa gggtctggta atggagcgcc   1380

gttgaagagc agtatgatga agtggtcagg accaacggac tctggagctg ggctgcttgg   1440

gatcaagtcg ctgcccctct gcttattaac gtgtgacctt gggccagtca tggacgctat   1500

ctgcttcagc tcagcattca gtgctctccg tcacccgacc ccatctatcc aggattatct   1560

ctccctggaa agctacaaac gtctcaccct atgtgggcca aatgttctgg ataggcctag   1620

ttaacctctt ctctccctgt tttctttgcg ctttcttgca gctatgtagt tatgctaatg   1680

aaaagagcat cctaggggga gcagagttgt ggattctagt cctgactaga ggactagtgc   1740

aaatgcgata ctcctgatga aaaatgtttc attcgttaga tataaatgtg ttaggcaggg   1800

ttatggacac tagatgaaaa aagaaatacc tctactttca tagagatcac tattggacag   1860

caaggcagaa ataattacaa ttcaagttgg aggcttatgg aggtgagctt gtaagaggtt   1920

acaagaggcg ccaaggcagg atcgccaaag acggaagact ttggaagagt ctcatacaac   1980

ggaagaggcg tt                                                     1992
```

<210> SEQ ID NO 284
<211> LENGTH: 497
<212> TYPE: DNA
<213> ORGANISM: Homo sapiens

<400> SEQUENCE: 284

```
gaaaggacag accaagtgca gtggttcgtt ccagcactta gggatgccaa ggtgggagga     60

ttgcttgatg ctaggagttg aagactagcc tgtgtaacat agcgagaccc atctctacaa    120

aaaaattaaa aagttacctt tagaacttac gatttttatg tgtagactcc atataagcag    180

agggtctatg cttattcact atttattacc ttccatagtc cctgcacata taataggtgc    240

ttcataaaca atttaatgaa tgaataaatt actgagaaaa cactggaagt ttttgggtta    300

gcattgtgtt aggtgcttga tatggtctgg ctgtgttccc acccttatct catcttgaat    360

tcccatgttt tgtgggaggt acctggtggg acataattga atcatgtggg caggtttttc    420

ctgtgctgtt ctcctggtag tgaataagcc tcacaagatc tgatggtttt aaaaatggga    480

gtttccctgc acaggct                                                 497
```

<210> SEQ ID NO 285
<211> LENGTH: 1667
<212> TYPE: DNA
<213> ORGANISM: Homo sapiens

<400> SEQUENCE: 285
agtgggatgc agctgaaaag atacccgaaa atatggaagc aactttggag ctgggtaaca 60
ggcagaggtc agagcagttt agagggctca gaagaagacc agaaaatgtg ggaaagtttg 120
gaacttccta gagacttgtt caatggcttt gaccaaaatc ctgataatga tatggacaat 180
gaaatccagg ctcatgtggt ctcagatgga gatgaggaac ttgttgggaa ctggagcaaa 240
ggtgacactt gttatgtttt agtaaagaga ctggtggcat tttgccctgc cctagagatt 300
tgtggagctt tgaacttgag agaaatgatt ttgggtatct ggtgggagaa atttctaagc 360
agcaaagcat tcaagaggtg acttgggtgc tgttaaaggc attcagtttt aaaagggaaa 420
cagcatgaaa gtttggaaaa tttgcagcct gacaatgtga tagaaaagaa aatcccgttt 480
tctgaggaga aattcaagct agctacagaa atttgcataa gtaatgagga tcccaatgtt 540
aatccccaag acaatgggaa aaatgtttcc agggcatgtc agaggccttc atggcagccc 600
ctctcatcac aagcctagag gcctaggaga aaaaagtgat ttcatgggcc agcccggggt 660
ccccatgctg tgtgcagcct agtgacttgg tgccctgcat cccagctgcc ccagctgtgg 720
ctgaaagggg ccaacctaga gctcaggcca tggcttcaga gggtgcaagc ctgaaacctt 780
gacagcttcc aggtggtgtt gagcctgcag gtgcacagaa atcaataatt gaggtttgag 840
aatctctgcc taggtttcaa agatgtatgg aaacgcctgc atgtccaggc agaagtttgc 900
tgcaggggtg gggtgctcat tgagttcctc tgctagggca atgtagaagg gaaatgtagg 960
gtcagagccc ccccacagag tccctactgg ggcaccacct agtggagctg tgaaaagagg 1020
gctaccattc tccagacctc agaatggtag atccacagac agcttgcacc atgtgcctgg 1080
aaaagctgta gacacttaac gccatctcat gaaagcaacc aggcagtgtg ctgtaccctg 1140
caaagccaca ggggcagagc tgtccaaggc tgtggttgcc cagctcttgc atccgcatga 1200
cctggacatg agacatagag tcaaaggaga tcattttgga gctttaagat ttgactgcca 1260
tgctggattt tggacttgca tggggcctgt agcccctttg ttttggccaa tttctcccat 1320
ttggaatggc tgtatttacc caattcctat accccattgt atctgggaag taactaactt 1380
gcttttgatt tgacaggctc atatgcggaa aggacttacc ttgtcttgaa tgagactttg 1440
gactggaatt ttgaattaat gctgaaatga gttaaggctt tgggggactg ttgggaatgc 1500
atgattggtt ttgaaatgtg aggacatgag atttgggagg ggtcatggca gaatgatatg 1560
gtttggctat gtccccacct aaatcccatc ttgaattccc atgtattgtg ggagggacct 1620
ggtgggagat agttgaatca tggggatgga tctttcccat gctgttg 1667

<210> SEQ ID NO 286
<211> LENGTH: 913
<212> TYPE: DNA
<213> ORGANISM: Homo sapiens

<400> SEQUENCE: 286
ttgaaagttg gtcttaggaa gaggaacttt ttgtggaaat ttcttaatat ttgaagaata 60
ttatgttatt gttcctctgt ttttcatggc gtagtaaggt tttcactaat gagcttgcca 120
ttctttctat tttattttt gtttactagg gttctgttga agataccact ggctctcagt 180

-continued

```
ctctggctgc cttgctgaat aagtgtaaaa cccctcaagg acaaagactt gttaaccagt    240

ggattaagca gcctctcatg gataagaaca gaatagagga gaggtatgtt attagtttat    300

actttcgtta gttttatgta acctgcagtt acccacatga ttataccact tattgtaata    360

tgcagttttg gaagtatatg ttaccattta actgtacaga gtacatagta atagagtggt    420

aattatttag attgattaaa gaactcattt ttttaaataa gttttttttt tttcactata    480

aaagtttatt ttatttgaga tggtatggta tcgaacatgt tcatattgtg tgtaatcgtg    540

ggtaaattac tcaaccttta tgtcatagtt tcttcacctt taaaatgaca ttaataaaag    600

agctacttaa taggattata agcatgagat gatttaatat acataaaata cttacagtct    660

gatatatagg aagcacttaa ctctttatcc tagaaaagat ttaaggtgac cttaacatat    720

atgtcagaaa atctttaaaa ttgtggaaat aaaaggttgt ataattctgc tatcctaaaa    780

ttactagtat ttcaatatat tttattttag tcttttcttt tagatacaag ttttaaaact    840

tttaagtgaa gtgtaatata cgtaagtact gcttgatgaa tttaaggtga tttctaaagc    900

caggtttgtt ggg                                                       913
```

<210> SEQ ID NO 287
<211> LENGTH: 907
<212> TYPE: DNA
<213> ORGANISM: Homo sapiens

<400> SEQUENCE: 287

```
agacgcccaa aatcaacaac aacaaaaacg atattggaat gattggatcc ccaaagataa     60

atgtttgagg tgatggatat ctcagttacc ctgagttaag tattatacat tgtatacgtg    120

tattaaaata ttacaaaccc ccaaatgtgt acaattatga ggtatcaata aaagagattg    180

gaaggactgg gtaatttgca agtaattaag gcaatttaca atttttaatt tttatttgtg    240

aataagtagt tatacgtgtc aaaattcaaa aaggacaggt ggatatacag tgataagtca    300

tccccccttc tctgtcagct ccataaagag cccctgtctt gcatggctcc agggtcacat    360

ttcctattgt attttgccac cacctgccct gggagcaaca gtgttagttt cttgaacatc    420

cttccaagca gagtctgggc ctacacaagc aaaacaagta tgtctattct ctctcctctt    480

taattttttt aaaggaagtg attgataatt taacactcaa gctataggtc attggttata    540

tttttaattt ccaatttatg ggaatagagg aagtgtcagt gatccccttc tggtttaaga    600

actggaggat gcatgtgttt agacccttta gaaacctgaa atgtcaccta atataattat    660

cagagtaaca ctttttagta agcaagctat ctatcaaaag taggtttttg aagaagaggg    720

taaggaaagg ttactttcat gggacatagc aataatttct aaaatctaat ggttttacaa    780

gacttgttca ttagaagtaa catctgtgag gatggcttta tgagtcaaaa tattatctgc    840

ttaatacccc acctgtaggg taagaagaaa tgtttttttc ttggtgacaa tttttagcag    900

caagcgg                                                              907
```

<210> SEQ ID NO 288
<211> LENGTH: 1137
<212> TYPE: DNA
<213> ORGANISM: Homo sapiens

<400> SEQUENCE: 288

```
tgattgccaa ggaagattca cagggcctag aatggcagtg gttatgcatc tacagtttat     60

tacaggagaa ggatacaatc cagtagcagg attatggtaa ggatatgcat cacagtcaaa    120

ggctgtcata gcaagtcatc cagagagttc gggtgcaagt tccagttttc ctttgttgtg    180
```

taaagtctgt ggtggggtgc attttctctc tcagagcagg atgtgtgcac aggacacctt 240
ggaacctagg agcccaaaat agagtcttca ctggactttt taatattttt cttgtcaagc 300
ggacatgttc ctgttctcta actagcctct tcagtggagg tcagaggaag agcctcattg 360
agaccaagtg caactcatca atcacatgaa acaatgctga taaataaacc acctaaatat 420
cccctgaccc acaaatacaa aacaacacca ttcaatcagt atttttcatg ccttgatcag 480
gggtcattgc catgcaggaa ctttaacaaa acagtacagg ctaataatag aattgttgga 540
attaactcac acagcacacc tatgagagag agttaagata gagggtcttg gtggtctcta 600
acagttgaat tcaaagtgaa gttaccagag taaagtgagc aaagacacat attagtacaa 660
tattggtaga taaaatcacg ttgctctaat aagcatagtt ttaaacttta accatgtttc 720
tccagtaatt ttagtaatta tattgttgtt atgtctaata cataaagcat tttttacttt 780
tttaaaaaat ttttaggcaa tgtggggtcc aaagtaatta aaaaaaaatt tttttaacat 840
aaagcatctt aaaattttac ttaatcatga tcacttagaa ccattaaaac atacgttttg 900
atattatggg gaagcttcgt tgttcctttg tagacagact taaagaaata caactttatg 960
atgacaagat ataagataat tatagattta aattttatag aaaccttttc ccttatctag 1020
tgcaagaggt agctaagtgc ttattttctc aaagtactgt gttataaaaa gtattcctag 1080
tgtagtcaaa gcttctcttt agactgataa aacttagagc acctgcattt acttcca 1137

<210> SEQ ID NO 289
<211> LENGTH: 457
<212> TYPE: DNA
<213> ORGANISM: Homo sapiens

<400> SEQUENCE: 289
tcattcttgg gtgtttctcg cagaggggga tttggcaggg tcacaggaca atagtggagg 60
gaaggtcagc agataaacaa gtgaacaaag gtctctggtt ttcctaggca gaggaccctg 120
cggccttccg cagtgtttgt gtccctgggt acttgagatt agggagtggt gatgactctt 180
aatgagcgtg ctgccttcaa gcatctgttt aacaaagcac atcttgcacc acccttaatc 240
cgttcaaccc tgagtggaca cagcacatgt ttcagagagc acagggttgg gggtaaggtc 300
acagatcaac aggatcccaa ggcagaataa tttttcgtag tacagaacaa aatgaaaagt 360
ctcccacgtc tacctctttc tacacagaca cggcaaccat ccgatttctc aatcttttcc 420
ccacctttcc cccctttcta ttccacaaaa ccgccat 457

<210> SEQ ID NO 290
<211> LENGTH: 564
<212> TYPE: DNA
<213> ORGANISM: Homo sapiens

<400> SEQUENCE: 290
gagggagagg gaacctttg ttttattcca gtaggaccag ctagaaacag aaggtgattg 60
accagtatta gggatggaat cagggtacaa ttatggagac aggctatcta aacaattcac 120
tctcaccatt taaatcagct gtttgatcat ttttttcca tatatcttta ccatcgcata 180
gtaaataata tccttttat tttcaagagg gagtattggc cttaagttag gaactctctt 240 aattttttc ccccatcatc ccacccgcac ttcttactcc ttacttccta cttgctttta 300
ttctttactg gctctttacc actgcgtatt tttaggtgca tacatctatt ttttaaaaaa 360
gcacccttgt tcctgggtcc tcttccagta ccatctatta atatatctct ctccctcttt 420
ccactcccag ctgggtttct gaaagcgtgc acttcccatc ttccattcat tcatctggtt 480
tccagccctg accacagtac tgaaatggca tttgctaggt gacctttatt tttttttaaa 540
tccagtgaat gcggtatagt cccc 564

<210> SEQ ID NO 291
<211> LENGTH: 2249
<212> TYPE: DNA
<213> ORGANISM: Homo sapiens

<400> SEQUENCE: 291
tgttgattca tgggcatttg ggttggttcc acgtttttgc aattgtgaat tgtgctgcta 60
taaacatccg tgtgcaagta tctttttgt ataatgatat cttttcccct gggtagatac 120
ccagtagtgg gattgctgga tcaactggta gttctacttt taaggaatct ccacactgtt 180
ttccttagtg gttatactgg tttacattcc caccagaagt gtagaagtgt tccctgttca 240
ctgcatccac accaacatct atttttgatt ttttgattat ggccattctt gcaggagtaa 300
ggtggtatcg cattgtggtt ttgatttaca tttccctgat cattagtgat gttgagcatt 360
tttttatgtt tgtttgccat ttgtatatct tcttgagaat tgtctattca tgtccttagc 420
ccattttttg ataggattgt ttgttttttt tcttgctagt ttgtttgagc ttgttgtaga 480
ttctggttat tagtcctttg tcagatttat agattgtgaa gatttttttc ccactctgtg 540
ggttgtctgt ttttgtctgt ttccttctgc tgactgttcc ttttgccatg caaaagctct 600 tttttttga gacagaatct cgctctgtcg gccaggctgg taacaaagac acaggtactg 660
gtaataactg ccatggctta ttgcctacat taatgatgaa agcaaatgct aaatttcagc 720
tagaggctag agaaaataag cctggaattt tcttttatgt ttatatactg ctatgaatac 780
caggagtcct tgggttaaga ctgtagggct ttctaaagcc tgtgatcact agtggagaat 840
gtagctttac aaagtctagt tggaaattgg caactggggg ttagtacaag ttacaaggaa 900
gggatggaat ttaagatgct agtgaaagct tggaggataa gggagcaggt gaactcataa 960
ggaagtttat gaactgagaa gggctgcagc aaagtgggct catgtgcttg aggagccaga 1020
ggacatgttg agggtgacat aggttctgaa gttcgtacag atacttatgc agtatggatt 1080
cttggaaaac cttctttagt catgtgatag aaaaataaca gcttatggaa aaaacagggt 1140
tgaggcagac ctgaaaatac atgaaatttt aaaaaccgct tctaacagaa gcataacaga 1200
ctgtaataaa aactgtggcc ttcctggcat ttgcacccaa acaacagcat tagccaactc 1260
tttgaagcct tagatctgtg gctcttgttt tctcctttga ggtgtaggtc cttgagggca 1320
tttgcttcta atagaggcta gtttcatcag aattaaaaat ctgaaccatg gtatgaaatt 1380
caattctttt tttttttct tttttgaaaa cactggcaaa tgttttgtat ccttgagctt 1440
tcccacatat cttaacatag tgagtggaaa gtacagtggc tgttaagcca actactctga 1500
ggtcttcact gctaaggctt actcttaatt gtgtgagagc ttaaccttga tccctttaaa 1560
acattaatgg gctagaaaaa aaaccattca taaaccagtg ccacctctga attttgctac 1620
cacaattccc ttatttacca atagtgcatg agctaatttg gaataaagaa ctaggcattg 1680
tagcacaaca gacattatgt gggcaaagtg ttgtttatat tctgtctaaa tagtgcttca 1740
catgtatgta ctattttcta aatatgtata gatgcttttg tgattaataa taaaacatga 1800
attcttaaaa caattttgct gacttcatag tagcttttca ccgttttttc agtagctgct 1860
aaaatttctg gagaagtttg ggaactattg ttttggagtg aaatgcagtg tgttagatat 1920
cacttgcaga attcttctaa gggtatttat tggcgattag aaaaaaaatc cttgtgttat 1980
accagtagta atacaaagta attgttcagc ttctgttaag tgtaaaggac tatacaagta 2040
ttgtgtatag ttatctcatt tattattttc tgggtagcta ttgttattat tacttcgtac 2100
aaaaagggaa aaggaggctc aaagtatcat gctccagata acagagccag taggtagcag 2160
agctgggatt gctacccagg tctctagtcc tgctttttca cactatatac tcattgcttc 2220
acttactcct tcatacatga ttccccagc 2249

<210> SEQ ID NO 292
<211> LENGTH: 890
<212> TYPE: DNA
<213> ORGANISM: Homo sapiens

<400> SEQUENCE: 292
catcaagcac agttccattg tgtaaaaact tggcttgatt taacctgtta attggaacac 60
tgtcattaat ggaaattagg aatatgaggt aagctagagg ttttatttta atgactttgg 120
gttattaaat ctataagaaa tgaaattcat ttagtcataa ttaatgtcat gtttctgcat 180
ctatattact tgttgggttt acagacgagg tagtgtatta ttagtgggaa gctttgagtg 240
ctacatcatc tccctttcta taaaataaat tgagtacgaa acaatttgaa ttaaaacacc 300
tgagtaaata gtaactttgg agacctgctg tactatttgt accttttgga tcaaatgatg 360
cttgtttatc tcagtcaaaa ttttatgatt tgtattctgt aaaatgagat ctttttattt 420
gtttgtttta ctactttctt ttaggaaaac accagaaatt attgttggca gtttttgtga 480
ctcctcttac tgatcttcgt tctgacttct ccaagtttca ggaaatgata gaaacaactt 540
tagatatgga tcaggtatgc aatatacttt ttaatttaag cagtagttat ttttaaaaag 600
caaaggccac tttaagaaag tttgtagatt tttcttttta gtatctaatt gtagcacctt 660
tgtggacagt ggatgtaata ttaagtgaca gatgggaaaa ggatttttaa aaaaatagca 720
actgtttcag tggatgaaat aaagattatt agcagagaaa atgaatattg ggcataactg 780
tcctggtgaa agacaatctc ataaatgaac aatttcataa tttcgtaaat gcaactgcat 840
tttattttca aagagaagga aaattatagt cactggaaac ggaaagagaa 890

<210> SEQ ID NO 293
<211> LENGTH: 1224
<212> TYPE: DNA
<213> ORGANISM: Homo sapiens

<400> SEQUENCE: 293
ggagcttggg aattcaactg acacacgaca gatttacagg agaaaagttt tatttcaagt 60
acacatgaga gcttcataga aaagaagtga agacctaaag aaacagactg gagagttcat 120
atgccatttt aataaaggat aatgtattag tctgttctca tgctgctaat aaatacatac 180
ccaagactgg gtaatttata aagaaaaaga ggtttaatcg actcacaatt gcacatggct 240
ggggaggcct tacaatcatg gcagaaggta aaggaggagc aaaggcacat attacatggt 300
gtcaggcaag agagtgtgtg caggggaact gccctttata aaaccatcag atctcgagag 360
acttattcac catcacaaga acggcatggg aaaaacctgc ccccgtgatt caattacctc 420
ccaccgggtc cctcccatga cacatgggga ttatgggagc tacaactcaa gatgagattt 480
gggtggggac acagccaaga catatcagat aataaattgt ggagaggcag taagattgaa 540
gaaaagaggt ttgagcttcg aggggtggta aattgtggga aggtaattat ttggggcaaa 600
ctaatggcac ataaggattg ttttagtaag gcttgttatg catacccaaa acaagtgcca 660

```
tctccagtaa tttaagagtc tatggtgatc aagagtagtt ctcttcctgc tagaagaggg    720

gtgggagaga acaccttcac aaagggaaat ttatattctg ccttcatgca gaaagggggc    780

gagcagagag ttcctacgta tactgtttct tcattatctt cctctcaaaa gaatacttag    840

gctaaagtgg catgatttgg ggtgacattc tgatcctctt cagtgacaat ccttgatatt    900

tttccttctt tctctccagg taaacagtgt taacatcctg gtatgcttcc cccaattcca    960

ttatactaac tctgtattgt gggttaaaga ttttttactt tgatcagcag tatttgaaac   1020

atacctgtta tactagatgt actctgactg taaaatagtg gtcagtgtta cttctttaat   1080

gatgctgtgg gattaaagga ttttattata aatgctggga agagcctgga tttgaggaag   1140

gtaagcagtg cagttaggtg gatgtagact agaagaggtc atttgttctc atttcattgt   1200

tgcccctatg acatgcccgt ttct                                          1224
```

<210> SEQ ID NO 294
<211> LENGTH: 1550
<212> TYPE: DNA
<213> ORGANISM: Homo sapiens

<400> SEQUENCE: 294

```
cagcctacgt gcccatttct taaagtagaa aatttagtag ttgatgatgt cagggaagaa     60

aagctttttc tctgccttac gttaagtagt tgggggcaaa ttaaattaat aaaagacaga    120

ttagtgagag aaaaggctgt aagaatttgg actttatata ccatcataat agaggaagta    180

aagggagatg aagggcactt aagggaaaac agatgacttg taggaaagat aaatgaaccc    240

ttaagagaat agatgagaaa tatgaaggtt ttgtgacaat gtctgtttag gtggttactt    300

ctcttcttgt tatgagagtc agtcttctgg ttgctggaaa ctgctaggag atttataaca    360

attgggctct ttcgagaggc tcttctttta agcagataag ggagttcaca aaaaagcctg    420

ttctcaaatg atttcagcac acacacacac acacttacga cacagttaag tactgtgcca    480

gtaagatgtg agttgtgcat ttcttttttt tctctgagta gactgtttga ggttatttat    540

atcaggactt gttatgcagg taactgaaaa ctcaacataa tctaggttat gtagttaaaa    600

gtatggagag aaggtaggct ttatttagag ttgcttgatc ctgtagatct cttctacctt    660

ttgtaatttt aatttcaacc aaggatggtt cccttttttgg ccctaggacc agttagcagt   720

tggggcacca ttccaagcaa gagtcctgca gtttgtagtg atgggaccat ttaaacagtg    780

attgtgacca gggacataga atgggatgat tggcccgagg taaccatggt tgggtatgga    840

gtcagcttcc ctgtaggaag agatagacaa agtctgagca ctcctgggaa gggggaggaa    900

gggaataact gttgtgtaaa tcatcagcag tgtctactaa gataccatct gtaaccatag    960

gcttctatgt tttataatat aaggctgtct tttaaataaa tcagattccc tgttaaagat   1020

ctgttctaga ttccctaggg ggttgacctc atatagtatc ttcttttttct ttggttacaa  1080

acttttaaac ttgtctgagg ttataaggtg aattcaactg tccactgtca atgtagatat   1140

ttttaatgga tttagggatt taaattacat gattcagaac cactttgagg aagtctaggg   1200

aatatcagtt gtttctgtat aatttctgaa agcttcactg ttttctaggt gtgcacttaa   1260

ttcatgtgat gaagggaaca gtatttacat gagtggtttg gttaattttt cccctcctaa   1320

gcttagcttt gtgtatcgtg cgtgcttcca gtgtttttgt ggctgcttta cataagtctt   1380

ttagaagtat tttctatttt tgaagtaaat gtggatcaaa accaccccaa gacaggattg   1440

aaaaaaagac agtttttcgc aagaaagtaa ataattttat ttagcttggg actttaaatg   1500

atatgtctta aatgtaaaca tttctatact gcattttggc catcttttga              1550
```

<210> SEQ ID NO 295
<211> LENGTH: 2828
<212> TYPE: DNA
<213> ORGANISM: Homo sapiens

<400> SEQUENCE: 295
gtgttgcacc cattaactcg tcatttacat taggtatatc tcctgatgct atccctcccc 60
cctccctcca cccctcaaca ggtgtgtgat gttccccttc ctgtgtccaa gtgtcctcat 120
tgttcaattc ccacctatga ctgagaacat gcggtgtttg gtttttttgtc cttgcgatag 180 tttgctgaga atgatagttt ccagcttcat ccatttccct acaaaggaca tgaactcatc 240 atttttttatg gctgcatagt attccatggt gtatatgtgc cacattttct taatctagtc 300
tgtcattgtt ggacatttgg gttgattcca agtctttgat gttgtgaata gtgccgcaat 360
aaacacacgt gtgcgtgagc ctttatagca gcatgattta taatcctttg ggtatatacc 420
cagtaatggg atggctgggt ccaatggtat ttctacttct agatccctga ggaatcgcca 480
cagtcttcca caatggttga actagtttac agtcccacca acagtgtaaa agtgttccta 540
tttctccaca tcgtctccag cacctgtcgt ttcctgactt tttaatgatc gccattctaa 600
ctggtgtgag atggtatctc attgtggttt tgatttgcat ttctctgatg gccagtgatg 660
atgagctata gaaatccttt ttagaaacaa cagagccttg ttgtaaaaca ggtaaatgta 720
cgtgaggact tcaaaaagtt tgtggaaaaa tggaattaaa agataaaatt taaaaacaca 780
ttttaaattt atttcccaac ataagctcct caagttcaag acacttttat aaatgatgat 840
ctcagctgtt tagttcatcc gtaaagaact gagggtacta gaaattttac catgtcaatg 900
cagtctcttt acattactaa ctaaagaaaa ataggtgctc tttaaagatc ttttaagatt 960
aggaacaaaa agaagtcaga agaagccaaa tcaaggtgga tgcttaacga ctttccatag 1020
aaacttacaa aattggcctt gtttgatgag aagagcgtgc aggaacgttg tcatggtgga 1080
aaaggacttt gatgatgctt tccctggcat ttttctgcaa aaacttggga taactttctc 1140
aaaacactct aataataagc agagcttatg ttctttatcc ccccagaaca tcagcaagca 1200
aaatgcctga acatcccaaa aaactgttgc catgaccttt gcccttgact ggtccacttt 1260
tgcttcgact ggaccacttc catttttggt agccattgct ttgattgtgc tttgtcttca 1320
ggatggcatt ggtaaagcca tgttttggct cctgttacag ttctttgaag aaatgcttca 1380
ggatcttgat cccttgttta aatttctatg gaaagctctg ctcctgtctg cagttaatct 1440
gggtgcaaca gttttgtcac ccatcaagtg aaaagtttgt tcagctttaa tttttcagtc 1500
agaattgtgt aaactggacc aattgttgag atgcctgtag tgttggctat tgtttctgct 1560
gttagtcatt agttctcttc aattagggaa tgaacaaaat taatttttcc tgaaaaattg 1620
atgtggatgg tctgccgctg tgggcttcat cttcgacatg gtctcatccc ttgttagaac 1680
aagttatccg tttgtaaact gctgatttcc taggagcatt gaccccataa aattttcata 1740
aagcatcagt tatttcatta ttcttctatg cagacttcac tataaatttg ctgtttggtc 1800
ttacttcaat tttagcagaa ctcatactgc tctgacatct aaactgatgt cttagccttc 1860
atagtgtctc tgactagatc ctattcagac gtgttatagc aaattagtaa agtttatttt 1920
ggtgccaaaa actttttgaat ccacgcatag ttttttcaca acacattttc catgaacttt 1980
ttgaagaccc ttcatatatt ataagaagaa agttaaaaat atccccctgca tctactactc 2040 agaaataacc actgttaaca ttaagtctgt tctcaactct aggcattatt gagggttttg 2100

```
aggacaggtc ttgaaaattt ctatggctac cttttactgg gtggagacta gcatgtatag   2160

ttgaccgcat aggttaatcc ctccactcaa aaagccacaa ttttaaagtg tagtattcac   2220

tagcatttag tatattcaca gtgttgtgaa atgaccacca ccatctagtt tgaaaatatt   2280

tcatcacaac caaaagaaaa cctcatatct attagcggtc tctcctgttt ccccagacac   2340

cggcaaccac taatgtactt tttgtctctg tggacttgtc agttctggac attttatata   2400

aatggaatca tgtgaccttt tatgattgac ctctttcact tagtataatg ttttagaggc   2460

tcatccacat tgtagcatgt gtcagtactt catttccttg tgtattggtc cattcttgta   2520

ctgctataaa gaaatagctg agactgagta atttataaag aaaagaggtt taattggctc   2580

atggttctgc aggccgtaca ggaagcatga tgatggcacc tgctcagctt ctggggaggc   2640

ctcaggaaat ttaaaatcat ggcagaaggg gaagtgcggc gtcttacatg gtggagcagg   2700

agcaagagag agaaggggga ggtgctccac acttttaaac aactagatct caggacaagt   2760

cagtcactat aatgagaaca gcacccaggg gaaaccgccc tcacgatcca gtcacctctc   2820

accaggct                                                            2828
```

<210> SEQ ID NO 296
<211> LENGTH: 1379
<212> TYPE: DNA
<213> ORGANISM: Homo sapiens

<400> SEQUENCE: 296

```
cacgatgcca gtccaattct tgtgtagttt tttaatcagc tgaatttaac attcaaattc     60

ttcttttaaa tcttccaata ggcagttatc tttataaaga tcctatataa tcaagacttt    120

gtttctgaat attttatgta tgtttttgct actgtaaatg agatctattt ctcattgtgg    180

tttcttgctg ttattactgg taagaattta gtgaaacaaa gtacttaaga gtatgtcttt    240

aaattgtgag attttgatga acttttaaga aataaaattc tttagtttct tagagctttt    300

tgagatttct aaggtagatc cttggtttgg gcaacatata actattacaa gttttgcaca    360

ttgaacgtta tttggtaatt tttagagagg acattttaaa tgtttaggaa aaatataaat    420

aaaatgtaga atactattgg gggcatatac atcatcagca ctgtaactgt ttcatatgaa    480

tcatttttgt acatatagaa ctctaaagtc ctaatgaaca gaattttaca tttctataaa    540

tagaaagtcc ttaatagttg tgactgaata acttatggat agcaaattat ttaactgaaa    600

acagtaaaat ttaagtggga ggaaatattt gctttataat ttctgtcttt acccattatt    660

tataggattt tgtcactttg ttctgtttgc aggtggaaaa ccatgaattc cttgtaaaac    720

cttcatttga tcctaatctc agtgaattaa gagaaataat gaatgacttg gaaaagaaga    780

tgcagtcaac attaataagt gcagccagag atcttggtaa gaatgggtca ttggaggttg    840

gaataattct tttgtctata cactgtatag acaaaatatt gatgccagaa ttattttata    900

agttccctgt ccccaagatg atgacttcac atctctgtca aacagaaatc gcccaacagg    960

cccttgtatg atgtcattta aacaagccct attttaaatg tcacctccac tggtaacagg   1020

atactcctag gaggatcacc aagcccaatt cttctaggag tagtgcattg attaggcttt   1080

ggggtttcca agcagttcat taatgtcact tttggaaaaa gtctgtcttt cataccagct   1140

tattaattcc ctatgggttc acacggtttt ttttcctgga ttttcatcaa acatgtgtaa   1200

ggtactcagt acaaagaagt ttagaaatcc agaacaaagc agtgtattta agtagtagta   1260

aacttccaga taatctgatg cccatatcta catatataaa aaatttgcaa atagttctgt   1320

agagagtcca aacatggagt agatccctaa ttaagagcct ttgcattaaa gtccacctt    1379
```

<210> SEQ ID NO 297
<211> LENGTH: 2455
<212> TYPE: DNA
<213> ORGANISM: Homo sapiens

<400> SEQUENCE: 297
ggagtgagag cgacaccttg tctttaaaaa aaaaaacaga ggaatgcatc atagtatata 60
ttaaattatt gcctattttt ttatctattt tattgagtgc taataagaaa attaatggca 120
aaaacttgtt ttttacagta taaattaagt ttaatttcat tttaaaatta agtaaatttg 180
ttttattaaa aagtatgttg aaagcaacat aaatagcact caaattgaga cagaaactgt 240
aactgtagta taagaagcat taggctggga attgggaaac acgagttcta gttgcagctt 300
ggaaactttt tctgaagctc tttacaaatt acttaatttc tctggttttc accacattgt 360
tctatagcat taacatgttg gattcattgc tttaattctt agacctacgt gtcatcagaa 420
atgccattac actttgagga tttgagcctt attttaaata aagttgtgat cctcatggca 480
gcctaggttt acatgtgtta aataaacagt attctgtaaa taccattgtc tttcatgttt 540
agtgatgttg ctgttgttaa cactgcagtg aaatgcatat ataagcaaac tacattacat 600
actcatgaac atggtccttt gttttgaaac tttgatcact gattgttcgc agtctttcat 660
tgtggaacta ctctttcact ttgaatgttt tgagaggttc ctttgttcag atcagtccga 720
tttcgtttct gggtgggtct ctactttccc ttttctcact ggtcaagcga ggtctgtcta 780
attgtttgct actactaaca tttgatggcc acgcttcagc aagtacattt gtagattctc 840
tctctctgtc tctcttaatt tgtggtctag agatcatatt ggttaatgaa attatgaaga 900
gggaatgtat ttataaaaac tcaaattctt gatgcagaag gtctagctga ttgtgaaccc 960
aaaatatccg agacaggtca caaccaattt agaaacttta ttttgccaag gttaaggatg 1020
catccatgac atagtctcac aaggttctaa tgacacatgc gcaaggtggt tagggtacag 1080
cttggtttta tacattttag ggagacatga gacatcagtc aacatgtgta agatgtacat 1140
tgattctatc cagaaaggca ggacaacttg aagcaagggg ctttcaggta ataagtagat 1200
aagagacaaa aggttgcata cttttgagtc cttgatcagc ctttcactga ataaacaagc 1260
ttagtcttgt tagtgaatct gcgtttttac ataaacagta ggtcagagga agcaatcaga 1320
aatgcatttg tgtcaggtga gccgagggat gactttctgt ccctcacctg tgaagataag 1380
ctatcagttt ccattgctag ggtgaaattc aacagaattg tttgagagtg aacatctgga 1440
ggcccacaag gactttcctt gtggagggga agtatgtagt gagggaagta tgtagttttt 1500
aaatctttgt cgctatctta tttagaaata agatggaagg caggtttgtc tgacatagtt 1560
cccagcttga cttttccctc ggcttagtga ttttgcggtt ccgagattta ttttcctttc 1620
acatatcagt cagatcattt ggtttgtgaa gtttcctatg cttaacagaa aatatgtgca 1680
ctagttttcc tagagtttca ttgtcagagt ctcaagtttt tgtttggaaa ttgtatttgg 1740
tcacattaat tatactctat gttagttcca aagaaatacc tttggttaag aaaagaattc 1800
tcatgcataa ctcctcgagg gtggggttac accttaatcc atcctcaggt gctcatggta 1860
attggggcaa atatgttgcc cagtgctggt gctctgcagc cttggatggg tttacccaga 1920
aagcagcttt caagtcagaa actaacattc ataagggagt taaggatttt ataaatagat 1980
atccataatt catgtagttt tcaagtaagt agtatttgaa tcttttctgg ttagataata 2040
attgtgagta tgttgtcata taataacagt atgtttttca ctatttaaat aattttagaa 2100

```
ttacattgaa aaatggtagt aggtatttat ggaatacttt ttcttttctt cttgattatc   2160

aaggcttgga ccctggcaaa cagattaaac tggattccag tgcacagttt ggatattact   2220

ttcgtgtaac ctgtaaggaa gaaaaagtcc ttcgtaacaa taaaaacttt agtactgtag   2280

atatccagaa gaatggtgtt aaatttacca acaggtttgc aagtcgttat tatattttta   2340

accctttatt aattccctaa atgctctaac atgatgtgaa tgttctatga taagttttac   2400

taatgtagtc atcaggtaag agtcaagctt tcttccatag agcagtcagc tgtcg        2455


<210> SEQ ID NO 298
<211> LENGTH: 2194
<212> TYPE: DNA
<213> ORGANISM: Homo sapiens

<400> SEQUENCE: 298

cacaatggga aaggatgtag caacacattt taaccctatg ttgagtttta ggtgggttcc     60

tttgaaattt tgttaaggct aacttttgtt aattttttta aaaaagtgta aattaggaaa    120

tgggttttga attcccaaat ggggggatta aatgtatttt tacggcttat atctgtttat    180

tattcagtat tcctgtgtac attttctgtt tttattttta tacaggctat gtagaaccaa    240

tgcagacact caatgatgtg ttagctcagc tagatgctgt tgtcagcttt gctcacgtgt    300

caaatggagc acctgttcca tatgtacgac cagccatttt ggagaaagga caaggaagaa    360

ttatattaaa agcatccagg catgcttgtg ttgaagttca agatgaaatt gcatttattc    420

ctaatgacgt atactttgaa aaagataaac agatgttcca catcattact ggtaaaaaac    480

ctggtttttg ggctttgtgg gggtaacgtt ttgttttttt tttttttttt ttaatcttgg    540

agtagaaata tatttaaaat tgatggagaa aattcccagt tcttaacatt agaaagggaa    600

tatattattc ttaccagtta gtaatctatt cacatttggt ttagagggaa gatttagaag    660

gtgagataaa agcttgtgag agaatagtgt attcatgtga aacttcttcc atgggttcag    720

agcatttaga aacaaacatc ccttcacact caaagcttac ctttgagcca gtcctccaat    780

agtgaggtct ttgaaggtca ggccaaattg gctgtgggag gacctcaggt taggatagga    840

attattttaa gacatggcac tatattcatg tgaaactcgc aaaaactagc cttgcatata    900

ggctcatgta tcatgtctca gctgagatgt ttgagagatc ttaactagat tctagaaaac    960

aaaaaaggaa gtagttttgg ggcaaatata tttgggaaac agtttattgt atttcctttc   1020

cccaaatgga ttttcaagtt cttcatataa tctaacccca acaaataaat tgcctgtttt   1080

tcaaaagaaa gatcatgtct tcaggttttt gtgtggggtt taaatgattc gaaagatttg   1140

accatactga tacattcact agtaacctta gttactaatg agtaatggtt ttgagttaat   1200

cagttaggcc tgaactactt ttctggaagt tagtaaatta tctcacaggc agccctgtga   1260

gccatgggaa aatgtgtata tggtctttct aggccacagt caaattacag gtatatttgt   1320

catggcttct cttgatgaaa ggcccagtat cggtttgtct gaagatatat aatagcattg   1380

cttttggggg taatatgggc agtaactctg tccacatctt tgggcaggct gtggttctgc   1440

ctttatatgc tatgtcagtg taaacctacg cgattaatca tcagtgtaca gtttaggact   1500

aacaatccat ttattagtag cagaaagaag tttaaaatct tgctttctga tataatttgt   1560

tttgtaggcc ccaatatggg aggtaaatca acatatattc gacaaactgg ggtgatagta   1620

ctcatggccc aaattgggtg ttttgtgcca tgtgagtcag cagaagtgtc cattgtggac   1680

tgcatcttag cccgagtagg ggctggtgac agtcaattga aaggagtctc cacgttcatg   1740

gctgaaatgt tggaaactgc ttctatcctc aggtaagtgc atctcctagt cccttgaaga   1800
```

| | |
|---|---|
| tagaaatgta tgtctctgtc ctgtgagaag gaaaagtata tttgcagatt ctcatgtaaa | 1860 |
| aacatctgag aatgtttgtc ttagtttaat agttgttttc ctgtggactt tatatacttt | 1920 |
| gtattgtctt aaaagagtga ttgatggtag ctacggaaaa ctttgatttt taaaattgtc | 1980 |
| tctttaagta gacaatttat aagctactgg tacgagttca ccttataaat ctccactacc | 2040 |
| atgtttttgc ttggactgtt cacacttcct ggaatggtcc ttcttgccgt ttatccaact | 2100 |
| tctttctaat ttttaagtcc ctaatgatgg gaattctatt tctgtagtga tttttctggt | 2160 |
| catacgaccg taaggtcatg ggtgtttttc tctg | 2194 |

<210> SEQ ID NO 299
<211> LENGTH: 571
<212> TYPE: DNA
<213> ORGANISM: Homo sapiens

<400> SEQUENCE: 299

| | |
|---|---|
| caccgtgatc ctccttattt cttagtatct tctaaagaac attaaatata gtaggtgcct | 60 |
| agtaaattat gtattgattt aacttctttg aggttctgtt gtttgtgaag aattataaaa | 120 |
| gcaatacaaa tgtttgtata gtaattaagc aacaggttaa tattcatgac ttaaaagatt | 180 |
| aaagaaataa gcaaaacatg ttagctggca actcacagaa aaagaattaa attgccaatg | 240 |
| agcacacgag cacatgaaaa attagcaaaa gtttcacccc tttacatata tttggttaaa | 300 |
| attgagaaaa gaatagtaat agatggtatt ggtaggactg tggcaggcac acaatttaca | 360 |
| tgaccaccaa aagtgtatgc aggtatccat gtcaccacac cctggtctca tcttcattca | 420 |
| gttttatttta ttttttttaa tctcggccta tttgattggc acgaaatgaa tgatagctgc | 480 |
| cttatttgga attcctttga ttactactag tgtgcttgat aatgtaaaac aatattcaaa | 540 |
| atctgttttt cctttcatcc gttgtttgtt c | 571 |

<210> SEQ ID NO 300
<211> LENGTH: 497
<212> TYPE: DNA
<213> ORGANISM: Homo sapiens

<400> SEQUENCE: 300

| | |
|---|---|
| gtggcatatc cttcccaatg tattgtctta attttgtttt tgtatgtgta tgttaccaca | 60 |
| ttttatgtga tgggaaattt catgtaatta tgtgcttcag gtctgcaacc aaagattcat | 120 |
| taataatcat agatgaattg ggaagaggaa cttctaccta cgatggattt gggttagcat | 180 |
| gggctatatc agaatacatt gcaacaaaga ttggtgcttt ttgcatgttt gcaacccatt | 240 |
| ttcatgaact tactgccttg gccaatcaga taccaactgt taataatcta catgtcacag | 300 |
| cactcaccac tgaagagacc ttaactatgc tttatcaggt gaagaaaggt atgtactatt | 360 |
| ggagtactct aaattcagaa cttggtaatg ggaaacttac tacccttgaa atcatcagta | 420 |
| attgccttat tctaagttag tataaattat tgatgttgtt atagaaccca tttacccctt | 480 |
| aattcacagt ctggggg | 497 |

<210> SEQ ID NO 301
<211> LENGTH: 3662
<212> TYPE: DNA
<213> ORGANISM: Homo sapiens

<400> SEQUENCE: 301

| | |
|---|---|
| gatgcagatc agggaaatgc aagtcaaaac cacaatgagc tacaacttca cactgattac | 60 |

-continued

```
gatagttaaa atcaaaaagt cagatggtaa gtactggcaa ggaagtggag aaattgaaac    120
tgtcatgcgc tcttggtgcg aatgtaaaat ggtgcagctg ctttggaaaa cagtctggca    180
gttcctcaga caattccact ccaacgtata tccaagtgga atcacaacat atgtccccac    240
aaacttgtac ataaatgttt atagcaggat tattcataat agccaaaagg tggaaacaac    300
ccgaatgtcc atcagcagat gaatgcataa atgaaacgtg gtctatccat acaatggagt    360
atattattga gccattaaag gaatgaagta ctggtacatg gtgcagctta gatgaacctt    420
ggaaacattg tgctaaatga aagaagctgg ttacaagagt caacacgtat gatttcattc    480
atgtgaaagt tcagaataga gacagcagta gagacaaagt agcagttcag ggttggtgcc    540
agggaatagg gggtaggtgg ggtgaaagct aaaggatacg gtgtttcttt gtgagatgga    600
aattctaaaa taggtgatgt ttatacatgt ctgtgaatat actaaaaacc attgaattgt    660
acacattaaa tggatgaatt gtataggaat tatattttaa taaagctatt taaaaaaatc    720
cagacacttc acccaagagg aaatctaagt ggtccataaa catgaaaagg tctttaatca    780
ccagtcagaa aaatgaaaat gaaaaccatg ccaggccacc tcccaccacc atagtgacaa    840
gcatttcaag tgtggcagtt ccagctgttg ttgaggatgt ggaataacac tggtaggggt    900
gttaagatta tctggtgaaa ttgaaaagac gcatacgacc cagcaattct gctcttaagt    960
gcatactctg gagatgcttt tgcccattgt gctgcgagat gtatacaaga atgttcctaa   1020
tacctccaca ctggaaacaa ctcatcagtg aaaatgaact acagctacac aaaatgacat   1080
agatggaatc ttaaaacgtt tagtaaaaga aatgatacaa aaggatacag tttttttttc   1140
atttatgtga agtttaagaa taggtggtat tgtttaggga tgcagtcttt gggatggcaa   1200
ctgtaaagaa aaagtgattg tgttaatcag agtgattgtc tttagggaaa tggagtgctg   1260
atggggaggg ggcacattag ggcttctgga gggccacagt tctggttttt aacctgagtg   1320
gtggttttgc acgtgcttgc tttatagtta gctgcaattt tttttttaa tgcagttaaa   1380
gtttggtatg agaacaaatg tatgaccgat gagtcctttc agtttaccaa gttctttttc   1440
gtcatcgtta atttagagtg ggttacatca gtttttcttt tctggctgcc aaaggcttag   1500
gaaaaaggca aactgacaga ggaagatttt aaatgtagaa atatttattg gtttacaaat   1560
ccttttaatc acttatacat gaaaagcttt catataattc aaaaagcaaa ttttaaattc   1620
caatgaaata gttcatcccg tggttgtgaa agagtgtttt tagattgctg cacagaagca   1680
tgtttaacgt ggaaatcagc tcatggtttt agttgttagg gctacaagaa attgggggag   1740
acttcattcc aagaaaacat gtagtctgtc aggctgtttt cattcctcta aaagagacag   1800
ttttctaaga tgtttttgaa aatgagaaaa tacgtaatag atctgcttaa gaagtttcaa   1860
acttaatctg tgcttattac atgaatatgc taatgtaaaa ccaggccttc agttagtgtt   1920
tccttccttt tagaatggtg tatgtaaagc aaaatataaa ctaatttctg acctgtcaaa   1980
ggttttttct taaaatttaa atttataatg tggtttggtt tttctttccc actcaaacat   2040
gaatttgggt aataccagaa taaagctgga tatataaatt ttatccaaaa tttagaactc   2100
tgttgttaag aaatctgttg accacataac catgtttctg agaaaataca tgattttttg   2160
catctttaaa aaaaattagc actaagaagc taagatgaag ttgtttttgt aatttgattt   2220
ttttttcctt aaaatactgt tttggagtta aaagttgtag caaaactggt ataagaaaga   2280
tgttttaaga tatatttaag tcttgtctca tactctattg actaagctag cccggtgact   2340
agggtagatg tatttaaaga ataacttttc ccccttaaaa tctcaatatt ccacatcctg   2400
ttagacttct tgagtattaa atacatcttc tatccttggt ctttctgcat ttagcttttt   2460
```

tgggaagtat gtttttaccc aagcatatgg tatgagctgc tgattcagta ttgagtggct 2520
ctttaagctt gttagttaca ttctgctgat taaaatggtg tacagaatag tcaggaaaaa 2580
ccagtccctg gtctgaaata aacaatgtta attagcttat ggggaagaac aaatgagtaa 2640
ggagaatttt catatacaaa ggaaatctct gattgtcttt ctggactcag tgtgtttggg 2700
ttaaggagat agggtgcggc tggagaaaat gatgaaaatg ttcagaatgt tacatgtatt 2760
tttacactga aactggaagt ggaagcccag tgtgatagtt ttctgcccga tgttggcctg 2820
tcttcacacc cacaccactt atcttgattg atagagctac tacttcctct tatactgctt 2880
cagaagttaa cctctgtggt gcagtgctag gatatcacag aggaaataat cccttgtaga 2940
cagtgtcttg ttgctgggag ttatcagtgc ctcctgttct ctctaaggag ggcaatggga 3000
agccctttcc ttgcatttgc tacagccgtt tccttgacct ccctggaaga acagtatttc 3060
atggtgtcag acaacattca gaacatgctc aaattaaatg tatgtcagta tgcatttgct 3120
ttggtgtgtg gtttgtccaa accaaagtgc ccatacatgt ctctggtcca gccatgtggg 3180
aaattcagca gtggggtgaa ccatatggaa atggcaggtg ttgggcagcc ttgactggac 3240
tgccctggtc ttacttctgg atttggtgag tagaagatca cactgttgct tgctgccctg 3300
ggttcacctc aaagagggaa agaagaatta gcaacttaaa tggttaaatt tagaaacaag 3360
aaaaagttct gtcagtgggc agtttcttac gtctaacaaa aaaaacaaca gcagtgaatt 3420
cttttgtgtt cagaattaac cagtaaacac aaccttagca attaacctat cactatcacg 3480
attgtttatt tcctggaatt ttgttgacag aattagtcca ataaatgtta tgaataataa 3540
ttttatgaat agagataggt taatgccaaa ttaagtataa ttgaatctga gacattaatg 3600
caactgtttt aaattcaacc actgacctgc aatttttata tgccttgtcc atccagcaag 3660
at 3662

<210> SEQ ID NO 302
<211> LENGTH: 1498
<212> TYPE: DNA
<213> ORGANISM: Homo sapiens

<400> SEQUENCE: 302
cttaatcctg aaaggcaggt gcttttatta tcttttatct tattatctac attttccaga 60
tgaggaaacg taggtacaga ggtttagtaa cttgcccagg tcacatagcc agtaagtggc 120
agagctggga tttgaacccc agtaccctat ctccagcgaa tctgagatgt acatgtgata 180
aatttaatct ttctcaataa attattaagt gtcaaagcaa gtggtatggg caatgcacca 240
ggattaagaa aaacagtgtg tggtaaagat gtaaaatatt tctaattctg ttgtgggctg 300
tggcactccc gtggaaggct tgccacagac acagccagag gcatccacgt gggcccctgc 360
tgcacacctg gtttgctgct accaaggctg ctctcccgag gcttgttcac acaaaggaaa 420
gtgagcagct aggaagctgc atatttgaaa gttgactagt caccaaatgc tggcatccaa 480
ccaagtgatt gcattgtacc ctgtttggat gaaagattgt gtttaaatga aaagagagat 540
gatgagccag aagtgtggca aatgagttaa aataaattgt cagcagtgtt tgaagcaggt 600
tgctgagggc tggtgtcctg aaatccggtc acttggagga tgtatatgtt ccatcagggg 660
ccggaaatgt tttatccaag ctttagggaa taaccctgga gattctcttc gttactctac 720
tgttaagtac gtgcttacgg agtaaacttc gcatgactaa ggtttacagg cctgaatgtg 780
caactgagtt caagtaagca gcaatgtggt gtattaggaa gactgcttga cttgggttct 840

```
aatccttgct tcaccaccta gctgtgtgac tttaaacatc actgtttttc ctcctgcctt    900

ccttctgtaa cttaaggggg ttggattatt agagttctca aatgccatac cttcaaggcc    960

aggtgcagga tgcagagaat agtgggttaa agtgaacacc tcaatgtaaa atcattcaaa   1020

aatttaaaaa catcacggac caaacaaata tgtctttaaa tctgaatttg gttaaaggtc   1080

acaagtttat gccctttgga gtactctctg acattttcat gatgatatga aaggattttt   1140

ccatacatac tcaaaaggcg ctcacgcctc tgttgcagtc agtctggcca cttccaaata   1200

gccaccccat gttggtctcc acttcttccc tccctcttta agtgctatgt taataatcta   1260

gcttataatt ctctaatcag cagtagagca ctttgctact ttattttttta ttgttagggg   1320

tgatcttagc agcccaagta tgctaagtct tagaaatatt catcagtgat gtttttccct   1380

gaagctcgtt tggtgactgc taaactagaa ccagaattgg agaaaaacga ccctgtgaat   1440

tccaagccaa caaagccggg gaagaggcat tgagcaacct gtggttgcct gagaaaca     1498
```

<210> SEQ ID NO 303
<211> LENGTH: 2415
<212> TYPE: DNA
<213> ORGANISM: Homo sapiens

<400> SEQUENCE: 303

```
gaaaccacag aatcgccttc ctccccagtt atttatactt caagtcatat tgtagagaga     60

aaatttctgt cagcaaaaat ctcaggaatc ctcctcattt ctatttgtat ggctttcaat    120

cgttgacatg attttttcac atatgtcatc ttctggggat ggattcgtat aaccctgctt    180

cacttgcttc cctgtgggag gctcacttgc ttctcgacag gctctggaag aactaggcag    240

tctggtacat ggttgtgcaa gaacccttga gggggccttg gagtgtgtgc ttgggccctg    300

gaactcatgc ctaggatgga gggctgagat tgccccttcc catccaccag ggagttgaca    360

agggggagaa gaaacttctt gtgagcttgc gatgacttgt ggcacttgca tcagaccttg    420

gagttccctg gggagaggca ctcttgggta tgacactgta tagtgccacc tgattgccat    480

ttgacccagt ttggccctgg atccttgagc aagagggctg gaaagaaaga caggccccact    540

ttttgggaca ctattagggt ctgtagcatt ggtggggaga gaattccccc aacccccaaa    600

agagctgaaa atgagacacg cgtggagggg tgaaagtgga gtgtggtcaa cagtgtggtt    660

acagagatgt gtgtcggggc cactcccact caccagggag actcatgaag cagaagggat    720

ggggcacaat gtggcttcca taggcacacc aagccacctg gagagcgcat cagccctttg    780

ggtaccccca agcggaagga ggttgggtct ttgggtctgg gaactttggt gcttgttctg    840

gtgggaaggg cagggagtca agaccagctg tgtcttccac tgctcttctt gtccactttg    900

gttactggcc tctgttggca tgaactgggg aggcagaggc tacctacaga cgaggaactg    960

tgtggagtgc gagtgtatgc agtaaagggt tagcttagct gacttgaggt actcacaccc   1020

atattccgaa gaaaagactg gccctcagcc tgagcctccg aaataatctc taagccctta   1080

gaatacctg ctttgtattc aaagagtatc tttgaatgct gaacttagaa ccactctaga   1140

aaatgtatgc taacaatgcg atttatgatg aacacttgtc tttgttcccc tggggccctg   1200

ggccacattg tatcagtttg agccctagag ggacagagaa tgagaaacta agatcagtca   1260

tgcaggtgct ccaggcctat gtgaccaacc accaataaaa accctgaaca tcaaggctca   1320

agtgagcaat acagctggtc ccaacttaca gtggttcaac ttgtgagttt tgcactctac   1380

aatgggttta ttgggacata acccagtgga ggaggatctg tacttcattc acatgtgttg   1440

tcacatcatt actgggagaa ttaagcactg tccacgtgaa tccactggga gaggataact   1500
```

```
ggaagcttgc acctggcttc tcctggattc tgctctgtac gccttttcc cttgttaatt   1560

ttaatctgta ttctttcact gtagtaatct acaactataa gcagaatagc ttttctgagt   1620

tctgtgagtc tttctagtga atcattgaat ccaaggtggt cttggggacc tctaacaaaa   1680

gatgtctgga cctgaacttc ctgttgtttc aaagatccta tagcaggctg tcttaccaac   1740

tttcagcatc aagaagctgg tggagagtgg gttagtttaa aaatgaaact ggggagagag   1800

atgaagccgg gggaagatgc cgtgaaatct caccttatag gcagcctctg attcacctga   1860

gggtttttcc ttgaatactt tctgggtaca agtatttgag acaggtgatg tgctggtcac   1920

tttattctca gctgcttgtg gcctagccct aacatgggca ctggaaacaa tgggggtagg   1980

ggttgatgat ggagaaatgg ggagtaaagg gatttaaaac tttgaaaaac tgagctgttt   2040

ccatgatttg tctcttttga ttctcacaaa acctttatga aatatgtgct gacattttaa   2100

gctctcactt atagtgagaa aagcaatctt cagcaaggtg atgacttgtc caagggaaga   2160

catggtcgcc cttgttcctt gggagatttt gtgctcccag gggaaagcat aagccctcag   2220

gagccatgat gagaacagct gtagaacagc aagtgaacag gtgtgtatca gtcaggatag   2280

gcaaggctaa gctgcagtaa taaataatcc ccggatctca gtggcggaac attgaggagg   2340

tttatttctt ctttatacaa atatgctgtg gatcaggatg actctccagg caactgtctg   2400

tgggactgtc caggt                                                    2415
```

```
<210> SEQ ID NO 304
<211> LENGTH: 6766
<212> TYPE: DNA
<213> ORGANISM: Homo sapiens

<400> SEQUENCE: 304

cagtgctttt gcatccttcc tgttaacttg tgtaggaata aaacattgtc acaataagat     60

ttttttcctt tttattgttt tgatttttta gccaatgaga aggaaaattc cttattaggg    120

agggcgaggg tgaggatatg tggggtgggg agaagcgaac gttccaagtt tcgaaaacag    180

cgactctctc ttggactctc tagccagtag aaacctccct cccactctct tgccccaaga    240

tctggtgctt agaagagaat caagggaagt tggaacccag aagacggaga cagattgagg    300

gactgctgtg aaatgttggg gtgtttggtg aataatatta gaagttgggc tggcagagac    360

cctgtcacat aaacattaaa tcaacactgg agactgagca tttgttagaa atgtaagcgg    420

gaatggcaga aaacttgttt ttaagggaaa gcatgttacg gcttatgttc agcctccatc    480

ctctgaaggc aaaagttagc aaagttgatg tatggcgttg ctttttctgg gaactttatc    540

tcgtttggtg gggttcccat ctctgtctcc caggagccaa gactttcccc tccctctgct    600

ccagcagaag ccagtctcag gcaaggctcc ctgtacctca tttacacttt ggtgtgaata    660

tgttattgta acctctctcc tggaggtgtc tgcattccaa gactgaactt ttctgtgaaa    720

gttactgtca ctgtgaaagg cagttcagcc cccagggatt gaaaaaggaa atcattttgg    780

gtaaggggac agttagtcca gattttttca gttgcaagta aacctaactc agccagtagg    840

caaaggggga aattgctggt ttgaactggt gggaagaaag ctgaggaaac tcctacactt    900

gggggaagaa ctgcaggtgc ctggctgcag ggaacgcagc gggggctcag gaccaggcag    960

atgccctgcc tctgcttccc ttggcacagt ggcctccttc tcccttcaag taggcagatg   1020

ctgcctgtgg cagaggacag cagctgattg gcagcccagc agggaggatg tggtagacag   1080

gcactgagca tctcttctac cctccttcta gagggctatc ctgtactgtt gaggctaaaa   1140
```

-continued

```
gactgaaaac cacatttccc agcctctctt gcagctacca atctggatga gagttagatt   1200
ctacacatta gatgcacttt agcaagattt tcaaaagcag attggagaag gagcccatgc   1260
ttctgctggt ttttttgct ggcaagtgag gggttctgtt tttcctggag tgactttatc    1320
atggtggcat ctgaaaaagg ctatttcttg atcagagaga cagcaaccct ctcagtgacc   1380
tagttctgtg ggtgtgtctc tcctgagagt taatcccaga gctcaaacta gagctcaacc   1440
ctagagtctc ttcaggcttc ccaggggtgg gggtgcattt aacagtccaa gttaaagaga   1500
aaataaaggc cattaaagac caaacattga gcactgagtg aaaaagtttt attgccaaac   1560
aggaaacctg attcaggcca gggtcttgga aggttgttca ggatgagatg gggaggtga    1620
aatggggtag gtctttgaaa accaacagat tgcaaattct ctgtcccata gcaggaaacc   1680
acagtctctg atgtcagctg gctgccaaca cgtcagttgt atcagcatta gctggctgga   1740
ggtggcctgc tgtgtgcaga tggtacctgg tgcaggattg tggtgtccag gtgtctctcc   1800
ttagcacata agaccctgtc cgaggactgt ggcatgacgt gctggagtca cgattctgtc   1860
acccagtcag gtcatcagtg tcagagagct aggtggccag gttggagttg attgccaatg   1920
ataggtcttt ttctgcttaa atcagctgga ctggattcta ttgcattaac ttgaccctga   1980
ctcatgccgc caggcctaat ttataaacca agacaagaaa gggctactcc accccctcca   2040
atttgtgtaa ggccagggga cttccccccc actccccaac ctgaggcatg caccctccct   2100
tagatcaatg gctgtttctc tgagaatgcg gaaccgtgat taatccagcc ttgatgggga   2160
ggcagcagga actgtaggca ttctcacttc acacccatcc caatcccctc cccttgctg    2220
tcctcttgta cagaggactg aaagcacaac actctctccc tccctccctt ataggtggtg   2280
acgatcatgt gactctcttc tggtcaatga gatgcagcag aaagtcctag ggaggtctag   2340
gaaaagtcct gttgggagag agcatttttt accttctccc tgctacttct tgctactagt   2400
aacatggatg tgagccttgg aggggtagct accatctggc acctggggtg gcaagccaac   2460
atggaaagga tggcagagcg ggaaggagga gccagcctta ccgatggcat cactgtcact   2520
gcgctagccc cagaccacct gctccagagt tctggttatg gtaatgaaat aaaccttgat   2580
ttttattcct taaaactacc cttcaatggg ttttctgttc attacagttg aatgctttca   2640
taactgatac aggagggacc ctgtgattgg cagttccact agactgcatg gagatgggtg   2700
gagttatcta aaagaacaga gatagtgtcc ctagaagaag gggacaggaa agcatcctgg   2760
gtacacaaaa gtcaaggctc caggatctgc cctgggggct atctcaacac ccctacactc   2820
tcaccgcacg tatttggtca gctatgaata tgaccaactc tcgtcgttta tctctattca   2880
gtggaacaca gcagcactgt gacctgccca cgagaagaag gatttttaga acttatctta   2940
gggcaatttt aggtagagga gcagacaaga tggtgtacag gagaaacagg tctattaacc   3000
ctggtattaa tattaactgg ctgcccagaa taaatgaaga atagcttatt ctttgccagg   3060
ttgaagatag aaaaggaatg aagggccgga gaagtacagc tgggtgaagc acagagcagc   3120
ctagtgcttg gcatgggact cagatctgaa gcagcctctc cgggacttct ctgagcctgc   3180
ccctggtggt atgactgtga tatccctgct tctatagttg gcaaccaaca tgtcctagct   3240
cctagaccat agagggccag attcatgtct cattgactgt gtaatctctg tgtggcccag   3300
tacagagcat gcacaccgta ggttctcaca tatgtttgtt gagtgaatga atacaatacc   3360
aaacgaatgg acaggacaga gctgtgggct agcaggaagg atatctggct tttgcttgaa   3420
ttagctagtg aattgctgtg tggcctcctt actgagcctc atttccctct gtctgcagag   3480
tcaagcaaat cttccatttt ttgttcccct gctgccagag catggcagag taaatgtgtg   3540
```

-continued

```
agttgaaggg agcaacctca tgaggttttg ctttgtgtct taattacagc catttgtgga   3600
attaggcttt taatataaat atttgtgtgc ctgcgcctgc atatatgtat ttggaccaat   3660
gctctcatgt gtgcaaatac atgtattcta aagaaatctg tccagaaccc cagcatctgt   3720
ggtgtctgtg gtgggagggg cttccatatt acagagagat gcccacagtg catgacgtta   3780
cccgcacagg tgtgacatca cagggtaacc aaatgctttt gccctggggg tgggagaggg   3840
atgggtgcac ggtgaacagc aggtgggggt ctttccatag gggatgagga agacaaggcc   3900
acttggaggc agaggagacc acagtggggc atgatggttg gggaaggcct tttacttctg   3960
ccccttaagg atgccctgga attcaggctt tcggatccca gagctctcat tagagcagcc   4020
ctgcgttgta gacttttctg cagtgacaga aatgttctat atctgtgcta tccaatatgg   4080
tagccacaag ttacatgtgg ctattgaaca cttgaaatgg ggttagtgca attgacgagc   4140
tgaaaatgta gtttaaattc acttacattt aaatagctgt gtgtggcttg tggctgccta   4200
ttggactgtg cagttctgga gaatggtact ttacttgtcc ttggggaagc agaaacaaat   4260
gaaaacgagg atctggagct catgaagttt ctcatggggt ggggtatgtg tgttgaagct   4320
gcaccttcag caggaacctg gccagtcctt agtggaggac atttctttcc atcctgcatc   4380
cagatggctg gtcctgctcc tcccagtcca tggagaaaaa agaattgaac aaactgtcta   4440
agctgggtca ggtactctgc agatgtttgc tgagtatcgt tcttgatgga aatccccgtg   4500
gaactcctac attttctcct ctcttctcct tcctttcaga acctcagagt gacagagcca   4560
aaagaccagt gcctcatttt gctgacatgg aaaaggaaac ttcgtggggg aaagagatct   4620
gcttgcagtc ggccagagag acagaaccag ggcagtggtg agctctcatg acctggtgtc   4680
tgttgccttc tggttaagtt tttcatttgt aattctacaa acatcccttc tgtaaacatt   4740
tccctcaaaa tggagcagga agctctcaaa aatggaccag aaaggggtca ggaatataac   4800
tttctctgcc cagattccag gacttacagt gagaaagcgc cttctgggaa cttcacaatg   4860
gctaaagtgt gctaatggga tgatgtgccc ttgtacaccc actgcctctg aactctgctc   4920
tgcattgctg agcaaactac atttcccaga actccttgtt ggattccttc caaacaggtt   4980
taccactggg agagcctgtt ggttggggag ggcaggaaga gggaggaaag aggaagggac   5040
tcacttcctg tttccagctg aagtctaaat caatccacta tcaacaggta gctatcatac   5100
taccctcatt gtcacccctc agaggtccca ctgcagctgc ataatgtccc ctcagtggcc   5160
tgaacatgag atgaacaaca ctcttcttgg gagtaccagc cttgcttggt tcatggccac   5220
ttttcctgat tatcttgcag ctatattagg tcatgtgaca aagttctggc cagtggcaag   5280
ggaacacaag tgataggtac agatagaagt gtctgatact acatagatta tgcttgcact   5340
cactcttaag agagagacat gaacttttac caacggaagc cagtattatt ttgaacctct   5400
gttagagtgg cttgaatctg tatcctaact tgtatcccta atgtgtgacc catgaaaatt   5460
agccaggcag caccagttcc aaagaagctc acactcccct gcggctgctt ctgccaaggt   5520
cactgatatt tccctttgct aaatcttgtg ggtgttttct tcagtccttg tcttaatcac   5580
tcagtggcac ttggcactta ttccttcttg aaacccttgt ttcccttggc tttgtggcat   5640
cctgtgctct tggttttctc ccatatctct gaccctcttt ccttagtctt ttttcttctt   5700
cctcctgtcc cttaaatgct ggttgtgatc ctctttttat ctcattctac acactcacag   5760
cctgagtaat tcacaccatc ttgatgctga gaacttccaa aatgttggtc tagcctgggt   5820
cattgttatg agctctagac tcacaaggcc aattgcttgg tgggaacccc tcccccatgg   5880
```

ttatctcatg ggtccctgaa gtccaacttc tccttcattg aactcatcac ctcttctgtt 5940
cctcctcctg ggttcccagg ctcagtggtg gcaccactgt ctacctggct gcttagcctg 6000
agacctggct ccgtcccaat tcctctctct cagtcttatc atccccatcc aggcaaatca 6060
ttgattctgt ggacctactc tttcgggtgt ccctcaaatc tctccacgtc tctgtgttct 6120
cactagcact accttggtcc accctgccat ctgctttcct cctccactcc tgcattctga 6180
gtcattttcg gcagcacacg catccttaaa acccctccac tggcttgcca gtgtcctcag 6240
gattaggcga aaagtctttg ctttgtttta caaggccctt cgctatctgg ccccctcatt 6300
acctcccttg ctctgcatgc tccagtcctg cagaactaca cacagttccc ccaacaaggc 6360
cctgctctgt tcttcccaca cactgctcct ctgcctgggc cactcttcct gctccttgtc 6420
agcaggcttg ctgctctcag gctcagcatg gacagctgct tctgagagcc ttctctgcct 6480
acccaggctg ggtggctgcc tctctttggt gtgcccatgg cagcccagaa tgcctggtgg 6540
acagggagcc ctcagcaggc cgtactgcag cgccctgccc ccgtcagcct ccaggagcct 6600
ggagtccagg gacatcaagg gcggtcctgt ctttctcacc cttgtctctc cagcccctaa 6660
cacaggggat gcctgacccc aaactagacg agttacttga cctctctgac ccaagacaaa 6720
atgggaggaa agtgccaaat ttccaagatt ggccagggga ttaaat 6766

<210> SEQ ID NO 305
<211> LENGTH: 5610
<212> TYPE: DNA
<213> ORGANISM: Homo sapiens

<400> SEQUENCE: 305
cacctgtgcc catcacatag ctggggcaca gctggagacc ccaacagaga ggagagctga 60
tgggtgacga gaaatcaggc ctctccgcca cggcagccta gctaatgggt cttggctgga 120
agctaacagg aaggcctctt tccagaaaca ctgtaagcca gtgtttctca gattgctggg 180
tgtaattcat aggcagatca tgaaatcagt ttaatagctt tgaccagcat taacctattt 240
atgcctagcg ttcccttatt ggaacactaa gtctgtgaga gttatttaca tcctactgct 300
taaggtcatc gccaaaatct gattttttac acaaaaaatt tgcaacctcc agcataaatg 360
ggttaaaaca agacaaaaca aaacaatacc agaatggaaa atagtgcatg atctgtacag 420
tatagttgta gaaaacttct tgttttatca tttgatgtca tgaaagtccc tgctgtagat 480
aaaagatgga gcttgtgctt ctgagtggtc atgctcaaca gggtggggag cccaggggag 540
tggggagtga tcgtatagac agaggtgggt ggggccagtg tgagcctgat ggtcaattac 600
ttctcatttc tagggaaaat tgaaggaaaa gaaggagggg gatgtggagg ggagagaagg 660
cctcagtaga gtttgcacta ttattagggc aagtaagctg cttctgaaaa gaaggggttt 720
gcaaagccaa cccaggcaaa agcaatctgc tggaagaact tcatccccag ctgacactgt 780
gggaaggacc ccatgcagaa gcaatagggc agcctggtcc catatcctca tgaaatgcct 840
cttataattg tgacatcttg caattgtgga ggactttaca cttttcggag ttcctagccc 900
ctcacttatt tctcgtaaga ccgctgggag gtggggggat ggtatcatca tcccacttta 960
gagatgagga aacaggatca gagtgagcta aatgactgcc agatccaaaa ctagaattca 1020
gacctcctag tttctaagtg gacgctcttt ctacaccacc ataatgtgag tgttctgtgt 1080
ttacagggtg tattcaagtc catgactgcc cattagaatc cccccaaaaa attccaggac 1140
tggcctgagt tgctccttag accaatgaaa tcagactcct gggagtacgg cccgggcctc 1200
gggatccttt aaagctccat ttggagagcc tcgggcacag ccaggttgga tccatctccc 1260

-continued agtcccccag ccttggctca gcctggccaa gctgcccagg aggtcccttg gtgccctggg 1320
ctctgtttca ctgttgtttt gtagagcaac ttcccagtga tgctgccact gggccccatc 1380
ctaacagtga agtcccccgg gccctcctga gaggaggtgt gaactggaag atggggaggc 1440
aggcggctct gacagacaga aagcaaacag ctcagagggg tggcaggctg cattttattc 1500
atcgttaatt taaacaccct tcaagtcctc tcttggaatg ctgctcagaa aaatagatgt 1560
attgtttgag aaaccctgca ggcttgtccc gcatgctcta gccccctcct gagagaacag 1620
atagcataaa aaatgatttg taaagcaagg gggagcttcc ttagggaaga aggggaaggg 1680
gaagagggtt tggggccagg tccgagtgca gaaatcctca atgcatgaga ctagcgtgga 1740
aggtgtagca attgtgctct ggggtgcctg aaagtgccag agctgcttca ggggcaagag 1800
tccaggcccc aagtccatgc tgatgagccc accctggggg tcaggaatgg cctcagcagg 1860
ccctccctcc ctccctctcc accctacaaa gtgaggagcc ttgagtcacc accagcacat 1920
tatacaacaa tacaagaacc ctgcaacaga taaagcccca gcgcctcttc tggactcaga 1980
tgccctaggc tggctgtctg gctgtgcttt ccagacagtg tgtatgtgga attgtgcttt 2040
ttgtttttta agaatgtaaa aagttacagt aagatcgaac cacagggccc gtcgctccta 2100
tggtctctgc ctgactgggc tgccgtctgc ctcagttccc cagaagcttc tcctttggcc 2160
atgagggctc agtcatccct caccccagag tccacaggaa gagggggtct gctgggaggc 2220
ctgtctgaag gacggaggat cctgggtcaa tttagcagct attttccagg gtttggcttg 2280
ggtttggatg ctggcttctg tgtgaaacct gaatacatgc aaattgtaca taaaactccc 2340
ccaaggcaga gagggatttt ccaggccctg gtacatctct agagagttaa aaatgggaaa 2400
tctttcttct taaagtggcc cagactgaga cttttccttg gggaaaaggg ttagtagctc 2460
tttgtaaggc tggtgtgtat gtgtgtgtgt atatatatat acatatatgc atgatgctgt 2520
gcaaatgccc agggctgtct ggcattttcc acaaaatgag agcctgagat tgcctaagcc 2580
ttctgatgcc ttctccaggc ctggaggcac tgcttcattc agaggacaca aaggcctgac 2640
cacctggctt tagcaagcta ggacacccag ggtggcttct ttacctttct cctcagctct 2700
gagaaggctg ctagccaaga ctctggattc tctgtggcca cagtcatatg gtgagggcct 2760
cttggagttc attcaaactt taagggagcc ccacagcacc ggcatgatgg gtaagtccag 2820
gcctaaggtt aggaagcaaa tcctggagca tgaggaaatt gtaggctaca gtgagctacc 2880
agtggtgtgc aaactggaga cccccaagac agtgagagag gccacagcat ctgagggaat 2940
ggagctcttt cttggcctga ggttcagaag aacctgcacc aaagaaaggc atccctatca 3000
atgtcactgt tcctgaaatg atgggagaac cacatccctg cttcagggaa gcagtccctg 3060
tcgtctgggg cgctgagccc tttggcctga gatgaaggat gatggtgtga tgtatcatgg 3120
cagtgtgact gagactggat tgggggatgg ggacagggga acataggcaa aaatacacat 3180
gtgccactgg atcctgagct gccattgtac cttggaggac tggcgtttct ctgggaagtt 3240
gggaggtggg aagaggaagg gtctcatttt cctgcccctt gaaaccatgc ttaccattcc 3300
tttagaagat tgctcaagct gcctccaatt gcctctttcc aaaaccaaag cataggaaaa 3360
caagtaaaaa cagctgaggc tgcagcataa gcaacttagg atagagtcta ggaagcaccg 3420
ccaacagaga agactgccaa gaaacatttt gagtttttct tctctggagg tgggtcctgg 3480
ttcctcccat ggagaccacg attctgtgta gtcctgcacg ctgggcgggg gattgcctgg 3540
aggtttcttt agacctgtct agctcacaca gtcttgatgc ctgggtttta ggctgctgta 3600
ctgttgctgg ggctcacttc ctgtgggtag gctgttattt tgcccgcaga tcaagtcctc 3660
actgtctaga tgcctctatc atggggatct cttcttccct ctctggatgg ctctgatccc 3720
caagttattt cctgttgcct aggtaacacc tctaattgga tgccttttaa tcgttccctt 3780
ttttaaaggg ataaatgtgg attttatttc caggtcctgt cagagggccc tgccctagag 3840
aacacgtgcg cccctgcgtg ggcaatccct tcactgtgac cgcaaccatg ggttggatgg 3900
ggggcactca ctgggctggc ctgacagtca cagtgaatcc tgaaagcatg gttttcacag 3960
gaacccacct tcaggattta gcaagactga cgtctctcct ggccagcgct gcttcactgg 4020
cttcacccca gattagggcc tgtgtttaaa aaccaatccc aactcaaatc agaaattacc 4080
caaaatagct ggagagtcac tgagatctca ggtaagcttt cccttcctgc catgaactag 4140
aaggggaaag aagagtttga cattcaagtt tgactctaat gctgggtgcg tgagcgcatg 4200
cgtgcatgtt tgtgtgtgtg tgtgttccac gcacatttgc cagggagaga gatttcacag 4260
catggctcca gctggaggcg gtgaggcggt gcttttctaa gacttcctat cagaagctgt 4320
gcatactggt gggtcacgcc gtgcctgtat aaactctggc acctgtcctt gccctcatca 4380
tatatgagaa aaatgggcag agagagtgtt cgtttacacc cccagaccac tatcctttca 4440
atgaagcctg ggtatctggc cttcctccag gtcagggacc ccctatgctg cagaaggcaa 4500
gtctgggaga atctgtccct cagcccgaga gcaaaactgt aatcctaaca ttacttccat 4560
ccaccagttt caccagctac ctccctcctg ccttcctctg cctccaatag gctgtgcatg 4620
gagaagacaa atcctcttga taaacaatat ttagaaaggg attctatctt tcctgacccc 4680
aaacacatca tggcctctgg agccaaatac cctgacattt gcaagatggc ttcttttggg 4740
ttcctggtgc tgcaggccct ggttcccaag gacgcagctg gcagaggtgc ctccttcaga 4800
ggaggaggag gagaagctgg agggctgcgc ccggcaaccc catgatctct taaaggggga 4860
aaagttgaac tgatcaacag tagttaagaa aaaaaaaatc cacaccaaca aataaatatc 4920
ttgtctgaga agactcagat attcctggtt aatattgaaa agcactgctg tggatgagct 4980
tgtgaaagaa aggacggttg ggggattcaa gatctgccga tccgagcctg gagatcagcc 5040
agctaaaagc ccagcagggc tcctgcagcc tcaccgctcc cctcctcaca ggtgccctgg 5100
accgcccacc attagaagta gctgccctgt gctctgtgct aaatggacta actctgagct 5160
gagaaaggcc agctaagccc ctcaccactg caatttccaa atctgggggga aatgccacag 5220 tccgcaagtt ggtgctatgt ttcatctcat tgcataatac tacaccattc tctgtgtgta 5280
gtggctgttc tatatatata catcgggagg caacatatgg ctgtcccaac ccccacctgt 5340
caaaactgtg actatatcac ttctgacgac cagaaggaag ctgctaggct gggccaggat 5400
tctaaatgct gaggaggtaa ttcagagcca cgaaaagttg caccatatgc tttggggttg 5460
ccggctgctt ctgtgcatgg ggacggggtt tagtgccagt ctgcaaaacc ctcctcgctg 5520
cggtatgccc tgggtgtggg cctgggggc cacgttttct ctccctgaag gagaatctgc 5580
tgggggccac ggttctccaa gaggggactc 5610

<210> SEQ ID NO 306
<211> LENGTH: 4189
<212> TYPE: DNA
<213> ORGANISM: Homo sapiens

<400> SEQUENCE: 306
aaagccattt ccagtgtcgg cccatttaat aaactggttc cacctggatt ttctcttcat 60
tgtggtgaaa gccaccacct aacaatgctg gccctgcctg catcatcgca tgtcatcatg 120

-continued

```
acaacctatg ggggagaaca gctccattca acagatgcag aaactgcagg ttaaagggtg    180
aaaagcagtt gcgaagtccc cacagcttgg aaatggtgga gccgagactg aaacccaggt    240
gtgctagcat ctaaagttca tgctctttcc accacattag actgtattct gagggcacca    300
aggaagctcc atttttctta agaaaccaaa ttgcagtcct ccaggaccac agccagggga    360
gcatcttcgt gggagagtgg ctgctgctca gagttgtgac tcccatcctt aagagtcctc    420
tgtcctctct ggcctccttt ctactgatca ttgctgtccc cttcacaggg gagaggggcc    480
atggcctatc ccctaaagag tctgccaagg tagactcata acctccccgt ggcacagctc    540
agacaagctg ggctatttac ataagacttg acccagggct tgaggacagc gcgaggaatg    600
aggtgcagag gagactgctg cttctgggtg acagtctgcc tggctgacca cagctggggt    660
actcattggc ctcttgaggc cccccacagg cctgccctgc ctgacctact cttgtgaggc    720
caaggccatc tcctccactc tctgggggcc tcttctgact cctccaaact cttccatgtc    780
tggactcctg gcttctgccc aaggccatct attggagttt gggtttccag ttgaggatct    840
gcctttttcc tggatgacca aacctagaat gtgaccggcc tcatgctccc tcctcacaag    900
ggtgtggctt tatccgaggg cctcagcaag gcaaccaaca ccagacatga agctggtaag    960
accaacatcc acctattcat tccttcagca aacatttact gtggacagca tcaggttggc   1020
agtatcatgc aaggctcaga aatatggtgg aaaaccagac agatgcagtt cctgtcctca   1080
gtctctaggc tgccttccta gaggcccctc actgggtttc ttagcagttt tgtacagatc   1140
ctacccccttt tgctgccagc aggctcacct ctgggacagg gcgcatatag tctgggccag   1200
aacttgtcct ggggtcttct tacggccctg gttcagcttg cattcagcat aacaacttag   1260
ctagggagtg ctgcaggccc caaatgatgc taaatactag actagctgtg taacaccatc   1320
tgcccagaat gaagggacag gtgaggcaga agggtctccg acagcgcaca gggcaaccag   1380
tgaaagcgtc cttactgtcc tgttcctgag gtctctctgt gcctgcttta ctgcccttcg   1440
ctttcctaca gagcacactc agctcatcct gggagacaag gtgggggtgg aggatggtcc   1500
atccttcttc cgcatcaagg tcagtaggtt cagagctctg ggggggtgct gagaccctgg   1560
gacaggcttc ctgctgaggg cactggggcc tatgcttgtg ccactgccta gccagttgcc   1620
tcccagagta gagaagcagt ctcccaagct cttgcaattt gtggggagcc aagctgctct   1680
ggagaggggc ctcaaagctt cagccagaga aaaggcaaac ccagccaccc tgagaatctc   1740
ctcctccccc tcaatcacac cctgcagagg cgtgatctgt ccctgggttc gcaccaagcc   1800
tgctattttg tttatgccac aattgatctg ccatcccagt ttgcaaagag cagacacttg   1860
ggggctttat tatgccactt tgacaaaagc tgtgaagctc gttcccacag cctgtctggt   1920
gccgccttcg caaatggggc cctggtgatg gggccttcgg agttcagctc agagagcatg   1980
gaagtgagat ggagaggcca gcactgatct gtatcgtgca gccctgggcg gcagcctcgg   2040
ttgggccctt gacacactcc tcccatccag gcccccagcc accctgtgag ggaggcacta   2100
ttacgcccaa aaatgcaggc aaggaaatgg gctgagggag gggaagcatt cactgaagtt   2160
agtttgtacg tggctgagct ggccctgaag cccatgccct ttccacttgc cagacagatg   2220
ggaagtcttg actcattacc cgctggagac ttttcctgct gggctctgca ctgtcaactg   2280
tgagagaggg aaataaaacg tactgtacag tccaatctgg gatacttctg agagtgaaag   2340
tggctctact agtaattacc ccaggacagc atgtataaac cagggctgtt ccaagcaact   2400
gggacacatg attaaaatgc agattccatg gcaggtcccg ctcagaggtt tatttagtgg   2460
```

```
gtcagaaaat gggcccagga atttcatttt aacaaatgtc tccagataaa tctgatgtaa   2520
atggaatatt cctttaagaa tgccattcct ttaagaaata atgttaataa ggtattccag   2580
atgaccctat tggttggaat ctgtccaact acaaatattt tgatttaaat ttccattgac   2640
ctaaaatttt tgtggtgggc actgcagctc tctccttacc aatcattctc ccagcctgta   2700
ctatattgag tagcagccag gctacttgga gaacagactg aactccagga atgggctcta   2760
ttagtctagg ccaatcagga taatccagtt ccttaccatg actggctcaa gaatgggtag   2820
acctaagtca atcagtgcag agcattttca tgactacaga gaaaccatgg gaaggctgag   2880
gcgtggactc agtgggcagg gatggaaaaa gactcagaaa tactgggcat ggcccatggc   2940
tcattagggt tgccaggtaa aatacagaac acccagttaa atatgacttg ggtaaacaag   3000
aaatcatttt ttaagtataa gtatgtccca aatattgcat aggacatact tatactaaaa   3060
tatagttgat tatctgaaat tcaaatttca ctgggcatgc tgtcttttta tttcctaaac   3120
ctggcaaccc tactcatgac tccacttgtc agcttggtac actcctctga gaagcttctc   3180
ccaatattcc catctcattt gatccttcct gactggccag tgttgggatt aagagcctca   3240
ctttaatcaa ggaacccaag gctcacacaa ggctgagccc tgcccagcca ggccagcggc   3300
caggcctccc catgtccctc tctctcctaa cagggaggag tgggagatgg gggagggctg   3360
tgggatggag ggcggggctg ccaacagcct gctccgtggc tggaactgcg acatcgcctc   3420
tctgggagta ggagtgggct tctggccaga ctcagtgggg gaggactgga cacttgagag   3480
ggcactgggc caaagacttc cctgggacat gtgccccagc cctggtacct cagggctgca   3540
catgtcagcc atctccatgt cacacccccg gggaggacaa ccgaccaccg tggacaagcc   3600
ctgaaccttt tgggaaagct ggtgctaaaa gaatagctgg agaagtcact actgaggact   3660
gaaaatgcgg agggtataat aactgctgtt gtgtatcgag cctcactatt tccacgcacc   3720
gtgccaagtg ctgcacgcgt atcaattcat ttaatcctca caacaactgc atgaggctcc   3780
atgttttcac tgattccaag tcacagcttt tttcctctca tgttaacatc tctaaaatcg   3840
tgcatcttac agtcaatggc ctgatagttt atttggcagt attttaaatt cctaatggta   3900
cgtaccatga tggtgtgttc ataaccaata gtgtcttaga tttgatgaac tatagtgggg   3960
atgattattg tccccagttg tgagattagt aaactgagtt gcatttaaca gataaagaca   4020
ttgaagttca gtaacttgcc caagatcaca aagcaagcac atggcagaga tttgaaacta   4080
gaggaaggag cttgcaatgt gataaagcag caaatgtaca agagtttgga agaaggagag   4140
gtaggttgct tttggcaaga gcagcaattc tcaattctgg ctgcacaat              4189
```

```
<210> SEQ ID NO 307
<211> LENGTH: 3729
<212> TYPE: DNA
<213> ORGANISM: Homo sapiens

<400> SEQUENCE: 307
```

```
ttcacagcaa agtggctcag gtgaggcagg caaggaatgg gcaaatcacg acatgacata     60
tggatttcca tggcagggaa atgccccgt aggcacagtc aagcctggct ctaccattgg    120
ctcgccgttc tcctacctcg ctgggcctcc atctccccac ctctggctca cttcctgctt    180
tggcccctac gctgggtagg aggcccggct agaggttagg caccatcttt tccagtcccc    240
aaagtgagag tgtgtgtgtg tgggagagat atttttaaat ggggctgttg tggaaaagct    300
gagaccgtgg gctgctctat ttgttggcgc ttgctggttt gtctgatttg cagagctgga    360
tggactgctc cctgaggaca gaagctcttg gttttcttcc ctccgaagcc aggcgtgggg    420
```

-continued

```
tgggagcatc cagtgcaccc ctcttgcatt gggtgcgcag tgatccggac agagaggctc    480
cagtcagcca ggcacagaga aaatggccct ctgcccctgt tctgcttgtt tttgtcttgt    540
tctctggggg cctttgaggt gactttcttc atttgatgac aacaagatgg gaggcgggga    600
cagctgaggt ggcaggagta ggggagctag ggacagagga tgaaccccac aggctcaggc    660
cagtgacttc taacattaga gaggttttgg ttaactggga gcaaatgcaa gtgacttctt    720
tgaatcgact ttgtacctcg gcacagcctt ccttgctagc agggctgact tcaaccaccc    780
cccactctgt gctttatctc tgggattaag gttttctctc ctcaccagaa atcattcagc    840
aaaatgagtt attaaaagcc ggttaaccac tcctgcctcc gggtagctcc cgtttaacaa    900
cctctcctgg ggagcagctg tcaagctcgg ccctgagctg gcgggaagat gactcattta    960
catacagccc gtctccaggc cccccccacc gccaccccaa gatctgtccc tgtctccctg   1020
atgactaatc ctttccaggg atgagatcac tgccccttct aaccccccc cccgccccca   1080
cacacagaaa gagcagagcc ctcatctcag cccagaattt tgggagaaga ctaaatccaa   1140
gaccaaggga ggcctttgat gggacaaaga cgtgactgat gaacccggag tgaggagcaa   1200
tgagatgaag aaagctctgc ccacctaccc cgtccctcac tcctccctcc cacctcaggg   1260
cgctcatgtg gggcttgtgt ggggaacagc tccagggtca taccacctct cagaagggag   1320
acagaccagc caggcgtgag gtgacagacc agcgggcagc tcagagcagc aagacaatgt   1380
caattcaatc actttacctc aattcctcta tcacacagga ggagatttta aaaggaagtc   1440
tctggtggtt tgtaaagcaa caaatcctgc tctcaagtgg atagttccaa gccctctcaa   1500
tgaattcagt tttatacacc tggagaagca cagcctcgtc ctttccatgg agctacaagc   1560
cacatctggg ggcgctcagt gcccaggctg agggggcacg cagagccctc ggggacgact   1620
caatgcacag aggccactcc ttaagggccc ggctccctca aactgaggtg tccccatgct   1680
tggtcttccc acagaagcca gcctggttgg ctgcttcaaa ggaggaataa agatgaggag   1740
ccatgatgca aacaaaccca cacctttcag ctgcagccag ggaggtgctc tagaggccca   1800
cggagagctg tgtgtctgct ctgctagccc gacctgcacc tgccctatgg gctggtaaag   1860
gggctgccca cagcacctca gcacatgggt ctctctctct tttcatccag cccaaaatgt   1920
caaagcacaa gggtctctgt cagggcctgg ctgtggtcac tggactgcgg ctgaggggta   1980
aggtgcaccc ctcctctaat gggggcgcac ccctcctcta atgggggtgg ggctggagct   2040
aatggcacat tccactctca gctgccacac acagatgggg aggttgatgg cccgcacaca   2100
ggaagtgagg gatggtgggg actgaattta tggagcccct atcccagacc aagcactctg   2160
ctggtacttt cacaggtgta atccccagag cagctcctgg gggaggtgtc attatgccgg   2220
tgaggaaacc aaggctcaga gaagtaaggc agcacaggtc ccagccccac tccacctctt   2280
gaggcctgac tcagccttag gttcagagaa tgcaactgtg atttttccct gagatgagca   2340
ttcaatcata ctgcgccagg gtacttgctg tggccaaaac gcctgccctg gatctgtggc   2400
atgactttgt gtcagaccct gtgcgataga aggagatgga agctgaggtt cagagacgtt   2460
aatgaccttg aaggtcaggg tcacagaaaa tggcacaacc gggattgcaa ctcagttctg   2520
cccaatttca aatctacctt cctgccacct ccttgccttg cctattgtcc ccctcccttc   2580
atatgacctg ggacccagac tccctggttt tctggaaata ttctctctcc ttttggctca   2640
ttctgtgcac tgtcccagtt ggtggtattg aggcacagct ctgcccagat cactctccag   2700
ctcagctgcc ctgagctccc cagccccacc tttcaaggtc aggaatgact tatttccttt   2760
```

-continued

```
tctcttcgcc tgtctgaatc ctcgccatca tctgacagca ctttcagctc accaggcatt   2820

taactgtgtg ctgtcttgtg acagcccctg tcctgaccat tgtcccagag atttaaccct   2880

ttgtgttttt ctatgttagc ttgccagtga ggacatggcc catgtcttgg acttcttgcc   2940

accctccaga atgcaggtcc tcagggagca gctgctaaat tcccaacaga actgacagtt   3000

tgtccagtga tcaccagcag acactgtacc agaaacattg tctccatctt agtttcagtt   3060

aactcaacat gtttttgaga cctgctgtgt gccagacatg agggcagggg aaggaagact   3120

atggtgaata agattgccca cagacctcca ggaacacacc tgtagtcaaa acacaattga   3180

gcttactggc tcactgcaat gaggaagctt ggccaccatg gattctgggg catctcagtc   3240

agagggtatc aaagagggct aattctagga gttgggcttg agttcttgag ttaggtgatt   3300

tatggaggac ttaaggaagc aggcttcgct ctggatggga tgctgccaaa gagcggaagt   3360

acttctatga ctgggcatct taattcttag ctggaagatg ggaacgacat agcgaggcca   3420

agctgtgatt ggccaagaag cagcagttgc tcatactaac cagatgaggg atgtttggtc   3480

tttttagtgg tttggacgat gttcttgttt tggtctgtgt ttggacatga ttatggggtg   3540

aatggtcttg tttttctctc actccatctt ggtcataagg cggccttgcc tgatcagggg   3600

ttctgtgaaa tgcttatgct ccatggcaga tcctcccagc cccactgtga gtgccaggcc   3660

agctctcggc gctcaggggc tgccttcatc tttctcaaaa tgctgctgtg ctttgcagcc   3720

cataatagc                                                           3729
```

<210> SEQ ID NO 308
<211> LENGTH: 774
<212> TYPE: DNA
<213> ORGANISM: Homo sapiens

<400> SEQUENCE: 308

```
ttcactccca acaagcactg ttaagtttat aaataaaaat gaataagata tgatccctgt     60

cctcatacat aatgaccaca atgccctatg aaaatgacag taagggagat gtcaggggat    120

tccgggaagc aagagaagcg gtttgggagg gtgccccaga gcaggtgcca ttggaactga    180

gtagtgaaga tgccttagcc aggagatgga ggcagttggg cacaaggtct gcaaggtcca    240

ggttggcatt caagggttca ggtgtcatgt ggataagact ttccagggag cacgtgtggt    300

atgagaatga aggcccctga ggaacttcag tatctaaagg gcagaagagg agtctatgaa    360

ggagaccaca ttcattcaac aaacatttat tgagggccta ctgtggccag gaactgtgct    420

aggcccttgg gattcaacag tgatctaaaa gacaaagtcc cctaccctca agaagcttac    480

atttcagtat gggagatgga ataataaact acaaacaatt acgtggcctg tgagaaagtg    540

gcaagtacta caaaaaataa aaaatagagc aggctaagag ggtgaggagt gtgcgggcag    600

ggaggaggca ggtcatggtt ttaagtgggg tgggtccagg gaggcctcgt taaggaacgg    660

atgtttgata aaggactagg gtaagagtgt ttcaggctag tcaacagcac gagcaaaggc    720

cctgaggcag aggggctgga aacagagaag aaaagagtga aaaaggactg ggca          774
```

<210> SEQ ID NO 309
<211> LENGTH: 1782
<212> TYPE: DNA
<213> ORGANISM: Homo sapiens

<400> SEQUENCE: 309

```
aatccctcct gcacactttc agggcaaagt ttaggtgata taaatgtccc tgaaatgaga     60

aaaaccatga ctttcatttg attttaatgt gagggagaaa cataaactag tagttttaca    120
```

aaaagaaaaa gaaatataat attcaagtag atttcaagca acagcagata tgctgaattt 180
atttgataac tgtcttcttt ttctctgtca gcagagtctc atgcaatttt aaaaggaaat 240
tcgatgaaac gaacacccat caacatcttt aatagctgca agcaatgtgg agcaaatttt 300
ttgtcttatt taatgtggtc atcaccataa cccagtaaag acaatatcat cattgctccc 360
attttgtaga cagggaaact gaatccagga taaataatgt agcttgcatg acaccaatct 420
tcctcaagtc tgagccagaa tttatatctc ccatttctca acctcatctc tcaagcctat 480
aatctttcag ttataagaag ggaaacactt gagggtgtat cagtttgtgt tttgttcata 540
gtgtttatat gctctcaatc aaggactgtt tattaaaaaa ttttaggagg tggtagtcaa 600
aaagtgtctc tggctgcagt actggggaca gactgcaggg gtgagttcag cgagtctagt 660
tcagaggctg tggatcaaac aggtggggtg gcccagacca ggagagtagc caaaagggga 720
ctaaggaagg gaggccaaag ggaggccaca aacgcaggag aggatgaagg tgctgaagct 780
agaggccatt caggaaggaa ggaatgacgg ggcaaggggt cagaaatttc tagaagaatc 840
tagtaagatg gaaacctaac agtcctactg ggatttggca actgggagga agctggctct 900
gtgcaggaaa gaagggggca ccgctgtgcg gacgccagac tgcgaagggc tgcagaagga 960
gccgaaaggg gaagaaacgg acgcaggtag gggtggctgc tgttaaagcc gcttcccggg 1020
gaggccaagg acatccacag ctgaagtgct caggaccatc cacagctgaa gtgctcagac 1080
actgcgtttt ctttatctca gagaggctgt gtgacttgcc cacgtatgag tacagtggct 1140
aaatcacaag ccctggagtc aagggtttag gttgatccag cccccactac tcactggtgg 1200
ctgtcagcaa gctactcgct gtgcctcagt ttccccatct atcaagtaga cagcactgcc 1260
ttacagatgg ttgtggggat cagaggggag gggacagctg gcggatttag cagagtacgt 1320
ggcacagagg aaacactaaa tatgcttctt cagctcctta tcaaggttag gcctccacaa 1380
agggtggagc agggaagaga aggcctcacc gggcagacct atcttggaga agatacaagc 1440
aatggtgctg aagtttcaca acagtgtcaa ccccctccct catgtgtgta ctcacagcta 1500
ctcactttcc tactctgtgc cagccatgag gtgtagtcac tgtgccaggg ggctgagtgt 1560
ccggcctggg acgtgagagg gcatgggctc acctgctcag ggtttgaatg agaccccggt 1620
aaccgcagca gtaaagaccc ctcaaatgcc atctctaaat taaaatgggt gatcagaaaa 1680
tagcaggtga acgatagtgc cctcactgcc cacagaagtg ccttcagtca gatttagcgc 1740
tccatcttct gcctttctga agggacagtg gaagcatcca tt 1782

<210> SEQ ID NO 310
<211> LENGTH: 1801
<212> TYPE: DNA
<213> ORGANISM: Homo sapiens

<400> SEQUENCE: 310
ccatctgtgc aattccttcc tcctagaatt cagaatctga ggtgctggtt tcctgaggac 60
acttgtgact tgctgccttt tattgaactc tgagtgccct attgcccagt ttgagtgttc 120
caatgggaag tgcagagcca ccgtggccat tcattgctgt agagctgcgc cccagtacct 180
gatacatccc tcaccctttt ccaattgatt tttagcttcc ttcatccctc cctctttccc 240
ttgtcctctt cgtgtccaca ggaagcctgt tgggagcctg ctatggcaag tgctgtgcta 300
ggacacggtc ctgcactctt agagtttgtg gttcagttat tccagtttca gcacttacat 360
tcattcaaat gctttgtgga agcaagctgg cttttagtca ccagcaatag caatttctga 420

-continued

```
aaatcaccaa gccacaccaa atatatgaaa tatctttctc taaggtggtc tttaaaattt    480
gggctgactc tcctccctct aggaatgttc tgatgagttt cagtctgaag gcagggagat    540
ggtctcggtg acctcctggg cccctgttct gcactgaact gtatgcccat acattcatag    600
gttgagatcg taacactcca gtacctcaga atgttactgc attggtagaa aggcttttta    660
aaaaagggaa tcaaggtaaa acgaggccat tagggtgagc cctaatccaa tatggctggt    720
gtcctcacag gaagagtgta ttaagataca gacatacaca aggaaaacca cgtgaagata    780
tggagaaggt ggttgtctgc aagccaagga gagagtcctc aggagaaacc aaccctgcca    840
gcccccttgat cttagacttc tggcctccag aattgtgaga aaatacattt ccattgttta    900
agtcccccag tccgtggtac tttgttatgg cagccggaag gagactgggg ccgcctgttt    960
gcttggctgc agaagcccca cgtggctgca ccctggctca ttctgttttc tgtagcagca   1020
gcagcagcag cagcggcagc agggagccca ggatgcaaag cttggtttct gagccctgat   1080
caggaggctg tgtttatatt tatcctgcta actgcagggg actgtttatt cccagagaaa   1140
taacctcctg gcaggatag gggcagccaa ggaaccagct gcttccatca ggcctgctgg   1200
gctcctccag gttctcatca taccacttct gtcgaggctc tctctgacgc agctctcctc   1260
actccacacc aggcttgggc ccaggggcac agcctggtct tcctgaggat gctcagacgc   1320
agggaccgac tgctcctcac aagcaccctg gcacatgcac agcccaggga ctggagcctt   1380
cgcaaacaag tcacagtcct agtctgagat tcagtgcaac actaggcgct tagtagatgc   1440
tcagtaaaca gaacaacaag gattttcttt tttagtttta aaacattagt ctacccatgc   1500
cttgataaac tgtaaaatgc ctctgccacc cattctccct tcttgctccc tttcatggga   1560
gctctgaggg gaaggtctct ggggtgggtt ccagcaaccc tgggcctgtt ctggggtcct   1620
gcagccaggt tgggctttca ggagcctata tttcatctgg gccccagtca cactacatag   1680
atttttgttt tatcacagaa atcactgcca cactgtgacc cttaaggtcc tcagcaggga   1740
tggcgcgagg tgagagtatc aaagccaggt gagagcactc agatggcttc tgcctttgaa   1800
c                                                                   1801
```

```
<210> SEQ ID NO 311
<211> LENGTH: 1032
<212> TYPE: DNA
<213> ORGANISM: Homo sapiens

<400> SEQUENCE: 311

gtctggattc tttcacaatg tagcataatg ctctggagtt tcagccatgt tgcagcatgc     60
atcagtactt catttctttt tatagctgaa taatattcca tagtatttat atatcaaaat    120
ttgtttatcc attaacctgt ggagggacat ttaggctgtt tccacctttt ggctattgtg    180
aatggtgcta ctataaacat gtgtacacat gcctgtttaa gtatatgttt tcagttcttt    240
ggggtatata cctaggagtg gaattgtaga atcatgtggt aattttgttt aactttttgg    300
aaaaatatca agctgtaccc aaagtggttg caccattttg catttccacc agcaaaatgt    360
gagagttcca gtttctccat atccttgcca atacttattt ttctttttaa aaaatagcta    420
tcctagtaca tgggaagtga cattcattgt ggttttaatt tgcatttccc taatgattag    480
tgatgttgag catcttttca tgtgtttatt agtcatctgg atatctttgg agaaatggct    540
attcaagccc tttgtccatt tttaactggg ttgttcggtt ttgttgttga gttgtaggag    600
ttcattatgt attctggata ttaatcactt acctgataca tgatttgcaa atattttctc    660
ccattctgtg ggatgccttt tcattctctt catagtgtcc tttgatacac aaaagttttt    720
```

```
cattttgatg aagtccaatt cacctgtttt tttcttgacc aaaaagtaga aacaactgaa    780

atgtccacca actcatgaac agataaacaa aatgtgtata taatgggata tattcagcca    840

taaaatgaat gaagtacaaa cacatacaac atggatgaac cttggaaact ttatgctaag    900

tgaatacagt cagatacaaa aagggaacta ttgtataatt ctatgcatgt gaggtacaca    960

gaatagtcat tttcataagg acaggaaatg gaatagtggt tagcaggggc tgaacagagg   1020

agaagattgg ca                                                       1032
```

<210> SEQ ID NO 312
<211> LENGTH: 627
<212> TYPE: DNA
<213> ORGANISM: Homo sapiens

<400> SEQUENCE: 312

```
aaccacccaa tgtgttcacc ttgcccgctg cctagacaga gccgatttat caagacagga     60

taactgcaat ggagaaagag taattcacac agagctggct gtgcaggaaa ccggagtttt    120

attattactc aaatcagtct ccccaagcat tcggggatca gggtttttaa agataatttg    180

gcaggtagga gtttgggaag tggggagtgc tgattggtca ggttagagat ggaatcatag    240

gtggttgaag tgagtttttc ttgctgtctt ctgttcttgg gtgtgatggc agaactggtt    300

gagccagatt cctggtctga gtggtgtcag ctgatccatt gagtgtaggg tctgcaaata    360

tctcaagcac tgatcttagg ttttacaata gtgatgttat ccccagaagc aattagggga    420

agttcagact ctaggcgcca gaggtggcat gatccctaaa ctgtaatttc taatcttgta    480

gctaatttgt tagttcgcaa aggcagactg gtccccaggc aagaaggggg tcttttcagg    540

aaagggctgt tattaatttt gtttcagagt caaaccatga actgaattcc ttcccaaggt    600

tagtttggcc tactcgcagg aatgaac                                        627
```

<210> SEQ ID NO 313
<211> LENGTH: 907
<212> TYPE: DNA
<213> ORGANISM: Homo sapiens

<400> SEQUENCE: 313

```
gccaaaggtg gaaaatgttg atgtagactt ctaagatttt gacaaaattt tgttttatgg     60

cctggtggtt atataaatat ttactgtata acaattcatt aagatacaca tttgtgtttt    120

ttgtatatat gtgttctatt tcacaatctt aaatgttcct taattaatta atggagcaca    180

ccttcagagt tgggtgggaa aataattctg cctagaaatc caaacttaga caagctagct    240

atcaagactg aggacaaact aaagccattc ttacacctgt aaggattcag ggtttatcta    300

ctatttatgc tatctgaagg agacaattga atatgttggc caggaaacca agtgtgagga    360

gtatgtagaa aacagaagat gatagtacta accctgttaa tctaataaaa agaaacccca    420

ggatgactgc ttgcagtggg gtttgaaaga aatctattca aattaaaaca ggaggtccat    480

gtgctccaaa aagatattct ttttttttaa atatatatat atcttttatt atactttaag    540

ttctagggta catgtacaca acgtgcaggt ttgttacata tgcatacatg tgccatgttg    600

gtgtgctgca cccattaact cctcatttac attaggtatg tctcctaatg ctatccctcc    660

cccctcccct accccataac aggccccagt gtgtgaaaaa acgatagtta gatgccacga    720

actaggtggc aatgccttaa ccgtatgtgt gttgtcaggc ctgagggcct cttccatcct    780

tgtcaagggg agtactaacc ttctcccctt tcatacaaca caaagatatt cttaagactt    840
```

ctagaatagaa ccctgaacaa ttttagagta aggaactaat agatatcagt gctttcatga 900
agaaggc 907

<210> SEQ ID NO 314
<211> LENGTH: 769
<212> TYPE: DNA
<213> ORGANISM: Homo sapiens

<400> SEQUENCE: 314
ccagaaggtg gaagctacag tgagccaaca gagtgagacc atctcaaaaa aaatttaaaa 60
aaatgaagaa ggaaggaagg aagagaggga gggagggagc gtgggcgggg gggggggggt 120
ggaggaggag gagagaagga gtgggaggag tggagaagga gggggaggag gagaaggata 180
aaaggttaca agtggttgtt actaggaatg ggggagaaga gaagtgggta atggcactga 240
agctttttat tatgtctttc agcattctct gattgttctt aaaccatcaa cagatctcag 300
tatgtagact aaaagggaat atttggtgaa gagatcttct ttcactattg tacacttgct 360
atggacatgt ccatgcctgc tgcctggcag gcaccattca ttaagtaggc ccctgttgcc 420
aaggaaacca gctcttcact gataccaaag ataatgcaga ggcctgccgc tcaccaagca 480
accttcctca tgagctatgc ccccaccttc ctgaactgtc tcttgctcct gtttgatact 540
gtcatgctgc acgaagctta cacttgctat ctctcacttc cctcttagtc atctgtgatg 600
ctggctaagg gagctaggcc agtcagcagt gacctgttgc ccttggttta ttataagcaa 660
actgttcaca agaaatgaac ttctgttgtt ttataaatga tatgcatcac agaacacaga 720
ataatatcaa aaccacatta gttttttcat acttgcttca ttgacccca 769

<210> SEQ ID NO 315
<211> LENGTH: 573
<212> TYPE: DNA
<213> ORGANISM: Homo sapiens

<400> SEQUENCE: 315
acatcgaccc agaaagttcc ttctgtcagt agcagttcac ccccccatgc ccccaaccct 60
tggcctccct gccttcccat ctccactccc aaccctcact gctctgattc tatcaccatt 120
gttttgattc ttctgctgtt gatcttcata aaaccagtat atttcctttt gtgtctggtt 180
tattttcctc agaataatgt ttttaacatt tatccatatt gttatgtgta tcagtcgttt 240
cttccagatt agtactctat tgtatggata gagcctattt tgtttaccca tttcctgttg 300
acagacattt ggtttgttcc cagttttgga ttataatgaa taaagctgct atgaacattc 360
ttgaacgatg aacatttttg tggacatatg ttttgatttt tttgtgtaaa tacctaggag 420
tgaaattatt gaggtatggt ataggtttat gcttaatttt atagagtact taaacttgat 480
tcttttattt aaaattgtga taaaatacac ataacataaa atgaaccgtc ttaactgttt 540
ttaactgtac agtgcagtgg tacgaagcac att 573

<210> SEQ ID NO 316
<211> LENGTH: 1465
<212> TYPE: DNA
<213> ORGANISM: Homo sapiens

<400> SEQUENCE: 316
agcgtgccat tgtactctcc ctgggtgaca aagcaaggcc ctatctaaaa caaacaaaca 60
agcaaacaaa aaaccccaaa actggaactc tgtatctatt aaacagtaat ctctcattga 120
gtggtgttaa gagtaaaatt ttttttaaca aaagaaaaaa gtaaaaagta aattttgaaa 180

```
aaagaattaa aaacaaaaaa tctccattac cccctccccc agcccctggc aaccaccatt    240
ctactttctg tctttctgaa tttgactact gcacataacc ttatataggt ggaatcaaac    300
agtatttgtc tttttgtgac tgacttattt cacttaggat agtgccctca gcttttaaaa    360
ggaaagacat tttgatatat gctacaacat aatattccat tgtatgtaca taccaaattt    420
tattaacgat ttcatctgtc aatgaacatt tgggttgctt ccaccttttg tctattgtga    480
ataatgctgc cgcgaacatg tttaagtcct tgctttcact tttttgtgta tacacccaga    540
agttgaaatg ctggattata tgtaattcta tttttaatat gagtgactgc catactgttt    600
tctatagtgg ctgtaccgtt ttacgttccc actaagagaa catgagtgtt ccagtttcac    660
catatcctca ccaacactta ttttctgttt tgttggtggt agccatccta ctggatgtaa    720
actttattca tttttcgaac ctttttaata tggaattttc aaacacacac aaaagatgag    780
agatctccag gtacccacca caagctttaa taatgattaa catttggtag caggtggaca    840
aagatatacc ttctctatag cagctataag atcagggaca aacaaagatc tatttggaac    900
tccaactaag aatggtgttt tgtaggctgc ctgatgaata aggttagata actaatggcc    960
agtctttcag cctgtgctca agggatagga taacaataaa gcatagttgg tgaaggagca   1020
gcagataaag gtcacaatag ataggccata agagaaccct cactatcact taccattcag   1080
accattcgct tcatattcta acaagttatt ttcctttcat aaaaggaagc tgaagctttt   1140
atttgtgttt gtggtgcatg tgatccatga gaggggactc aaccaggtgc tatgtgtgag   1200
tagtacttaa tccgacagta ttagtgggct ggtgggcttt cctggttaca tgggaaccct   1260
agaaacccaa gccaagcaca aaagccaaga ctgaattctc cagtaagtca cctggtagcc   1320
ttgacatgct catgcttaaa aaagagccag tgacctatta ataggaagct cctgaaatga   1380
gtcctctgaa catctgcaag tatggtcagc tacacctgag ctgagacttg cctgtttccc   1440
tgccaggaaa tcatgggctc agaaa                                         1465
```

```
<210> SEQ ID NO 317
<211> LENGTH: 1399
<212> TYPE: DNA
<213> ORGANISM: Homo sapiens

<400> SEQUENCE: 317

gtgcccagct agttccattc ttttcagata aattttttca aatcctctag aaacaggtaa     60
tatttgtgct ttttaaacag ttcagaatac acacaaaata taaaatgttt ctaatattta    120
ttatatatct aacatattga taatctaata gaattccaga ttcctaaagg atttctgtat    180
aagcactgag agataacctg tcttagccat tgctagtcag aaccaaagaa aataccatga    240
agattctgag gtcttccacc aaaaaaagtt tcttaaaaga aatggaggca tgaaggcagt    300
caggtaatga cagcaatgac agaatgagaa aagtactgca acagttcaaa aaactgcttt    360
ttcttcctgg ttctgctaca taattcaaga taactttaac cacctctctg ggcccaatt     420
tctttacatt gcaaagaagt tatggaccct ttaatactca gttccacaaa ttctgactca    480
gagggttcag tgagaactcc aataattggg aggcaataaa ctcactggat agctttgagt    540
aagacgactt ttggtgtgcc tgtcagttca tatcctccta taaagtctct aacctcaacc    600
catcccaacc acaggcctgg gggcctgtag ctatgtatta tggatccttt taggaaaaag    660
tatcttgcta gtcacaacta tgttctccct tgaagaaaaa tgagcaggtg aagctgctgt    720
tcagacagaa tgaagcggat gtgcaaaggg accacagaca accatcacgg taggaaatac    780
```

-continued

```
cgcttgcttt actgctgaat ctccagtgcc tagatcagtg cctggcccta gcaggttttc    840
atcaaataat tattgaagga ccactgaatt tcattccctc atgtggtttc catgagatac    900
ttctgtattt ctctaatcat tcaattattc ctccccctta agctagcaca agtttctttc    960
ttacaaccag aaagcccttc caaatacatt atgatattct ccccttcata gccaccactt   1020
acttcactac aggtatatgt cagacctcag gaaagacacc accgaagact ggatcacatg   1080
tccccactca ggaatacaga attggcacat gagattaggt cagttggtca gcagcactaa   1140
aggtggtgat agacaccaat gcagcgcata aaggctggcc ggcaggcgaa gtgataagaa   1200
agcagacaca aacaggaaag tagacaatgg tggttctgag acatccctat attttcctgc   1260
tatggactga atgtttgtgt ctcccacacc cccattcata tgttgaaatg ctaacatcca   1320
acagtatttc gaggtggggc ctttgagagg caactagttc ataaatgtgg agccctcatg   1380
atgggattag cgctcttga                                                1399
```

```
<210> SEQ ID NO 318
<211> LENGTH: 1332
<212> TYPE: DNA
<213> ORGANISM: Homo sapiens

<400> SEQUENCE: 318

tgcacatgct cactgaaaga cagatgtgat cattttcata gtaactttat tcataatgac     60
cacaagctgg aaacaaccta aatttctatc aacggtagaa tgggtaagtt gtgatgtagt    120
cacacaatgg aatactacac agaagtaaaa catgaactgc tactacatat aacatggatt    180
actctcacag atacaatgtt gaacaagaca cggaagagtg catataatta tttcacttac    240
ataaagtttt aaaacaggca aaactaatcc gtggtgataa aaggggttgg tgggggcctg    300
gggaacataa ggacacctac tgaagtgcta gaaatattct atattttgac ctgggtggtg    360
cattcaaggg catatataaa aacccactga ggtgtacact taatatcggt acacttttaa    420
attttacctc agtaacaagt tgaaaatata ttggaagaaa gcatataaat gaagatgtta    480
atcagtggtg ttgtcttcca aatatttctg gtttttctcc caggtatatg caaggatcac    540
actcctccta gaactttaat gtggctatgt gatttgcttt ggccaatgaa agtcctttaa    600
gagtccttaa gtgatttgcc atactctttt ttcatttccc aaagttagca cccacactcc    660
tgatggtatc tgctttgtca gcctgagacc cagaatgaag gcaacttaga gcacaaattg    720
gtgaactttc tctgtaaagg gccacagaat aagtatttta ggttttgtga gatgtacaca    780
ctctgtagca actactcagc tgtgccattg tagaaccaaa gtagccacag ataataaata    840
aatggacaag gctatattcc agtaaaactt tatttagata aataaggagc tagacagatt    900
ttgcccatgg accatagttt gatcatggcc aacctatgat ctaaaccaaa gtccctaggc    960
aagttgcaat agaaaagttg tgtgagacag tgagattttg cctttgttat tcaatggcaa   1020
gctagcccat gctgacacag aaattggtcc cttgtttttt aaaatgctaa aatactgaac   1080
actggcttaa tggttagctg gcaggcattc aggaaattgc tatcagaaga tggaagaaat   1140
aacttacaca agggtaattt atattatgga aaggtgaaac tgccccttga gataacctga   1200
aaggcagatc atctaccctt tactaaagaa aaagacagaa aaacaaaata ttttgtagtt   1260
gctgttcact gcacttgaca aaacgtacag aagagatgaa ctcagaaaag actggtcagt   1320
ttgcaggcaa aa                                                        1332

<210> SEQ ID NO 319
<211> LENGTH: 4336
```

<212> TYPE: DNA
<213> ORGANISM: Homo sapiens

<400> SEQUENCE: 319
cagcaagcac caaatcactg gatgactatg acacctactg ttaagatctc tgaatgactt 60
aatatgcctc agactaaaac tccaactaag attatactag ttaatcccat aaattggtca 120
aaatggctta aggaaacaga ctaagggtgt ggctttccca cctaagcctg aaaagcctca 180
gttacccaga aattaagttc agagaggcat gggaacaaga aggcaaagga atacagcaaa 240
ctttagaagt atacattaac tagatgtcac ttttgggtca tctccctttg ggtgataagg 300
acattctgca ggtgtaaaaa caagtgaact gaatatatag tgaccagaag ggctgagtca 360
gtcttctact ttgttaaatt tacttacttt taaatcccag aagagccaaa aatcatctgt 420
aaaggaaagt agcaagtaaa tagcatgcca ttttctccta gtgttgatgc ctacaaaagg 480
aaaaatgatt attaactctt aggcggcatt atctttttcc aatactaaat gtaacattta 540
gtaaaaacat attgttttag ttcactaagt agttgtctaa tcttttccct ctatatgtag 600
gttcctttgg aaatttaaaa aaaaaaaaaa aatatatata tatatatgac actgtttaca 660
aagggtaaaa aaaaataaga ttctatacat ggatatgcaa acttaatatt acatagtgga 720
tttggtgtgt atatttggtt ttgaatcctg agtttactac ttactgtgtt taccagggaa 780
aaccgcaatt tgttatcctt ctctcctttc atacaacaga gaaaaccaca atttgtttaa 840
cagtcacata atacatattt aagtcacatg ctaagcacta cactaaattc tgagaataca 900
acgaggtccc tagttacaaa gaacttgtct tcatttttca attagtaata tgtggataaa 960
agttacccaa tggacagtct aaggcagaat gactgtgaag gtcaaataag actgtgaaag 1020
agcttcaaaa attgtaaaac actacacaaa tattcgtttg tccaaacatt tattgaaatg 1080
ccaggcattg tgctaagcac tagagatata acagtgaaca aggcttatat ggtccctgcc 1140
cttacaaagc ttacagtcta gcagtgatca ataagcagta acaataaagt gtgccaagtg 1200
tatgtctggg aaagaacagg gtgtataggg aatggatagt aagggcacct aatctagagg 1260
gcatcaatga aggtttccta gatgaagtgg catactgaga ccttaaagat gaagataaat 1320
ttgtattgta ccctaagagc aatggtgaaa gcaatgcagt gacatgatca gtaagtcttt 1380
tggagcaatt tggttgtagt gtagaaagga ataaaaataa aaaacaggga gactaataag 1440
gaggctgttg ctataattta ggtaggttga tggcctgaat taaaatggca gcattggaga 1500
attggtaaaa aggacaaatg aatggttggt agtggtaatg ccatttagtc aaagaggaaa 1560
catgagagga ggagcaggat tgggggcaag atcaatgaca tgtagtgcct gagacagcaa 1620
agagcatttg ttagcaatta gatacatcaa ttagggaaga tctagaaagg agatatgaat 1680
ctgacagtca tttgcatata aatggtaagg aaaccatgga aggaaatgag atcagctagc 1740
gagctgacac agaacaaggc agtctaaaac aaattttttt aaaaatacga agaacagata 1800
ttgaagggaa gaggtgcctg caaagactaa gaaagcacac ctggagatgg tatctcctca 1860
aagctaaagt catcaagtgt tcaagtgttt caaggagggt aagactatta acaaggactt 1920
agcatagtag agcaatttga gtggcaatac gggacactgg gaatacaaat ctgtcaagaa 1980
aactagtagg aatgagctat aggacagtaa ctggtaagga cctaataatt tttttttaa 2040 tgtacgtatt ttaactatat tcactgctac aacaggacca gtaacaacta tatttattta 2100
aaaaaaaaaa gactgccatg cagttacaga attacttaat acagaaaaca gtaaaataca 2160 ctttttttctt tttcttttt ttttttttt tttacaaaca agactagctt atagcaaatt 2220

```
ctctatagct aagggtcaat ttaaaatcct tggcttatat ctccccctca ctcaatgact   2280
acatgatgca aactaatttt attaacacct taagcaaaac atactggaat ttcacaaaat   2340
gtacaagatt tcaatattta aggaactggg gttagaaagc agaagtggct ttcaggtctt   2400
ccagtctttc tctcaagtaa taaagctctg ctgtgaatat tcaaagctat tgggaaatta   2460
ccggtagatt tttctgtttt ttttttttcgg ttttccacta tgttgtttct ctagatatgt   2520
aagcttactc tattaaccaa aatctcagct tgaccattct tgataagtac ctaatcgaca   2580
tgtaactttt tttctgcctt aaatatgtat aacaggacag agcccttaaa tctgattcaa   2640
ttattaattc ctgatttaca agtgctatgg tgagctaaca gaacttatca atgcctttat   2700
tgcactttac tagccaaatt tagaaggttg gaattagtct ctcctatcta gtattctgtc   2760
agtttgccca gcttgtactt ttaattttgc ttctaatggt aatctgccct atcccttgaa   2820
ataaaataat ctacattttg ggagggctaa ttcttcattg tgccaggctg tcccatgcac   2880
tgcaggggtg agtgtcttta ggcttaaatg ccaacagaag cccctagtaa atatgacaac   2940
caaaaaagtg cccctacaca tttctcagca tcctctggaa tgacaggtta ctgcctctag   3000
ttgaaagcca ctggcacaac tttggttttt aagctcttat gccatttatt ttaattgccc   3060
agacatcaat tccacctaaa ttcttagtca tagcctggtt ccttgaattt gctggattag   3120
taaccacaga ttaaggtgtt tcaatagtta agacaggact ttggaacaag agtttttaaa   3180
ttgtataata cttgagagga tctatgaata taaattgggt cctgtttata attagtttta   3240
cataatgaac tttaagattg ccttttcatg gtgaacagaa gtttggaaat tactgttttg   3300
gcacaaagca gattatctta gtagaaatac agaattactg caatctgtga ataagactgc   3360
ttttaaatat ttctacttgt gtgctatctt acatatagaa tgtgtacgac agttccaaat   3420
tttagaataa atccatttct agcatctaac aaaatctgat actgtatcat tttaaaacaa   3480
agtgtttact ttaggcagga ttttttaaaa taaagcagca atacccacgc agataagaca   3540
aaaaagctaa aatatctcac acctcctaat cctggagtgc aatctttttt cctcatcgtt   3600
tttgataggg ccaaacttgt gtctacagta aaaaaaaaaa aaaaaagaat tactaactgg   3660
caaccattaa gattctatac ttaccatagt cctttaatag gcaagctgat aaaatagccc   3720
ccagttatta aaaaaaaaat ccaaggaaaa cccccaataa ttagtcttat ctccaaattg   3780
catgaagtct cctatatctg aaacttaaaa atgattctaa tgacttcctc tatcagtaat   3840
gtgttatcac tgaggtgggt gatggggagg gaagagggaa gaaatctgtc agtattacct   3900
tcgaactcag aaatgtttaa aaaaaagtct caaacatttt gatggttaga caaaacacct   3960
ccactgttat gtatgggctt ccttttttgga aacttatgaa cttgctatgt gagcttctgc   4020
aaattggttc aaaagcacat ttaaggagtt gataatttaa gactatatga atcagaattt   4080
taacactcca ttaaaataag agctgaaatt tttggcattt atcttcagaa cacctaaaaa   4140
acagactgca aattcaactc acattaatac taaatctctt taaaattaac tatatcataa   4200
aagacaatga ctttgtcact aaactaagtt ttaaaaaagg tggcattctc atgtttcagt   4260
cccatgctgc catttgagat gaaaaaaaag gcaactgtca gaattttaat tgtgatcagt   4320
ttggacggct ggtact                                                   4336
```

<210> SEQ ID NO 320
<211> LENGTH: 1612
<212> TYPE: DNA
<213> ORGANISM: Homo sapiens

<400> SEQUENCE: 320

```
cctggccaga aaattcattg acttcctaaa gatttattaa ctttctgcat tacttttttt     60
tttcccctcc atcgtaaata taaaagggaa tagtagagaa aatcattcag aattttattt    120
tttagtgaca ttatttagtg acattttatt agagtcactt aggaacctga ggctgaataa    180
agttcaggta aaagtaaaat tagttgagaa gagacatctg ccaaaagaaa tctattttta    240
acttcacttg ctgtctttcc tagaggaaca gaaatagtgc tgaatgtcct attagaaatg    300
atggttgctc tgcccgtctc ttccctctct ctcacacaat atgtaaactc atacagtgta    360
tgagcctgta agacaaagga aaaacacgtt aatgaggcac tattgtttgt atttggagtt    420
tgttatcatt gcttggctca tattaaaata tgtacattag agtagttgca gactgataaa    480
ttattttctg tttgatttgc cagtttagat gcaaaatcca caagtattca agtgattgtt    540
aaagagggag gcctgaagtt gattcagatc caagacaatg gcaccgggat cagggtaagt    600
aaaacctcaa agtagcagga tgtttgtgcg cttcatggaa gagtcaggac ctttctctgt    660
tctggaaact aggcttttgc agatgggatt ttttcactga aaaattcaac accaacaata    720
aatatttatt gagtacctat tatttgctgg gcactgttca ggggatgtgt cagtgaataa    780
aatagattaa aatctattct cttctgatgc ttacattata gtggtgggag acaaaatggg    840
tataataaat attatattag atagcattaa gtgctgtgga gaaaactaaa gcagggagga    900
agataggagt gtgcaagcca gaaaggttgc aattaaattg agtagttcag gaaggcttca    960
atatggatgt gatatttgag agaccggtgg aagtcaagga gcaagttgtg aggctattta   1020
aaggtattct tggcttacag aacaatatac gcaaagacta ttaaatggaa gcatacctga   1080
catgttaaag gactatcaag gaggccagtt tgtctagagg ctgaaaagga aagagtaata   1140
ggagatgagg tctgagtgaa aacacgtaaa tccttgtggg ccaaggtaaa atctttagct   1200
ttttttctga atatggtggg atactgttag agggttttaa gcagaggtta cgtggtgtgg   1260
tgagtttttt ttttttaatc ctttgtcttt ctgtgtggaa aatagcagga cagggcagaa   1320
gcagtctgtc ctgcagactg cttggtcgca gtagagatgt aagaagcagt gagattctgg   1380
gttaattatg gaggcaaagt tctcagaatt tgctgatata gggtatgaga gaaagaggaa   1440
tcaggaatga tttcaaggtt ttggtctgct aaatggaagg agttgccatt tactaagatg   1500
ggaaagacta tgaaagaagc agattttcag agagatcaga agttcatttt ggggcatgtt   1560
caatttaaga tgcctgttag ttggatgttt atgtgagttt ggaatgcagg gt           1612
```

<210> SEQ ID NO 321
<211> LENGTH: 831
<212> TYPE: DNA
<213> ORGANISM: Homo sapiens

<400> SEQUENCE: 321

```
gcagtccttt gaggatttag ccagtatttc tacctatggc tttcgaggtg aggtaagcta     60
aagattcaag aaatgtgtaa aatatcctcc tgtgatgaca ttgtctgtca tttgttagta    120
tgtatttctc aacatagata aataaggttt ggtacctttt acttgttaaa tgtatgcaaa    180
tctgagcaaa cttaatgaac tttaactttc aaagactgag aattgttcat aaataaacta    240
ttttacctgc agagacctct gatatatgtt tcttgatgga agtacccagt accacctatg    300
aagttttctt gtcaaaaaat caaatgtgaa tctgatcatt acttagatct aagtaccaat    360
atatgaaaaa tataggagac aaggaagcat ggtaaatgat actgagattg ggagactaca    420
tggaaaaaga cttgttccct tcaacagata gacagcaggg aaaaaagaat agagaaagga    480
```

-continued

```
gtaaagaacc tgtagattaa aagacattta agggacatat gaaccaggtc cagtgtatag    540

atcttaccta aatcctgatg gagcaaacta taaaaaaatt tttttgagac aaatgtttga    600

atacaggttg actatttgat ggcattaagg agaaattatg aattatcttg gtataagaat    660

attgtcatgg gttttttttt ttgagtcctt acctgttaag atacatacta aaatatttgt    720

gggtaaaatt atatgacgta taggagtata tgatttagaa aacggattaa aatataaaag    780

gataaaatag gatcttatat tttgtgactc acttcctgtt ggatatcttt c             831
```

<210> SEQ ID NO 322
<211> LENGTH: 997
<212> TYPE: DNA
<213> ORGANISM: Homo sapiens

<400> SEQUENCE: 322

```
tggccttgtt taaggtcctg atgagtattc ttataggtac actgtgtttc gtttaattat     60

ttccttagga taaatttata gaaataacat tccttggtaa aagaatacat attttaaaaa    120

ctgtattagt ttcctgttgc tgtcaaaaaa tttccagaaa cttagtggca ttaaacaata    180

caaattaatt attctacagt tctggagatc agaagatacg ggtcttacta ggcctcacta    240

ggctaaaatc aaggttttgg cagggctgtg ttcctctatg gaggttccaa gggaccagag    300

aaactacttt acagtagtta ttttaaggga atgaaagtga agatggggtt gggcagtcaa    360

agaggctgtt acttttcatt tttggccttt cagtagtttg aatttttttta tcatatacat    420

gtattacttt aatttttaaa aagtaaaaag cagctgtgat tcagtctctg taatttagat    480

caatttacat caaactaggg tggtctcatg tgttgtcttg ctcacagtga ccactagatt    540

attccaagaa gggacaattt ccaagacttg gtttacactg agacggctcc tgattttaag    600

gataccttag atcaaactct aggaaggcag tttcattttg gccttgcagt tccctgggtc    660

attttccaag cccatggcct cctggagtct tcgcctagct gtaggttatc tttgtggcta    720

ttatttcact gtaattatac aggaagattt attgagggat ttctgtgtac cagccgtggt    780

tctcagcact ttgtatactt tgtattaact ctgactcctg acagtaactc tacagaggtt    840

ctgctgttac ccagttttac atagaaacat ggccagcgga cgcagttaga aaatggcaaa    900

gtggggatta gaaactaggc agtttgactc cagagtctgt gcccctgtcc acttggctcc    960

actgctgggg aagaggcctc tgaagcagca ggaccat                             997
```

<210> SEQ ID NO 323
<211> LENGTH: 1165
<212> TYPE: DNA
<213> ORGANISM: Homo sapiens

<400> SEQUENCE: 323

```
accccgtcat agcacagttc ctgagttaca tctttacata ctgtagtatc cttcttgtga     60

aaaaagatac agattccaaa ggtctgagaa accaatcttg gttataaagg ggaaaaatgg    120

tcatgggttt ttaaaatttg ttttgtctta attgcatttc aaatttacat ttctaaatga    180

ataattgctt atataaagca gttttgatta acaatataaa acactatcta tttggagtga    240

ttcctttacc catttctgaa ggcaagtttt aaaaattact agaagacact tcattgagaa    300

tattattaaa catgcctata gttctaccac ctcaacacaa ttgcttatta acacattaat    360

gttttggtgt gttttggact ttttaatatg tatttttcac ttgttctagt aattatgcta    420

cagattgatc atttcttttt caacatgtca tcaaagcaag tgagcaaagt gctcatcgtt    480

gccacatatt aatacaaaat ggaagcagca gttcagataa cctttccctt tggtgaggtg    540
```

acagtgggtg acccagcagt gagtttttct ttcagtctat tttcttttct tccttaggct 600
ttggccagca taagccatgt ggctcatgtt actattacaa cgaaaacagc tgatggaaag 660
tgtgcataca ggtatagtgc tgacttcttt tactcatata tattcattct gaaatgtatt 720
ttttgcctag gtctcagagt aatcctgtct caacaccagt gttatctttt ttggcagaga 780
tcttgagtac gttttctttt ctccttattg ataaattgat aatcctcaag gatgattatt 840
aggtgatact cttacttcat ggattcttaa aagatatgat ttaacatatt acaagtgcct 900
agcaaggtgt ctgttacacg taggtatttt aagtaaatgg tagctgctga tgtaatttct 960
gcccctttgc ccttcagttg gggtattgct ttggaccgat tagagggctg tggctgggat 1020
gctaaaggtt catgtttcct tagctggctc ctgagccacc agctcccacc acctgtgtat 1080
acctgtgcta gtttgccttc ccacaagtag ctgctggcta tctgttatgc tggtacagtt 1140
ttcagaaact gatgaatggc ctttg 1165

<210> SEQ ID NO 324
<211> LENGTH: 1275
<212> TYPE: DNA
<213> ORGANISM: Homo sapiens

<400> SEQUENCE: 324
gtggcgtgat atccttgatt ctatcagcaa cctataaaag tagagaggag tctgtgtttt 60
gattcagtca cctttagcat ttttatttcc atgaagtttc tgctggttta tttttctgtg 120
ggtaaaatat taataggctg tatggagata tttttcttta tatgtacctt tgtttagatt 180
actcaactcc actaatttat ttaactaaaa gggggctctg acatctagtg tgtgtttttg 240
gcaactcttt tcttactctt ttgtttttct tttccaggta ttcagtacac aatgcaggca 300
ttagtttctc agttaaaaaa gtaagttctt ggtttatggg ggatggtttt gttttatgaa 360
aagaaaaaag gggattttta atagtttgct ggtggagata aggttatgat gtttcagtct 420
cagccatgag acaataaatc cttgtgtctt ctgctgtttg tttatcagca aggagagaca 480
gtagctgatg ttaggacact acccaatgcc tcaaccgtgg acaatattcg ctccatcttt 540
ggaaatgctg ttagtcggta tgtcgataac ctatataaaa aaatctttta catttattat 600
cttggtttat cattccatca cattattttg gaacctttca agatattatg tgtgttaaga 660
gtttgcttta gtcaaataca caggcttgtt ttatgcttca gatttgttaa tggagttctt 720
atttcacgta atcaacactt tctaggtgta tgtaatctcc tagattctgt ggcgtgaatc 780
atgtgttctt tcaaggtctt agtcttgaaa atatttatag tgtagtagaa ctattttatc 840
ctccaatgct ccttcttttc cttgtatttc cattatcatc actttaggat ttcacttatt 900
tatcattcaa catttattaa ttgcctctca tattccaggc tttgtgctag aagttaggga 960
tataaagaca aataagatat ttcctgccct taaagactag attcgtgttg ctaagtcttc 1020
attatcaaga aaagcataag tggggaaaag tgcttgcatt atggattcct catagttgct 1080
cccctctgca tgtaaaaatc accatttcca tcatagattc ctagcggtct caggacttta 1140
taaagcccaa agtgcctatg tcataaatatg aggaaaaata ctgagaccct tccatatatg 1200
ggaggtatat ggatgagaca gctcctgact tcacttttcc cagaaatctg aaaagcagca 1260
gcagtcattc cagag 1275

<210> SEQ ID NO 325
<211> LENGTH: 3164
<212> TYPE: DNA

<213> ORGANISM: Homo sapiens

<400> SEQUENCE: 325
tgtgctagat gcctcactgg aaaaataaag gacatgatgg aaaactctgt agggtcagag 60
aaagggatca ttagagaagg ttctttgaag aaatattttt tgaaatatga aggataaata 120
ggaattaact aggtaccaat aggttaggag tagagctttc cagacagagg gactagttct 180
tgggaaggtc tccagacaga aataagtgtg gcttgtctga ggacctctta ttcgcctatt 240
aaccttccct ccccagtaaa cactcctggg aacaacacac attgtagaac cacgttgtgg 300
tgctgttcag tatagcaagt aattcagcag agataagttc ttggaatctc atctttggga 360
tttagttact aagatacatt caagtttgag caaaataagg tctcagagct tggattcatt 420
gttctgttcc agcaattaga gcagtacctg gcacatagca caagtgcttg aaaacactga 480
ctgagtaggg taggtgggtg agtgggtggg tgggtgggtg ggtggatgga tggatgggag 540
gatgggtggg tgaatgggtg aacagacaaa tggatggatg aatggacagg cacaggagga 600
cctcaaatgg accaagtctt cggggccctc atttcacaaa gttagtttat gggaaggaac 660
cttgtgtttt taaattctga ttcttttgta atgtttgagt tttgagtatt ttcaaaagct 720
tcagaatctc ttttctaata gagaactgat agaaattgga tgtgaggata aaaccctagc 780
cttcaaaatg aatggttaca tatccaatgc aaactactca gtgaagaagt gcatcttctt 840
actcttcatc aaccgtaagt taaaaagaac cacatgggaa atccactcac aggaaacacc 900
cacagggaat tttatgggac catggaaaaa tttctgatcc ataggtttga ttaaacatgg 960
agaaacctca tggcaaagtt tggttttatt gggaagcatg tataattttt gtcctaagtc 1020
tgtgctcagc cctcccacat gtgctcattg ctggttgact gttggagtct ggttcttacc 1080
tctaagagga agcccaggag agggcataaa gccagcacac tgtcctcacc tgatggtgtc 1140
agagtcctta cgagtaagcc ctagccagaa cattgctgga agagatcaag ggccactgtt 1200
tgaaattgca cagcaggata cggaaaaggg gtaccttagg tataggcatt gtcattaaag 1260
aaattgctaa gatacttgag attttcctgt ttaaggaatg agctttatga tacaaagagc 1320
agttctaaaa attagggagg gaattaacta aattaattag gatatttctc aaattccttt 1380
acagtttttg tctctctgct gatatagtgt ttacatgatt gttatttact aaacaaatgc 1440
tattttgtat tgtgctcctt ataacttaat tgtttattac aaggttttga tggtgaccta 1500
ccaacaacaa gtaatcccaa acacagtctg aattttttgt tttccatcca gaaataagat 1560
gaatctttcc atttccgtgt tttcagtttt catcattttt atcctatagg ttacttatct 1620
ttattttaaa gcatttcata ataattttat agtttttgtt ttgtttgctt gtttgctgtt 1680
ggaaatggaa tattccctcc ttccatttag actgctaacc agctgtaaat gtttcaaaat 1740
atgcatgttt tacagcagtt gttcaaagca atacaggaac agtaaggaca gagccagtca 1800
ttttacaacc acattctgtt aaactgatgt ctattagcag ggtttttcct attttattag 1860
gaaggactta cacctgatat ataacaaagc ttgttttaat caaggctcag aaaatgtttt 1920
tcattagttt ttttcctaac catgaagaat aactgctttg taacacacat gctggctata 1980
aagcagacaa aaaattcact gtaggtgctg cctgactggc ctctgtccgt gtttctgttg 2040
gggctgctta ccacagcctc tgcattatca ttagctagtg tgttcacaat accaagttcc 2100
cagtagcaaa gaaaggtcaa gctcttacgc atgccattca tttatctaca ctgtgcaggc 2160
gcactcaggt ggcagggaca aagaccactc ctttggcgca tctcaagttc agaattctca 2220
gtagaggggc tccagctgtc cttttgtcag gtgcccatgc ctgctccagg cctgtgtggt 2280
caggacacgt gttacagagt acagtgacat taatgatggg gccatggata tggtcagcac 2340
tcagaggatg ttagtctctt cattgataaa gtcacaacca cttttcctgt tggaaataaa 2400
aagatttgac gtatccttgt ctacagcaac acaggacaac agataatcag caggtcatct 2460
aaatctgttc agagagaaag gagagctgtt tcctgaaaat acatcttccc ctgattttag 2520
tcttattttt ttctgccttt attgctttct accctcttca aaccagcctc atttcctaaa 2580
ttaccttgaa tatgcattga cacttgtact gcctgaaatt ctggaaaact cagtatggct 2640
actccaccgt cagaacttcc tgagcaaagt tagttgctct ctcggctcac tgttttgttt 2700
tgttttgttt tcctgcctca ggtttatttg tacaaatagc acaggaggac cagccccatg 2760
cagatggtag cccaggggcg ggggtagggg gtcacaccag tccttctgtc ctcatgttgg 2820
cagagatatc tactctgaag cctttgtagg ggcctgggca cctttgggag cctgagctgg 2880
aactgaaggt ggagctgcag cctgggcctt ggtttgatcc ttggccttgg cctttggccg 2940
gcacagcctg agccccttgg caatacgggc acgagcacgc ttcccaagct tgggatgggc 3000
aatgtaggca agtcgatcga gcttgcggct gacacccttt gggatcttgg gcttaacctc 3060
cttgggcttt acgagggcct tgatagcctc ggcacgtgca ctcatggcct tggcattgtt 3120
ggcctgcatc ttctttaggc ccttcttgtt gtgcttcttg gcaa 3164

<210> SEQ ID NO 326
<211> LENGTH: 2468
<212> TYPE: DNA
<213> ORGANISM: Homo sapiens

<400> SEQUENCE: 326
cggaggctct actgttggac tgctgtccac tctggaactg cggaggctct actgttggac 60
agacctgggt taccagccgt gtgactagcc ttccctggcc tccatatccc cctcagtaat 120
gaaggaatgt gtcatcccca aatccaggga cagttacaag cagtcagtga acagaaagtg 180
tctggtacag gttctaagtg cttattattc taagtcactt cacttacctg agttctcagt 240
tttcctatct ataagataag caggttggat aaaatgttct ccaatatact cctggtcctg 300
agatgatgtg attgtgggca gccctttaat catggtgaag atgttcatca taagcacact 360
gaaactacaa aataggaata taaatatttt ctccattaaa ttatgctgga tcctagaagc 420
aaaaactgga actgtgaaac cctacttcac agaaaactta aaattcccaa gcagatgaat 480
gcttctcgga aggacactga cagttaccta cctggaaaga atctagatgg aggtggcatg 540
ggcactaagc ggtgagatta aacccagtta gggcagcccc accagccttg gaacccacac 600
atctggagat tgttgatgca gagagaaagg ttcctactgg tgagacctga aagggatatg 660
tggcaggtgg gaggaagaag ttctgtctgg aaaccaaccc ttgttcctcc gttattgatt 720
gactcctggt accaacatga gccctaggtc ttatagaggc cataagtccc tatgccttat 780
agtgcccatg gatgagatga ggccacacat gcccccagtg ggttaacatg tctagcgtgg 840
gtaaggctct tggagcacta tgatacacag gaaatgccca gtaactctta gttggtttga 900
tatctgttcc cattgctcac ttaagctcag tgccccttta ctgatccttt tattctgcct 960
ccctctgcac atgtgcattg agactcctat ctgagacaca cactgtgttg ggtgcccagg 1020
gatgcagcat agatgttgct gccttccaca gaagcgctca tggtctgcta gagaatatat 1080
cccatgggag agaaaaacag actcgggaga atatagcagg ggcccttgtc ctggactttg 1140
gcagttagga aagggaggga agagacatgg aggctgggac ccaaaggcta aataggaatt 1200

```
tgctgggcca aaggggaggg ggaatgaaaa gagtgtttct ggcagaggaa atggcaagga   1260
taaaggcctg gaggcgcaag agaatatgtg tttgaggatc tgaaagttga gtgcagtggg   1320
tccagtgttc tctaccctgg ctgccattag aattacctgg gaaactttta gaaaattcca   1380
gtgtctgggc cctccctaaa acaataaatc attcttgggt ggtggggtct gggcatcagg   1440
attgtttaaa accctcccca ggtactgtca tgtgcagctg gggttaagct gtgctggggt   1500
ctgagtatgg atctgttagg gcaagtggcg gtgatggagt tgaggctgca gaattcaggc   1560
caaatagaga ggttttcatc aggatattaa agagtttaga tttcaatttg gtgggaatgg   1620
atgggatctt atttgcattt tatgaagagc tccctggttg caatatcaga atggattgga   1680
gaggagcaag atggaagcct acagtgattt gggagaagtg gtgagggact tgagacacag   1740
gaagtagccc cattcactaa tagttgagta tgtagatttg ctaggacctg gaaatggttt   1800
ggctggtggg gagtgggaag aaaggcccaa agtgtgaaat gaagatggag agcacattgc   1860
ctagcccaga gtgattgcca tttgctctgt cccagttgag gtccaagggg ttggccagag   1920
atcatggagt ctgtggctcc atggggagaa gaacctctca gcatgcctcc ttgtcttatc   1980
ctgggttagt cagattcatt ttgttagatt acattttttt tccagtggaa ctctgcttaa   2040
gtcctgacca gtatgttttc agaaggatca gagggcctgc ccttgtccat tggtgcatga   2100
caccagcttg gtgggttcct tgctgctccc tgttttcata gggttatcag aataccttct   2160
ctccctgcca ccagcaggtc acactggctc ctgacttttt ggcccatgga accaccatct   2220
ttctgcttct tagattgtgc cttgtactcc actgatcatg gccagtacat cagaagccct   2280
ggtttgcagt gaatgcattt gatatggaaa tcaggaaccc tggggatacc actcatcata   2340
tttggttgct gtgtttttcc tccaatcttt caccataaca acaatcaact caaaagattt   2400
ctataaccac ttgtgtgggg gtttctcccc acacactaaa caagcagtca gttccagagt   2460
ggacagca                                                            2468
```

<210> SEQ ID NO 327
<211> LENGTH: 2826
<212> TYPE: DNA
<213> ORGANISM: Homo sapiens

<400> SEQUENCE: 327

```
acatcagaag ccctggtttg cagtgaatgc atttgatatg gaaatcagga accctgggga     60
taccactcat catatttggt tgctgtgttt ttcctccaat ctttcaccat aacaacaatc    120
aactcaaaag atttctataa ccacttgtgt gggggtttct ccccacacac taaacaagca    180
gtcagttcca gagtggacag cagctggtct cctccaattt aattccaaca ctgtctactt    240
ggagatagca ttagatccca caggttgagg gtgcagtccc ctagactgcc cccagtctcc    300
tgcttcagac accagtcaca agtccaggac tctagaagtt ctgaccagtt tcaagttggg    360
gttcccacaa ccccccactt tatttttgat taatttgctg gagtggctca tagaactcag    420
ggaaacactt agtttctgg acttattaca aagatttaaa aagataccaa taaatagcca    480
aataaagaga tatacagggc tagatctgga agggtctgga gcgcaggagc ttctgtcccc    540
atctacttgg ctcccagcag atggatgagt tcttattcat tttcttgtca gcttcgacat    600
gttcagctct ctggaagccc gcaaactctt gtcttcttgg gccttttatg gagacgtcgt    660
taggcaggca tgattgaaac atggacaact gtgtcgaaat atgattggac ataaaggggt    720
ctaaactcag tgaggcctgt ttgttcagat tcttcttggc ctctctgtgg ccattctttc    780
ctccaggata tggggcagga cccctatgga atgagggtct tatgacccac aatcaaatta    840
```

```
gagtcctgcc ttgggcaagt gaaaggaaag caggagaagg taagagaaat tctgttgcct    900
aagaccttct gaggcctaaa gcaccccaac attataacag aagacgataa caggactatg    960
ggagttatga gctgggaacc ttggacaaaa atatatacat attaaataaa tattaagtgt   1020
atatatatac ttacgtatat taagtgtatg tgtgtgtgtg tatatatata ttttttttaat   1080
ttactggttg gttttgggaa gcagaaatta ccataactac tcttaaaaat cttttaagtc   1140
tctttgaagt tagaaaagtc actgtacctt tttgtttcca ttggccctgt acttcttatt   1200
ataccccagc aggaggagca taatgtgttg ttatatcatt ctggtgataa gattcataag   1260
tgggttcagc tggtgacagc ctgattccct cattgtaaac ttatccatca acatgtagct   1320
taatcgtttc accttttgtg atgaccatta cctgaatcag ttatttcatt agattgcaag   1380
attatgcttt tctgatttta tcatttcttc tgtattgact gtaattcttt ggtatagaag   1440
aactttccct tgttaatagc tatttggttg tcctgaagta cagttcttac tagaaagtaa   1500
gaccaaatgc tgaattatat ccctctagct atcaattttc gaaggaatga atggtgtcct   1560
agtaatttcc agtggtgttt aattacgttt tcccttctct ttctccttct cttattccct   1620
ccctctccat ctcctccctc ctcactttca gtttttgct ctttcagtat tttgtcatag   1680
ctgttaacag agcaacatat tttaatcaat tgtagtcatt tttctttttg gtgctcaaat   1740
tatcccgtct tagtcccatg gaagcaagcc cttggagcta gggccctcta ccttttgatg   1800
gatttccatt tgtcttgata atttccttgt ttctgacaag acaagatgtt gcaggcacat   1860
tttatacttt cccagcccaa accctggaat aggccttttc tccgaggagc tctagttcat   1920
tttagtggga aatggtattt agagactata atctgggatc tgggagtcct cattgctact   1980
gagtagtcat tacttttagg cttttccagt ggtcagagct aggaaatatg tatatttaaa   2040
aatggacagt tgaatggttg ttgccaggag ctgggaggaa ggggaagtga gaaattgttt   2100
aatgggcaca gagtttcagt ttggggaaga tgaaaaagtt ctagagatag ctggtggtga   2160
tggttgcgca acaatgtaaa tgccactgag ctctcattta aaaatggtta aaatggtaaa   2220
ttttatatat attttaccac aataaaaaaa agtcttcttc tgggagcacc cccccaagac   2280
aaaaatatga aaattttaca ctgatacttc catttcaaga taattttaag attataagga   2340
ttttgcttaa ttcttgaatt ttatacctgt aaacctttta tacttcaaat ttcgggcaga   2400
attgcttcta taacaatgat aattatacct catactagct tctttcttag tactgctcca   2460
tttggggacc tgtatatcta tacttcttat tctgagtctc tccactatat atatatatat   2520
atatatatat tttttttttt tttttttttt aatacagact ttgctaccag gacttgctgg   2580
cccctctggg gagatggtta aatccacaac aagtctgacc tcgtcttcta cttctggaag   2640
tagtgataag gtctatgccc accagatggt tcgtacagat tcccgggaac agaagcttga   2700
tgcatttctg cagcctctga gcaaacccct gtccagtcag ccccaggcca ttgtcacaga   2760
ggataagaca gatatttcta gtggcagggc taggcagcaa gatgaggaga tgcttgaact   2820
cccagc                                                              2826
```

<210> SEQ ID NO 328
<211> LENGTH: 3843
<212> TYPE: DNA
<213> ORGANISM: Homo sapiens

<400> SEQUENCE: 328

```
tcggtctcag tcaccatttg tctaagcaaa ttcaggcagg cttcaccttg cctttctaca     60
```

-continued

```
tttgttccct tttcttagca ttttgggcct ttgtttacac gtgggaaaag acccacaggt    120
cgtctctccc tttgggcagg atacaggctt cctgtgactg aggttttgct agctgtagaa    180
gtggctgcca attggcttct ggtttttatt tccatgattt gctccagtgg ctcttccctt    240
ccatcattgt tagctttcaa gctaggaact tttaaaatgc ttttaaataa aagtgagctg    300
ttacttgatg catttagcag tcttcctcac agtggttttg atagacagac tccctcagtt    360
tggaatttat gagttttctt taagggtttg tctccctcat gtatagcagg ctgttgaaag    420
ttacaatgtc aataactttc tgaatagtat caaactgttt tcagtgcagt gtattaacaa    480
aactaacctg cctcaagttt ggtcagcttt ggagtcttac tgaggctaaa atgataaatc    540
taaatgattt aaaattgtgt attcctacac agtatctcac ttaattatgt aatagtcttg    600
tgagtgaggc agagcagatg ccgttttctc tattttaaag atgaggaaaa tggaatggaa    660
aatggaaagg acagactaat tgcaacatcc tcgcaatcaa aaacaggccc aggttcatgc    720
cttgttggca gtgggttgct actggctgtg gccttcatgc aggaaggcta gatgcataac    780
caggtcaaca gcccgtgcag gacaagcacg ccatgtaatt ctgattccat cgactgaggc    840
tggtgttttc aaacgtgctg gtgtagggtc ttacagacag agtcatctgt gctatgggga    900
atggaatgtg ctcttgcttt ggagccagaa ctcctctgaa gctcccacca cctacaccat    960
tcagaggcca gacagaaatt tgttcaccat tttgggcatg attttcgtgc ttttgtaaaa   1020
tgtgcttcac tgcagccctt actgggctgt ggtgatgaac acttaagata ctgtgtgtgt   1080
gctttataat ctgtaaggca ctgttcaagg ggagggacct ctgccatgag cccctaccca   1140
ctggtatctg gttgacatcc aaagccccag cctgggagaa gctgattctc tagttgaatg   1200
ctgtataggg atttgactga ggctcagatt tggtgaggaa gaccactaac cttaacagac   1260
caacaggctg gctactccct gatgaagttc cccaggccat gaaagaagta agagatacat   1320
tccttgtaac agctttctta gttgcacctg tatgattatt tgatcagtgt gttgtctgtg   1380
cagggatcat gtctgtggag ctcaccacct cgtcctcggt gctgagcaga gtgcctggca   1440
tgtgtactca gtagatattt gctaagggag cgagtcagtg attgagagga gcagcctggg   1500
aggtaaagcc ctagaatctt tattttaaag ggatatcaaa gttgaacatt cagttagaca   1560
gttctcttga gtccagggat ttacccatcc atggtggaca cactttcagt taaaaagtaa   1620
ggttaatttt gacaggttgc agtatccagg caagcattct atggaataag gctcatctca   1680
gggattagta atgactgaat taacttactg ctagtcccat aattttgacg ttaattaatg   1740
gggttaagaa atgtcataag ctatttggta ccatttaaag tgaaaatacc cttaacgttt   1800
tttgcctcca gatatccaca cttaatttca ttttcttgct ctttggtgaa cagtcctggg   1860
tctgaatgta tatatccatg gtttgtcact aggtgacagg ttttttgga acaagaaatc   1920
agttcagtga acatttgtca agtatcttct ctgtaaaaag tgtaatgtgc caagctcaga   1980
agtaggaagt gaaatggata aactatgacc cctgccttaa agaacaccat ggtgttgtat   2040
gggaattgtt taggtagaat gaaagaaatc ctctaataga gatatgaggc cagttcagca   2100
gaaagccagg gtgagatctc ctgagaggga tggaagggtg tcttgatcat ctctggtagc   2160
agcaaaggca ctggcataca gtggccactg gaagacaacc agcaggggat gggggcgttt   2220
acccttgcaa gtgagcatta ggaactagag gactgattgc cctttcttca gctttggttt   2280
cccttgctgc agaaaaagat gctgagactc atggcctcgg ttatgaactc agatatgtgg   2340
tttggctttg aagcacagat ggattttgtc cgattttggc agggaaatgc ctacagacag   2400
cactatgggc atatttaggt tagggacgaa atgcaagttg attaagtcct gataagaggc   2460
```

-continued

```
tgtgaagagg tccaagaagc ctcacaatgc ccaatgaaga aaagccctgt gcttggtgct   2520
gccgcctccc ttccccgtcc tgctggcagg gctgcgcttc agtagctctg gatgcgtcag   2580
agcagtccat gaacattctg tgtggaaaat ctctgactgt tttagtggat tacactgctc   2640
tccctttcct ccagtgcctc gttattcagt attatttgat gttctccagc ttttaaaata   2700
atcattttcc gcctacgcag aacatcctgt agagacgttg aggttccagt gggaacagag   2760
aggaatactt attctaaaaa tgaagaaaat aaaccttttt ttatggagtg ggtgatagta   2820
ttgcagaact tctataatag tatgagaatt cacttgtggt gccaaagctt aaaaaaaaag   2880
tatagtaaaa acataatgta taggcttatt gctgtgctat gacccatgcc ccgttttctc   2940
caacctctct tgtcctcact cttccttttt gctggtgata tttttactta tttcatgaaa   3000
aaaaagataa catatacaca cacatagata tatgcacaag tatatgtata tatgtgtgca   3060
taacacacat aaacatatac attggtaaat ttaaaaacat atttatgaaa tatatgtagc   3120
atctacagaa aaacatgaac acttgtgaga atagcatctg cctaaaaaat aggacatcac   3180
catcaccttt gaggctctta tgtgctgctc ccctgtgcca ttcccttccc ttcttcctta   3240
gaggtgatta ctattctaaa ttttgggatt attatttcct tttttttatta tagtgtttta   3300
attacagttt tattacctgt atttgtattc ctaaaaattt gtttactttt gcaagcttta   3360
gattttataa aagtagaatt acactgtaag tttaattttt ctgtaattta tatatagcta   3420
cacatatatt cctaagattc atccatcttg ttacatatag ctctggttta ccttttctgt   3480
ataatataga ttctgcttcg tgaatttaca gttcattcat tcttctgtta aaggacagtt   3540
ggaggactca tatggcctca gtctctgtgt ccccacatgc caccctgctt cccagcctca   3600
tatgagttga ttggtggcct ggcatactgg atgagaagct ctaggtcata tatttaagag   3660
agttattgct gggtcataaa atgacagatt gttttccaga ggggtcatat tgatttaaat   3720
tatcaccaac aattatattg tcagattttt accagtttgg tgattgtgaa acagtgtctg   3780
atggtagttt ttatttgcat tttcttggtt gaaataaagt tgtgtatttc agccaggtgc   3840
gtt                                                                 3843
```

<210> SEQ ID NO 329
<211> LENGTH: 4221
<212> TYPE: DNA
<213> ORGANISM: Homo sapiens

<400> SEQUENCE: 329

```
tgaacctgca atatctcaga ggtatgcctg tatctacttg ttctgtgata cttgttattg     60
tcagtttgtt tggatttacc acatattatt tgatcataat tctttcctgt agatgtttta    120
tggtctgcct aaacctttag tggggccttt gatggcttag tcctttcagg cttaagacaa    180
tagaagttta tttctcagag ttctaaaagc tgggaagtcc aagatcaagg caccgacaga    240
tttagtgtct agtgaaggcc cgcttcctca tacatggcac cttctagctg tatccttaca    300
tagtggaagg gaatagctag ctctctggag tttctttcat aagggctaat cccactaatc    360
ccaattatga gggaagacct aatcacctcc caaaggcccc acctcctaat agtatcacct    420
tgggggttag gatttaacat atgaattttg tggggacaca gacattcaaa caatagccat    480
ggcaaacttt tttgctttgt ctaattcact cttattttga aaagtatttg tgttgggttt    540
aaaactccag attggtaatt attttttctt agtgcattga aggtaatagt gtatcatttt    600
ctgatttcta ctcttgctct tgaaaattca gctatcaatc ttaaaattta ttacctgttg    660
```

-continued

```
aaaatccagc taccagtctt atattttatt tacttagtgg gtaatctctc ttctgagtac    720
ctttaagatc tcctttcaga aataccatgt agtaaccctg tgtgtcacgt gtggattttg    780
ttgggcttgc tagctgagac ttgacagttt tcatcacttc tgggatattc tcaggtattt    840
tgtcttcaaa gtcttcagat attgtcctct tcctgccctc tctccgactc cttctggaac    900
atgagttatg tatttattat ctcccatgtg cataagttat ctttacatat tttcaatttc    960
tttatctttc tgtgctacat tctggataat tttgttgatc taccttccag ttaattagct   1020
tgttaacttt gtcaaatctc tttttaagtc tatcttgatt tttcttttca attattgtat   1080
ttttcatttt taaaaacttt atgtgctctt ttggaaatct tgatcccagg agatagtgga   1140
tagtgtcctg ctgcttactc atggttttaa tagttcttga gcatgctgaa catacttatt   1200
ttatgttatt tgctaatctt tccaattcct gaaaccttta cagatctcat tctgtggatt   1260
cttctggatt ctaattcatg gggcattttt tttgtttttt gttaattcct catactttat   1320
ctgtggggaa ttacttgaag cctgggttga caatgaaatt ctgcagagag aatttgcatt   1380
tgattctact ggaggaacag tcagccccga tatcagttta aattaaaatc tctgcttaag   1440
gttttcaggc aacctgctta gcatgaatcc tggctggaaa agcatgtgag gaccagttta   1500
tgattacaca ttcacagggt gtcatgtttt cttccaacac caatgctaga ggtggcagtt   1560
ttgcttactg cccttggagg gacaggggag tgggcatggg catagtagta tggttttcct   1620
tttcactggg ggtgcagccc ttggagtctc agcttaatgt gttggggaag tggtctccta   1680
ttagactctc catttcaaac cattccatga ttttgtcctc cttttgccac cttccgagcc   1740
tgtaaaaact aatgtttgtg attcctgagg tttctctaat gtcttttaat aaagttgacc   1800
tcagagatct cgttacctct ctgagttcct gctttgtctt agattttgat ccttgagtgt   1860
tctttaatct tttagcaatt ccttgttgca tgttaaaaga ttagttatat tttattcctc   1920
atttgtgttc gttttcacca ggaggctcaa ttcaggcttc tttgcttact tggtgtctct   1980
agttctggtg cctggtgctt tggtcaatga agtggggttg gtaggattct attacttacc   2040
tgtttttttgg ttttattttt tgttttgcag ttctccggga gatgttgcat aaccactcct   2100
tcgtgggctg tgtgaatcct cagtgggcct tggcacagca tcaaaccaag ttataccttc   2160
tcaacaccac caagcttagg taaatcagct gagtgtgtga acaagcagag ctactacaac   2220
aatggtccag ggagcacagg cacaaaagct aaggagagca gcatgaggta gttgggaggg   2280
cacaggcttt ggagtcagac acatgtggtt tcaaatccaa gttcgaccat ttcccattta   2340
tttgactgta gacaagttac attcctaaac tatgtctcag atttctcatc tgtaagttgt   2400
ggtattacta gttaacatgc aggggttttg tttgtttgtt tgtttgtttg tttgtgaggg   2460
taagaaataa cccaagaagc ctagtccttg gtagttgctc agtgccctat aaatgttgtg   2520
aaccaggtgg tgagggtttg gtgctgctag agaattctgg tatctgctct gtgcaacaga   2580
gtactgtagg tgatgcaaga gaaagaagac ctgatgcctt ctttcctccc agctttgaga   2640
atggagcaaa ggcctacccc agccaccaag tgagccagtg ggcttgatca gcacaggaaa   2700
ggtgaccccg gcagtttcat ttgactattg catggctggc aacatttcta ttgattgttt   2760
ccagggacct tggcggatga gctcctgttg agtctagcat ctctgttaaa tctgttctca   2820
aataggtaat gcatatggga ggatgctgcc accttgcatc tactagacat cacctatcta   2880
ctgtgagact ctccctctaa gccctgctgt ggcctcagag tgcttattgg ccctgtgagt   2940
ggggcagcca ctatacattg catggagttg gtacatgaga tagaaaccta ttcgccatcc   3000
cttgaaactg ccccagtcca gaagcttcct gttagcacat gtacctcctt gtatgtattc   3060
```

agaactcatt ccatttaggc ttggaaaccc gtttggtgca actctgttca agttccattg 3120
tctgctttga gaatgcttgg gcttgtatag tgagctgtca ctttttaatt tgttaggaat 3180
tctactcgcc ttgcttttc ttttccagca tgtttaaggg aatgacctcc aaggccccaa 3240
atcacagttg tattcatgtt ctttcatttc acagatacaa tccaggccag tcccagattt 3300
gcagctgtta ataaatgtga atggttttcc agtaaggggg tagaaaaaca tagggagaga 3360
accgggttca gagttcaata tctggattca agtccttcct ttagcacttt actaactgat 3420
gtagaataag tcagctactc aataggtgcc tcagtttccc caccaaaatg cagacataga 3480
aggtgctttg tctgctttga tgagaagtct ttaagcaagt ctatggggtt caatgtgttt 3540
taagaactat aaagtaccat ataaatgtgg cctttattcc cattgtgttc ttggaagtaa 3600
ttcaatatag tgtgtacttc atagctgctt ttggactatt gccagccagt gtatcatcct 3660
aaactacatg tcagcatagt ataatcctgc cttaggtcta cttttgatta tttaggaaga 3720
ctccctgccc ttcctataca tttcacataa tttttaataa gttgtaaaaa agtgatttat 3780
aggattcttt gtaagtgggg gaagttaagc agacaaaaag tttttaaatc ttactgcaga 3840
gtgtcaggaa ccttttatag caccagacag gtagggacag aacatgagtg gcagcaagcc 3900
agacttggtc ttagtgctct aacctgtctg ttagaggctg gccagtcaga cccctggttg 3960
aagacgttgg gaatcccagc tctttggagg ggtaagagat tttgttagac tgttaaccag 4020
attccacagc caggcagaac tatttctgtc tcatccatgt ttcagggatt acttctccca 4080
ttttgtccca actggttgta tctcaagcat gaattcagct tttccttaaa gtcacttcat 4140 ttttatttc agtgaagaac tgttctacca gatactcatt tatgattttg ccaattttgg 4200
tgttctcagg ttatcggtaa g 4221

<210> SEQ ID NO 330
<211> LENGTH: 683
<212> TYPE: DNA
<213> ORGANISM: Homo sapiens

<400> SEQUENCE: 330
cccagcccat atattttaaa gctctgttat tgggtacata aacatttagg attgttatat 60
ccttttgata atggactctt ctattatgaa aagataatat actgtgggtt tataacatat 120
gtaaaagtat gagtaacata ttatcagaag gggagaaatg gaagataact taggcatctt 180
atttttaagc atagttttcc ctttgtttct gcattagatg atttacctga aatgtcattc 240
aatttaactt actctccatc ctcacccgcc cagctttggt tatgaggcag tagaaagaaa 300
tgatctgcct gtggttttct agaaatacga aagttgagtc cttaaggcta cacagaaaga 360
aagtacctcc ccagggcttc acccttccca tcctttcagc aggctttttg tctgtcgtat 420
cttctctgtt gaaatggcca ttgacaagag gaggaaaggg gttttgttgt ggattgttca 480
ggcacttcct ttggggtata tgggggatga gtgttacatt tatggtttct cacctgccat 540
tctgatagtg gattcttggg aattcaggct tcatttggat gctccgttaa agcttgctcc 600
ttcatgttct tgcttcttcc taggagccag caccgctctt tgaccttgcc atgcttgcct 660
tagatagtcc agagagtggc tgg 683

<210> SEQ ID NO 331
<211> LENGTH: 1799
<212> TYPE: DNA
<213> ORGANISM: Homo sapiens

<400> SEQUENCE: 331

```
gacatggaga gccgaatccc tgcaggccat tataaatgag attatgccat ttgctcccat      60
ttcttcttat tctttcattt ttggggctct ccatcttgat gtgttctttg gatcgtgaac     120
agatccaaag aaaaggttgt tctgccgtgc tgtttgtcag gatgaaaaac tcttttttaa     180
gtgtttaggt ctgcccccag tgcccagccc aatcaagtaa cgtggtcacc cagagtggca     240
gataggagca caaggcctgg gaaagcactg gagaaatggg atttgtttaa actatgacag     300
cattatttct tgttcccttg tcctttttcc tgcaagcagg aagggaacct gattggatta     360
ccccttctga ttgacaacta tgtgcccccct ttggagggac tgcctatctt cattcttcga    420
ctagccactg aggtcagtga tcaagcagat actaagcatt tcggtacatg catgtgtgct     480
ggagggaaag ggcaaatgac cacccttga tctggaatga taaagatgat aagggtggga      540
tagctgaagg cctgctctca tccccactaa tattcattcc cagcaatatt cagcagtccc     600
atttacagtt ttaacgccta aagtatcaca tttcgttttt tagctttaag tagtctgtga     660
tctccgttta gaatgagaat gtttaaattc gtacctattt tgaggtattg aatttctttg     720
gaccaggtga attgggacga agaaaaggaa tgttttgaaa gcctcagtaa agaatgcgct     780
atgttctatt ccatccggaa gcagtacata tctgaggagt cgaccctctc aggccagcag     840
gtacagtggt gatgcacact ggcaccccag gactaggaca ggacctcata caatctttag     900
gagatgaaac ttgcccatct ctaaaatttc gggatttctt tgtacccaac aaggttcaaa     960
cacaacagtc agcttttatt catgattttt acttccatct gctgatgtag aacatacctc    1020
cagagtgacc tcagaaattg tcaaatgtga aaacacaagc catcacagtg agaaatggga    1080
ggttgagtta gattgtctaa ggctggagag tccatatact cccactgtta gctctgaagt    1140
gtgtagccag tcttcagatt ctgggtcagt tgcctcagtc tctcttagct tttgccttac    1200
tctttatccg accactgccc tgccaggaaa acaaggctct ataactcctc ttacaggtca    1260
gcttgacaca aaaagggtgc ctggattcct aatgtttcat tgtcactttt cccagtcaga    1320
tgataatgct tttcaaatca acatatattt tgggggaggt tggaagggag agttgaaata    1380
ttctaagaat caaagagtag cccactttaa tcagagtatg acccctgatt gctcacagtc    1440
atctcctgag cagtgtgagc gagtttcaga tgaggaggct gaaggccagt caggcatgct    1500
cgaggattcc aagtctgtag gtgggagggc agagatttag tcctgttggc caaagcctct    1560
agggaatttc tcactccagt ggagaaggca acacacttac caaactgtgt ggaaactatc    1620
tcatttgatt agaaatttta cctcaagaag aggaaggaca gttgagaaag aacattttct    1680
tacacatgag acagctaagg cttacaagaa ggagaggaat aatgaggcaa aataatcctc    1740
attaatattt tcattcctcc cctggggatt agaactactt tcagacccga ttttaatgg     1799
```

<210> SEQ ID NO 332
<211> LENGTH: 545
<212> TYPE: DNA
<213> ORGANISM: Homo sapiens

<400> SEQUENCE: 332

```
tccagaccca gtgcacatcc catcagccag gacaccagtg tatgttggga tgcaaacagg      60
gaggcttatg acatctaatg tgttttccag agtgaagtgc ctggctccat tccaaactcc     120
tggaagtgga ctgtggaaca cattgtctat aaagccttgc gctcacacat tctgcctcct     180
aaacatttca cagaagatgg aaatatcctg cagcttgcta acctgcctga tctatacaaa     240
gtctttgaga ggtgttaaat atggttattt atgcactgtg ggatgtgttc ttctttctct     300
```

gtattccgat acaaagtgtt gtatcaaagt gtgatataca aagtgtacca acataagtgt 360
tggtagcact taagacttat acttgccttc tgatagtatt cctttataca cagtggattg 420
attataaata aatagatgtg tcttaacata atttcttatt taattttatt atgtatatat 480
tgtgtcagtt cagatgccaa aaagaggtct tgaacatgtc acaggctctg atggcactga 540
ccatg 545

<210> SEQ ID NO 333
<211> LENGTH: 578
<212> TYPE: DNA
<213> ORGANISM: Homo sapiens

<400> SEQUENCE: 333
agcctcccaa agttaagtgc tgggattaca ggcatgagcc actgcggccg gcattaagta 60
tgagttttta agttagccca ctttgttaat gactatgagt actaatagct taagataaag 120
aagtttctag gtaatcttgt ttgaaggatg atgtaaaaat ataaatttaa actgtgagtg 180
acaaaataaa cttccttaat atttgcctac atttagagaa atggagcatt cagctcagaa 240
aggaagaatg tctgtggttt taaggtaaaa tccatattcc aagactcagt gaagaaagtt 300
cagtgataaa gaacagacta ctctcatctt atgaagaaat ggagcaattt cacttggaaa 360
gactaggaag acaaaatgtt acagacgtat ttgttgtgcc acaaaatagg caaggtcagt 420
tttgaacaat aagaactcca taaagtagac cagggcatct cagaagtgag gttccatgag 480
cccaggtggg gcacaggctg ggtgatcttg agtggagagg aagaggggtt ttctgagctt 540
caagagctgg gccacacagt gtgttggttt tagctggg 578

<210> SEQ ID NO 334
<211> LENGTH: 2355
<212> TYPE: DNA
<213> ORGANISM: Homo sapiens

<400> SEQUENCE: 334
tgccctcagc tactcactcc cacagtcata taccagatct catcattaga caattgtaat 60
ccctacacaa tttagttcca tgtatcctct ctctaaccac tattcctcat ctttccaggt 120
cattctctct agacccgaat tccaacaacc cttcaaccac actggtacca ctaatctaca 180
gattacatct tctttctact ataccttgat gtgttcctga atatctcccg aatcctcttc 240
atccagttta atttcaaggt ccatcattat aatcattttc ttacatactc cctcacctct 300
cctgccccat taatactgtc ctagtaaaat ctagctctct acccactcca tgcctgcccc 360
tatgctgctg taagtagcca gagaaacaca tataataaat gcattcacac aaaccttcta 420
acatatcata taatattgtc tgatgtcttc ctactagaat gcctctcagg caggaatttt 480
ttttttctaa actaatttat tcactgaaat atcccagtgc ctagaatagt gcatgttaaa 540
tagtagaatc tcactcaaca tttgttgaat gactgaatag gagttccaaa atagagaaca 600
cagcatatgg gaggggaaaa aaatcagtaa caaaatcatt caagaaattt tcccagaact 660
aaaggatggg agctcctaga attgacaggg gcccagcatc acacatgaaa acttcaaatc 720
acatgactat cttcaaatta caccagaatg ctagagagaa agagaatagg atacaagctt 780
ccacaaagag gagaaaaata gatcacaaat cagaaaagat cagaactcaa aatgttcatg 840
aaaactcaac agccatgctc gaagtcacag cacaatgaag aaatgtcctt ttaaaaaatc 900
ttaaggagaa ccatggcaac tcaggattct ctacccagcc aaactatttt aatcaagtga 960
gagggtagaa tgaagacatc ttcaggcctg caaggtcatg aaaaattaac aatccacaaa 1020
ccctcttctc aggaagctac tggaagatgt accaaaataa gagaataaat aaggagaaag 1080
gcatgagaca ccggaaaaag ggaacccaac ctaaatcaca tgcaaagaaa atctccagat 1140
gccaatgaag ggtgaccaca tctatgtacc gagagggcaa gtcactagtt tagaaaggga 1200
caagtcagat gcaccaagat tcaacaaact ggaactgaaa taacaccaga tgcatctgaa 1260
aatactgagt gggattaatc tactcttgga gattctgtgg ctaaattgat gatagaaaac 1320
caagcaaata caaagaaaaa ccataacatt aactttagag gaaactaata gttctgaggg 1380
agatgatcct agaatgcaac ctggctccac tgtgtgagta gtgtttagag ggtcctaatg 1440
acacaagcag gctggaatta cactgttcct ttattaggag gatataagag tggaaaataa 1500
gtatgtgtgt ggcagggaca aaggatgaaa aacagctaaa tcctcatctt ccataaaagg 1560
atgtcaatat agaatgcctg aagcagaaca atcaagatgc aacataagta tgttatacag 1620
agatacaagg acagtacaca agaatcagct aaaagtattt aacagaaatg gtcaggggcg 1680
aggtcagagg agccagggca ggggactgct gtgttcataa caagctttgt aaaaaactat 1740
atgactcctt aaactatgtg tccttaaaaa aatgttttaa gaacagaaaa taacaaagag 1800
gtaaaatatg aattatctat ccttcatatc tcacttgagt actgatgttt gaaagaagca 1860 tatttttta atgaacattt caattagcca gtattttacc atgtaacttt gttaaaatta 1920
tattacactc caataagaat gcctttacct gtgacagtag ttcttccttc tctccagcaa 1980
gttttcgtag ccttacatct aaaacaaatg aaaaagatca taaactaaat atgtgatgat 2040
atagtacata aacaattaaa aatttttcaa actcataaac agctaatatt atctgataaa 2100
ttacattact tacagctctg aatatctaaa gaaataaagg tgttaatagc attacagaaa 2160
agttcttaac tatctaaaaa gtatttccac acaactgata tttatcaggg caccaaatcc 2220
aacatttgtt ccccacagca gtgatttgcc acttaaagac aaacagaagt acaaaggagg 2280
tcatttcctt gtttcaagct ttcactagta gacagacaac tcaaatgtca agtgtgttcc 2340
taaaggctga gccct 2355

<210> SEQ ID NO 335
<211> LENGTH: 4683
<212> TYPE: DNA
<213> ORGANISM: Homo sapiens

<400> SEQUENCE: 335
gccagactct cgttccattc tccagatctc tcttgctcac ccagcatcct gttttattca 60
aagtgcccta caatcacatt tctggaatgc acattagaga atgtgcttac taactttcaa 120
aatgtttttc agtttgcttc acacttgtat ctctcactcc tctaagaagc ttacacatat 180
atgaaaacaa gatgaaaaac aaaaaaattg ttttttttta aaataaaagt gagctaatga 240
tacagtatct atctgtgcca tttttcttcc tctagagtag atttctttgt ggggtcaatg 300
gatgggtgac tttgatttct cagacagagg tgtcagcaac tttgtggttt cctggagaga 360
ggtgtcagat tctcaaaggg ttaaatttaa gaggtttaga ctttaagagt ctgggaagcc 420
ctgctctgga agtcatactt ctctgatatc tttttggtca tctgtttctt ggcttaagaa 480
atgtggtgga aaagaggtac agaaccctgg ggtaagcagt ggaacataaa accagatgtt 540
ccaaggatga gaaacttata acacacttga gaagtctcct gctagcctac tgctccccta 600
gcacaggtat actagactat ctctttgcag aacagtttgt agttaagtaa aaaccgatgt 660
gtataggccc atagtacttc catccacagg ccttacagtt acacttattg ccttacagtg 720

```
acccagatgc tgatttccca aggtcaagga tgtctgaaga caatgtgcca atgtgcccag    780
attcttctag ttaaggatct acttgagtct cagcccttat gctgtttttg ttttccaagc    840
tgggatatga aaaagcagaa aacccaatag ggtaacatta atccaagtca acatagcaac    900
cagtatctta cctaatggcc cttctcctgc tgactccaag acctgagcag cttcctgaga    960
cacaacagtg atggctccag ccactggttc atgactgaca tcaccattgg gagtgccatc   1020
ggggattata actaagccat gtttctgcag gggggaaaaa cccaccatca caaaaggccc   1080
gtatggaagc tgtaagctct gtgaggtcac tctgcaacaa tacatgtttg ctacaggtaa   1140
aacctggtta gaatcagtta catgaaatat agctctgtgt aagaaatagc ttcaacctac   1200
caaatctgga ttagagaata aacactgtag tttgtattta ggctaggaaa gatggcagga   1260
tgaaaggaag gaagatagag agtaaaacag tgagggacct gaattccagg ctaatgctaa   1320
catacctctc ccgtcttcac tgtctcctgc aggtcagcca gctcctctct gagcatatct   1380
cgctcattcc taaggcaggc aatgtattct ttctgtttct ctagggcctg gttttaggta   1440
aggtagcaag ggaaacaatg gcacagaaaa agagcaggtg aaaggtagca gagaagtacc   1500
taattcaaat aagcaaagat aaaggcataa aaagcaagaa agcagtcaaa agattggaaa   1560
caaacagtca gatatgggag gaaatacaga gttacatgga tatacatctc cagaagagac   1620
ttctcataga aactggttct catgcatcaa tttggcaaaa catgtttaat cacatcaagc   1680
agggaaataa atcttttcca gtcaatgaaa aaaataaaac aggaaaagga agataaagag   1740
agaagccaga gtaaaataaa gctttcctta ctgactgcct aagtgcattt ttatttggtg   1800
aacaaaaaaa accccacatt tcatgtttaa ctaaactagt ttattcaaga atacagttga   1860
ttttttaaaa aatagttctg gaataaaaat aactattata cataggtatt ttaatttaat   1920
attggctgta gatttttctc caagtagtgt ggcaaaatac tcaaatacca cttaattcaa   1980
aatagttaac ctccaaaagg attcaaagat caacttctga caacttaatt aaatataact   2040
gagactcatt tggctttctg ttatactccc aaaatgtgaa aaacaaaaat aaacactgac   2100
aaaataaata cagccaagct atgaagagtt acagaatatg gatttcagaa tcaggctttt   2160
gggttctggc acatacttgt cctatgcctc agtttcctca ctggaaaaac agaagggata   2220
atagcaccca tcccaagggc agaggcataa atcaaggtaa agcattgcct gtaatgccta   2280
gatagcaggg acagttcagg agaatcaggt tggtgatttc atttgtaaat tccctgccat   2340
ttccttaatc tcacaactgt cagctgagga caatgcagaa gcaggaacat actttggtca   2400
tcaatgaaaa ataaaatcta ctatgaaaaa ataaaatcta ttgtaaaaga aaataaccca   2460
gaattaaaaa tacacccaag gtaagtagtc tatgcaggaa tctgattact ggcctatttg   2520
aaaaagcctt tccccaaata tttttgttca tatatttaat gtcttctgtt agcattccca   2580
ttaatccaag aagttaaact atatcaggta actttcctct cagttcactg ggtttggaag   2640
tgggacagcg aattgctgag aaattgatag ctgaatagct gggcaattca aaaaatcatt   2700
ataatcctgt tttgcaacca aatagggagc aagtaaataa gggatgatag caactacgat   2760
ttgtatagca caaattatat ggcaggcact attttatata atttctctct tatacattat   2820
tttacatttg aaacctctac atatcctgtg aggtacttgt attatcccca tttaacagat   2880
cagaaaattg aggctcacag tggttatatt ttttcgccca aagtcacagt aagtggcaaa   2940
accagaaaat gaatctggtt gtttttgttt ccaaagccct taaatagttt tttaaatatc   3000
acagctctat gaaggccaca ttatattccc ttattgttag cccagatgat gctaggaaag   3060
```

gagtccatac ggcaaatcct actctttact tatccaaact gcaatgtcaa tatctgactt 3120
cttttcaaca atttacattc acactatatg atgtgtctca agtctgcctg tgaattaaca 3180
atgtgcattt ctagcaccat ctagctagtg ttaacactcc attatgttaa taattaataa 3240
taactgaaac attgggaaaa caaagcacaa caatactttc ccatgtgttg agtgtcactt 3300
tatggattag gtatttttgg ttactggtat ctgcatgcat agttatgtca tgtatcacca 3360
catataagtg ggtaaatgat cactgtcaca acatgctcta cataaacaac aacactgaat 3420
aaaaaagacc tctgaggaac aggccaattt gaaactagga attctagcaa atgatataca 3480
tgacatttgc tcttcttcca catcgtattg cactgggttt tatttttacc ttcggacttt 3540
ttaatttcct cttcccataa ttacagatga gaaaataaaa tacatcctgt aaattcaccc 3600
acttcaccac aaagtttgaa gactactaaa ataccttata attggatcaa atgtattcaa 3660
gctggatcta aaaccctctg tattacctga ccatataacc actacccttg tgtttgtgtg 3720
caacaatagc tcctacagta gatttttttt agggtaaaaa gtacacgctt gtagagttca 3780
aaataactct ttatccctga cctaacctca aatcctacca cccggaagcc aaaaggatgt 3840
gtataatggg ctgaactttt gggcaagggg ttaattctcc acataattgt actggggaac 3900
aaatatcttt ggtcagaatg gaagtgagtt tatgctgggc tatagagata cgcaagttct 3960
tcatacgcac ctattctata catgggctcc tggtgtttag aaccgcagtg gagctagagg 4020
caagaccact aatgaactga actttaacct gggaataatg gacatatttc ttcattaagt 4080
tactaaatgt aaatcttaaa aatgaagcta gagacaagta gttactgacc atactgaaaa 4140
tgtgtcttaa aagtcaaggg aggaccactg cccttgtatt ataatgataa caaatgttgg 4200
caaggacatg gagaaattgg aaccccttgtt cactagtggt gggaatgtaa aatggtacat 4260
ctgctacaga acacagtata actgttactc aaaaaaatta aacacagaat taccatatga 4320
tccagcaatt ccacttctgg gtacataccg aaaacaactg aaggcagagt cttgaagagt 4380
tatttgaata cccatgttca cagcagcatt attcacaatg gccaaaaggt agatgtgttg 4440
atatatcaac agaagaatgt ggtatataca tacaatggaa tatgattcag ccttaaaagg 4500
gatggacatt ctgacatatg ctgcaaaatg aaccttgagg gcataatgcc aagtgaaata 4560
aatcagatac tgtatgattc cacttacatg aagtacctag agcagtcaaa ttcacagaga 4620
cagaaggtgg aatggtagtt gccattccac caggggtttg ggagaaggga ctgaatgggg 4680
agt 4683

<210> SEQ ID NO 336
<211> LENGTH: 3430
<212> TYPE: DNA
<213> ORGANISM: Homo sapiens

<400> SEQUENCE: 336
aggcacaacg tcaggttttc ctatggaagt ctctgtctcc tactgactca tttttcatac 60
tgtgtaaatg ctcaagaaga atcaaaagga caggtttttt caatctctag gttaaattct 120
actgtagtcc tcatcaatga gcttctaacc aaagcccaat ttcatttcat accccaattt 180
ttttatcttt ccaaagaagt gtctcctgga ggtcaaacac ctcttttgtc atggtgtcta 240
ttttctgctg catgcgctgc ttctcctgca gaggaagagg ggaagagaag taataaaaga 300
gcagaaagaa aagggagagg aggtttgagg gaggaaacaa aaataaagcc gataaagaaa 360
cttaaccaaa agggaaagtc tgtgatgaac aggaaaagca aaattggtct gccaaaagaa 420
aagatgacat tcacagtctt ggccacaaga ttcttattgg cttgccccta caaaagtaag 480

```
caaaggaacc aggaataatt gttccaacca cagctacgtg gcagcaagcc agctagaatt    540
tctgtgtaca tacagctcca tatgtatatt ctttctttga taactgcctt tttaccaaac    600
aagaacttac attcctagag agggaaattt aggtttgctt atgaacaaat gatctttcat    660
cttagagaac aagcagtttt gaattttatt ttttaagcag aactgatcat tttgaatttc    720
tgttagcaaa atctatgaca gcaagaacac catgaatttt gtattatttt aaaattatat    780
tattttgaaa catttaaatt tagcatttaa caatccttaa atgacctttc taattaggca    840
atggtgctta acaggttttc ttcttatgca ttattggtaa attattatgt cctcctttcc    900
ctactcatac attaggtact ttaccatgga attttcaatt ccaaagacca aaaaacatta    960
tttgtaatat ttaaagtttt tcagcataac catagatact aacatctaaa agatgttcat   1020
tctagatgta aaaaacatct aaaactatag ttctcaaagt ttgtatacct agcaccctaa   1080
gcttttaaag aagccacagt gatgaactat agaaatcaag cattatattc ttcttaaatg   1140
caattacaat taattactag aacactttac cagtcctaac ttaagctatt gaatttgaga   1200
agcagccccc aaagcaggtt tattatttta tgtggttggc attttggcac aaaaagataa   1260
aagaacaaaa agggaaagaa tttcacatta ttttaaaata ccagcaggat acagattctg   1320
gaaaatatgc ttcctacctt atatggagaa aaaccaagaa aattaacttc acatgtaatc   1380
tgatagatcc aaaaggttat ctgtatctgc acttgaaatc cacaaattct gagtatgttc   1440
aattattctt aatgatgaca aaaattaaca cgtcttcaaa tttaaagtca tttcttttttc  1500
tctattaaat ggtttttaaa aatcatttgt agagagacat attaagaggt aggtccgagg   1560
ggaaagagag aaagagggag agaaaaagaa aggctaaggt ctgagtagcc aggaatgtgg   1620
acaagtgtgg ttgtgagatc tctctcctgg gatcattaac aatctatgct tcctgacatc   1680
tctggcgtgt caacactaac ttaacattag atgcctttga tagccacacc tagatagtgg   1740
gcaggatccc ccttcaaact tatttccata tttatctaaa aacatcgtct caggagggaa   1800
aaccacattt aaagaaaaaa gatgcatgca atgtagcagg cctgcaagga tgactaatgt   1860
tttcaaagag ttcttggtag actatgcttc attccattcc taagatgttg ccagcaatgt   1920
ggcagagtcc cttcgcttgc agaaacctga accttcagac taaccattct ttacctttt    1980
gtacagaacg tatcttgatg tttcttcttt tttcatttag ccacctgaga aatgtattta   2040
cctgagtgaa aatcaaactt attccccaag aatcatgtcc caaaagatgg cattcactaa   2100
ttccaaagaa taatgttatt ctataatttt tccttttgcc catttcctaa gatatctgta   2160
ggaaacagtg tgcttaggaa taaaagacac aaaaatttct gctaccaaag tggggtaatg   2220
tttataggat ttatagtatt aatttttaag cataatctgg tttatgtttg aaaatttgta   2280
gtgtacagtc aaatataaag agacaaactc tgatgcatct taactctcct tccctcccaa   2340
cacatcctca tcccattcaa ctcatttttt ttcaaaatta agtattccca cagttcatgt   2400
acatacctca ataagctcat ctctttgccg caggccttct ttaagttctt ccatcttatg   2460
ctgcagcaca ctacacatat gtttctgcct ttctaactcc tgttattaaa caaataatat   2520
catttacaca ggtcatggca cacaagaaat ttgaacatac acaatacaac acagaggtta   2580
agtatgacct ccagaaacat gcccaaactc ctgattcata gtaacttaga aaaattgtgt   2640
attctataga aaagttaaga aaattttaaa attccatctt gtataattat caggaaaacc   2700
tgaactaatc aatggcaaaa ttattaaaaa caaaagataa tttagtaaag taacaggtta   2760
taaaatgaac atatacaatt caatgacatt catatacaaa taaaattcaa agaaggaata   2820
```

-continued

```
ataaatgcaa tatcaaaata aaatcaatat taaataaaaa acatacatgt aaacttacaa   2880

aatatatcaa aaacctatat gaggaaaatt atataaagca ttcccaaaag acagagaaat   2940

aggattgaat aaatggaaag gcataccgtc ttcttggatt aaaagtctca caacattata   3000

aaaatgccag ttctccctaa attaatctat acatttaatg tagtacaaat aaaaatacca   3060

tcaggttttt cttttatcat catcagagca agttgatttg aaagaaaaac acaagaaaaa   3120

gtagccagaa aaatacatac tgaaaaagaa gaaagccggc cttattaggt attaaaacat   3180

attataaagc ttctataatt aaaacaatgt tgttatggca catgaatata gaccaaggga   3240

gcagaataga gaattcagga aaaacccact taaatataca aatatattta aaaacaataa   3300

aaataagagc atctcaaatc aatgagaagg aaagactttt aaattagtaa tgttgggata   3360

actggatatc catttggaaa aagataaaat tggaactata cctcatacca cacaccagga   3420

caaattccaa                                                          3430
```

<210> SEQ ID NO 337
<211> LENGTH: 1323
<212> TYPE: DNA
<213> ORGANISM: Homo sapiens

<400> SEQUENCE: 337

```
caccattgcc aacacttctg catacagagc atgcttgggc tgcagaatgg gccctgatac     60

ctttagttct ttaagcccct gcatgtatct cccttctaca tcctgtatct ggtccttaag    120

gtcatagata tcctgcagga cataggaatg aaccattgca taaaaccatg cacaaacgta    180

tcttaaatcg caaaggattc agatgaaatg tgactcactt ttgtatattc cagactaaaa    240

gcagagaaat caaagtacaa aaacataact cccactccca accactgaaa agggcaaata    300

ggtcagggga tagtgggact gggggaaggt ctagagtaat caatctaatg ttaaatattt    360

tcttggcatt aaattctgtt aataacagtg tagcaaatgg ggacagggct atatatggag    420

gaaaaagcta tataaattat aatatttaaa atcatacaac ttttaatatt ttataaatca    480

cttaaaattt ttttagcaca atgcttcacc tagaactagt aaaatataca gtaaattaat    540

aagaggtggc aaattttaat gattcatgca aaagtttttt aaaaatataa taaatgaata    600

tgaacaaagt tttctttcaa tgacttggtt actggccaca attaacttga gagaaaggga    660

gtaaagggag ggaagttaaa cattttgaac agaatgtcaa atgagatatt ctatcctgag    720

gataccattt aaatgatgag aaaagcactt gctccaaatg ttactataat ccttataaga    780

aaagtgaaac aggtcaaatt ttaaatggaa aatactgttt ccctgtgtct gaccttgtta    840

tataaggtct attctgaatg ctcgatttat gtccgaaata actgcacagg gccctaaata    900

caattctgca attacaagca ggatcaatta ttaaaggctg attatacaca tttttggtat    960

tatattttcc ctgcctcctt cattgcctct ccagtaggtt tgactgtctt ttacttatcg   1020

attcattcaa tacacattta tgaaggacct atttaggagg cagatggtag gatacaaaaa   1080

taacacttcc ttcaagaagg tcattctctc aaggaagaaa aaacaagcaa caagtagtat   1140

gacaaaagaa agctaagtct aaggctggaa ggccttgtcc tctcatatcc ttttgtccca   1200

ttagaatgca gtagctaaag gcaagagttt atcttattca actttccacc ctggcattta   1260

tgtctggtac atagtaagag ctggtaagag ctcaattaat actgtcacct tcaaaccaat   1320

ggc                                                                 1323
```

<210> SEQ ID NO 338
<211> LENGTH: 2268

<212> TYPE: DNA
<213> ORGANISM: Homo sapiens

<400> SEQUENCE: 338

```
cttagtcacc gcctgtcctc tacctcccct ccagtgaaga ggggacctcc agtccaggca     60
agctcatcca tctgagtcct ggactctcct ctcacccacg caggtatttt gatctgtcag    120
ttacccctct ctccttcctc aaccttcctc ctctctctac tggttcaacc caaccaaaga    180
aaataataat cactctcacc tttaaaagaa agctaaaaac cttttcttaa atttctctct    240
ccctaccaat tgcccaacca attcccagtc tctcgtattc actccagagc aagtttctca    300
tattttctcc ccttgcagtt ttgacttgct cacctcatcc tcactgttga accacagggt    360
tactgaactt ctggcctgca atgcttcctc tgactgtgat caaagttatt ttttaagaat    420
gcaaagcaga tagtattgct ctcctattta atatcccaca gttgtcaggg taaaactgaa    480
ttcctttcag gctagcatac aagatgcttt gtgatttggc ccctcactac ttttccagcc    540
ttctctctta cacgctacta ttcttcactt ctcatgccac cctctggcaa ctttgctata    600
caggtagctt tctgggttgt ctgaatgcat ctctttgagg aagccttccc ccttcaatta    660
ctttccttgg ttaattttta tttttccttc aaactttagc tcagagtttg tcttttctga    720
aaagcctttt gttacctctt ctcctagtcc aatttaaatg atgctttctt gaattacctt    780
aacagcccca ttcttgctac taccattgta taacaccacc tggttttatt ggtttgtatc    840
agtttgtctt ccctatgaaa aagggaaatc ctgaaggcca gaacatattt tgcctcttaa    900
atctccaagg ccaagtgctc aataaatctt gaatgaacaa atgtatgcaa tttctctcac    960
tatcccctgc ctcacaaaca gcaggttcag caaataaaat atatattttt taaagttctc   1020
tttttccaag taaaggggtt aataaggatg gagacttaat gagtcaaata agcttttcat   1080
tatctcaggt atttctgtta cccaaatatt attacacttc tattactatg aaaaactgag   1140
agataactat attcaagcag ctgaatacca tcaaggctca aaagactaat aattcccaca   1200
atctagttct ttgtacactc acatattttc catttaaaac atggccagtt gtttctgaga   1260
gaattacttt tacatacatt acaaagtggg tttttttgg catttgtaaa ttagcagaaa   1320
ttccaacacc attaaattta caggaaagag gacagaaaaa agaactatct aatctccttc   1380
ctttcaagct ctgaaacact tgagtcacac ttttgtacag tacttatttt ttaaaaagaa   1440
atcatattcc ttctttctac taagtcacat taaaggttaa aagttccagt atattaccaa   1500
gtcaaaaaac tgcttttaaa aagaaaacca aaaacttcag tttacccgca attcacttaa   1560
tgaagtgtct ggatctatta agctgctggt gtccccactt cctcgtctgg atgagtttcc   1620
acttagaggg gttgttgctg aggcagaatt tcgagatgaa ggctagaaag agaaatatga   1680
cccttctaag tctcatttct ttaaaaatat gtttgctgtg gaaactaaaa acagggcagg   1740
gtggttgggg gaagatgtgg gtttcagatg aagaagttac catgtgtaat caatggtcaa   1800
tttagattgg ctttgcaggt atccaggtat acagagaagg gcccaagcat actaagcaaa   1860
atttcatgac acaaatacct tatcaaaatc tataattcgt aataaccaaa aagaaaatcg   1920
tttttatgag ggttattttc taagtttatc tttgctatcc tgtaaacaat acttaagtga   1980
gcacatcaga ttaacttaaa gcagttttag aattttataa ctgatatgct aatcagcact   2040
tccccttttt aatttctgaa ctgcttatca atctcttctt tctctaatac tctgttgagt   2100
tgataaaggt gaagatacta tttgcagcag agagtagcaa cactggatat cactatgaat   2160
gtagactgtt cttcccaaaa ttcatttaaa cgtgagatta tgctattgat taataaactg   2220
```

-continued catgaatctg tgctgtccaa tatacttgcg attagccaca tgcagcta 2268

<210> SEQ ID NO 339
<211> LENGTH: 2183
<212> TYPE: DNA
<213> ORGANISM: Homo sapiens

<400> SEQUENCE: 339
tgtggctcgc attacatttc tactggacag agttaattta tctttcttgg gtatagcata 60
aaattaatct tgataaatca tctccctgac tttctaataa tactttcaga agaaagagac 120
tttaacacaa agcaaattct agaaaggagt tattttactt caagaaacaa tttatatata 180
taaaaggaaa aaatatctca gagtttgtca ccaccattcc taaagaaact tcattttcag 240
tgtttactgg cttcttctca ggatcaattt ctagaggaat gaaaatcaaa agagcagcca 300
aaagctaaag aggtgacatt caaggaaata aaatgcagtg cctcttctct tcccagggcc 360
tcacatgatt taactccgaa ggaattttgg agggtcaagg acaggaaata gatgaaggga 420
ggaagagcag ctacatcaga ccaattgttg taaaataaat aatgaacaag ttacagatag 480
caagtttaat tgaccttgag aatttccctt aggaatttac atactcactc ttgtataatt 540
ttcagcatac tgtttgtcag atttttcatc caactagaaa agaacaaaga taaaaatcag 600
taaagatgct tagcaagttg actttttttg ggaggaaaaa agtgatcttg agttttccaa 660
gttcaatgat gtttgaagcc taaaaataaa catattaaaa atgaaattaa aattccagtt 720
taacataaga taaaatgtca gcaactttaa tttttatcct aagggagaca ctgagtaagc 780
aatctatgtt tactcaaaag tttagaactt ttgggtaaat tttctgttta aggtatttaa 840
aacacattaa agaaggctac atataaagtt ttagcactgc aaatgttaat acaaaaaaag 900
cttgtacata tcaaaaagaa aagtctgata aaaccaaaag cgaaaaactt ttatttctaa 960
acattattag gacacaggac acacagataa agactagtac actcagccaa aaaagttcag 1020
attagattaa agcatgttaa atatgtcacc aaaatatttt cccccacatc aaggattttt 1080
tgttttctca gtaatacatg cacatgacca aaaaaaaaaa aaaaatcaaa cagcacaaaa 1140
gagtatgagt agggctctct ccctaccatg ccataccctg accaccagtc tctaatagca 1200
accaaccaca aagtctttaa aaaaattcta gtaagtgtcc catatatgtt ctacatcttc 1260
tttttcccct taccaagtct cagagatttg agaaattact tcatctttct tcatagcatt 1320
tatcactccc tgacactacg gtatttatcc atttatttat tgtctgctct ctttctataa 1380
tgtaagctct atatcagtat gttcttttct gtactcctag tatcaagaat agtgtctggc 1440
atagagaagg gctcaaaatt tgttggatga atgaataaat cataccccat ctatactaat 1500
agacttccct catttatttt aaacagcttc atagtagcct gttatctcaa cttgccacaa 1560
ttaaattaac ctatcttctg tagataggcc ttaaggttgt ttcagacagt atttcaagaa 1620
gggaggtacc ttaaaagtct agtccaaacc ctgagtttta tagctaagga aaaagaaatt 1680
cagaggtgac agattttgct gaaggttgca gagctgaatc caacccttag ttttgtaaat 1740
tttcaattca gtgttcatat tgtttacctg aatatatatg ttattccaat tatcaccagg 1800
agaaaaaagg cacataggga tgtaactaaa tgaaaataac tccaactcct acacaaacct 1860
tctagaccca atctagagaa gagatctgaa aaccttctca gttaattatt aaaacatgaa 1920
acatcatttc tggctctact cagaacactt caccctaact tccacatatc tgaaagtttt 1980
tagtgttctt tttattaccc acacttatgt ttataaatat tctttattat gatgatagta 2040
ttacatcagt aatataaaca ctatttttag acatttaact ctttgttact tcttgctgta 2100
aaaactctga aaaagaaact aattttagtt cattttaatt tttaaaacaa catataaatg 2160
tttcaaagca ggtaatgaca gcg 2183

<210> SEQ ID NO 340
<211> LENGTH: 892
<212> TYPE: DNA
<213> ORGANISM: Homo sapiens

<400> SEQUENCE: 340
tgacctccaa aatcatccag tttttaatag actgtccatg gaataatctt atatttcaga 60
ggttgcatca ctgaactaat ccatcacaat gttgactcta ttgctttcac catcttctga 120
gagatcccaa ttgtcgcaac ccaaactgat catgcaccaa acctcggaga ttgtcaagcc 180
agcaaaaatt acccaaagca accatgccat agttctctta ttttggctac actaacttgg 240
caagttctca cttcttagac ttgtactatc ttgtgtgcta tcttccattt agacaaaaac 300
ctagctgaaa cttggtattc taaaagccca ataggatcca acagccaaga gttctacatg 360
gctgcaatgc aataacaagc taatgttcat aatgatgatc cagagtctgc cagatccaga 420
aaaaagcttt ttaaacagaa taaaatttaa tcatatttaa tatattaagc tgtaaaactg 480
tagtttaata aagtatttac agtgtagttt cttcaatgca gtcattggat cttgatcttt 540
tgttaatttc taatttatat atatactaac ttgataatgc tactcaaaaa ttgtttgaaa 600
aaatatctga tttccacaac cacagaaggg aagacatcaa tcaattttaa caatttccta 660
aagcaaaact ggctaaggat tccatttaga aatgggttta attattaaca atcagcaaaa 720
tttcagtttt gcttaaaaaa catttacatt tgtttgcttt attgtagcct gacttacaaa 780
acagaaataa agccaatgta gaagaaaata agaggctaga acccccaaaa atattatata 840
ggcttgcaga aacatgacct ggcacccttt ctcagcacct cctagctcag aa 892

<210> SEQ ID NO 341
<211> LENGTH: 433
<212> TYPE: DNA
<213> ORGANISM: Homo sapiens

<400> SEQUENCE: 341
ccagatttgt aaatccctgt tctagagaac tttttcctta tgttaaagag ttacagttaa 60
ctagtagggg caggggggaga ttttttaaac tgtcagcact ttcacttata tgtaagtact 120
aaagtaaatc atcacaaaat aaatataagg aagacataac tattaattca gatattataa 180
attaagaggc tgacagaatt cagtttttaa gagaacagat gtaaacagta agtttaattg 240
tccatactta tgggggaaaa acggggattg ctaggcaatt taatataaag ggcaatattt 300
caggggaatg acttggaaac cagtcttcta actttgtatg cagagagagt tattgattag 360
acccacacca agatgatact gttgcatagc cagatttgag aaccaatgat ctggaatgct 420
taagaaccac aca 433

<210> SEQ ID NO 342
<211> LENGTH: 2961
<212> TYPE: DNA
<213> ORGANISM: Homo sapiens

<400> SEQUENCE: 342
tcagtccatc agcctcctcc agcttccttg tacctcctct ccaatctata cctcactgaa 60
tatcacctta cccacttgcc tgccaggagc ttcggtgctg ttaagaaaaa ttattggctg 120

-continued

```
ggcacagcgg ctcatgcctg taatcccaac acgttgggag gccgaggcag gcggatcacc    180
tgaggtcagg cattcaagac cagcctggcc aacatgatga aaccctgtct ctactaaaag    240
tacgaaaaat tagccgggct tggtggcaga tgcctgtaat cccagctact tgagaggctg    300
aggcaggaga atcgcttgaa cccaggaggc ggaggttgca gtgagccaag atcgtaccac    360
tgcactgcag cctgggagac aagagaaaaa ctgtgttaaa aaaaaaaaaa aaaagagaga    420
gagtccgggc acagtggctc atgcctgtaa tcccagcact ttgggaggcc aaggtgggtg    480
gatcacctaa ggtcaggagc tcaagaccag cttgaccagc atggagaaac cccgtctcta    540
ctaaaaaaat acaaaattag ccaggtgtgc tggtggtcgc ctgtagtccc agatgctcag    600
gaggctgagg caggagaatt gcttgaacct gggaggtgga ggttgtggtg agccgagatc    660
gtgccattgc actccaggtt gggcaagaag agtgtgaaac tctgtctcaa aaaaaaaaaa    720
aaaaaaatgt atccaaaact tggaaacaag aaaagaggat gactgcatgt cctttcaaag    780
ttgtttaatg tggtttacag gctcactcaa ggattattta attatttaga agaataaatc    840
ctcttagaac cctgggtttt taggccaaag tctcacctat ttatttttctt tttttttctt    900
ttcttttttt tttttttttt gaggtggaat ctcgctctgt tgcccaggct ggagtgcagt    960
ggcacaatct cagctcactg caacctctgc ctcccgggtt caagcaattc tcctgcctca   1020
gcctccggag tagctgggac tacaggcaca tgccaccatg cttggctaat gtttctattt   1080
ttagtagata cagggtttca ccatgttggc caggatggtc tcaatctctt gacctcgtga   1140
tccaaccatc tcgacctacc aaagtgctgg gattacaggc gtgaggcact gcgcctggcc   1200
agcctcacct atttcattat attcccttaa atgtacagtc atgggtcact tcacaatggg   1260
gatacattct gagaaatgtg ttgttaggtg attttgtggt tgtgcaagca tcatacagtg   1320
tgcttaccca aacttggatg atgtagcctg ctatacaact aggctatatg gtgtagctta   1380
ttgttcctag gctataacct gcataacatg ttactgtact aagtactgta gacagttgta   1440
gcacaatggt aagtatttgt gtatctaaac atacttcaac agaaaaggta cagtaaaaat   1500
atggtataac agattaaaaa tggtacatcc atatagggaa gttaccatga atggaacttg   1560
caggactgga agtgagtgag tgagtgggtg agtgaatgtg aagtcctagg atatgatcat   1620
acactactat agactttata aatgctgtac acttaggcta catgaaatta aaaatatatc   1680
tttttcttgg acgggcatgg tagctcatgt ctgtaatccc agcactttgg gaggccgagg   1740
tgggtgggtc acttgagatc agcaattcaa gaccagcctg gccaacatgg tgaaaccctg   1800
tctctaccaa aatatacaaa aattagccac atgtgatggc gtgtgtatgt agtcccagct   1860
actcgggagg ctgaggtagg agaatcgctt gaacctggga ggcagaggtt gcagtgagca   1920
gagatagcac cattgcaccc cagcctgggc aacagagtga gaccctgtct caaaataaat   1980
aaacaaataa aaataaaaag atgtccagtg cctaatctaa tcaacattga ttggaaaggc   2040
agatgattaa gcacaaataa agcctgttta gtcaagaaat ttactattgg atacataaga   2100
tgaatctata tataaaaatg aaaaggcaat gttagagcta tgtaggaatg aatgcaaatt   2160
aataaaatgt cattggagta agaacagaac ttactgacaa gacaagattt ccattgaaat   2220
cttagtgtgt gtggcttttt ttttttttag atggagtctt gctccgttgc ccagtctgaa   2280
gtgcaacggc tcgatctctg ctcactgcaa cctccacctc ccgggcttaa gcaattctcc   2340
tgcctcagcc tcctgagtag ctgggattac aggcacccat cactacgtct ggctaatttt   2400
tgtattttta gtagagacgg gttttcacca tgttgcccag actggtctta aactcctgac   2460
ttcaaatgat ccaccagcct cagcctccca aagtgctggg attacaggca tgagccactg   2520
```

```
tgcccagcca tcctagtgat ttttttaatc tatatatata tatatatata tatatatttt   2580
ttttttttg agacaggtct cgctctatca cccaggctga agtacaatgg cacaatcatg   2640
gctcattgca gcctcgatct cccaagctaa agcgatcctt ccacctcagc gtcccaagta   2700
gctgaggcta caggtgtgtg ccaccatacc catttagttt ttttaaattt atttttcttt   2760
tgtagagaca gggtctcacc atgttaccca ggttggtctt gaactcctgg gctcaagcga   2820
tcctccaagg cctcccacct cagcctccca aagttctagg attataggta tgagccactg   2880
tggcccctct agatttttaa atgatgttat tatttgcagt aattcttcaa ttcataggaa   2940
cttaatctca gggcacagca a                                             2961
```

<210> SEQ ID NO 343
<211> LENGTH: 2915
<212> TYPE: DNA
<213> ORGANISM: Homo sapiens

<400> SEQUENCE: 343

```
acttaatctc agggcacagc aagagacaga acttcaatgc attttttttt tttttttttt     60
tttgagacag agtctcaccc tgtcgcccag gctggagtgc aatggtgcga tctcagctca    120
ctgcaagctc cgcctcctgg gttcacactg ttctcctgcc tcagcctccc gagtagctgg    180
gactacaggc atctgccacc acgaccagct aatttttttt ttgtattttt ggtagagaca    240
gggtttcgcc ctgttagcaa gaatggtctt gatctcctga cctccttcgt gatccaccca    300
cctcggcctc ccaaagtgct gggattacag gcatgagcca ccacgcctgg caatgcattt    360
tttaaataac catttttttcc cataccattg aatgaattat ccatctcttt ccaggggaat    420
gaaattcccc tgtaaagatg agcccttgac tcacacctct aatcccagca ctttgggagg    480
ctaaggcggg cggatcactg gaggccagga gtttgagacc atcctggcca acatggtgga    540
aacctgtctc tgctaaaaat gcaaaaagca gtcaggcata gtgcatgcac ctgtagtctc    600
agctacccgg gagtctgagg cactagaatc acttgaacct gggaggtaga ggttgcagtg    660
agccaagaca gcactactgc actccaatct aggtgtggag agacactctg tctcattaaa    720
aaaaaaaaaa aaaaaagatg agccctcaat tacaaacttc ttttgggatc aatatcaatc    780
agaagttatt aagtgctata gtttgtctga tgcagaagta aacatttaaa gttttgacat    840
aaactttagg gttggcaaga gcattaagtg agttaatgca tacatgttag ctattacatc    900
acaaatcact gaaatgttgt agtttaatgt caaattatta caagttgcta aaatagactt    960
gcatgggaat ctaaagtaca gtaaaaataa tgcttaatta ttagccaaag tgctctctca   1020
gctaaaatgt ttactcattg gtctgccatg aatgctttca aataacaatc attctttttg   1080
gtgttcagga aaagatcagt atccagactt aaatttggga gctctgaaag gaaagcaatg   1140
aactttccct ccaacacttt tggatgtttt tatgtactcc ctcaacccca tgggccccca   1200
cggtaccctt atgatacttt tgggaaccat gatgtctctt tcttctgaaa agctcaatgc   1260
tgcactctgg tactattgcc tgatattaat atgtagttat ttattttta actttatgtg   1320
tatgtctgat ccctcccaac tgggatggaa gcttctcaag aacaggatct gacttggcac   1380
agtggctcac gcctgtcatc ccagcacttt ggaaggctta ggcaggagga tcacttgcac   1440
tcagcagttt gagatctgcc tggacaacat gacggaacca cgtctccaca aaaaaacaca   1500
aaaattagct gggtgtggta gcgcttgcct gtaatcccag ctactcagga ggctgaggtg   1560
ggaagattgg ttaagcctgg gaggttgagg ctgtagggag ccatgattgt gccattgcac   1620
```

-continued

```
ttccagcctg ggcatgactc tgactaaaaa aaaaaaaaaa aagtaaataa gttacaaatt   1680
aataccatac gagcctgtgc ttcattacag tgattagaaa ggtcctaaaa ggctctgatg   1740
cctgaaatat gtctctcaaa gacatgcttc tgtgccttag agcctccact attgcttact   1800
tcttttattt ttatttacgt atgtatgtat gtatgtatgt atgtatttat ttatttttga   1860
gacagaatct tgctcttgtt gcccaggctg gagtgcagtg gcgtgatctc agctcactgc   1920
aacctctgcc tcccaggttc aagcaattct cctgcttcag cctcccaagt agctgggatt   1980
acaggtgtcc gccaccatgc gtggctaatt tttttgtatt tttagtagag atgggttttc   2040
accatgttgg ccaggctggt cttaaactcc tgacctcagg tgattgccca cctcggcctc   2100
ccaaagtgct gggattacag gtgtgagcca ccgtgcccgg ccatgtattt atttttttga   2160
gacagggtct cgctctcttg cccaggctgg agtgcagtgg tgtgattatg gttcatggcg   2220
gcctcagcct cctaggctca agagatcctc ctacctcagc ctcctgagta gctgggacca   2280
caggcaccac cacattagcc accacgcctg gatgattttt tatttttatt ttttgagaca   2340
gagttttgct cttgttgccc aggctggagt gcaatggcgt gatcttggct cactgcaacc   2400
tccacctcct gggttcaagc gattctcctg cctcagccac cctagtagct gagattacag   2460
gcatgtgcca ccatgcccag ctaattttgt atttttaata gagatggggt ttctccatgt   2520
tggtcaggct ggtcttaaac tcccgacctc aggtgatttg cccacctcgg cctcccaaag   2580
tgctgggatt ataggcgtga gccactgctc ttggctgatt tttgtatttt ttgtagagat   2640
ggggttccac cgtgttgccc gggcttcgct tgcttttttt agataaaatg ttgtctccag   2700
gccagatgtg gtggctcaca cttgtaatcc cagcgttttg agaggtcgag gggggaggat   2760
cacttgagcc taggagtttg agaccagcct gggcagtata gtgagacccc tgtttctaca   2820
aaaaataaaa aattagccag gcgtggtgtt tcgtaccagc tacttgggag gctgaggcag   2880
gaggattgct tgagcccaag aggctgaagc tgcag                              2915
```

<210> SEQ ID NO 344
<211> LENGTH: 3182
<212> TYPE: DNA
<213> ORGANISM: Homo sapiens

<400> SEQUENCE: 344

```
cgtggtgttt cgtaccagct acttgggagg ctgaggcagg aggattgctt gagcccaaga     60
ggctgaagct gcagtgagct gtgagtgtgc cactggactc cggcctgggc aagagagtga    120
gactctgtct caaaaacaaa caaacgtggc cgggtgcggt ggctcatacc tgtaatcccg    180
atactttggg atgctgaggc gggcggatca cttgaggcca ggagttcaag accagcccgg    240
ccaacatggc gaaactccat ctctactaaa aattcaaaaa tcagccagat gtggtggtgt    300
gtgcctgtag tcccagctac tcgggaggct gaggcacgag aatcacttga acccaatagg    360
tgggggttgc tgtgagccaa gatcatacga atgtattcca gcctgggtga taaggcaaga    420
tcttgtctca aaacaaaaaa caataacaac aacaacgaaa acacaaagaa caaaacaaaa    480
ccaaagaaac acaaactttg tctccagaag gcctctatta gaatctaaat acctaacctt    540
cgaggtgtaa ctcactagca cgttgtctct ctaacagttt cctagcagac agttcaggtc    600
taggattgta tccagggaca gagctagaga agccggagcc ccactgtggg gatgctgatg    660
aggcagaccc ctcagtgagg ccagtgaaca gatgagtcca ctgggctggg cacctgtgag    720
atggggcaga ggaacaccca gataggttaa agggcatctt gacacaacca gagtttatct    780
gtagcatagt cttcacaaac caagccagaa cccaagccag agccgcatga gagtgaattc    840
```

```
ccatctggct ttgggggaca aatgactcat ccaaggctac actcagcgct gagtggtgac    900
tgggagccag tgcgctctgc tgactgctcc actttcagaa atacttgcag atctcaatta    960
tctaattgca attgcaacga gaaccaaagc aggggagcag agacaaacaa tttctgaggt   1020
aaccagatgg ctttattaac tcaagttctc acctaaaatt gccctcaaga atcctgtggg   1080
aatgggttgc agtggtgtgg ccctggattc acaaccgaca gagcttctga attctgagtg   1140
atctgtacac aaacacacct ctgcctgggt tacacggtaa gggcctcatg tacataatcg   1200
cagcatgctt tcctagaaat cgcttggtag cgtgatgggt gggattcaga agtcagcagg   1260
aacccaaagt gagtggagag gtcatggcca tgagtcagag gcctctatcc ttcagcagcc   1320
tccaacagga agcagacagg gaaggttcct atagttacaa gggcttggct ggtttattac   1380
tttcattcta atgggcgttt ttataagaca taagcaaagt acgaaatatt ttatagccat   1440
tcggagagga agtccgccac acatttcaaa gaatgaatgc cctctgtaag gataagcagc   1500
taactacaag cttcttttgg aattgactag aagttattaa gtaccaaagc ttatctgata   1560
ctcaaataaa tatttctcta agttttgact cttgagaggt aaacttcaag gttgacagca   1620
ccgaggctat gtggtatact aaaagggtgt gggatttaga gtcccacaga cctaggatca   1680
agatttatgg ccaccattca ccaacaccaa caataggatc ttgggtttta cttaattttg   1740
gttaactagt tttctcattt gtaaaataaa aataaatgat acctagctca cagtttctgt   1800
gaagattaag tgagataata tgaaagaaat cacattgtac ttaccaaatg tttcgtgttc   1860
ttttctcttc cttcatatgt gttaagctga attaacaaac tactaagtaa gatttctttt   1920
tttttttttt ttcccgagac agggtcttgc tctgccgccc aggctggagt gcagtgacat   1980
gatcatggct cactacagcc ttgaccttca cctcccaggt gcaagccatc ctctcgcctc   2040
agcctctcat gtagctggga ccacaggcat aaaccaccat gcctggccaa ttttttttaat   2100
ttttagtaaa gacagggtct cactgtgttg cccaggctgg cctcaaattc ctgggctctc   2160
caatcacatt tgggattagg taaaaaatta aaaacaaaaa aaaataaaaa aaaacttctg   2220
ggctcaagtg ttcctcccac atcagcctcc caaagtgctg gaattacagg gatgagtcat   2280
aatgcctggc ctaaaccact tactcttttt tttttttttt ttgagacgga gttttgctct   2340
tgttgcccag actggagtgc aacggcacaa tcttggctca ctgcaacctc tgccttccta   2400
gttcaagtga ttctcctgcc tcagcctcct gagtagctgg gattacaggt gtgtgccacc   2460
acggccagct aattttgtat tttcagtaga gacggggttt ctccatgttg gtaaggctgg   2520
tctcgactcc tgacctcagg taatccgcct gcctaggcct cccaaagtgc tgggattaca   2580
ggcatgagcc accatgccca gcctttttgt tgttgttgtt gtttttgaga cagggtcttg   2640
ctgtgttgcc caggctggag tgcagtggta cgaacttggc tcactgcaac ctcttcctcc   2700
caggttcaag ccattctcct gcttcagcct tcccagtagc tgggactaca tgtgggcacc   2760
accgcacctg actaattttt gtgtttttag tagagacagg gttttaccat gttggccagg   2820
ctggtctcaa acttcttctt tctttctttc tttctttttt tttttttcct tgagacagag   2880
tctcactctg tcacccaggc tggagtgcag tggcgtgatc tcggctcact gcaacctcca   2940
cctcctggga tcaagcaatt cttctgcctc agcctcccga gtagctggga ctatgggcgc   3000
acgccaccac atccagctaa tttttgtatt tttagtagag atggggtttc accatattgg   3060
ctaggctggt cttgaacttc tgacctcaag tgatccaccc gcctcagcct cccaaagtgc   3120
tgggattaca ggcatgagcc actgagccca gccctactaa ggaagatttc tggccagtag   3180
```

cc 3182

<210> SEQ ID NO 345
<211> LENGTH: 2974
<212> TYPE: DNA
<213> ORGANISM: Homo sapiens

<400> SEQUENCE: 345
cccagcccta ctaaggaaga tttctggcca gtagccaaat aggactttga aaatctttaa 60
gaataggaag aatctgaaaa ataatcttca aaaaagaaag cagcatgttt catgaaaatg 120
tgtaattatg tataactggt agtggccagc caatgctaat tctactaatt ctgtgtacta 180
gagttatcta tgtggatatc tagaaactcc tcaagggaat gtgtgaggat ggagaattca 240
tcttgttgac catgaatctc tacagaacta agtacagagc cttatagttt gataattcat 300
tgaaacagaa tcattttata tccccttcgc actaactggt tctgaaatac cattctcctt 360
gggtaatttt gtttttttgt tttttgtttg tttgagacag tctcactccg ttgcccaggc 420
tggagtacag tggtgggcac tatatcgtct cactgcaacc tccacctcct gggttcaagt 480
gatgctcctg cctcagccaa ccgagtagct ggaattacag gcatgtgcca gcacgcccgg 540 ccaattttg ttttttagt acagacgaag tttcaccatg ctgggcaagc tggtcttgaa 600
ctcctggcct caagagatct gattgctttg acctcccaaa gtgcaaggat tacaggcatg 660
agccactgtg cctggcctct tcaggtaatt ttggatcccc taaaggctca ctcacaggcc 720
ggctctcaca tttttgccca cactttatgt tcaaaacatg tatcagtggt tacctatgct 780
ttcggacaga atattcctac aagagtgagc cagcttgcac cacagacaag ccaaactatg 840
cctgtgtcct tatctatcgc tgcataatcc caatggttag tgatctccat tccacggacc 900
ccgtgctgtc tcatacaaag catttcggac ttaaggatag aagcaaactg ccatgtcctc 960
tatgccatga tgcttactaa tcctttacca ctctgagatt ttcttggagc tatttatagc 1020
tgattttcct gggctgactt tcgaccaaag aggagatgga aactttgttc ttaacagtgc 1080
tccaactgtg tgattcaact tggctgcatt ccagcaagtt ctgtgagttg ttaatggagg 1140
tgagaaagga gtggggtggg gagtcacagg gatgctaact gtagatctgc tttttctctt 1200
ttttttaaat gtttgttttt agagacaggg tcttgctctg ttgctgagcc tggagtgtag 1260
tggcataatc atggttcgtt gaagcctcaa actcctgggc taaaacgatc ctcccacctc 1320
agcctctcaa gtagctggaa ctacaggtat gcatcaccag gcctggctaa ttaaaaaaaa 1380
aaaatttata gagacagggg tcttgctatg ttcctcaggc tggtctcaac tcctgtcctc 1440
aagcaatcct ctgaccttag cctcccaaag tgctgcaatt tcagttgtaa gccaccatgc 1500
ccagccctgc agatttgctt tttttttttt tttttttga gacggagttt cgctgttgtt 1560
gtctaggctg gaatgcaatg gtgcgatctc tgctcaccgc aacctctgcc tctggggttc 1620
aagtgattct cctgccttag cctcctgagc agctgggatt acaggcatgc accaccacgc 1680
tcggctaatt ttgtgttttt agtagagacg gggtttctcc atgttggtca ggctggtctt 1740
gaactctcaa cctcaggtga tctgcccacc tcagcctccc aaagtgctgg gattgcaggc 1800
gtgagtcaca gcgcccagcc tagatttgct ttctatagga ctttatattg tcatcctcat 1860
caccactatt ttaacaagct gctagtttac ctagtaaatc ctacatgaaa tagaaatgtg 1920
gtcattattg gctggtgcag tggctcacgc ctgtagtccc agcactttag gaggccgaag 1980
cgggtcgatc acaaggtcag gagttcgaga ccagcctggc caacatggtg aaacctcgtc 2040
tctactaaaa atacaaaaat tagccaggtg tggtggtgcg cacctgcaat cccagctact 2100

```
ggggaggctg aggcaggaga attgcttgaa cccaggaggc agaggttgca gtgagctgag   2160
atcgcgccac tgcactccag cctgggggac agagcaagac tctgtctgcg tgggggggaa   2220
aaggaagaag tttgagacca gcctggacaa catggtgaaa tgctgtccct gctaaaaata   2280
caaaaattag ccaggcgtag gccgggtgcg gtggctcaca cctgtaatcc cagcactttg   2340
ggaggccaag gcaggcggat cacaaggtca ggagattgag accatcttgg ctaacactgt   2400
gaaacgccgt ctctactaaa aatacaaaaa aattagccag gtgtagtggc gggcgcctgt   2460
agtcccagct gctggggagg ctgaggcagg agaatggcgt gaacccagga ggcagagctt   2520
gcagtgagcc aagatcatgc cactgcactc cagcctgggc aacagagcga gactgtctca   2580
aaaaaaaaaa aaaaaaaaaa aaaaattagc caggcgtggt ggctggcggc tgcaatccca   2640
atcccagcta cttgggaggc tgaggcagga gaatcacttg aacccaggag gcagaggctg   2700
cagtgagcca cgatcacacc actgcgctcc agcctgggtg acagagcaag actccatctc   2760
aaaaaaaaaa aatgtggtta ttactttatc tattcacaac acttccctac agactcctgg   2820
agttcacctt ctttccgtaa acagggaacc aaccaacaga cacgacatat cctccctctc   2880
ccactactct atccacattc ttggtttcct tttttctttc acttccttct ggaacttgag   2940
agcttgtttg gaggttctag caggggagca cagc                               2974
```

<210> SEQ ID NO 346
<211> LENGTH: 3199
<212> TYPE: DNA
<213> ORGANISM: Homo sapiens

<400> SEQUENCE: 346

```
tcgtcctctt cgacctagca tgcagctttg ggagggacgc acatggagcg gtgagagagg     60
aaggagacac ctacctatcc agccagatca gctgaatcaa ccctggcgat caatggggtg    120
acagatgtcg taggaacctt atcaatctgg gtattctgag tcagtttcgt gtacagtgat    180
gatgatgatt atgtatagct cagccagact atgacacttg acaactccct catcctgagt    240
aggagtacaa ataaaattaa gtttgtgaca tttagttcat tctttttttt ttttttgagg    300
tggagtctgg ctctgtcacc caggctggag tacagtggtg caatctcagc tcactgcaac    360
ctctgcctgc tgggttcaaa tgattctcct gcctagcctc ccaagtacct gggattacag    420
gcacacacca ctatgcccgg ctaatttttt ttgtattttt agtagagacg gggttttgcc    480
atgttggcca ggctggtcaa gtgatccaac tgtctaggtc tcccaaagtg ctgggattac    540
aggcatgagc caccacgcca ggcccgttta gttcattctt actacacacc ttgattttcc    600
atgaacatct caggaatcgg aacatacaga taattccaga aaggagagga atctgtgtat    660
ttttcttctt ttgtttcctt attatgcctt gtgagaggcc aatgcatgag tttttaacta    720
ggtccatgag aacccacaga gacagcctcg tttgacccag tctggttatc agaagaggga    780
agttccttat aattgtgtat gtatacctgg ttggttcaca gatgtcctta aacatgagaa    840
cgactatgtc tgaaaaaaac tctcaagttt caccggggct gttgcacacc ctataaatga    900
cccatcataa agacctcacc cctctctgat aggataaggc aaaggttaag gtccatcctg    960
ttagccacac tctattttcc ttctagctag gccagaacat aatatctgga accaactgtt   1020
ctctctctca gctggctgta agaatgctgt atgctttttt tttttttttt ttttgagaca   1080
ggctcttgct ctgtcgccca ggctggagtg cagtggtgtg atctcggctc actgcagcct   1140
ctgcctcctg ggttcaaacg attctcctgc cccagcctcc tgagtagctg ggattacagg   1200
```

-continued

```
cacacgccac catgccaggc taatttttat atttttagta gagacagggt ttcaccatgt   1260
tggccaggct ggtctcgaac tcccgacttc aggtgatccg ccccccctcgg cctcccaaag   1320
ggctggggtt acaggctgta tgctttttat agtgttgggt ggttaagtct tacacaaagt   1380
aaatgcccag taaatactta ttactggtca tgactcaacc attcaggttg ttactaagct   1440
aagaccagtc accccatagt ccctgccata ccatatgctc ccagagagag cacttctggc   1500
cctccctatg atggctgcca ccaccactac tttgtgggga agaatagtca tcctgacggt   1560
tagtcatccc taacctttgg actaactatt cacaattcag tttaggctga tttctctttg   1620
caccttatat tcctatgtgc ctcagtcact agaagaataa gccttctaga tcatccaaca   1680
tggatagatc atcaacagtg gatactatcc cagtaccctg agtccactgc taatctgatc   1740
aagcccctct ccctctcctt cccaaattct tcaatgtgcc tttgcaactc cagatctgtc   1800
gccatcaaat gtctttgtag cctcgtcctc ttctttgaat gttcccttca ccacttggca   1860
ataaatgaac ctggctgtcc ctgagcagcc catctcctga gcagtcctct gaggtagaag   1920
ctgctttact tttcccctga catttcaggc tcctaagggc caggggggtat agtaggtttc   1980
ctacttgcca tttccaaact gttccttgcc tctcctcctt cagacacgca gcttctttga   2040
agcctctctg atgacctcct aaccttccag ctcacttact caagaactcc cactgtctca   2100
gttcttcaac tgtatctgac accatttctc tcttctctta tcttcacttc ccaacctcac   2160
ttaagttcca gggcccagca tttttattcc acatttgcaa atactgtcca caacaaactt   2220
atccttctct cttctatcgt attttatttc taaacagagt ctcgctctac aatagtcact   2280
tttaaaatta tttattagcc aggcgaggtg gttcatgcct gtaatcccag cattttggga   2340
ggccaaagcg ggcagatcac ctgaggtcag gagtttgaga ccagcctggc caacattgcg   2400
aaaccccatc tctaccaaaa atacaacaat tagccaggtg tggtggcacg tgcctataat   2460
cccagctact ctggaggctg aggcaggaga attgcttgaa cctgggaggc ggaggttaca   2520
ctgagctgag atcacgccac tgcactccag cctgggcaac agagcgggac tctgtctcaa   2580
aaaaaaagac taccattcag accattcagc aaactccagt gcccaggcgg cctggtcctc   2640
catctcaccc ttcgctccat cttgccctta gcctgagcaa ccctgcaccc tgctccttct   2700
ccccctggtc atttgcggtc acagtgcacc aagagaagag gacgccacct tcctggtctc   2760
atccctactc aggtgtgcac cctttgctag ggcccgtgcc tccacccagg tcagagcttg   2820
gagattcacc ctcttgcttt cacgtttaaa taagatgcaa gcaagggccg ggcgcagtgg   2880
ctcactcctg taatcccagc acattgggag gccgaggcgg gtggatcacg aggtcaggag   2940
atcaagacca tcctggctaa cacggtgaaa ctccgtctct actaaaaata caaaaaatta   3000
gctgggcgtg gttgtgggcg cctgtatatt cccagctact caggaggctg aggcaagaga   3060
atggcgtgaa cccaggaggc ggagcttgca gtgagccaag atcacgccac tgcactccag   3120
cttgggcaac agagccagac tccgtcccaa aaagaaaaaa aaaagatgca ggcaaaggct   3180
gctgtagaat aggcgctgc                                                3199
```

<210> SEQ ID NO 347
<211> LENGTH: 3054
<212> TYPE: DNA
<213> ORGANISM: Homo sapiens

<400> SEQUENCE: 347

```
tcttcccaag agagccaaga tttcttcttt cctcttcttt cttttttttt tctttctaat     60
ttcaaaggag tataattaaa ttgccaggta aaagctcaaa ggtctttttt atagtgttct    120
```

-continued

```
ggaaggttct ctgcctgtgt ttgtatttcc tttagcctcc acgttcctct atccagttcc    180
cgcacccttc cccccaggcc ccattcttca aggcttcaga gcagcgctcc tccggttaaa    240
aggaagtctc agcacagaat cttcaaacct cctcggaggc caccaaagat ccctaacgcc    300
gccatggaga cgaagcacct ggggcggggc ggagcggggc gcgcgggccc acacctgtgg    360
agagggccgc gccccaactg cagcgccggg gctgggggag gggagcctac tcactccccc    420
aactcccggg cggtgactca tcaacgagca ccagcggcca gaggtgagca gtcccgggaa    480
ggggccgaga ggcggggccg ccaggtcggg caggtgtgcg ctccgccccg ccgcgcgcac    540
agagcgctag tccttcggcg agcgagcacc ttcgacgcgg tccggggacc ccctcgtcgc    600
tgtcctcccg acgcggaccc gcgtgcccca ggcctcgcgc tgcccggccg gctcctcgtg    660
tcccactccc ggcgcacgcc ctcccgcgag tcccgggccc ctcccgcgcc cctcttctcg    720
gcgcgcgcgc agcatggcgc ccccgcaggt cctcgcgttc gggcttctgc ttgccgcggc    780
gacggcgact tttgccgcag ctcaggaagg tgaggcgcgg attggagcag agttgtggag    840
ctgggctggg ctgggggggca gcggccccg gccctcggcc cccgaaacgg gcataatagg    900
gaggggacca agaggccgcg ctttccagcg tggagaccgg acggtgcggc cgtgctccgg    960
ctcaggccct ccgcgcggta ggaaacggcg agggccgtcc cggggagcag cctcacttcg   1020
cagctttgct cgccttggta gggaaatggc cttgggcgga ggcgggggac aggcagggaa   1080
cggagtggcc acgtccaggt ttcctgcggc caccgaaccg gtgcctcgcg ccctggcgca   1140
cccacgtcct cggttcgggg tggacttggg gttccaaaac agccccagcc ggtggcggag   1200
tctttacgac agggaccagc gggctcgccc ttgtccttgc agcgggcccc ggatgtgggc   1260
ctcaggcggg gacaggcgcc cgcagggagg cctccagggc cgctatgcac ctgcgcgcgg   1320
caggcggccc ggaccacaca gggcgtgtgg gtgttttccc ttttctaagg atcatatgag   1380
taatgccagg cttattgtag ggaacgcaga aataataacc gtaaagagta aaaacatata   1440
atcccagcat tttgagaatc ccataattag taattaggtg tatctttctt tctttttatt   1500
tatttattta attttttgag actgagtctt gctctgtcgc ccaagctgga gtgcaatggc   1560
gcgatctcgg ctcactgcaa ctttcgcctc ccgggttcaa gtgattctcc tgcctcagcc   1620
tcctgagtag agtagctggg attacaggcg cgcgccacca ccccccgcta atttttgtat   1680
tgttagtaga gacggggttt ctccatgttg gtcaggctgg tctctaactc ctgagctcgt   1740
gatccgcccg cctcggcctc ccaaagtgct gtgattacag gcgtgagcca ccgtgcccgg   1800
cctattttat ttttttattt gaaacagcct tgttctgtca cccaggctgg agtgcaatgg   1860
caagatcttg actcattgta gactacgcct cccggcctca gaccatcctt ctgcgtcagc   1920
ctttatgcct ggctaatttt tgtatttatt atttattatt attattatta tttttgagac   1980
agagtttcgc tcttgttgcc caggctggag tacaacggcg cgatctcatc tcactgcaat   2040
tcaggcgatt ctcctgcctc agcctcccga gtagctggga ctacaggcat gcaccaccac   2100
ggtcagctaa tttgtatttt ttgtagagag gggtttcgcc atgttggcca ggctggtctc   2160
gaactcctga cctcaggtga tccaccgacc ttggcctccc aaagtgctgg gattacagac   2220
gtcagccaca gtgccagccg aatatttgta tttgtagaga cgacatctca ctatgttgcc   2280
caggctggtc tcgaactcct gggctcaagt gatcactccg tctgggcctc ccagagtgct   2340
gggattacag gcgtgcatca ccacacccgg ccttaaaaac aagatttaaa atggtgactg   2400
gtatgttgca ccgttattca aatgttagac atgtagtttg atttcagttt ctcttaactg   2460
```

```
tggaataaac aacttggctg ccgtctctct ctctctcttt tttttggaaa cagtgtctcc   2520
gtctgtcgtt cagcctggag tgcagtggca catttacatg tcactgcgtc ctccatttcc   2580
caggctcaag cgatgctctt acttggacct cccaaagtgc tgggattaca ggcatgagcc   2640
accggtccgg catctcttgg tttatttgta agatggtgcc tagaagtgga gtggcgtttg   2700
ccaaaggtct ctggaagggc ttttacactt tcaccaatgg agtggcctaa attcagtaat   2760
tatactctca aagtaatgca gttttagtca actcatgttt ttctggcttc aatctgggac   2820
tacgtactta atgttaaatt gctttaaagt ggtcatagct gctacaggtt tgtgctcaga   2880
aagtctgcac ctgactggtc tgatttaaat tttacgcccc ttaggtatga acagtgtgtt   2940
ttaaacaagt acaggatggg gctgcagaag atttaaacgc ttgagaacaa gtgctgtatt   3000
ttccccttt gtgaccccag tattgagttt agtgttgggc agattaaagg tggt          3054
```

<210> SEQ ID NO 348
<211> LENGTH: 3179
<212> TYPE: DNA
<213> ORGANISM: Homo sapiens

<400> SEQUENCE: 348

```
tgttgggcag attaaaggtg gttcatatcg actataactt gaacagggaa aaattgaaat     60
caacttaggg tacttgggat acgaaggatc aatataaaaa ctctggtttg tcatgctagc    120
tttttctttt ttttcctctt cagttgaact gaggagatag tttttgtttt taatgattgt    180
gctcttttaa ctagacaaaa ggaattagat agtcttgcct attcgaagtt aaatgaactt    240
ttgaggttgt taaggacaaa actattaaac tgacatcaat aatacagaat gggctgctta    300
gtatcacttt ccttatcagg tactaggatt taatttagtt aggaaactca cttaaaggga    360
ggactataac tgcagttgaa agtgtaattt ttccaagata taaaattgtt taaagattga    420
atatattcct gttaagcccc aaaggaaaca tccctcattt aagaaaatgg ggtgggagag    480
caagagaagg tgaggattca cagatcctag aattggaata gttgattttt ttttgtaaaa    540
gaggcggtga cagccgggca tggtggctca cgtctgtaat cccagcactt taggaggccg    600
aggtgggtgg gttacctgag gtcaggagtc ctagaccagc ctgaccaaca tggtgaaaac    660
ccgtctctac taaaaataga aaaaaaaagc cgggcgcggt ggctgacacc tgtaatccca    720
gcactttggt aggccgaggc ggacggatca tgaggtcagg agtttgagat cagcctggcc    780
attatgctga aaccccgtct ctactaaaaa tacaaaaatt agccaggtgt ggtggcatac    840
ccctgtagtc ccagctactt gggaggctga ggcaggagaa tcgcttgatc ctgggagatg    900
gatgttgcag tgagctgcga ttgtaccact gcaatccagc ctgcacgaca gagtgagact    960
ctgtctcaag aagaaaaaca aaaaaaggca gtgactaaca gggatgttac ttagcaggac   1020
aggactgtgg aaggagctaa gactgggagt ttcacaaaga caaagctaga aatgatactt   1080
ggagagctgt gttcttgttt taaaaaaatt gtaacaggag gccaggcaca gtggctcatg   1140
cctgtaatcc cagcactttg ggaggctgag gcaggaggat tgcttgaggc caggagttca   1200
aaaccagcct gggcaacatg gcgaaacccc gtatctacaa aaagttaaaa attagccagg   1260
catggtggtg catggctgta gtcccagcta cttgggaggc tgagacagga ggatcacttg   1320
agccctgtag gtccatgctg cagtaaacca agattgtgcc actgcattcc agcctgggcc   1380
acagagtgag accctatctt taaaaaaaaa aaaaaaaaaa aaaaaaaaaa acaggaatgc   1440
atgcagatta aactatgtgt ctgtatacag tatgcaaact ttagcaagtg ccaggcactt   1500
aggcagtagt ctatagctga aaaataaaac attcagaacc actttttaag gttttgtgtc   1560
```

```
cttgtaactt taggcattat tattacaata taacttagct gggacatgag agttaataga   1620
tccacatttt aaagtagatt tttttttaa ttttctagaa tgtgtctgtg aaaactacaa   1680
gctggccgta aactgctttg tgaataataa tcgtcaatgc cagtgtactt cagttggtgc   1740
acaaaatact gtcatttgct caaagcgtga gtaaaatatc ctaattacct gtaagcttta   1800
ttttgactta atacttcttt aattgatgtg ccttgagttg gaaagagttt tattggctta   1860
aatctgaatc atgttacaaa gtaagtgtgg gaacacataa atttcaaata atctttgacc   1920
ctggaacttt agagttaatt tttttttcc cgtaatcatg aaatcagtta tttttcagtt   1980
tggcattaag gtttcttttt cagtggctgc caaatgtttg gtgatgaagg cagaaatgaa   2040
tggctcaaaa cttgggagaa gagcaaaacc tgaaggggcc ctccagaaca atgatgggct   2100
ttatgatcct gactgcgatg agagcgggct ctttaaggcc aagcagtgca acggcacctc   2160
catgtgctgg tgtgtgaaca ctgctggggt cagaagaaca gacaaggaca ctgaaataac   2220
ctgctctgag cgagtgagaa cctagtgagt ggggctgcct atactacttg ttttcatgct   2280
gttcagattc atttaattaa atttattttt gattatgtaa tatgatttca tggtttagaa   2340
ttcagaagat atgagtgtcc agtgaaaagc ttccttctca ttccagtccc cctcgctacc   2400
cattggacct ccacagaatt gatgttattg attattctat aaccttccag agatagttga   2460
tgaatttgtt atatatctgt tttattattt ttacataaat gatagcatac taggtataat   2520
ttttctttta tatctttact taacattatt cagtatttca ttgttgcatt agtagtaaat   2580
gtatgtaatt taacctatgt atttgcttat tgattgtgtt ttaaaagtga gatatgcttg   2640
ttttagggat tgtttaatga aaaggcacag aaacccactc aagctagctt aagcaaaaaa   2700
agacttcatt ggaagggact agaaactgga aaggatgtca ggaccaaagt gggcactttg   2760
tttttctgtt ctggtcttct ggagcctcgt tgtcagtttt ctctttgtgc cctttctttt   2820
gtttttttctt ttttctttc ttttctttt ttttcgagat ggaatttcca ctcttgttgc   2880
ccaggttgga gtgcagtggc acaatctcag ctcactgcaa cctctgcctc ccgggttcaa   2940
gcaactctcc tgccttagcc tcctgagtag ctgggactac agctatacca cacctgacta   3000
atttttgtat tttagtagag atggggtttc accatgttgg ccaggctggt ctccaactcc   3060
tgacctcagg caatccaccc acctccacct cccaaagtgt tggattacag ttgtgagcca   3120
ccatgcccgg gcctttcatg ccttttcatc tttttagttg aacagggcat gacactgcc    3179
```

<210> SEQ ID NO 349
<211> LENGTH: 3187
<212> TYPE: DNA
<213> ORGANISM: Homo sapiens

<400> SEQUENCE: 349

```
tctttgtgcc ctttcttttg ttttttcttt tttcttttct tttcttttt tttcgagatg     60
gaatttccac tcttgttgcc caggttggag tgcagtggca caatctcagc tcactgcaac    120
ctctgcctcc cgggttcaag caactctcct gccttagcct cctgagtagc tgggactaca    180
gctataccac acctgactaa tttttgtatt ttagtagaga tggggtttca ccatgttggc    240
caggctggtc tccaactcct gacctcaggc aatccaccca cctccacctc ccaaagtgtt    300
ggattacagt tgtgagccac catgcccggg cctttcatgc cttttcatct ttttagttga    360
acagggcatg acactgccag ctaaactttg acttaatgtg actttatgta ttgtgtccag    420
agaacagagg gtcaatatta gaaaaggtgt tccctcctgg gtgtgtcctt tatgaaggat    480
```

-continued

```
gtgtaaggga agaaattata ggaatagcta ctgcataaat tttttttctc ttagtcctta    540
taattcgaga attttaggat tagcttatta ggaaaatagt atggaagact gagttatagt    600
caactgacat tgtcttttta ctttatagct ggatcatcat tgaactaaaa cacaaagcaa    660
gagaaaaacc ttatgatagt aaaagtttgc ggacgtaagt gcaattaaat gcatcatatt    720
cttgcacagt tggtggctca aatcttccat cctacaccat tagaaaaagc aagtctaaat    780
gctttttat atttctgaaa aataaagtta cttgaaatag agttgcaaga atagcacaga    840
gattctggga atacacttca ctcagattca ccaattaaca ttttggcaca tttgcttttt    900
atatgtgtat gtgtggatga atatgtgtgt gtgctttaca tcagtgtatc tatgcatgta    960
taaatatttt tcccagaagc acatgagagc aagttgtaga catcaggccc ctttacccct   1020
aagtacttca gtgtatgttt tcctaagaac aaaaggcatt cttttatata aaccactata   1080
caacgatcaa atttaggaaa aatttttttt ttttttttta gacggagtct cgctctgtca   1140
cccaggctgg cgtgcagtgg cgtgatctca gctcactgca acctgcgcct gccggtttca   1200
agcgattctc ctgcctcagc cttccaagta gctgggacta caggtgcctg ccactacgcc   1260
ctgctaattt ttgtagtttt agtagaaaca gggtttcacc atattggcca ggctggtctc   1320
gaactcctga acttgtgatc ctcccgcctc tgcctcccaa agtgctgcaa ttacaggtgt   1380
gagcttccgc gcccggccag gaaatttaac gttatatcac gttgtgccca ttttcccaat   1440
attgtccttt gtagtaattt ttcccctctg attcaggacc cagtccaaga tccatgtatc   1500
acatttagtt gtcatgactc tttagtctct taatatcgaa cagtttcttg gcctttcttt   1560
gtcttccatg aacttgctat ttttaaagag catgggcaag tcattatata taatgtccct   1620
caaatttga tttgtctgat atttcctcct tttttttttt ttttttgag ttggagtttt   1680
cccttttgtt gcccaggctg gagtgcaatg gtgcaatcac ggctcaccgc aacctctgct   1740
tcccggattc aagcgattct cctgcctcag cctcctgagt agctgggatt acaggcgtgc   1800
gccaccatgc ctggctaatt ttttttgtat ttttagtaga cacggggttt ctccacgttg   1860
gtcaggctgg tctcgaactc ccaacctcag gtgatctgcc cacctcagca tcccaaagtg   1920
ctgggattac aggcatgagc cacctcaccc gagccttgat gttccctctt aactaaaagc   1980
aggttatgca tttttgacag gaaaactact taagcgatct tgtgtccttt ataatacttc   2040
acattaggag ttgcatgatg tcagcttgtc cctttactag taaagtaaac tttggttaaa   2100
gtggtatcca ccaggttttt ccactgtgaa gttaccattc tccctttgta atccataaat   2160
aatctatggg cagatacttg gatactaagt aaatgttctt tttctaatta aactggtacc   2220
cagcagtttg aatatcaatg gatgattcca gcctgaatca attattatta tgatagttgc   2280
aaaatggcag aaaaatttta actttaatga cagttttaga ccctgagctg tctgcttaaa   2340
gagtagtgct tcttactgtt gtgtggtaca aacatttttt tttaatacag attttaaatt   2400
ctttacagtg cacttcagaa ggagatcaca acgcgttatc aactggatcc aaaatttatc   2460
acgagtattt tggtatgatt ttttaataag tgagctttag cagacagttg gtgagacagt   2520
atgttttgag tataaggaca gccagtgatt taagtggtgg ttaaatgcac ttactggagc   2580
aacagtttcg gatctgggta cttaatgtga atttcctgtt actgtttttt tttgtttgtt   2640
tgtttcttta agacagacta ttgctctctt ccccaggctg gagtgtcatg gcaagatctc   2700
ggctcaatgt aacctctgct tccaaggttc aagcaattct catgcctcag cctcccgagg   2760
agctgggact acaggcacat gtcaccatgc ccagctaatt tttgtatttt tagtgtcggc   2820
ggggttttgc tatgttggcc aggctggtct cgaactcctg gcctcaagtg atctgtctgc   2880
```

-continued

```
ctcagcctct caaagtgttg ggattacagg tgtgagccac cacgcccggc ccattgtttt   2940

tggttatcgt tgttttcctt ccatagcctt tgaaaagcct agttttactc ctaaagaaaa   3000

cgtagtatct cttagtatcc ctaaaacatt tgagttttct tatcctggag aacctgtccc   3060

tgtggatgag ctccagtaac atcttaaagt aaatatgcac caaaattact tttggtaaat   3120

acagttttgg tgcatattta ctttaggatg ttactggagc tcccatcttc tctgctttaa   3180

ggaacta                                                             3187


<210> SEQ ID NO 350
<211> LENGTH: 3128
<212> TYPE: DNA
<213> ORGANISM: Homo sapiens

<400> SEQUENCE: 350

acctgtccct gtggatgagc tccagtaaca tcttaaagta aatatgcacc aaaattactt     60

ttggtaaata cagttttggt gcatatttac tttaggatgt tactggagct cccatcttct    120

ctgctttaag gaactagtcc ttaactagtt agcccttact taactcttta aactctggtt    180

taaaaaataa aaagaagctt gaatagtgtg acggaactct ttaaaggtag tatgaattta    240

ttcaagagtc tttagaaaga atgtactttt tttactcttt aaaaacaaaa tgatggccgg    300

gcacggtggc tcacgcctgt aatcccagca ctttgggagg ccgaggcagg tggatcacaa    360

gatcaggaga tcgagaccat cgtggctaac acagtgaaac cctgtctcta ctaaaaacat    420

acaaaatagc cgaatgtggt ggtgggcacc tgtagtccca gctactcggg aggcttgagg    480

caggagtatg gcgtgaacct gagaggcgga gcttgcagtc agctgagatt gtgccactgc    540

actccagcct gggcgacaca gcaagactcc gtctcaaaaa caaaacaaaa aaacaacatg    600

gaaaatgcat gctgcgtttt accttgcatt tctttttctt ttcttttttt ttttttttt    660

ttgagacgga gtttcgctct tgttgcccag gctggagtgc aatggcgcca tctcggctca    720

ccacgacttt tgcctcccag gttcaagcga ttctcctgcc tcagcttccc tggtagctgg    780

gattacaggc aatgtgtcac cacgcctggc taattttgta tttttagtag agatggggtt    840

tctccatgtt ggtcaggctg gtcttgaact ccggacctca ggtgatccgc ccacctcagc    900

ctcccaaagt gctgggatta caggcatgag ccactgcacc cggccttacc tttcatttct    960

ttagtaattt agttttaaag tagttctaat ccaaataaaa tactttcata tcttatttaa   1020

aaatcttttc aatataagaa aatcctctta ggaaaaattg tacattgtaa ttatgtttgg   1080

ttgcatggct gtcttatttc cctttgatag atttagagac ctcccaaaga tttcttgatt   1140

agtgataaac ttagttatcc actaatggaa aggaacagtg atgcatgtag attatagaaa   1200

atcaaacact gaatattctg attctcaatt aatgttattt tcaaatgatt ttgattatat   1260

tagtattaat ttgtattatt caattttttt ccccagtatg agaataatgt tatcactatt   1320

gatctggttc aaaattcttc tcaaaaaact cagaatgatg tggacatagc tgatgtggct   1380

tattattttg aaaaagatgt gagtatcatc ttctttattc ctgtgttcag gaatgtagtc   1440

tatcatgcct caatgaatta aatatatttc atcacctttt tatccactta cagatcaacc   1500

aaatggttcg ctgctgccgt taattttgtc ctccctgtca ctcacatgca tcttgcttgt   1560

ttgtatattt atgcctctta tcaaattgtt ctgcctaaaa tatctcccct ctttcttata   1620

attcttattt attatctact tggtggttac ttagtttgtg catatatgct cccctatgat   1680

atttataatt tacacaaata aaagtctgtt aaaaaagact gtaactgata tgattaaaat   1740
```

-continued

```
attttgttga aactttaata tattatagtg aggtattttc tgctgaaata tgaggtttgc   1800

ttcaaaataa tctgggcggg ggtgaaagga tgaaaggaag aaaagatgaa gtaagagagg   1860

ctatgtgttg ttggccttgc atctgggtga taggtacatg ggcatcattg cactactctt   1920

tctactttcg tgtatgttga aaggttcctg taataaacag ttttttaaag ttccaataaa   1980

ttagattgtt atcactaaaa ccataaagat tcttggcagc ggttcttttg gcatacaatt   2040

tgtatgtaat tatatgtggc catggttggt ttccttaaat atttttaatt ccttttctcc   2100

ttttcaatac aggttaaagg tgaatccttg tttcattcta agaaaatgga cctgacagta   2160

aatggggaac aactggatct ggatcctggt caaactttaa tttattatgt tgatgaaaaa   2220

gcacctgaat tctcaatgca gggtctaaaa gctggtgtta ttgctgttat tgtggttgtg   2280

gtgatagcag ttgttgctgg aattgttgtg ctggtgagta cagaacaagt aaaatttcat   2340

ttaagggtat atttttcaa gaaaaagtaa tagtggctgg gcgcggtggc tcaccacacc   2400

tgttatccct acactttggg aggctgagac aggtggatca cttgagccca ggagtttgag   2460

accacactgg gcaacatggt gaaaccttat ctgtagtaaa aatacaaaaa ttagtcagat   2520

gtgatggctt gcacctgtgg tcccatctac ttaggaggct gatgtgggag tggtcagttg   2580

agtccaggag gtcaaagctg cagtgagcca tgatcacacc actgcactcc agcctgggca   2640

acacagcagg accctgtctc aaaaagaaga aaaaaggaaa tatgaaaaag taacatccat   2700

attccaaaac attcagggaa aaaaatcttc atttttaaat aatttttta tggtgaatga   2760

atctattgta tctctggtct ctttttacaa aagtcatttt atgaagcaag aaaggatgct   2820

aatattaaaa agcttgtggc tgtgcacctc acaggccagt taaattgcca tctagcagca   2880

agcgtctttc agttgtcact gcaaacaatt caacacctag tgcaaaatac ctgaaccccc   2940

aaaccactca ataagatgga acaacagaac acaaagttaa cgttagccat acaaaagagt   3000

taaaagtgat atgtgaatca atacttccaa gtaaagatga gcaaattgaa tttaacagtg   3060

cttcagcaaa agaatgtatt gcttgaagaa gtgaaaggtt tattttagga atgtaaggat   3120

gcttcggt                                                            3128
```

<210> SEQ ID NO 351
<211> LENGTH: 2155
<212> TYPE: DNA
<213> ORGANISM: Homo sapiens

<400> SEQUENCE: 351

```
atacctgaac ccccaaacca ctcaataaga tggaacaaca gaacacaaag ttaacgttag     60

ccatacaaaa gagttaaaag tgatatgtga atcaatactt ccaagtaaag atgagcaaat    120

tgaatttaac agtgcttcag caaaagaatg tattgcttga agaagtgaaa ggtttatttt    180

aggaatgtaa ggatgcttcg gtatcaagaa atcttactaa cactggccag gtgtgatggc    240

tcaggcctgt aatcgcagca ctttggaagg ctgaggcggg tagatcactt gagatcagaa    300

gttcgagacc agcctggcca acatggtgaa accctgtctc tactgaacat acaaaaaaat    360

tagctgggcg tggtggcaca tgcctgtaat ctattcggga ggctgaggca ggagaatagc    420

ttgaacctgg gaagcagagg ttgtagtgcg ccaagatcat gccactgcac tctaatctgg    480

gtgacagagc aagactctgt ctcaaaaaaa aaaaaaaaaa aaaaaaaaaa aaggccaggc    540

acagtggctc atgcctgtaa tcccagcact ttgggaggct gaggcgggtg gatcacccga    600

ggtcgggagt tcgagaccag cctgaccaac gtggagaaac cccatctcta ctaaaaatac    660

aaaattatcc gggcatggtg tctcatgcct gtaatcccag ctactcagga ggctgaggca    720
```

```
ggagaatcac ttgaacccag gaggtggagg ttgcagctga gatcatgcca ttgcactcca    780
gcctgagcaa caagagtgaa actccgtctc aaaaaaaaaa aaaaaaaaaa gaaatcttac    840
taacacaaca gaattcagaa agaggtttga gggtatttag gaacttagat ttccagttca    900
atcaaccatg tttggctatc catctggaac aaaatgaaag ttgaattcct atttcactcc    960
accaggctgg ccatattgcc cagctgtgtg agggtggcat gtccagagca cagtagtagg   1020
aaaggcgttg ggcagtgtat ccattttcaa agacatttac atatttaaaa atacaaaaaa   1080
gtaaactccc aagaaaatta attgagggaa tgtttgtaca accttgtggt aggggaaatt   1140
atgtaaggca agaaatctgg aatccatgaa agaaaagata catatatgtg tatgtatatt   1200
ttgagagagg gtcttgctgt gtcacccagg ctggagtgca gtagcatgat cataactcac   1260
tgcaacctcc aattcctgga cttaagtaat cctcctgacc tatcctccca agtagcaagg   1320
actacaggta tgtgccacta tacctggcta attttttaat ttttagtaga gacgaattct   1380
tgctatggct gccgaggctg ggcttgaact cctaggctca agcagttctt ttggcttagc   1440
ctcccaaact gctgggatta caggcatgag ccattgcacc tagtcctata tatatatatt   1500
ttggcttcat taaaattaag cattttatat ggcaaagaaa ctgtaaagta aaaaataacg   1560
atgggcatga aaaaaatatg gcgcataaag caaaaatgga tattatacat aatatacaaa   1620
gagttcttac aaattgatga ggaaacctaa agaaagaatg acaacaggta gggatagaca   1680
gttaatagaa atttcagatg gcaaatgaac acaagtggtt aatgctggaa gtctaattgt   1740
tctgtagaaa taaatgaaaa cacaagtgca ataaggaagc acattgttat tgtatcatag   1800
cattgcttgt aaaggtgaat ctggccaggc gtggtggctt acgcctataa tcccagcact   1860
ttgggaggct gaggtgggca gatcacctga ggctgggagt ccgagaccag cctgaccaac   1920
acggagaaac cccgtctcta ctaaaaatac aaaatgagcc aggcatggtg gtgcatgcct   1980
gtcattctgg ctactcagga ggctgaggca ggagagtcac ttgaacccag gaggcagagg   2040
ttgtagtgag ccgagatcat gtcattgcac tccagcctgg gcaacgagag caaaactctg   2100
tctcaaaaaa tgaataaaaa caacaacaaa agtgaatctg gaaaatagcc tgagt        2155
```

<210> SEQ ID NO 352
<211> LENGTH: 3118
<212> TYPE: DNA
<213> ORGANISM: Homo sapiens

<400> SEQUENCE: 352

```
catgcctgtc attctggcta ctcaggaggc tgaggcagga gagtcacttg aacccaggag     60
gcagaggttg tagtgagccg agatcatgtc attgcactcc agcctgggca acgagagcaa    120
aactctgtct caaaaaatga ataaaaacaa caacaaaagt gaatctggaa aatagcctga    180
gtgtgtatca gtaagagagt aaattatgtt tattgtatct acgataggga ataatgtgaa    240
tggtgaatga gttcgatctt tatctttgga tctggaatgg ttgctatgat gttgatacaa    300
gctgtgcaca ggtggtgatg atactgcatg gtcccatttt tagaccccaa aacttagatg    360
catgtgttta tatatgatat ttgtattagt gtggaaaagg aggatgtgga agaatgcaca    420
ccaaactgtt aaatttcttt cttttttttt tttggaatgg agtctcgctg gccggacgtg    480
gtggctcact gctgtaatcc cagcactttg ggaggccaag gcagctgggt cacgaggtca    540
ggagatcgag gccatcctgg ctaacacggt gaaaccctgt ctctactaaa aatacaaaaa    600
attagccagg tgtggtggcg ggcacctgta atcccagcta cttgggaggc tgaggcagga    660
```

-continued

```
gaatggcgtg aacctgggag gcggagcttg cagtgagccg agattgcacc actgcactcc    720
agcctgggtg acagagcgag actccatctg aaaaaaaaaa aaaaaagaaa aggagtctct    780
ctgtgttgcc ctggctggag tgcagtgtca tgatctcggc tcactgcagc ctccacctgc    840
cgggttcaat tgattctcct gcctcaccct cccgagtagc cgggactaca tgcagaagcc    900
accatgtcca gctaattttt gtatttttg gtagagacag ggtttcacca tattggccag    960
gctggtctcg aactcatcac ctcgtgatcc gcctgcctcg gcctctcaaa gtgctaggat   1020
tacaggcatg agccactgtg cccggcttct tcttttttt ttttttttt ttttttttt   1080
ttttttttt tttttttgag atggagtctt gctctgttgc ccaggctgga gtgcagtggc   1140
acgatctcgg ctcactgcaa cctccatctc ccaggttcaa gccattttct tgcctcagct   1200
tcccaagtag ctgggactac aggcgtgcac caccatacct ggctaatttt tttgtatttc   1260
tagtagagat agggtttcac catgttggcc aggctgatct cgaaatcctg atgtcaggtg   1320
atctgctcac ttcggcctcc caaagtgctg tgattatagg cgtgaaccac catgcctggc   1380
ctaaactgtt aaatttcttt aaagattatt cattgtttcc ttttttttctt tctctttctt   1440
ttctgttgtc ccattggatc cagcattgtt tttgattttg atttttgttt gtttgtttca   1500
cttgtcgtgg tagacttttt tttgtttagt agtgaaagtt tttattttat tttatttatt   1560
tatggagaca gagtctcctt ctgttgccca ggctggagtg caatggtgca tgatcttggc   1620
tcactgcaac ctctgccccc caggttcaag ctattctcct gcctcagcct cccgagtaga   1680
tgggattaca ggcgcctgcc accacgcctg gctaattttt gtatctttag tagagatgag   1740
gtttcacaat attggccagg ctggtcttga actcctgacc taaagtgatc cacccacctc   1800
agcctctgaa agtggtaaga ttacaggcat gagccatcat gcctgaccta ttttatttta   1860
ttttaatttt tttttagaga tggagtccca ctctgtcgcc caggctggag tgcaatggcg   1920
ccatctcggc tcactgcaac ctctgcctct cgggttcaag tgattttcct gcttcagtct   1980
cccaagtagc tgggattaca ggcgaccacc accgcgcctg gctaattttt ttgttttttt   2040
agtagagtcg gggggtttca tcatgttggc caggctggtc ttgacctcct gacctcaagt   2100
gatccgccca cctcggcccc acaaagtacc ggtgagccac cacgcccagc ccaccttatt   2160
tatttttaag agacagggtc ttactctgta gcccaggctg gagagcagtg atgccatctc   2220
cactcactgc aacctctgcc tcctgggttc aagcaattct ggtgccttag cctcctgagt   2280
agctgggact acaggtgcgt gccatgacac ctggctaatt tttgtatttg tagtagagat   2340
ggggtttcac cgtgttggct gggctggtct gaaactcctg acctcagatg atcttcccgc   2400
ttcggcctcc caaagtgccg ggattacagg catgagccac tccactggtg tgaaattttt   2460
aatttaagaa gcaataaatg tttatggata gatgttaaaa ttagtttttt ttcagatcaa   2520
aattatgtcc attaaaagca tatatgtctg tttagataat cttttttga atagcagtcc   2580
taaaacaata gttgtctttc ttccactcag gttatttcca gaaagaagag aatggcaaag   2640
tatgagaagg ctgaggtaaa tggattactt acctaaatag aaaggccctg ttgaatctct   2700
tactcctaat cactctacct tcctacacac tgatgcattt cagttatact ggagtccctt   2760
tatactgttg tctttagggt cttagggaca gtcttagaat gtactcttac ctaaatattc   2820
ttgcgtgagt tccatggcag atcaccatct gttttctgcc tcatagaaga gtggaatggg   2880
aagcctatgg tttttattct acaaagagtc aacatctaac agaatcttct gaaggcatac   2940
tccagtggat tcaccttgga gaaactcatt gtgactgatg atctgattta ttatctctat   3000
gccagtgaaa taatcattta atatgaactt aatttgtcat aatctattgt gtactaacta   3060
```

gtctatacta gtgtgacatc aaagtgtcag attgttagtg tgtttcagtc ccttggaa 3118

<210> SEQ ID NO 353
<211> LENGTH: 2346
<212> TYPE: DNA
<213> ORGANISM: Homo sapiens

<400> SEQUENCE: 353
tagtgtgttt cagtcccttg gaattgaata tgaacactta tccttgaacc ctatcaataa 60
catttttcac atatctcaat ttttgtgtgt ctttgtagtt gtatgtgggc cacttactaa 120
tattttagca agtaataaaa atagaaacgt aaaggaatat tggaaaaagt ctaatggaac 180
cagaaagttc tagcattttt ttcccattct gtagtaggtc atctggttta tttggtttgg 240
tgaccgcaag tctagaagac taaccctgaa ttgaatggta acagacaggc agaatgacaa 300
tgtagtgttg cagtgcagag cagtacagac ctgggtttgg ctgggcaaaa ttatataact 360
tctttaagcc tccatgtttc ctcatctgta aaatgaggat aatagatagt atggacctgt 420
tgcaaggatt aaacataatc agtgtaaagt gttggtccca tgcttgccac ataagaaaat 480
atttgtcaac agagtggtag ttgtcattat cattgtctca gtttgcctgt aactagttgt 540
gtgatctgag acaaacacta attttgaact tgagtttccc cacatgtaaa atgaaagatt 600
gataatagaa agtaaatcaa ttttttctag cattaaaaat agtatgcatt taataaaaat 660
cttattctta atgatctagc ttacctccaa cttgccctag tcactttggc gatcttgtct 720
ctaaatagaa ccttgaaaac acttaaatgt gtgtttcctt gcaatataac tttttctttt 780
tttatttaaa taagtcttat aaatgtggga aaaaattatc ttgtgttcct ttaatttcat 840
ttttatttaa tactattttc agaatgaaca aaagattgaa aaattattta gaattttttt 900
ctgtgctttt tcctgtttca gataaaggag atgggtgaga tgcataggga actcaatgca 960
taactatata atttgaagat tatagaagaa gggaaatagc aaatggacac aaattacaaa 1020
tgtgtgtgcg tgggacgaag acatctttga aggtcatgag tttgttagtt taacatcata 1080
tatttgtaat agtgaaacct gtactcaaaa tataagcagc ttgaaactgg ctttaccaat 1140
cttgaaattt gaccacaagt gtcttatata tgcagatcta atgtaaaatc cagaacttgg 1200
actccatcgt taaaattatt tatgtgtaac attcaaatgt gtgcattaaa tatgcttcca 1260
cagtaaaatc tgaaaaactg atttgtgatt gaaagctgcc tttctattta cttgagtctt 1320
gtacatacat actttttttat gagctatgaa ataaaacatt ttaaactgaa tttcttaact 1380
ttgacatttc aaatttcttc ttctttttct tttctttttt tttttttttt gagatggagt 1440
cccactctgt tgccaggctg gagtgcagtg gcacaatctc ggctcactgc aacttctgcc 1500
tcctaggttc aagcgattct tctgcctcag cctcccgagt agctgactac aggcgcccac 1560
caccattcct ggctaatttt tgtattttta gtagagacaa agtttcacca tattggccac 1620
gctagtctcg aactcctgac ctcacgatcc acccacctct acctcccata gtgctggggt 1680
tacaggcgtg agccaccgcg cccggcctct ttttttcttt ttgttttgtt ttttcttttt 1740
tttttgaga caggatcttg ctctgtggcc taggctggag tgtagtggtg cgatctcagc 1800
tcactgcagg attcaagcga ttctcctgcc tcagcctacc aagtagctag gattacaggc 1860
tcccactacc atgcccggct aatttttgta tttttagtag agaaaaggtt tctttttctt 1920
ttttcttttc tttttttctt tttttttttt tggggggggtg agacagagcc taactctgtt 1980
gcccaggctg gagtgcagtg gcacaatctc agctcactgc aacttctgcc tcctgggttc 2040

```
aagcaattct cctgcctcag cttcccaagt agctgggact acagatgtgc accaccatgc   2100

ccggattatt tttgtatttg tagtagagac agagtttcgc catgttggcc aggctgatct   2160

cgaactcctg acctcaagtg atccacccac cttggtctcc caaagtgctg ggattacatg   2220

tgtgagccac catgcctggt cctatttact ctttgttaag tggaagtgga tcatcataaa   2280

ggtcttgatc ctcatagttt tcactttgag taggctgagg aagaggaagg gttggtcttg   2340

ctgtct                                                              2346
```

<210> SEQ ID NO 354
<211> LENGTH: 3104
<212> TYPE: DNA
<213> ORGANISM: Homo sapiens

<400> SEQUENCE: 354

```
cacattacga gctcagtgcc tgccggaaat ctcccacctg gtggcaacct acccttgcat     60

acaccccacc caggggcttc aagccttgca gctgagtaaa cacagaaagg agctctacta    120

aggatgcgcg tctgcgggtt tccgcgcgac ctaggcgcag gcatgcgcag tagctaaagt    180

caccagcgtg cgcgggaagc tgggccgcgt ctgcttatga ttggttgccg cggcagactc    240

ccacccaccg aaacgcagcc ctggaagctg attgggtgtg gtcgccgtgg ccggacgccg    300

ctcgggggac gtgggagggg aggcgggaaa cagcttagtg ggtgtggggt cgcgcatttt    360

cttcaaccag gaggtgagga ggtttcgaca tggcggtgca gccgaaggag acgctgcagt    420

tggagagcgc ggccgaggtc ggcttcgtgc gcttctttca gggcatgccg gagaagccga    480

ccaccacagt gcgccttttc gaccggggcg acttctatac ggcgcacggc gaggacgcgc    540

tgctggccgc ccgggaggtg ttcaagaccc agggggtgat caagtacatg ggccggcag     600

gtgagggccg ggacggcgcg tgctggggag ggacccgggg ccttgtggcg cggctccttt    660

cccgcctcag agagtgggcg gtgagcagcc tctccagtgc ggaggcacgg gggcggaacg    720

ttggtgcttg tgcggattcc gccgtcccca ggttctgctt ggctccggag ggacgccccc    780

ctcagccctg aaacccgtgc ctctccagcc gccccggatc tgaacttgtg atcacggagt    840

gtttacgtcg tgccaggcat tttaatgcat tgttctagtt cattttccag cagtcgcatt    900

cctcgccttg gccctacatg tagcgctcat tacaaacacg gccagaatct cttattaaca    960

aacagcagcc aggagtgaga tttaaaatag actgggggtt taggagaccc ttttatgaca   1020

cgtaattctg ctcccacgac gctcccattt ataccgccgg tccagctaag ggtctggtaa   1080

tggagcgccg ttgaagagca gtatgatgaa gtggtcagga ccaacggact ctggagctgg   1140

gctgcttggg atcaagtcgc tgcccctctg cttattaacg tgtgaccttg ggccagtcat   1200

ggacgctatc tgcttcagct cagcattcag tgctctccgt cacccgaccc catctatcca   1260

ggattatctc tccctggaaa gctacaaacg tctcacccta tgtgggccaa atgttctgga   1320

taggcctagt taacctcttc tctccctgtt ttctttgcgc tttcttgcag ctatgtagtt   1380

atgctaatga aaagagcatc ctagggggag cagagttgtg gattctagtc ctgactagag   1440

gactagtgca aatgcgatac tcctgatgaa aaatgtttca ttcgttagat ataaatgtgt   1500

taggcagggt tatggacact agatgaaaaa agaaatacct ctactttcat agagatcact   1560

attggacagc aaggcagaaa taattacaat tcaagttgga ggcttatgga ggtgagcttg   1620

taagaggtta caagaggcgc caaggcagga tcgccaaaga cggaagactt tggaagagtc   1680

tcatacaacg gaagaggcgt tatatgagac accaaagtcc acgttgagtc ttggtggact   1740

agaagtttgc tagggagagg gcttgaaacg aggtagattg gcgttgctgg tgtagaaaag   1800
```

```
gaaggagact ggcccaggtg ggtggggtta gatgaccaaa ggcttttagt gtggtgttga   1860
gctgttgaaa ttttatgctg tagccaatga aaagtctgaa atgttttttt tttttttttt   1920
tctgagacgg agtcttactg tgtcgcccag gttggagttc agtggtgtaa tcctggctca   1980
ctgcaacctc cacctcctgg gttcaagcga ttctcctgcc tcagccaccg gagtagctgg   2040
gattacaggc acgtgccacc acgcctagct aatttttgta tttttagtag agatggggtt   2100
tcaccatgtt ggccaggctg gtctcaaact cctgacctca agtgatccac ccaccttggc   2160
ctcccgatgt gctgggatta caggtattag ccactgcacc tgacctacat agattttaca   2220
taagacttta aaacagggcg ggcgcagtga ctcacgcttg taatcccagc actttgggag   2280
gctgaggtgg gcggatcaca aggtcaggag atcaagacca tcctggctaa catggtgaaa   2340
ccctgtctac actaaaaata caaaaatccc agcactttgg gaggctgagg tgggcggatc   2400
acgaggtcag gagatccaga ccatcctggt taacactgtg aaaccctgtc tctactaaaa   2460
atacaaaaaa ttagctgggt gcggtggcag gtgtctgtag tcccagctac ttgggaggct   2520
gaggcaggag aatggtgtga acccggaagg cagagcttgc agtgagccga gattgtgcca   2580
ctgcactcca gcctgggcaa cagagcgaga ctccatctca aaaaaaaaaa aaaaaaaaaa   2640
aaagacttta aaaaaaatta taagaaagga cagaccaagt gcagtggttc gttccagcac   2700
ttagggatgc caaggtggga ggattgcttg atgctaggag ttgaagacta gcctgtgtaa   2760
catagcgaga cccatctcta caaaaaaatt aaaaagttac ctttagaact tacgattttt   2820
atgtgtagac tccatataag cagagggtct atgcttattc actatttatt accttccata   2880
gtccctgcac atataatagg tgcttcataa acaatttaat gaatgaataa attactgaga   2940
aaacactgga agtttttggg ttagcattgt gttaggtgct tgatatggtc tggctgtgtt   3000
cccaccctta tctcatcttg aattcccatg ttttgtggga ggtacctggt gggacataat   3060
tgaatcatgt gggcaggttt ttcctgtgct gttctcctgg tagt                    3104
```

<210> SEQ ID NO 355
<211> LENGTH: 3131
<212> TYPE: DNA
<213> ORGANISM: Homo sapiens

<400> SEQUENCE: 355

```
gggttagcat tgtgttaggt gcttgatatg gtctggctgt gttcccaccc ttatctcatc     60
ttgaattccc atgttttgtg ggaggtacct ggtgggacat aattgaatca tgtgggcagg    120
tttttcctgt gctgttctcc tggtagtgaa taagcctcac aagatctgat ggttttaaaa    180
atgggagttt ccctgcacag gctctctctc tttgcctgcc gccatccatg taagatgtaa    240
cttgctcctc cttgccttcc tcaatgattg tgaggcctcc tcagccatgt ggaactggct    300
gcagagtcat taaacttcgt tcttttgtaa attgcccagt ctcaggtatg tcttttttta    360
tttttttttg agacagagtc tggctctgtg gctaggctgg agtgcagtgg tgcgatctcg    420
actcactgca gcctccgcct cccgggttca agcgattctc ctgcctcagc ctcccaagta    480
gctgggacta taggtgcacg ccaccatgcc cagctaattt ttgtattttt aatagagacg    540
gagtttcact gtgttggcca ggatggtctt gatctcttga cctcgtgatc ttcccgcctc    600
cgccttccaa agagctggga ttacctaccc agctgggtat gtctttatta gcagcgtgaa    660
aacagactaa aacagtaaac tgataccaat agagtgggat gcagctgaaa agatacccga    720
aaatatggaa gcaactttgg agctgggtaa caggcagagg tcagagcagt ttagagggct    780
```

-continued

```
cagaagaaga ccagaaaatg tgggaaagtt tggaacttcc tagagacttg ttcaatggct    840
ttgaccaaaa tcctgataat gatatggaca atgaaatcca ggctcatgtg gtctcagatg    900
gagatgagga acttgttggg aactggagca aaggtgacac ttgttatgtt ttagtaaaga    960
gactggtggc attttgccct gccctagaga tttgtggagc tttgaacttg agagaaatga   1020
ttttgggtat ctggtgggag aaatttctaa gcagcaaagc attcaagagg tgacttgggt   1080
gctgttaaag gcattcagtt ttaaaaggga aacagcatga aagtttggaa aatttgcagc   1140
ctgacaatgt gatagaaaag aaaatcccgt tttctgagga gaaattcaag ctagctacag   1200
aaatttgcat aagtaatgag gatcccaatg ttaatcccca agacaatggg aaaaatgttt   1260
ccagggcatg tcagaggcct tcatggcagc ccctctcatc acaagcctag aggcctagga   1320
gaaaaaagtg atttcatggg ccagcccggg gtccccatgc tgtgtgcagc ctagtgactt   1380
ggtgccctgc atcccagctg ccccagctgt ggctgaaagg ggccaaccta gagctcaggc   1440
catggcttca gagggtgcaa gcctgaaacc ttgacagctt ccaggtggtg ttgagcctgc   1500
aggtgcacag aaatcaataa ttgaggtttg agaatctctg cctaggtttc aaagatgtat   1560
ggaaacgcct gcatgtccag gcagaagttt gctgcagggg tggggtgctc attgagttcc   1620
tctgctaggg caatgtagaa gggaaatgta gggtcagagc ccccccacag agtccctact   1680
ggggcaccac ctagtggagc tgtgaaaaga gggctaccat tctccagacc tcagaatggt   1740
agatccacag acagcttgca ccatgtgcct ggaaaagctg tagacactta acgccatctc   1800
atgaaagcaa ccaggcagtg tgctgtaccc tgcaaagcca caggggcaga gctgtccaag   1860
gctgtggttg cccagctctt gcatccgcat gacctggaca tgagacatag agtcaaagga   1920
gatcattttg gagctttaag atttgactgc catgctggat tttggacttg catggggcct   1980
gtagcccctt tgttttggcc aatttctccc atttggaatg gctgtattta cccaattcct   2040
ataccccatt gtatctggga agtaactaac ttgcttttga tttgacaggc tcatatgcgg   2100
aaaggactta ccttgtcttg aatgagactt tggactggaa ttttgaatta atgctgaaat   2160
gagttaaggc tttgggggac tgttgggaat gcatgattgg ttttgaaatg tgaggacatg   2220
agatttggga ggggtcatgg cagaatgata tggtttggct atgtccccac ctaaatccca   2280
tcttgaattc ccatgtattg tgggagggac ctggtgggag atagttgaat catggggatg   2340
gatctttccc atgctgttgt gatagtgaat aagcctcatg agatctgatg gttttaaaaa   2400
cggaagtcta cctgcacaag ctctttcttt gcctgctgcc atccatgtaa gacatgactt   2460
gttcctcctt gccttctgcc atgattgtga gacctcccca gccatgtgga actataagtc   2520
cagtaagcct ctttttcttc ccagtctcgg gtatgtcttt atcagcagca tgaagtccag   2580
ctaatacagt gcttgaacat gtaatatctc aaatctgtaa tgtacttttt tttttttaa    2640
ggagcaaaga atctgcagag tgttgtgctt agtaaaatga attttgaatc ttttgtaaaa   2700
gatcttcttc tggttcgtca gtatagagtt gaagtttata agaatagagc tggaaataag   2760
gcatccaagg agaatgattg gtatttggca tataaggtaa ttatcttcct ttttaattta   2820
cttatttttt taagagtaga aaaataaaaa tgtgaagaat ttaattgtgt tttagtattt   2880
taagtagatt gtgatagtag aatggtttga gacactttaa tagcaattag catgtggttt   2940
ttaaaaagtt gcagtttggc tggtcgcagt ggctcatgct tgtaatccca gtattttggg   3000
aggctgaggc aggtaggttg cctgagccca ggagttcaag accagcctgc ccaacgtggt   3060
aaagccccat ctctactgaa gataaaaaaa tttaaaaaaa ttagctgggg ctattggcac   3120
acacctgtgg t                                                        3131
```

-continued

<210> SEQ ID NO 356
<211> LENGTH: 3085
<212> TYPE: DNA
<213> ORGANISM: Homo sapiens

<400> SEQUENCE: 356
agttgcagtt tggctggtcg cagtggctca tgcttgtaat cccagtattt tgggaggctg 60
aggcaggtag gttgcctgag cccaggagtt caagaccagc ctgcccaacg tggtaaagcc 120
ccatctctac tgaagataaa aaaatttaaa aaaattagct ggggctattg gcacacacct 180
gtggtcccag ctaatcaaga ggatgaggtt agaggatcac ttgagcccag gaggttgagg 240
ttacagttta actttcagag gccaaggcag gaggattgct tgagtccagg agtttgagac 300
caccctgggg aatgtaggga gatcccatct ctatagaggg atagattaga tagataattt 360
ctgaggggag gggaggggga gggccaggga aggggaggga aaggggaggg gagggcaggg 420
ccagcagtaa ggtcataata gagacatgta tctgtaagat ccttataata ggtgaggatg 480
gccacaaatt agcgccacag atttgtattt ttagtagaga caaggtttta ccatgttggc 540
caggctggtc ttgaactcct gacctcaagt gatccgcctg ccttggcctc ccaaagtgct 600
gagattacag atgtgagcca ccatgcccaa ccacaagcat ttatttattt atttatttat 660
ttatttattt atttatttag agacagtctt gctctgtcgc caggctggag tgcagtggcg 720
ccatctgggc tcactgcaaa ctctgactcc ctggttcaag cttttctccc gcctcagcct 780
cccgagtagc tgggattaca ggtgcatgct gcaacacccg gctaattttt gtatttttag 840
tagagatggg gtttcaccat gttggccagg acggtctcga tctcctgacc tcgtgatccg 900
cctgccttgg cctcccaaag tgttgggatt acaggcgtga gccacagcac tcagccagtt 960
atttttttat aagaaaacat tttactggcc aggcctggtg gctcacacct gtaatcccag 1020
cactttggga ggccgaggca ggcggatcac gaggtcagga gttcgagacc agcctggcca 1080
acatggtgaa accccatctc tactaaaaat acaaaaatta gccaggcgtg gtggtgtgcg 1140
cctgtattcc cagctactgg ggaggctgaa gcaggagaat cgattgaacc cttgaggcag 1200
aggttgcagt gagttgagat cgcaccattg cactctagcc tgggtgacag agcaagactt 1260
catctcaaaa aaaagagaaa acattttatt aataaggttc atagagtttg gatttttcct 1320
ttttgcttat aaaattttaa agtatgttca agagtttgtt aaatttttaa aattttattt 1380
ttacttaggc ttctcctggc aatctctctc agtttgaaga cattctcttt ggtaacaatg 1440
atatgtcagc ttccattggt gttgtgggtg ttaaaatgtc cgcagttgat ggccagagac 1500
aggttggagt tgggtatgtg gattccatac agaggaaact aggactgtgt gaattccctg 1560
ataatgatca gttctccaat cttgaggctc tcctcatcca gattggacca aaggaatgtg 1620
ttttacccgg aggagagact gctggagaca tggggaaact gagacaggta agcaaattga 1680
gtctagtgat agaggagatt ccaggcctag gaaaggctct ttaattgaca tgatactgtt 1740
tcatttaagg aaaaataata aaaaaactct tttttttgta tctaattaaa ataatgttct 1800
gatgtttaca gaaactttgt atatttaatt ggacattaga acaagctgtt tgttgtgtaa 1860
gatttatttt acctcagatc ttttctcccc cctttccttt ctgtcttgtg ttccaaaaga 1920
gtaattatta cggtaaatat tactgtaatt atggatttat caaataagat gcagttcttt 1980
agcatttttt gataaatcga gtggaacttt agcctgttat tttactattt gttttatttt 2040
aactaaattc tgattgtgtc attttttttt ttttttttg ggaccgagtc tcgctctgtc 2100

-continued

```
gcccaggctg gagtgcagtg gtgcgatctc ggctcactgc aacctctgcc tcccaggttc   2160
aagcaattct tctgcctcag cctcctgagt agctgggatt acaggtgtgt accaccacac   2220
ccagctaatt tttgtatttt tagtagaggt gaggtttcac catcttggcc aggctggtct   2280
tgaactcctc acctcgtgat ccacccacct gggcctccca aagtgctggg attacagcca   2340
tgagccacca tgctcggctt tgattgtgtc atttgtatag gcatgtggtt tattatttag   2400
ttattttttt ttttttcttt gaggtggagt atcactcttg gtgcccaggc tggagtgtaa   2460
tggcgtgatc tcagctcact gcaacctcta cctcctgggt tcaagcaatt ctcctgcccc   2520
agcaggagta gcttgggatt acaggcatgc ccccaccacac ctggccaatt ttgtgttttt   2580
agtagagaca gggttccacc atgttggtca ggctggtctt gaactcctga cctcaggtga   2640
tctgcccacc tcagcctccc agagtgctgg gattataggc atgagccacg gtgcccagca   2700
tatttagatt tttttttttt tgagactgag tctgactctg tcacccaggc tagagtgcag   2760
tggcacgatc cacgatcttg gctcactgca gcctccacct tatgggttca agcgattctt   2820
ctgcctcagc ctcccaagta gctgggactg caggcacatg ccaacacgcc cggcttattt   2880
ttgtattttt atagagacgg ggtttcatca tattggtcag gctggtctct aactcctgac   2940
cttgtgatcc acccgccttg gcctcccata gttctgggat tacaggcatg agccacagcg   3000
ccaggcctag atgtttctta aggtatgtat ctcccaaaga ttctttttgt ggtcctcaag   3060
taccataagc accgctggag ataac                                          3085
```

```
<210> SEQ ID NO 357
<211> LENGTH: 3148
<212> TYPE: DNA
<213> ORGANISM: Homo sapiens

<400> SEQUENCE: 357
```

```
accataagca ccgctggaga taacacatgt gatgggcatt tttagcatag attgtatcta     60
agcaactttc cacaagtaat agttctgtta agggttgtta ttgtggccgg gcgcggtggc    120
tcacacctgt aatcctggca ctttgggaag ctgaggcggc cggatcacct gaggtcaggg    180
attcgagacc agcctgtcca atgtgctgaa accctgtctc tactaaaaat gcaaagaaaa    240
aaaaaatcta gccaagcatg gtggcttgct cctgtaatcc tagctacttg ggaggctgag    300
gcaggagaat tgcttgaacc tgggaggcag aggtagcagt gagccaagat cgtgtcaccg    360
cattccatcc tgggcgacag tgagactctg tctcaaaaca aaaaaagagt tgttaccgtt    420
gggactattt tttgaaagct ttatgtgaac gtaattttat attttgatga aaatttagtt    480
tattgatgta aaaagtgtat cagtacatca tatcagtgtc ttgcacattg tataaacatt    540
taatgtaggt gaatctgtta tcactatagt tatcaatgtt ataattttca tttttgcttt    600
tcttattcct tttctcatag tagtttaaac tatttctttc aaaatagata attcaaagag    660
gaggaattct gatcacagaa agaaaaaaag ctgacttttc cacaaaagac atttatcagg    720
acctcaaccg gttgttgaaa ggcaaaaagg gagagcagat gaatagtgct gtattgccag    780
aaatggagaa tcaggtacat ggattataaa tgtgaattac aatatatata atgtaaatat    840
gtaatatata ataaataata tgtaaactat agtgactttt tagaaggata tttctgtcat    900
atttatctca aaacctaaac tgtgtatcaa tgatattaag cttttttttt tttttgagac    960
agagtttcac ttttgttgcc caggctggag tacaatggcg cgatcttggc tcaccacatc   1020
ctctgcctcc caggttcaag tgatcctcct gccttggcct cctgagtagc tgggattaca   1080
ggcatgtgcc accacgcctg gctcatcttt tttgtatttt tagtagagat ggggtttctc   1140
```

tatgttggtc aggctggtct caaactcctg aacctcaggt gatccgcccg cctcgggctt 1200
ccaaagcgct gagattgcag gcatgagcca ctgtgtctgg cctattttta tagtttatgt 1260
acttggaatt atataatata ttctgcctag cttctttcat tcaatatttg taagatttat 1320
ccatattatt gagtgtagtt gtggattttt gcatttatat ttcatagcac gagcatgtca 1380
gaatttatcc attttacttc ccttctgccc gccactgcta ctctccccat tttacctttt 1440
tttttgtttt tttgagatgg agtctcagaa tttcgctctg tcgcccaggc tggagtgctg 1500
tggcacggtc tcagctcact gcaacttctg cctctgggtt cagctgcacg ccaccatgcc 1560
tggctaattt ttgtattttc agtagagggg attttgctat gttggccagg ctggtcttga 1620
actcctgacc tcaggtgatc cacccacctt ggcctgccag agtgctgtga ttacaggcgt 1680
gaaccaccgt gcccgacccc cattctaatt ttgatggaca tttgggtaat tttcattttt 1740
ggctgttata aatactgctg caattacagt taattttcac agtttttttt tttttttttt 1800
tttttttttt tttttgaggt gagtttcgct cttgttgctc aggctggagt gcagtggtgc 1860
gatctcagcc cactgcaacc ttcaccttct ggattcaagc aattctcctt tctcatctcc 1920
taagtagctg gggtttacag gcatgtgcca ccatgcccag ctaattttttg tattttaatt 1980
tcacagttct ggaggctggg aagttcagaa ttaaggcact ggctgatctg ttgtctggtg 2040
agggcccact tgttcataga taaccatttt ctcactctaa cctcacaagg ttgaaagggc 2100
ctaatttttg tgtttttagt agagacgggg tttcactatg ttggctaggc tggtctcaaa 2160
ctcctagcct cgagtcatcc acccgcctcg tcctcccgga gtgcttggat tacagcatga 2220
gccactgcgc ccggccccca ttttagtttt gatggacatt tgggtaattt tctttttttgg 2280
ctattctaaa taatgctgca attactgtta attttcacct tgtaaaaacc attttcaaat 2340
ctcaagagat taacctttag ttttcttggt ttggattggg aaggaacacc aaggaaaatg 2400
agggacttca gaatttattt tcattttgca tttgtttttt aaaatcttta gaactggatc 2460
cagtggtata gaaatcttcg atttttaaat tcttaatttt aggttgcagt ttcatcactg 2520
tctgcggtaa tcaagttttt agaactctta tcagatgatt ccaactttgg acagtttgaa 2580
ctgactactt ttgacttcag ccagtatatg aaattggata ttgcagcagt cagagccctt 2640
aaccttttttc aggtaaaaaa aaaaaaaaaa aaaaaaaaaa agggttaaaa atgttgaatg 2700
gttaaaaaat gttttcattg acatatactg aagaagctta taaaggagct aaaatatttt 2760
gaaatattat tatacttgga ttagataact agctttaaat ggctgtattt ttctctcccc 2820
tcctccactc cactttttaa cttttttttt tttaagtcag agtctcactt gttccctagg 2880
ccagagtgca gtggcacaat ctcagcccac tctaacctcc acctcccaag tagttgggat 2940
tacagttgcc tgccaccatg cctggttaat ttttatattt ttagtagggt tgcggggaca 3000
gggtttcacc atgttggcca ggttggtctc aaacttctga ccttaggtga tcctcccacc 3060
tcggcttccc aaagtgctgg gattacaggc ttgagccatc gtgcccagcc tactttttac 3120
ttttttagag actgggcttg gtggagtg 3148

<210> SEQ ID NO 358
<211> LENGTH: 2176
<212> TYPE: DNA
<213> ORGANISM: Homo sapiens

<400> SEQUENCE: 358
ttagagactg ggcttggtgg agtgaagtgg caagatcata gctcactgca gtattgaact 60

```
cctgggctca agcgatcttc ctgcttcaac ctcatgagta gctgggtcta caggcacaag    120
ccaccatgct tgcctaattt taaaattttt gcagagttgg agtttcacag tgttgcccag    180
gatgttcgct cactcctgac ttcaagtgat tcttctgcct tagcctctag agtggtagct    240
gggattacag gcatgaacca ccatgctctg ctattttttt tcaaggtttt tttttttttt    300
tttttttttg agagactggt atgactatgt atgctcccta ggctggagtg cagtggctat    360
tcacaggaag tgccatcaga gtgtactaca gcttcaaact cctgggctca agcacttcta    420
tcatagtctc caaagtagct gggactacga gtgtgtctca ttgtgccttg ctctcgaatt    480
gctttttttt tttttttctg gtttcaagct atctatgtgg tattagtcct cactttatga    540
ataattttgt atactactaa tagcaatttt tttttttttt ttttttttga gacggagtct    600
cattcttgtc gcccaggctg gagtgcagtg gtgtgatctt agctcactgc aacctctgcc    660
tctccggttt gggcaattag ctgggattag aggcgcctgc caccatgccc agctaatttt    720
tgtattttta gtagacatgg ggtttcatct tgttggctag gctggactct aactccaggt    780
gatctgcctg cctcggcctc ccaaattgat gggattacag gtgtaaacca ctgggcctgg    840
cctagcaatt taaaatgaca ttctaagaag ttttatgtct aaatctgcag taagtggctg    900
ggtgacgtgg ctcatgcctg taatcccaac gctttgggag tccagggtgg gaggatgact    960
tgaggccagg agttgagacc agcctgggca acatagtgag actctgtctc tacaaaagaa   1020
aaaattagcg gggcttagtg gcgtgcgcct gtagtctcag ctactcgaaa ggctgaagtg   1080
ggaggattct ttgagcccca agggttctgg cttgccgtga gccaggatgg caccactgca   1140
ctccagtctg ggcaatagag tcagaccctg tctcaacaaa taaaataaaa ctgtagtaat   1200
tataaagtgg ttttggctgg gggagaaatg tacagttgaa catacggatt aagaggttga   1260
aagttggtct taggaagagg aactttttgt ggaaatttct taatatttga agaatattat   1320
gttattgttc ctctgttttt catggcgtag taaggttttc actaatgagc ttgccattct   1380
ttctatttta ttttttgttt actagggttc tgttgaagat accactggct ctcagtctct   1440
ggctgccttg ctgaataagt gtaaaacccc tcaaggacaa agacttgtta accagtggat   1500
taagcagcct ctcatggata agaacagaat agaggagagg tatgttatta gtttatactt   1560
tcgttagttt tatgtaacct gcagttaccc acatgattat accacttatt gtaatatgca   1620
gttttggaag tatatgttac catttaactg tacagagtac atagtaatag agtggtaatt   1680
atttagattg attaaagaac tcattttttt aaataagttt tttttttttc actataaaag   1740
tttattttat ttgagatggt atggtatcga acatgttcat attgtgtgta atcgtgggta   1800
aattactcaa cctttatgtc atagtttctt cacctttaaa atgacattaa taaaagagct   1860
acttaatagg attataagca tgagatgatt taatatacat aaaatactta cagtctgata   1920
tataggaagc acttaactct ttatcctaga aaagatttaa ggtgacctta acatatatgt   1980
cagaaaatct ttaaaattgt ggaaataaaa ggttgtataa ttctgctatc ctaaaattac   2040
tagtatttca atatatttta ttttagtctt ttcttttaga tacaagtttt aaaactttta   2100
agtgaagtgt aatatacgta agtactgctt gatgaattta aggtgatttc taaagccagg   2160
tttgttgggg aagagg                                                   2176
```

<210> SEQ ID NO 359
<211> LENGTH: 3128
<212> TYPE: DNA
<213> ORGANISM: Homo sapiens

<400> SEQUENCE: 359

```
ccagtttcaa gcgattaagt gattctcctt cctcagcctc ccgagtagct gggattacag     60
gcgtgtgcca ccacgtcgcc accacgtctg gctaattttt gtatttttag tagagacagg    120
gtttcgccat gttggccagg ctggtcatga actcctgacc tcaggtgatc cacctgcttg    180
gcctcccaaa gtgctaggat tacaggtgtg agccactgtg cctggcttaa gttttgtatt    240
tttagtagag acggtgttcc atcatgttgg tcaggctggt gtcaaactcc tgaccatgcg    300
atccgcctgc ctcggcctcc caaagtgctg agattacagg cgagagccac cgtgcccggc    360
ctgtttgagt atcttttaaa accagtaagg acaaactaga ggtgtcagct ctcttcatgg    420
gctttggaga aacaagacaa aaaggaaaga gatgtttcgc cgggcgcggt ggctcactcc    480
tgtaatccca gcactttggg aggctgagga cagcggatca cccgaggtca ggagtcaaga    540
ccagagccat tgcactccag cctgggcaac aagagcacaa ctttatctca aaaaaaaaaa    600
aaccaaaaaa gaaacaggaa agagatgttt tgattttta agtctagagt gttctgttct    660
tactctacag cacttagcag tagtccatct atcctccttg tttgttcttt acaacaaaac    720
cccattggtt ctctcttacc aagtttgctt tattcttggt ttatcctttg taagatgtga    780
aagggatatg aagagcaaat aggaagtgtt actcttgctg cttgagagaa agctgtttta    840
caatttgttg gcaaacaatt tgtaaaagta caacaaaagt gtgcattttt ggcttcttat    900
ttatgtttta tcattgctat atctcataat ttgtgatttt taaaataact ttttatttga    960
aaagcactac agggtcacgt catgttttta aaaaataaat taagaaggta aacacccgta   1020
cttctacttt acctctagtc ctagtctatg gtggtaatca gtgttaacag tttagtttgt   1080
gttcttaccc ttccaggggt tttttttctc tatgtataca gatatatgca tttttaaaaa   1140
catagttaac acttaaaaac aatatgggat cgtattagga atacaatctg tattccttcc   1200
caacagtata tacagttttt ttccatttca ctatgtatct atttataaat tttttatttc   1260
taataatttc tcttgaatag gtgagacatc atatagtata aaattcagta gaaaatcagt   1320
ttttcagagg tacaaaattg gctgactttg cacagactcc tttcatttca caggtaggga   1380
tgcacagcca cctcttccac cgacgagagg aaaggatatg tgtgcctgtg ggctcttcaa   1440
ctctgttgat tagttatgat ttattttctg gtcagtttga gaggaaacag tgataaaata   1500
ctgggaacag ggaagaagca taagattatt attgtttttt tttttttttt tgagacagag   1560
tcttgctcag ttgcccaggc tggagtgcag tggtgcgatc tttgctcact gcaagctccg   1620
cctcccgggt ccatgccatt ctcctgcctc agcctcccga gtagctggga ctacaggcgc   1680
ccgccaccac gccctgctaa tttttttttt gtatttttag tagagacagg gtttcaccat   1740
gttagccagg atggtctcga tttcctgacc tcgtgatcca cccgcctcgg cctcccaaag   1800
tgctgggatt ataggcgtga accaccgcgc ccagctttaa tttttttttt tttttttttt   1860
ttgagacaga gtcttgctct gtcgcccagg ctgaagtgca gtggcgcgat ctcggcttgc   1920
tgcaagctcc gcctcccagg ttcacgccat tctcctgcct cagcctcctg agtagctggg   1980
attacaggca cccgtcacca tgcccagcta attacgggac ctcgctctgt cgcccgggct   2040
ggagtgcagt ggcacagtct cgctcactgc aatctggcaa gtgattctct tgcctcagcc   2100
tccagagtag ctgggactac aggtgtgcgc cgctacgccc agctaatttt tgtattttta   2160
gtagagatag ggtttcgcca tgttggttgg ccaggatggt ctcgatctct tgacctcgtg   2220
atccgccctt ctcggcctcc caaagtgctg ggattaccgg tgtgagccat cgcacctggc   2280
cttcctactt tattaagata cctaagggat ttctgtgatt gttaggattc aaatttctgt   2340
```

gagcataaga atcaagctgt gtgcataata attgcatggg atttcacagc tgggccccat 2400
tcccagggat tttgtattat ctacctccaa gtgattttga tgctggtgat ccttggacca 2460
gacttggtga agctcaatgc ttagctagga aagccccaaa aatttgcttt attggattgt 2520
gtaatttgac tacatccatt gtttcttttt tcaaatgtag agttatatgc cacaaaaata 2580
ttttccgtag cagtaggcat cctaattaat ctcgatgttt gtttatagcc ccattgatgg 2640
ggctataaac ttggcagcaa attgttttcc cactaatttg gcattttcca taaatgtttg 2700
tttatagccc cattgatggg gctataaact tggcagcaaa ttgttttccc actaatttgg 2760
cattttccat aaaaaacacg tatctgttgt tagctgccta gacgttagct ggacatggtt 2820
taggttactt ttctcttaaa aagtaaattt taattcaagt tcctttaagc cagcagtctc 2880
aacctggggc agtttttccc tccaggggac attcagcagt gtctagagac atttttggtt 2940
gtcatgctga ggaagagagt gtatagtggg tagaatccag ggatgctgtt aagcatggaa 3000
cagcccctta caacaaaaaa ttatgtagcc taaaatggca gtgttgccaa gattgagaaa 3060
ttatgcttta aatgtgtttt tatatatggc cattttgtgt ttactctgga gataacatgc 3120
ttttcctc 3128

<210> SEQ ID NO 360
<211> LENGTH: 3145
<212> TYPE: DNA
<213> ORGANISM: Homo sapiens

<400> SEQUENCE: 360
tccgtagcag taggcatcct aattaatctc gatgtttgtt tatagcccca ttgatggggc 60
tataaacttg gcagcaaatt gttttcccac taatttggca ttttccataa atgtttgttt 120
atagccccat tgatggggct ataaacttgg cagcaaattg ttttcccact aatttggcat 180
tttccataaa aaacacgtat ctgttgttag ctgcctagac gttagctgga catggtttag 240
gttacttttc tcttaaaaag taaattttaa ttcaagttcc tttaagccag cagtctcaac 300
ctggggcagt ttttccctcc aggggacatt cagcagtgtc tagagacatt tttggttgtc 360
atgctgagga agagagtgta tagtgggtag aatccaggga tgctgttaag catggaacag 420
ccccttacaa caaaaaatta tgtagcctaa aatggcagtg ttgccaagat tgagaaatta 480
tgctttaaat gtgtttttat atatggccat tttgtgttta ctctggagat aacatgcttt 540
tcctcatata acatgcttga taaacatttt ggtaacacag gaattgtaaa tgctggtgat 600
gtcagtaaat agttaagaaa tttagggctg tgcgcggtgg ctcacgcctg taatcccagc 660
actttgggag gccgaggcgg gtggatcccg aggtcaggag atcgagacca tcctggctaa 720
catggtgaaa ccccgtctct actaaaaata caaaaaaatg agccgggtgt ggtggcaggc 780
acctgtagtc ccagctactc aatttagaaa gcagatttgt ttcctttcta tacctgtgta 840
atttgaggtt tagtttactg tcacatcgtt tataaacata aggaagatcg ttgctcatct 900
gatagcattc cgaaccttga gtcatctgta atgcctatgg cctccagaaa agcttctcta 960
atactgtact tagagatgtg taaaatatgt aggaacattt tcccaccttc gattgttagt 1020
ttacctttca gcttcagtaa tttacctttc agctattact ttagtaacat cttcaacatt 1080
gtttttcaaa ctgcaaggtg tgacccagta gtgggtcgtt aaattagtag gtgacagagc 1140
atttttgaag aattaaatac aatagaacat agcagagtgg gctcacgcct gtaatcccag 1200
cactttggga ggcgaggctg gcaggtcaca aggtcggcag gtcacaaggt cagaagatcg 1260
agaccttcct ggctctaaca tggtgaaacc ccgtctctac taatagtaca aaaaattagc 1320

-continued

```
ggggtgtggt ggcatgcgtc tctagtccca gctactcagg aggctgaggc acgagaatca   1380

cttgaatccg ggagctggag gttgcagtga gccgagattg caccactgca ctccagcctc   1440

agcaacagag caagactatt tcaaaaaaaa aaaaaaaaaa aaagaaagaa agaaaaaaag   1500

aaaatagagt gtatcacata attagagtag caagtattga tttgtgaaac ctattttaat   1560

catagatcta tgtatgtatg tgctggattg tgatgtaaag acatttcttg ctgtggttac   1620

actgaaaaaa atgaaaagtc actgatttcc aataacttac agaagcagta tgaactacat   1680

attctgtcgt tcttgaaaca agctgagatt ttattgactt tgggaagcag tagaattatt   1740

ttagtttttt aattaacagt ttttggcttt gtactgtcaa gaggtaattt tagaaagcat   1800

tctaaaaatg taagtactgg atttggcaac attcttgaac tgtaattctg tttcgttaaa   1860

catcactatt tacatgtgca acagcgtgtc tgtaacaatg tcccagtaat gaaattcttt   1920

cttctattta aggcatgtct gtttgataaa agtcaaacaa aattgggtat atgtcagtgt   1980

cttatgatac tgcttaatta aacattaatt tgactcttag ctaatcagga aatgtttgcc   2040

tcacagtctt acagagcttt ccaccttcta aaaaagctaa cgtttcagaa tagattcagg   2100

attcaacctt ctttctgtct tttttttttt ttgtttgaga cagagtcttg ctctgttgcc   2160

caggctggag tacagtggcg ctatctcggc tcactgcaac ctccgcctcc tgggttcaag   2220

caattctcct gcctcagcct cccgagtagc cggggttaca ggcgtgcgcc accatgccca   2280

gctaattttt ttgtattttt agtagagaca gggtttcacc atgctgggtg gccaggcggg   2340

tctcaaactt ctgaccttga gatctgccca ccgtggcttc ccaaaatgct gggattatag   2400

gcgtgagcca ccgcacctag cctagattca ggctgcttct tttttttttt tttttgaga   2460

cagagtcttg ctcttgttgc ccaggctgga gtgccatggc atgatctcag tgcaccacaa   2520

tctctgcttc ccaggtttaa gcgattctcc tgcctcagcc tcccaagtag atgggatcac   2580

aggcatgagc caccatgcct ggctaatttt gtattttttg tacagacggg gtttctccat   2640

gttggtcagg ccagtctcga actccctacc tcaggtgatc tgcctgcctc ggcctctcaa   2700

agtgctggga ttacaggtgt gagccactgc gcccagcaga ttcaagcttt ttaaatggaa   2760

ttttgagctg atttagttga gacttacgtg cttagttgat aaattttaat tttatactaa   2820

aatattttac attaattcaa gttaatttat ttcagattga atttagtgga agcttttgta   2880

gaagatgcag aattgaggca gactttacaa gaagatttac ttcgtcgatt cccagatctt   2940

aaccgacttg ccaagaagtt tcaaagacaa gcagcaaact tacaagattg ttaccgactc   3000

tatcagggta taaatcaact acctaatgtt atacaggctc tggaaaaaca tgaaggtaac   3060

aagtgatttt gtttttttgt tttccttcaa ctcatacaat atatacttgg caatgtgctg   3120

tcctcataaa gttggtggtg gtgac                                         3145
```

<210> SEQ ID NO 361
<211> LENGTH: 3080
<212> TYPE: DNA
<213> ORGANISM: Homo sapiens

<400> SEQUENCE: 361

```
cccagatctt aaccgacttg ccaagaagtt tcaaagacaa gcagcaaact tacaagattg     60

ttaccgactc tatcagggta taaatcaact acctaatgtt atacaggctc tggaaaaaca    120

tgaaggtaac aagtgatttt gtttttttgt tttccttcaa ctcatacaat atatacttgg    180

caatgtgctg tcctcataaa gttggtggtg gtgactcact cttaggacac attcagattt    240
```

-continued

```
cttttttttt tttttttgag aaggagtctt gctccgttgc caaggctaga gtgcagtggc    300
acaatctcag ctcactgcaa cctctgcctc ctgggttcaa gcgattctcc tgcctcagct    360
tcctgagtgg ctgggattac aggcatgtgc caccatgccc ggctaatttt tgtactttta    420
gttttaccat gttggccagg ttcgtctgga actcccaatc tcaggtgacc cacctgcctc    480
ggcctcccaa agtgctggga gtacaggcgt gagccacaga gcctggccat gttcagactt    540
ctaataacag gtttgtattg actcttagcc tcatggcaga agccaagaga catgagacag    600
cttagaaatt tttgcttttt ggaaatgaat gttagagtta ctggtttgtg attaaggcct    660
attgcactga cagaggcagt gaaaaagggt ttgattgcca aggaagattc acagggccta    720
gaatggcagt ggttatgcat ctacagttta ttacaggaga aggatacaat ccagtagcag    780
gattatggta aggatatgca tcacagtcaa aggctgtcat agcaagtcat ccagagagtt    840
cgggtgcaag ttccagtttt cctttgttgt gtaaagtctg tggtggggtg cattttctct    900
ctcagagcag gatgtgtgca caggacacct tggaacctag gagcccaaaa tagagtcttc    960
actggacttt ttaatatttt tcttgtcaag cggacatgtt cctgttctct aactagcctc   1020
ttcagtggag gtcagaggaa gagcctcatt gagaccaagt gcaactcatc aatcacatga   1080
aacaatgctg ataaataaac cacctaaata tcccctgacc cacaaataca aaacaacacc   1140
attcaatcag tatttttcat gccttgatca ggggtcattg ccatgcagga actttaacaa   1200
aacagtacag gctaataata gaattgttgg aattaactca cacagcacac ctatgagaga   1260
gagttaagat agagggtctt ggtggtctct aacagttgaa ttcaaagtga agttaccaga   1320
gtaaagtgag caaagacaca tattagtaca atattggtag ataaaatcac gttgctctaa   1380
taagcatagt tttaaacttt aaccatgttt ctccagtaat tttagtaatt atattgttgt   1440
tatgtctaat acataaagca ttttttactt ttttaaaaaa tttttaggca atgtggggtc   1500
caaagtaatt aaaaaaaaat ttttttaaca taaagcatct taaaatttta cttaatcatg   1560
atcacttaga accattaaaa catacgtttt gatattatgg ggaagcttcg ttgttccttt   1620
gtagacagac ttaaagaaat acaactttat gatgacaaga tataagataa ttatagattt   1680
aaattttata gaaacctttt cccttatcta gtgcaagagg tagctaagtg cttattttct   1740
caaagtactg tgttataaaa agtattccta gtgtagtcaa agcttctctt tagactgata   1800
aaacttagag cacctgcatt tacttccaac aaagcagaat taaagaaaat gagacttggc   1860
cgggtacgtt tgtaatccca gcactttggg aggccgaggc aggtggatca tgaggttagg   1920
agatcaagac cattctggct aacatggtga aaccctgtct ctaccaaaaa tacaaaaaat   1980
tagctgacat ggtggtgcgc acctgtagtc ccagcttctc aggtggctga ggcaggagaa   2040
tcgcttgaac ccaggaggtg gaggttgcag tgagctgaga tcacaccact gcgctccagc   2100
ttgggcaaca aaaaaaaaaa aaaaaaaaag aaaaagaaaa tgagtcttta ctggctgggc   2160
acagtggctc acacctgtaa tcccagcact ttgggagacc gagacgggca gatcacctga   2220
ggtcgggcat tcgagaccag cctgaccaat atggagaaac cccatttgta ctaaaaatac   2280
aaaattagcg gggcgtggtg gcgcatgcct gtaatcccag ctattcggga ggctgaggca   2340
ggagaattgc ctgaacccgg gaggcggagg ttgcggtgag cagagatcgt gccgttgcac   2400
tccattctgg gcaacaagag cgaaactctc catctcaaaa aaaagaaaat gagtctatac   2460
tttgctgttt tcatactctc ttagtgtggt gtaggcagcc atgtatcccc cttgtgcctc   2520
tatttctcca ttctgtgaat gagtgtcttc cactgctgtg cttttctgat tccgtaacct   2580
ttgtttgttt gtttgtttgt ttgtttgttt gtttttttatt gatcattctt gggtgtttct   2640
```

-continued

```
cgcagagggg gatttggcag ggtcacagga caatagtgga gggaaggtca gcagataaac   2700

aagtgaacaa aggtctctgg ttttcctagg cagaggaccc tgcggccttc cgcagtgttt   2760

gtgtccctgg gtacttgaga ttagggagtg gtgatgactc ttaatgagcg tgctgccttc   2820

aagcatctgt ttaacaaagc acatcttgca ccacccttaa tccgttcaac cctgagtgga   2880

cacagcacat gtttcagaga gcacagggtt gggggtaagg tcacagatca acaggatccc   2940

aaggcagaat aatttttcgt agtacagaac aaaatgaaaa gtctcccacg tctacctctt   3000

tctacacaga cacggcaacc atccgatttc tcaatctttt ccccaccttt ccccccttc    3060

tattccacaa aaccgccatt                                               3080
```

<210> SEQ ID NO 362
<211> LENGTH: 3029
<212> TYPE: DNA
<213> ORGANISM: Homo sapiens

<400> SEQUENCE: 362

```
ccaaacaaca gcattagcca actctttgaa gccttagatc tgtggctctt gttttctcct     60

ttgaggtgta ggtccttgag ggcatttgct tctaatagag gctagtttca tcagaattaa    120

aaatctgaac catggtatga aattcaattc tttttttttt ttcttttttg aaaacactgg    180

caaatgtttt gtatccttga gctttcccac atatcttaac atagtgagtg gaaagtacag    240

tggctgttaa gccaactact ctgaggtctt cactgctaag gcttactctt aattgtgtga    300

gagcttaacc ttgatccctt taaaacatta atgggctaga aaaaaaacca ttcataaacc    360

agtgccacct ctgaattttg ctaccacaat tcccttattt accaatagtg catgagctaa    420

tttggaataa agaactaggc attgtagcac aacagacatt atgtgggcaa agtgttgttt    480

atattctgtc taaatagtgc ttcacatgta tgtactattt tctaaatatg tatagatgct    540

tttgtgatta ataataaaac atgaattctt aaaacaattt tgctgacttc atagtagctt    600

ttcaccgttt tttcagtagc tgctaaaatt tctggagaag tttgggaact attgttttgg    660

agtgaaatgc agtgtgttag atatcacttg cagaattctt ctaagggtat ttattggcga    720

ttagaaaaaa aatccttgtg ttataccagt agtaatacaa agtaattgtt cagcttctgt    780

taagtgtaaa ggactataca agtattgtgt atagttatct catttattat tttctgggta    840

gctattgtta ttattacttc gtacaaaaag ggaaaaggag gctcaaagta tcatgctcca    900

gataacagag ccagtaggta gcagagctgg gattgctacc caggtctcta gtcctgcttt    960

ttcacactat atactcattg cttcacttac tccttcatac atgattcccc agcatgtact   1020

cttttttttt tttttttttt tttgtttgag atagaatctc gctctctgtt gcccaggctg   1080

gcaggcagta gtgtgatctt gggctaactg caacctccat ctcctgcatt caagcagttc   1140

tcctgcttca acctcctgag tagctgagat tataagccta tgctaccacg cctggctaat   1200

ttttgtattt ttagcagaga tgaggtttcg ccttgttggc caggctggtc tcaaactcct   1260

gaactcaagt gatctgccca cctcagcctc cgaaagtgct gggattatag gcatgagcca   1320

tcatgtccgg cctccccatc atgtaccctt aaataccatc aagcacagtt ccattgtgta   1380

aaaacttggc ttgatttaac ctgttaattg gaacactgtc attaatggaa attaggaata   1440

tgaggtaagc tagaggtttt attttaatga ctttgggtta ttaaatctat aagaaatgaa   1500

attcatttag tcataattaa tgtcatgttt ctgcatctat attacttgtt gggtttacag   1560

acgaggtagt gtattattag tgggaagctt tgagtgctac atcatctccc tttctataaa   1620
```

```
ataaattgag tacgaaacaa tttgaattaa aacacctgag taaatagtaa ctttggagac   1680
ctgctgtact atttgtacct tttggatcaa atgatgcttg tttatctcag tcaaaatttt   1740
atgatttgta ttctgtaaaa tgagatcttt ttatttgttt gttttactac tttcttttag   1800
gaaaacacca gaaattattg ttggcagttt ttgtgactcc tcttactgat cttcgttctg   1860
acttctccaa gtttcaggaa atgatagaaa caactttaga tatggatcag gtatgcaata   1920
tactttttaa tttaagcagt agttattttt aaaaagcaaa ggccacttta agaaagtttg   1980
tagatttttc tttttagtat ctaattgtag cacctttgtg gacagtggat gtaatattaa   2040
gtgacagatg ggaaaaggat ttttaaaaaa atagcaactg tttcagtgga tgaaataaag   2100
attattagca gagaaaatga atattgggca taactgtcct ggtgaaagac aatctcataa   2160
atgaacaatt tcataatttc gtaaatgcaa ctgcatttta ttttcaaaga gaaggaaaat   2220
tatagtcact ggaaacggaa agagaagtta gaggtaaaca taggacacac aagaaaactt   2280
tcattttgtt tatttttcttg tttttctttt gagacagggt ttccctctgt tacccaggct   2340
taagtgcagt gacactatca tagttcacta acccctcaaa ttcctgggtt caagtaatcc   2400
tcctgcctta gccttagtag gtgtaaatac aggtgtgtac caccatgcct ggcgaatttt   2460
aaaaaaactt ttttatagag atgagctctc gccgtgttgc ccaagctggt cctaaaacgc   2520
tggcctcaag ctatcctccg gcctcagtct tagcctccca aaatgctggg gtttcagtag   2580
aagccaccat gccgggccac ttctgtttct tttccatgta gagttctttg caggaggagg   2640
ttagaatagg tgtgcatctc ctaaatagtt gtcgaatata actaaaaagt taaccaggac   2700
tctaaatact atttacttct aaaatttgtt aattgggaac atttagggtt taactgatct   2760
atatcttatg tctttaacaa ttttgaatga taattatatg taaagtaaga acagtttgtg   2820
aaatagttga aaatatcctt acatgaaagt gaattttaaa gcacagttta tgtaatgtta   2880
atgttttgtt ttgtatctgt taaaaatttg tttatatgaa caagtttaca ggtttactgt   2940
ggtgagcccg ttgaatatag tgggtttttt ttgtttgttt tgtttttgtt tttgagatga   3000
agtctcactc ttgtcccgag gctgatgtg                                     3029
```

<210> SEQ ID NO 363
<211> LENGTH: 1685
<212> TYPE: DNA
<213> ORGANISM: Homo sapiens

<400> SEQUENCE: 363

```
gagcccgttg aatatagtgg gtttttttttg tttgttttgt ttttgttttt gagatgaagt     60
ctcactcttg tcccgaggct gatgtgcaat ggcgcgatct tggctcactg caacctctgc    120
ctcctgggtt caagcgattc tcctgcctta gcctcccgag tagctgggat tataggcacc    180
tgtcaccaaa cccggctaag ttttgtattt ttggtagaga tgggatctca gcatgttggc    240
caggctggac tcaggtgatc cgtctgcctc ggcctcccaa gtgctgggat tacaggtgtg    300
agccaccatg ccgagcctga atatagtgtt tttaagttgc aggactttaa aaataatatt    360
ttgaaatttt tctaagttaa attccctgtt aaaatggtca tgcaggaata tacgcttgca    420
ttattcatat tagggtaact gtttggtttg ctagttgtta gattctttgc attccttttt    480
ttttttttt tttttttttt ttttgagacg gagtttcact ctttttgaca aggctggagt    540
gcaatggcgc tatctcggct cacctcaacc tccgcctcct gggttcaagc gattctcctg    600
cctcagcctc ccaagtagct ggaattacag gaatacgcca ccaagcccgg ctaattttgt    660
atttttagta gagatggggt ttctccatgt tggtcaggct ggtctcaaac tcccagtctc    720
```

```
aggtgatcag cccacctcgg cctcccaaag tgctgggatt acaggagtaa tcccccaccc    780

ttttaaaaaa atgagacaga gttttattct gtcacccagg gtggagtgca gtggtgcgat    840

catggttcac cgcagccttg aatctgggct caagtgatcc tcccacttca gcctcccaag    900

tagttggaac catagatgtg catcaccaca cctggctgat ttttaaatta tttgtagaga    960

tgaggtcttg cttgttgtct aggctggtct taaacttctg ggcttcagca gtcctcctgc   1020

ctcagcctcc cagagtgctg agatgataga catgggccac tgcccctggc cgcatttttc   1080

ttttcttttc ctttcttttt tttttttttt ttttgaaacg gagttttgcc attgtcgccc   1140

aggctggagt gcagtggcac gatctctgct cactgcaacc tctgcctccc gagttcaagc   1200

cattcttctg cctcagcctt ccagttatct gggattacag tcatgtgcca ccacgcccag   1260

ctaatttttg tatttttagt agaaacaggg tttctctatg ttggtcaggc ttgtcccaaa   1320

ctcctgacct cagatgatcc acctgcgtct gcctcccaaa gtgctgggat tataggcgtg   1380

agccaccatg cccggcccta actgcatttt tcttagtatt tgtggtttga gttaatactt   1440

gccctatgtg atgttgattt attattactg gatcattaag tgaggtttaa agaagctaaa   1500

tgccatttgc tctatgccct ctggatttta aaagtgcatg ggtgtgcacg tgtgtaggta   1560

taaatgtttc catattctag tatattctgt gtcagtgata gagcagtctt agagctgtct   1620

tttccattta cttgtaggtt aagaagccaa aaaaagttgt gtcatcatcc cgtttaggaa   1680

aactt                                                               1685
```

<210> SEQ ID NO 364
<211> LENGTH: 2998
<212> TYPE: DNA
<213> ORGANISM: Homo sapiens

<400> SEQUENCE: 364

```
tgggtgtgca cgtgtgtagg tataaatgtt tccatattct agtatattct gtgtcagtga     60

tagagcagtc ttagagctgt cttttccatt tacttgtagg ttaagaagcc aaaaaaagtt    120

gtgtcatcat cccgtttagg aaaacttaca ttttggctat tgtttcctct agtgctgcta    180

ttagtggaat gattttaggt gttcaacttt cagatcaatg ggagacagaa atattgttct    240

gagacatctg gaagccgaat gtgttttatt cctgcctgtc tgaggatgtg gtcttgcctt    300

tgatagggca aagttatttg taaacattgc tttaaataaa aacatgtaaa ggtgtttttg    360

atggttaaca aaaactatga gtataataga gcctagtccc tattacggac tggtattgat    420

ctggtgtggg aagagtattg agcttttcag tgtcacctac ctgtattccc ttgaagggac    480

ccagagccca ggcaaagctc tgctgaggtc gggcgtggtg gttcacgcct gtaatcctag    540

cattttagga gaccaaggcg ggtggatcac ctgaggtcag gagttcaaga ccagcctagc    600

caacatggtg aaaccctgtc tctactaaaa atacaaaaat tagctgggtg tggtggtgca    660

tgcctgtaat cccagctatc tgggaggctg aggcaagaga attgcttgaa cccaggagac    720

ggaggttgca atgagccgag atcatgccac tgcactctag gtgggtccct gagtgagact    780

ccatctcaaa aaaaaaaaca aacaaaaaaa aaaaaaaaaa aaaacctctg ctgaaatgct    840

acagttaatt ttgccatttg tggtcagcat tcttcttcta aattgctata atcttgcctt    900

catattatgt gtctcaaatt taagcaggta tcagaatgtc cacgggaaca aattgccatg    960

gctctaagcc cagaatcaga ttcttcagat ctggagtagg gctggggaat ttgcatttct   1020

aacacacaag tttgttgatg ctgtttgtct ggggtccacg cttgcctaac ttctgatgtg   1080
```

```
atttatttct gccagtttct ttttttgttg ttgttttatt tttttgagat ggagtctcgc   1140

tctgtcactc aggctagggt gcagtggcat gatcttggct cactgcaacc cctgcctcct   1200

gggttcaagc gattctcctg cctcagcctc ctgagtagct ggggttatag gcacactgca   1260

ccacacccag ctaatttttg tatttttcgt agagacaggg tttcaccatg ttggccaggc   1320

tggtcttgaa ctcctgacct caggtgatcc attggcctcg gcctcccaaa gtgctcggat   1380

tacaggtgtg agccacccac catgcctggc ccttcctacc aatttctatc ctccctgaaa   1440

tgctgcacac ttaggcagtc actggacaat atctgcccca aaattggttt gtataattga   1500

gaatatttaa gaggttgtta aaatttgaac cactttctat tcttctatta agtgtacaca   1560

tctattaaag atccccttgt agctcttttt atctgggcca tcacatttct gcccagcaga   1620

tgcagaggcc ctgtcctctc ttccacctcc ccactacctc tccttcccta cttttggact   1680

gtaaaagctg tctttctgca gttaattgtt ttattctttg taggttctac tcgttgataa   1740

tgttatctac tgctataata attacagacg gcaacaggat gatcaaatct tggatatttt   1800

aaatttacat tatgcctttt ttattttatt tttttaaagt ctctgcttga cagcaaataa   1860

gcctaacgtt ccctaacaaa tgatgatgtc ccattaatga tttgatgact tcctgtttgt   1920

agtttttatt tagagtgctt gtgggtagtt tttcataacg acatttaaaa atcaggatat   1980

aaataatttt ttaagttttt tttttaggcg gggcacagtg gctcacacct gtaattccag   2040

cattttggga ggctgaggtg ggcagatctt gtgaggtcag gagttcaaca ccagcctggc   2100

caacagggcg acaccccatt tctactaaaa atacaaaaat taggccgggt gcggtggctc   2160

acacctgtaa tcccagcact ttgggaggcc gaggcaggca gatcacaagg tcaggagatc   2220

gagaccatcc tggctaacac ggtgaaaccc catctctact aaaaatgcaa aaaattagcc   2280

gggcatggtg gcaggcgcct atagtcccag ctactcggaa ggctgaggca ggagaatggc   2340

ttgaacccag gaggtggagc ttgcagtgag ccgagatggc gctgctgcac tccaacctgg   2400

gcgagagtgc gagactctgt ctcaaaaaaa taaacaaata aaaaataaaa aaattaacca   2460

ggcatggtgg cgcatacctg tagtcccagc tacttgggag gctgggacag tagaatcgct   2520

tgaactcggg aggtggaggt tgcagtgagc tgagatcacc cactgaactc cagcctgggc   2580

aacagagcaa gactctgtct ccaaaaaaaa aaaatgtatt tttctttgaa gcttttctac   2640

ttttaaatgt aatgtatagt attataacaa gtgaacaaaa tgatacaaag aagtatggcg   2700

ggaaaggtgt ggtagagatg ggaaaacata tttcctccag cctcttaggt tcattggagg   2760

agcttgggaa ttcaactgac acacgacaga tttacaggag aaaagtttta tttcaagtac   2820

acatgagagc ttcatagaaa agaagtgaag acctaaagaa acagactgga gagttcatat   2880

gccattttaa taaaggataa tgtattagtc tgttctcatg ctgctaataa atacataccc   2940

aagactgggt aatttataaa gaaaaagagg tttaatcgac tcacaattgc acatggct     2998
```

```
<210> SEQ ID NO 365
<211> LENGTH: 2076
<212> TYPE: DNA
<213> ORGANISM: Homo sapiens

<400> SEQUENCE: 365

cttgcatagt ttgcttctgg tatgttaaag tgtgctctct ctaagtgggt agtaattagg     60

aacaatttat ctcaacctca tttattgaat gttttaaatc aagagaacgg actctgttat    120

attaagcttc tatatataat tgtctgtttc actgtaatgc ctagtaagga tacacttcat    180

tctttttta gatgttcttt cacaatttca tgtaaatttt agttgttttg tttcaaaaaa     240
```

caattcctat tgaacaatct ctaggaatag atagcttaat aataatatta gatctagttt 300
tctcttttca tagtttacct cttctttctt ttctttcttt tttttttttt tttgagacgg 360
agtctcgctg tgtcgcccag gctggagtgc agtggtgcga tctctgctca cagcaagctc 420
cgcctcccag gttcgcgcca ttctcctgcc tcagcctccc aactagctgg gactacaggt 480
gccccccacc actcctggct aatttttttt tttttttttt tttttttttt tttgtatttt 540
tagtagagac agggtttcat tgtgttagcc aggatggtct caatctcctg acctcgtgat 600
ccgcccacct cggcctccca aagtggatta caggcgtgag ccaccgcgcc cagcctctgt 660
ctctcttttc tttttctttt tcttttcttt tcttttcttt tcttttcttt tcttttcttt 720
tcttttcttt tctttccttt cctttccttt cctttccttt cctttccttt ccttttcttt 780
tctttctttt cttttcttct ctcttctctt ctcttctctt ctcttctctg tcttttttttg 840 acgagtctca gtatgtcacc taggctggag tacagttgca caatgttggc tcattgcaac 900
ctctgcctcc cttgttcaag tgattgtcct gcctcagcct gccaaatagc tgggactaca 960
ggtgcgcact gctacgcccg gctaattttg tatttttagt agagatgggg tttcaccatg 1020
ttggccaagc cggtctcaaa ctcctgacct caagagatcc acctgcctcg gcctcccaaa 1080
gtgctgggat tacaagtatg agccacgatg ccagtccaat tcttgtgtag tttttttaatc 1140 agctgaattt aacattcaaa ttcttctttt aaatcttcca ataggcagtt atctttataa 1200
agatcctata taatcaagac tttgtttctg aatattttat gtatgttttt gctactgtaa 1260
atgagatcta tttctcattg tggtttcttg ctgttattac tggtaagaat ttagtgaaac 1320
aaagtactta agagtatgtc tttaaattgt gagattttga tgaactttta agaaataaaa 1380
ttctttagtt tcttagagct ttttgagatt tctaaggtag atccttggtt tgggcaacat 1440
ataactatta caagttttgc acattgaacg ttatttggta atttttagag aggacatttt 1500
aaatgtttag gaaaaatata aataaaatgt agaatactat tgggggcata tacatcatca 1560
gcactgtaac tgtttcatat gaatcatttt tgtacatata gaactctaaa gtcctaatga 1620
acagaatttt acatttctat aaatagaaag tccttaatag ttgtgactga ataacttatg 1680
gatagcaaat tatttaactg aaaacagtaa aatttaagtg ggaggaaata tttgctttat 1740
aatttctgtc tttacccatt atttatagga ttttgtcact ttgttctgtt tgcaggtgga 1800
aaaccatgaa ttccttgtaa aaccttcatt tgatcctaat ctcagtgaat taagagaaat 1860
aatgaatgac ttggaaaaga agatgcagtc aacattaata agtgcagcca gagatcttgg 1920
taagaatggg tcattggagg ttggaataat tcttttgtct atacactgta tagacaaaat 1980
attgatgcca gaattatttt ataagttccc tgtccccaag atgatgactt cacatctctg 2040
tcaaacagaa atcgcccaac aggcccttgt atgatg 2076

<210> SEQ ID NO 366
<211> LENGTH: 1960
<212> TYPE: DNA
<213> ORGANISM: Homo sapiens

<400> SEQUENCE: 366
aacagaaatc gcccaacagg cccttgtatg atgtcattta aacaagccct attttaaatg 60
tcacctccac tggtaacagg atactcctag gaggatcacc aagcccaatt cttctaggag 120
tagtgcattg attaggcttt ggggtttcca agcagttcat taatgtcact tttggaaaaa 180
gtctgtcttt cataccagct tattaattcc ctatgggttc acacggtttt ttttcctgga 240

```
ttttcatcaa acatgtgtaa ggtactcagt acaaagaagt ttagaaatcc agaacaaagc    300

agtgtattta agtagtagta aacttccaga taatctgatg cccatatcta catatataaa    360

aaatttgcaa atagttctgt agagagtcca aacatggagt agatccctaa ttaagagcct    420

ttgcattaaa gtccaccttc ctcatttcat agctaaggat attgaggctc agagagttta    480

tgtgtctgga gttaaagtta ttttgtgttt ccttaatttt tgacttacta gaaagttaaa    540

gtacctacag atttctgtgt ttcactatat gttaacttgc ttggctggaa gtttttctgc    600

tgataattgg ttttatgaag gaagaatcct gttaagaatg catcattgga ctgggtgtgg    660

tggctcacgc ctgtagtgat cctagcagtt tgagagaccg aggtgggcag attgcttgag    720

tccaggagtt tgacactaac ctgggcaaca tgatgaaacc ctgtctctac aacaaataca    780

aaaattggcc atacatggtg gcacgcacct gtggtcccag ctactcagga ggctgaggtg    840

agaggatcac ttgagccagg gaggttgagg ctataatgag ccataattgc actactgcac    900

tccagcctgg gtgacagggt gagatcctgt ctcaaaataa gaaaagagaa tgcatcattg    960

gccaggcaca gtgactcatg cctataatcc caatacttta ggaggatcac ttcagcccag   1020

gagttcaaga ctagcctgtg ccacatagac cacatttcta ccaaaaatca aaaggaaaaa   1080

acttgctggg tgtggtgatg cacacctgtg gtcccagcta ctcgggaggc tgaggtgaga   1140

ggattgcttt agcttaggtg gttgaggctg cagtgagcca tgatagcacc actgcattcc   1200

atccagcctg agggacggag tgagagcgac accttgtctt taaaaaaaaa aacagaggaa   1260

tgcatcatag tatatattaa attattgcct attttttat ctattttatt gagtgctaat   1320

aagaaaatta atggcaaaaa cttgtttttt acagtataaa ttaagtttaa tttcatttta   1380

aaattaagta aatttgtttt attaaaaagt atgttgaaag caacataaat agcactcaaa   1440

ttgagacaga aactgtaact gtagtataag aagcattagg ctgggaattg ggaaacacga   1500

gttctagttg cagcttggaa actttttctg aagctcttta caaattactt aatttctctg   1560

gttttcacca cattgttcta tagcattaac atgttggatt cattgcttta attcttagac   1620

ctacgtgtca tcagaaatgc cattacactt tgaggatttg agccttattt taaataaagt   1680

tgtgatcctc atggcagcct aggtttacat gtgttaaata aacagtattc tgtaaatacc   1740

attgtctttc atgtttagtg atgttgctgt tgttaacact gcagtgaaat gcatatataa   1800

gcaaactaca ttacatactc atgaacatgg tcctttgttt tgaaactttg atcactgatt   1860

gttcgcagtc tttcattgtg gaactactct ttcactttga atgttttgag aggttccttt   1920

gttcagatca gtccgatttc gtttctgggt gggtctctac                          1960
```

<210> SEQ ID NO 367
<211> LENGTH: 3160
<212> TYPE: DNA
<213> ORGANISM: Homo sapiens

<400> SEQUENCE: 367

```
agtccgattt cgtttctggg tgggtctcta ctttcccttt tctcactggt caagcgaggt     60

ctgtctaatt gtttgctact actaacattt gatggccacg cttcagcaag tacatttgta    120

gattctctct ctctgtctct cttaatttgt ggtctagaga tcatattggt taatgaaatt    180

atgaagaggg aatgtattta taaaaactca aattcttgat gcagaaggtc tagctgattg    240

tgaacccaaa atatccgaga caggtcacaa ccaatttaga aactttattt tgccaaggtt    300

aaggatgcat ccatgacata gtctcacaag gttctaatga cacatgcgca aggtggttag    360

ggtacagctt ggttttatac attttaggga gacatgagac atcagtcaac atgtgtaaga    420
```

```
tgtacattga ttctatccag aaaggcagga caacttgaag caaggggctt tcaggtaata    480
agtagataag agacaaaagg ttgcatactt ttgagtcctt gatcagcctt tcactgaata    540
aacaagctta gtcttgttag tgaatctgcg tttttacata aacagtaggt cagaggaagc    600
aatcagaaat gcatttgtgt caggtgagcc gagggatgac tttctgtccc tcacctgtga    660
agataagcta tcagtttcca ttgctagggt gaaattcaac agaattgttt gagagtgaac    720
atctggaggc ccacaaggac tttccttgtg gaggggaagt atgtagtgag ggaagtatgt    780
agtttttaaa tctttgtcgc tatcttattt agaaataaga tggaaggcag gtttgtctga    840
catagttccc agcttgactt ttccctcggc ttagtgattt tgcggttccg agatttattt    900
tcctttcaca tatcagtcag atcatttggt ttgtgaagtt tcctatgctt aacagaaaat    960
atgtgcacta gttttcctag agtttcattg tcagagtctc aagtttttgt ttggaaattg   1020
tatttggtca cattaattat actctatgtt agttccaaag aaataccttt ggttaagaaa   1080
agaattctca tgcataactc ctcgagggtg gggttacacc ttaatccatc ctcaggtgct   1140
catggtaatt ggggcaaata tgttgcccag tgctggtgct ctgcagcctt ggatgggttt   1200
acccagaaag cagctttcaa gtcagaaact aacattcata agggagttaa ggattttata   1260
aatagatatc cataattcat gtagttttca agtaagtagt atttgaatct tttctggtta   1320
gataataatt gtgagtatgt tgtcatataa taacagtatg tttttcacta tttaaataat   1380
tttagaatta cattgaaaaa tggtagtagg tatttatgga atactttttc ttttcttctt   1440
gattatcaag gcttggaccc tggcaaacag attaaactgg attccagtgc acagtttgga   1500
tattactttc gtgtaacctg taaggaagaa aaagtccttc gtaacaataa aaactttagt   1560
actgtagata tccagaagaa tggtgttaaa tttaccaaca ggtttgcaag tcgttattat   1620
atttttaacc ctttattaat tccctaaatg ctctaacatg atgtgaatgt tctatgataa   1680
gttttactaa tgtagtcatc aggtaagagt caagctttct tccatagagc agtcagctgt   1740
cgcaacacca tttgttaaat agtccgtctg ttctccattg actgaagtgg tactttgggt   1800
ctattttaaa gactctactt ttacctcgtc tcaccattct tttgtctaca caaaatatat   1860
tttatcgctt attctgtgtt accatatcta ttagagctag ttccccctca tatctctgct   1920
ttagttattt tcacatgttt cttttatctt tttttttttt ggagatggag tctcgctctg   1980
ttgcccaggc tggagtgcag tggcatgatc tcggctcact gcaagctccg ccttccgggt   2040
tcacgccatt ctcctgcctc agcctcccga gtagctggga ctacaggcgc ccgccactgc   2100
gcccagctaa tttttgtat ttttagtaga gacggggttt caccgtggtc tcgatctcct   2160
gacctcgtga tccgcctgcc tctgcctccc aaagtactgg gattacaggt gtgagccacc   2220
gcgcccagcc ttatcttttt tttttttccc cctgagacag agtcttgctg tgtcgcccag   2280
gctggagtgc agtgacgcgc agtcttgact cactgcagcc tccacctccc ggattcaagc   2340
gattctcatg cttcagcttc ctgagtagct aggattatag gcatgcacca ccacgcctag   2400
ttcatttttg tatttttagt agagatgggt tttcaccatg ttggacaggc tggtctcgga   2460
ctcctggcct caagtgatcc acctgcctca gcttcccaaa gtgctgagat tacaggtgtg   2520
agccaccgtg cctgacccac atgtttattt tttctaagaa aactttacta tcatttatca   2580
agttaagaaa attattctga tatttcaatt gggtgtttaa attagttgag ggaaatatga   2640
ggccattcac tagatgatag gtttttttg ttttaatcat gtttcatgtt gaaacaaaaa   2700
agttttttcc tgccagtttt ctggctaatc tcaggaagtc cctgaaacaa attattgata   2760
```

```
agtaaaaaaa attatttaaa aaattttaaa ttatatttaa aatcttctgt gacttatggt   2820
gggggaggc taaagccttt ctccttctgt actgttctgg aaactatggc ctgttctact   2880
ccctcccctc ctgaattttc ccagaacttt acaggtagct tttatatata tgatcccctg   2940
tcgtctgttt aacaagtact ttgagtgtct attatatgca gacattctag gtgttcagac   3000
accctagtaa ttagtttgtt cctcataatt ctcagtaaag aagacatgta tatttctcat   3060
tttataggtg aagaagctaa gactttactt ttcctcagtt agacagctag tgctggtggg   3120
tgcctaaact tagatcttcc attgccaaat ctaggtgtgt                         3160
```

<210> SEQ ID NO 368
<211> LENGTH: 2985
<212> TYPE: DNA
<213> ORGANISM: Homo sapiens

<400> SEQUENCE: 368

```
tccattgcca aatctaggtg tgttgttttt ccagcacact agaatcctcc tggttcaaga     60
aatgtatata ttttagcttg gataagatac aacttttgga gtgttctaat catcttcaag    120
tttttcgtgg attagttata acatatgaaa aaagataggg ctgaatgggc cacatgatgc    180
caaaagtgaa aaagtcactc actagattat gacctgcaga atctggtcct tgcctgcctc    240
tgcttttata ttttgcagct tgtcccttca cacagtggtc tcacttttat aatgtctttc    300
cctcatgcat ttctttaatt ctttttattt gcctgttcca tagtagtctg tttgtgctgc    360
tacttgcccc tgtactgttc ttgagctata catatacatg tctgctgtgc cattgagtga    420
ttccatcaag gccacaatta tcatcttgat gaactgattt tctcccactg ctgataatta    480
cttctctctc ctttctttct cctttacatc acctcttttt gttcttaatt tcattccctc    540
cttgatgcca gtgagtattt ttttcttatt ttattctcat cttccttgag tattgtttat    600
ttcaacctct tttttttttt ttttttttgg agaagggttt ggctttgtcg ctcaggctgg    660
agtgcagtgg cacaatttg gcccactgca acctccacct cctgggctca agccatccca    720
cctcagccac ccaagtagct gggactacag gtgttgccca ctgctttgta tttttaatag    780
acacaggatt tccccatgtt gctcaggctg gtctcgaact cctgggctca agcagtccac    840
ctgccttgcc ctcccaaagt tctgggatta caggattaca gatgctgtgc ccggcccaac    900
ctctaatttt aattttctct tcaaattgtt caataagatt tagtttcaag acattttcct    960
ggccgggcat ggtggcttac gcctataatt tcaacacttt gggaggccga ggcaggtgga   1020
tcacttgagg tcaagagttc aagaccagcc tggccagcgt ggtgaaaccc catctctact   1080
aaaaaataca aaaattagcc gggtgtggtg gtacatgcct gtaatcgtag ctattgtgga   1140
ggccgaggca tgagaatcgc ttgagcccgg gaagcagagg ttgcagtgag ttgagatgac   1200
accactgaaa tccagcccgg gcaacagagt cagactacgt ctcaaaaaaa acaaaacaag   1260
ctgggcgccg tggctcacgc ctgtaatccc agcactttgg gaggccgagg ccggtggatc   1320
acgaggtcag gagatcgaga ccatcctggc taacacggtg gtgaaaccct acctctagta   1380
aaaatataaa acattagccg ggcgtagtgg ttggtgcctg tagtcccagc tactcaggag   1440
gctgaggcag gagaatggtg tgaagccggg aggcagaggt tgcagtgagc ctagatcgcg   1500
ccactgcact ttagcctggg tgacagaaca agactccgtc tcaaaaaaaa aaccattttt   1560
cttattttga aaacttttgg tattgaaaga tatttatact acagtaatga gaaatactgt   1620
gtgtgtgtat atatgtttgt gttttttttt ttgttttttt ctttctctct ctctcttttt   1680
tttttttttg acagagtttt gctcctgttg tccaggctgg agtgcagtgg tgctatctcg   1740
```

```
actcaccaca acctctgcct cccgggttca agtgattctc ctccctcagc ctcccgaata   1800
gctgggatta caggaatgtg ccaccacacc taactttgta tttttagtag agacgggttt   1860
tccccatgtt ggtcaggctg gtcttgaact cctgacctca ggtgatccac ctgcctcggc   1920
ctcccaaagt gctgggatta caggcaccct gcctgtgttt gtgttttaaa aggggtaata   1980
gcttcagtct tttttttctt tctctgagac ggagttttag ttttgttgcc caggctggaa   2040
tgcaatggtg tgttcttggc tcaccacaac ctccatttcc tgggttcaag cgattctcct   2100
gcctcagcct cctgagaagc tgggattaca agcacgcgcc accatgctgg gctaattttt   2160
gtatttttag tagagacggg gtttctccat gttggtcagg ctggtctcga actcctgacc   2220
tcaggcaatc caccgacctc aggtgatcca cccgcctcag cctcccaaag ttctggggtt   2280
acaggcgtga gccaccacgc ccggctgtct tcaatcttaa ataaggattc catttaaata   2340
ttttgtaaaa ggacacagat cacagtttta ctcaggggaa tataattgtt atagcaggaa   2400
ttgtgccatt gcgctattcc aaacagtgta aaagaacatt aataaattga attctaacta   2460
catttgtccc taaggagttg ttcgttttcc acttgtattt ccattttaat tatcattatt   2520
tggatgtttc ataggatact ttggatatgt ttcacgtagt acacattgct tctagtacac   2580
atttaatat  ttttaataaa actgttattt cgatttgcag caaattgact tctttaaatg   2640
aagagtatac caaaaataaa acagaatatg aagaagccca ggatgccatt gttaaagaaa   2700
ttgtcaatat ttcttcaggt aaacttaata gaactaataa tgttctgaat gtcacctggc   2760
ttttggtaac agaagaaaaa tcatgatatt tgaagtgtgt tttgttattt tcgcaagcca   2820
ttacattctg actatttaat atgttaggtt tcctatataa aataaggcat ggtatgttac   2880
agtaggacac ataactggaa gttactcttg cacatagaaa caaaaaatgg cagaaaagca   2940
caaaacttac tatagttgta acagggaaag gaaacactag ggcct                   2985
```

<210> SEQ ID NO 369
<211> LENGTH: 2138
<212> TYPE: DNA
<213> ORGANISM: Homo sapiens

<400> SEQUENCE: 369

```
aggaaacact agggcctaca acgtactaat gtcttgggtc atctatgggc tcatgaggct     60
ctaggttatg gaagtaaata ccactgaaaa gcaaatatta attacacatg aggcaagcct    120
ttttgagttc tgtatgtcat tttgtagatt ttgagttcat tctagtggca ccatttgaga    180
tcattttcat gtaattaaag gaacacagca acctggcact gtgttattgc ccttagaatg    240
gaatgaatat atgtttagca caaggtagga agtgatgcgt taagttggaa ggctttgccg    300
atcatggtgt gtatgttgac taacctttat tgtgccttta aaaaatatac tcaagaacta    360
ccttaaccaa gtaattaaag tcaagattac cagttgtggg acaaatgaca tgtacttcct    420
ggtgtgatat agaaggaagg acacagtatc acctatatag tattcttgac cagaatattt    480
aacctgattt taaacaagaa gtaaaaattc aaataaattt agattgtggt gcattcaagg    540
cctgaacttt aataaatgtc catgtcacgg cagcaaaaaa gaaatcaaca ggtcttaaag    600
agacagggca accaaacgca gtaggcagta gttgattaga tcccaattta gaggttggag    660
ttggggaata gctatagagg acactattgg ggcgaattga gaaagtttaa tatgagacaa    720
tatggtgtta gtgtcagatt tcttgtgtga aatggtagtg ttatgattag gagaatgtcc    780
ttgttctcag gatatgcatg ctaaattatt taaggacaaa tattttttta aaaggttatg    840
```

```
tgcatgagta attctataaa ttgtgttgct attatgaatt gtcatggtaa atcaaaagga    900
aacataaaac tcaaaaggtt ttatttttaat acactttatg tattgaaatg aatggaattg    960
atttgtaaag attacatttt tgcttgttgg tgtcagataa ctgtgacgta ataatctttt   1020
gctgaattat gtttcttagg ctagatttca ttttaaagaa ccctgtaaat accatttatt   1080
tgaactgtgg atcttcctta aaaaataata tttattaagc acctagcagg gtaaagtttt   1140
tagattttaa catttaaatt gaaggtttta tattagaagt caacctgaat ttaaatgaaa   1200
cttcttcttg gtctgatatt acatattatg agctattttt atttaaaaat gtaatggcgg   1260
ccagacatgg tgattcacac ctgtaatccc agcactttgg gaggctgagc tgggaggatt   1320
gcttaagccc agaagtttga gaccagccta gccaacatag ggggacccca actctacaaa   1380
aaaatccaaa aaatattagc cggctgtggt ggtacatgcc tgtagtccca gctactcagg   1440
aggctgaggc aggagaatca cttgaaccca ggaggtcgag ggtgtggtga gccataatta   1500
tgctactgta cttcagcctg ggcgacagag caagactccc atctcaaaaa gtgtaatgga   1560
tcactttaat aattttctat catacaatta agtcataaaa ggtcatgcta ttaagagcca   1620
gttatgtgac atgccaagta tagactctta attaagatgc tttggtttgc tttttattta   1680
tttatttatt tttcagatgg ggtcttacca tgttgcccag gctttagtgc agtgatgcga   1740
tcatgactca ctgcagcctc aacctcctag gttcaaggga ttctccccac ttagcctccc   1800
aagtagcttg ggactactac atgtagtagt gccaccacac ctggttaatt tttttttaat   1860
tatcttttgt ggagatgaag tctcactctg ttgcccaggc cagactcaag cagtcttcct   1920
gccttggcct ccgaaagtgt tgggattaca ggcgtgagcc accctgccca gcctagtttt   1980
cttttttta ctataaactt attcttgtca gtatgctagc aattttacaa gttttaaagt   2040
agttatagca agtacttcac tcatgtttaa ttcttaaagg cttctattgc tatataatag   2100
ggtagtctga attcttcaaa agtgtactga ggccaggt                           2138
```

<210> SEQ ID NO 370
<211> LENGTH: 2491
<212> TYPE: DNA
<213> ORGANISM: Homo sapiens

<400> SEQUENCE: 370

```
gggattctcc ccacttagcc tcccaagtag cttgggacta ctacatgtag tagtgccacc     60
acacctggtt aatttttttt taattatctt ttgtggagat gaagtctcac tctgttgccc    120
aggccagact caagcagtct tcctgccttg gcctccgaaa gtgttgggat tacaggcgtg    180
agccaccctg cccagcctag ttttcttttt tttactataa acttattctt gtcagtatgc    240
tagcaatttt acaagtttta aagtagttat agcaagtact tcactcatgt ttaattctta    300
aaggcttcta ttgctatata atagggtagt ctgaattctt caaaagtgta ctgaggccag    360
gtgcagtagc tcacacctat aatcccagca ttttgggagg ccgaggcggg tggatcacct    420
gaggtcagga gttcgaaact ggcctaacca acatgttgaa accctgtctt tactaaaagt    480
acaaaaatta gctgggtatg gtggcaggtg cctgtaatcc cagctactca ggaggctgag    540
gcaggagaat cgcttgaacc caggaggcgg aggttgcagt gagccaagat cacaccattg    600
cactccagcc tgggcgacag agcaagactc tgtctccaaa aaaaaaaaaa aaaaaaaaaa    660
aaaaaagtat actgaaacag aggaagataa ttaggtctgc ttggccattg ttaagttgat    720
ttttattttc aaaacatttg atcactgttg tggggaacaa gggaataaaa aataagttaa    780
atttccagcc cctagattaa actaataatt tttggttttc ctagaattaa atgcttttat    840
```

```
cttgaatgtt ctgtgaagct tttgacatga ttgatagctg tatgatagtc tgaatgacat    900
gtgggtcatg caccagcccc tccaacctgt taacatttag aatctattca gaaaaattta    960
agcattgtta atttcctttg tttttgtct agcatgtgtc agattttttt aaatgtattt   1020
attaatagct tttaatgtta atactctaga acagtagaat cttgaaaatg ttttaagtga   1080
caattagaga tttaaattta tgctgacatc ctctgcatgt gatactgatg aggaaagaaa   1140
gccaaactgt cttacggtca gttcgtacaa tataccaggc cttgatggtc acatttcaac   1200
ttgctacctt tttgcttaca tttttcttat ggtgattttg aggtgtcatt ctggtttctc   1260
agatacttaa aatataggaa aaggtgtgtc ttaaaattga gagaatgtct tggataagca   1320
gctgtgtagt tttatatttt gctgataagg gaaggtactc tatttttgtt ttttgtgtgt   1380
ttttgtttgt ttgtttttga gacagaattg cccaggctgg agtgctgtgg cgcaatctca   1440
gcttactgca acttccacct tctgggttca tgcaattctg gtgcctcagc ctcccaagta   1500
tctgggttta cagacatgca ccaccatacc tggctaattt ttgtattttt ggtagagatg   1560
gggtttcgcc gtgttaccag gctggtcttg aattcctggc cccatgtgat cccccggcct   1620
catgcgatct gcccgcctca gcctccctaa gtgctgggat tataggcgtg agccacccaa   1680
cccagccagt actctgtttt tgatagctat tcacaatggg aaaggatgta gcaacacatt   1740
ttaaccctat gttgagtttt aggtgggttc ctttgaaatt ttgttaaggc taacttttgt   1800
taattttttt aaaaaagtgt aaattaggaa atgggttttg aattcccaaa tggggggatt   1860
aaatgtattt ttacggctta tatctgttta ttattcagta ttcctgtgta cattttctgt   1920
ttttattttt atacaggcta tgtagaacca atgcagacac tcaatgatgt gttagctcag   1980
ctagatgctg ttgtcagctt tgctcacgtg tcaaatggag cacctgttcc atatgtacga   2040
ccagccattt tggagaaagg acaaggaaga attatattaa aagcatccag gcatgcttgt   2100
gttgaagttc aagatgaaat tgcatttatt cctaatgacg tatactttga aaaagataaa   2160
cagatgttcc acatcattac tggtaaaaaa cctggttttt gggctttgtg ggggtaacgt   2220
tttgtttttt tttttttttt tttaatcttg gagtagaaat atatttaaaa ttgatggaga   2280
aaattcccag ttcttaacat tagaaaggga atatattatt cttaccagtt agtaatctat   2340
tcacatttgg tttagaggga agatttagaa ggtgagataa aagcttgtga gagaatagtg   2400
tattcatgtg aaacttcttc catgggttca gagcatttag aaacaaacat cccttcacac   2460
tcaaagctta cctttgagcc agtcctccaa t                                  2491
```

<210> SEQ ID NO 371
<211> LENGTH: 3126
<212> TYPE: DNA
<213> ORGANISM: Homo sapiens

<400> SEQUENCE: 371

```
cttacctttg agccagtcct ccaatagtga ggtctttgaa ggtcaggcca aattggctgt     60
gggaggacct caggttagga taggaattat tttaagacat ggcactatat tcatgtgaaa    120
ctcgcaaaaa ctagccttgc atataggctc atgtatcatg tctcagctga gatgtttgag    180
agatcttaac tagattctag aaaacaaaaa aggaagtagt tttggggcaa atatatttgg    240
gaaacagttt attgtatttc ctttccccaa atggattttc aagttcttca tataatctaa    300
ccccaacaaa taaattgcct gtttttcaaa agaaagatca tgtcttcagg tttttgtgtg    360
gggtttaaat gattcgaaag atttgaccat actgatacat tcactagtaa ccttagttac    420
```

taatgagtaa tggttttgag ttaatcagtt aggcctgaac tacttttctg gaagttagta 480
aattatctca caggcagccc tgtgagccat gggaaaatgt gtatatggtc tttctaggcc 540
acagtcaaat tacaggtata tttgtcatgg cttctcttga tgaaaggccc agtatcggtt 600
tgtctgaaga tatataatag cattgctttt gggggtaata tgggcagtaa ctctgtccac 660
atctttgggc aggctgtggt tctgccttta tatgctatgt cagtgtaaac ctacgcgatt 720
aatcatcagt gtacagttta ggactaacaa tccatttatt agtagcagaa agaagtttaa 780
aatcttgctt tctgatataa tttgttttgt aggccccaat atgggaggta aatcaacata 840
tattcgacaa actggggtga tagtactcat ggcccaaatt gggtgttttg tgccatgtga 900
gtcagcagaa gtgtccattg tggactgcat cttagcccga gtaggggctg gtgacagtca 960
attgaaagga gtctccacgt tcatggctga aatgttggaa actgcttcta tcctcaggta 1020
agtgcatctc ctagtccctt gaagatagaa atgtatgtct ctgtcctgtg agaaggaaaa 1080
gtatatttgc agattctcat gtaaaaacat ctgagaatgt ttgtcttagt ttaatagttg 1140
ttttcctgtg gactttatat actttgtatt gtcttaaaag agtgattgat ggtagctacg 1200
gaaaactttg atttttaaaa ttgtctcttt aagtagacaa tttataagct actggtacga 1260
gttcacctta taaatctcca ctaccatgtt tttgcttgga ctgttcacac ttcctggaat 1320
ggtccttctt gccgtttatc caacttcttt ctaattttta agtccctaat gatgggaatt 1380
ctatttctgt agtgattttt ctggtcatac gaccgtaagg tcatgggtgt ttttctctga 1440
attcctcttg agatgcctgt aacttgaacc acgtttttat tctagacatt actgaaatgt 1500
tttgtcttta tttcactttt taggagcttc cttgaaggta gggactatac cttctatttc 1560
ttggtatctt tttctttctt tttttaaaag ttttttagag agacagggtc tcactctttt 1620
gcccagactg gtctcgaact cctgggctca ggtgatcttc ctgccttggc ttcccagagt 1680
gctgggatta caggcatgaa ccaccgtgat cctccttatt tcttagtatc ttctaaagaa 1740
cattaaatat agtaggtgcc tagtaaatta tgtattgatt taacttcttt gaggttctgt 1800
tgtttgtgaa gaattataaa agcaatacaa atgtttgtat agtaattaag caacaggtta 1860
atattcatga cttaaaagat taaagaaata agcaaaacat gttagctggc aactcacaga 1920
aaaagaatta aattgccaat gagcacacga gcacatgaaa aattagcaaa agtttcaccc 1980
ctttacatat atttggttaa aattgagaaa agaatagtaa tagatggtat tggtaggact 2040
gtggcaggca cacaatttac atgaccacca aaagtgtatg caggtatcca tgtcaccaca 2100
ccctggtctc atcttcattc agttttattt attttttta atctcggcct atttgattgg 2160
cacgaaatga atgatagctg ccttatttgg aattcctttg attactacta gtgtgcttga 2220
taatgtaaaa caatattcaa aatctgtttt tcctttcatc cgttgtttgt tcatgttcat 2280
gaccttttt tttttttcct attctcctcc ctccctccct ccctccctcc cttccttcct 2340
tccctccttc cctccttccc tccctccctc ccacacaaag gtgtgtgcta ccatacctgg 2400
ctagttttta attttttttt tttttttttt ttttagaggc aaggtctcac tatgttgctc 2460
aggctggtct gggctcaagt gatcctccca cctccgcctt ccaaagtgct gggattacag 2520
acgtgagcca tcatgcctgg cccttgccca tttttctatt gaagttttag tgctttttat 2580
tgactttgtt tatatattaa gataatccat tatgtttgtg gcatatcctt cccaatgtat 2640
tgtcttaatt ttgtttttgt atgtgtatgt taccacattt tatgtgatgg gaaatttcat 2700
gtaattatgt gcttcaggtc tgcaaccaaa gattcattaa taatcataga tgaattggga 2760
agaggaactt ctacctacga tggatttggg ttagcatggg ctatatcaga atacattgca 2820
acaaagattg gtgctttttg catgtttgca acccattttc atgaacttac tgccttggcc 2880
aatcagatac caactgttaa taatctacat gtcacagcac tcaccactga agagacctta 2940
actatgcttt atcaggtgaa gaaaggtatg tactattgga gtactctaaa ttcagaactt 3000
ggtaatggga aacttactac ccttgaaatc atcagtaatt gccttattct aagttagtat 3060
aaattattga tgttgttata gaacccattt accccttaat tcacagtctg gggtaggaa 3120 catgta 3126

<210> SEQ ID NO 372
<211> LENGTH: 2920
<212> TYPE: DNA
<213> ORGANISM: Homo sapiens

<400> SEQUENCE: 372
ttctgcatca gttggttgca catgagtgag ataatcttgg ttctttatcc tttgttattt 60
gtacttcatt gggaatcctt ttgagttagt atatttgagt cattattatt attgctgtag 120
aattcaggaa cttttagtag atctggcagc ataaaatttt gcttttaaat cattgtttgt 180
gttttgtatg ctatagaaat gggttcagaa tattttttaa aaggccagat gaagtgtgaa 240
gatagaaaaa cttcatcctt cactgtgaat gtttaacaaa catttgcttc tactttattt 300
ttgtttgctt cctttagttg tgcaaagtat tcagttctag aatgcatgag atatatgaca 360
aagccaaaaa attctttata gttgataaat aattgtggca aaaacagctg tatagtaact 420
ttgcaagcat catttgatta aatgcttaaa aagtcttgac tcagttttaa ctatttcctg 480
caaataatca atatttaatt aaagctactc caaattagtg acactttacg tgtctgtctt 540
tctccctccc cttctccctt ctcccttccc ccttctccca ttctcccatt ctcccttctc 600
tcttcttcct ttcctcttcc cttcccttcc cctttccctt ccccttccc tcttctcttc 660 ccctccccct tcccatcccc catcccttcc cttcccccat ccctttcctt tccccttccc 720
ttccctcctc ttcctccttc ccttccccct tcctccttcc cttcccccctt cctccttccc 780 tttcctcttc cctttcccct tcccttcccc cttcccttcc ctcttccctt ccccttcccc 840
tttcccctcc ccctctcctc ccctccctta ccttcccatg aaatgagaaa gcctcagaga 900
tagtggcttg attaattttt ctttagatta agatatttgt ctaagccttt aaggtttatc 960
tattgagctt ttttgtctcc tatttttatt tttcctacta tgtttgtcga ggataaaata 1020
cagcactgtg tgccaagtca taatcacttt tcatttgaga cttaattaaa atgcctttat 1080
tttaatgata tatttggcta atgtatttga agtaatccga aattaagttt tctaatgaca 1140
aggtgagaag gataaattcc atttacataa attgctgtct cttctcatgc tgtcccctca 1200
cgcttcccca aatttcttat aggtgtctgt gatcaaagtt ttgggattca tgttgcagag 1260
cttgctaatt tccctaagca tgtaatagag tgtgctaaac agaaagccct ggaacttgag 1320
gagtttcagt atattggaga atcgcaagga tatgatatca tggaaccagc agcaaagaag 1380
tgctatctgg aaagagaggt ttgtcagttt gttttcatag tttaacttag cttctctatt 1440
attacataaa caggacacta agatgaaggt tttttgttgt tgtttgtttt cctctgtgtt 1500
tctagtgctt attttttaat cagttttttt gatggcaaag aatctatctc tgtgttattt 1560
tgatttctgc agtatataca tctgcatgat caatattcga tttcaagtac caaagtagga 1620
gtaaaggaat attaacctag gtttaaaatt agtcatttca ctaaaattag ttattatgga 1680
cgatagatgt ctaggtatat ctttgttcat aaacgaatat atcaagttca gttattaaat 1740
tacacattag gtaagaaaag gacaaagaaa taaaaaagca tgattcataa ttcctgccct 1800
ctatttgtct agaatttagt tgggaagata agaataacga acgtgacaca gagaataaag 1860
tggcatatga caaatattta ttcaagaaag ctatatgtgg acgggatgtt tcagttctca 1920
tgggagaagt ggattttatg gtgcctttga gtaatgggtc atatttgggc gttcacacag 1980
aaagacccaa gcatatgcct aatttttat tattattatt ttttatttat ttatttattt 2040
tttagacgga gtctcgctct gtcgcccagg ctggagagca ggggcgcgcg atctcggctc 2100
actgcaaact ctgcctcctg ggttcacacc attctcctgc ctcaggctcc cgagcagctg 2160
ggactacagg cgcctgccac cacgcccggc taaatttttt gtatttttta gtagagatgg 2220
ggtttcaccg tgttagccag gatggtctcg atctcctgac ctcatgatct gcctgccttg 2280
gcctcccaaa gtgccgggat tacaggagtg ggccactgtg cccggccctt tttttttttt 2340
ttttttttaa attagaggat tactagttct cttcaattat aaaaataaaa gaatcttatt 2400
tcactgcctg gtcctggaaa catgtactgc aatatacatt gtgacaactt tttacctgtc 2460
atgtttttag cttttacctg tgaatgtctt atcattgttc ttatctgaag gatagatagt 2520
tgctacaata ataatagatg gtgtgtatgg tttttgagcc taaaaagtgt agttttatct 2580
gttgtaccta tacaagcagg agaaatataa cttgttaata attttaggta tggcaggctg 2640
ccatcctaaa tatgaagtgg tctttgtatt tgcactttaa tgtgttgaaa tcatagcttt 2700
cagtgatcca ggattaggca gactctttta tgcaatctct tgtttccagt tagaatagaa 2760
gtcgtgtact tttgataaca ttaattataa tatattttga gccctgtgag gttggtaaca 2820
ttattcccat tttatgaatg aggaatgtgt gttaaggagt ttgcccaaga gtcacatagc 2880
aagtcatagt catgctctct gaagcagcaa taacttggca 2920

<210> SEQ ID NO 373
<211> LENGTH: 3092
<212> TYPE: DNA
<213> ORGANISM: Homo sapiens

<400> SEQUENCE: 373
gccctgtgag gttggtaaca ttattcccat tttatgaatg aggaatgtgt gttaaggagt 60
ttgcccaaga gtcacatagc aagtcatagt catgctctct gaagcagcaa taacttggca 120
ataaaataaa aatgaagcat cttctgtatg tgttaacttt tcagtgactg tttatgcctt 180
ccagtattct ttgtaaacct tgaattcttt ttttcacaga tgattaaagt ttatcaattg 240
taaaggtgga ggaatttggg aactagacag tgcacacata aataataaat atgttcttca 300
aatattgggt gggctaatgt gggaggagtt tgagaccagc ctgggcaaca tagtgagacc 360
ctcgtctcta aaaatatgaa aaataaaaaa aaaatttttt aaatgtgtga tatgtttaga 420
tggaaatgaa acaatttgtc actgtctaac atgactttta gaaaagatat tttaattact 480
aatgggacat tcacatgtgt ttcagcaagg tgaaaaaatt attcaggagt tcctgtccaa 540
ggtgaaacaa atgcccttta ctgaaatgtc agaagaaaac atcacaataa agttaaaaca 600
gctaaaagct gaagtaatag caaagaataa tagctttgta aatgaaatca tttcacgaat 660
aaaagttact acgtgaaaaa tcccagtaat ggaatgaagg taatattgat aagctattgt 720
ctgtaatagt tttatattgt tttatattaa cccttttcc atagtgttaa ctgtcagtgc 780
ccatgggcta tcaacttaat aagatattta gtaatatttt actttgagga cattttcaaa 840
gatttttatt ttgaaaaatg agagctgtaa ctgaggactg tttgcaattg acataggcaa 900
taataagtga tgtgctgaat tttataaata aaatcatgta gtttgtggaa tttgagatgc 960

-continued

```
attgtagttc ttcgcagtgt gacttcaaat attttggaag aaacaaatag ctcagagacc   1020
tcgtaaaata tcttaaactg gagggctcca tggagatcat tgcgagtgac tcccccagaa   1080
tgtccatctg ttgacaggag ccaggctggc tgcatacgaa ttagctaagg agcttattat   1140
atatccagag tcctaccgtg agcctccatc ccgtctgcca ttctcccatc cctggtctat   1200
gataagactt agaaatctgg attttaacaa aacgtttcag attgagaacc ttgatttagt   1260
ctacttctcc tattttacaa taaagagatg aagcggttaa gaattagcta atcctacgca   1320
aagtgaggga aaaaggacag tctttttaat aaatgcggcg ggctggtggg gtatccatat   1380
aggaagaaat gacattggac ccctactcca tgtcatatat aaaaacctcc actttgggag   1440
gcgaagcagg caatcacttg aactcaggag atcaagacca gcctggacaa catgacgaaa   1500
ccccatctct acaaaaataa atgcaaaaat tagccgggca tagtggtgct tgcctgtagt   1560
cccagctact caggaggctg aggtgggagg atcacgtgat ctgggagagg ttgaggttac   1620
agtgagctgc actccatcct gggtaataca gtgataactg tgtctcaaac aaaacaaaac   1680
aaatcacctt cagtgatttt tagaccaaat gtacaaggta atactctcaa ggttttaatg   1740
ttttatagtt ctgcagaaga taacatagga aaatattttt atgtccttgg ctttgggaag   1800
aatttaagtc acagaaaaac accatccata aagtttgact tatttagcta tttgaaatta   1860
acaacttcta ttaaaaggca ccacaagtga aaagacatga atcgtaatgg aagaacatac   1920
tggtacgtta taaaatatca aagagttggg catggtgtcc catgcttgta gtcccagcta   1980
ctcaggaggc tgaggcagga ggatcacttg agcccagcag ttcaagtctc agcagttcaa   2040
gtccagcctg ggcaatatag caagactgca tttcttttct tcttcttttt taatacctgg   2100
aataaagaac tcctataaaa tcactaagaa aaggggtcac ttaagaatct cattaacaaa   2160
aagaatttga atatttttcc aaggaagata tgcaaatgga ctgtaagcac atgaaaagat   2220
gcagatcagg gaaatgcaag tcaaaaccac aatgagctac aacttcacac tgattacgat   2280
agttaaaatc aaaaagtcag atggtaagta ctggcaagga agtggagaaa ttgaaactgt   2340
catgcgctct tggtgcgaat gtaaaatggt gcagctgctt tggaaaacag tctggcagtt   2400
cctcagacaa ttccactcca acgtatatcc aagtggaatc acaacatatg tccccacaaa   2460
cttgtacata aatgtttata gcaggattat tcataatagc caaaaggtgg aaacaacccg   2520
aatgtccatc agcagatgaa tgcataaatg aaacgtggtc tatccataca atggagtata   2580
ttattgagcc attaaaggaa tgaagtactg gtacatggtg cagcttagat gaaccttgga   2640
aacattgtgc taaatgaaag aagctggtta caagagtcaa cacgtatgat ttcattcatg   2700
tgaaagttca gaatagagac agcagtagag acaaagtagc agttcagggt tggtgccagg   2760
gaataggggg taggtggggt gaaagctaaa ggatacggtg tttctttgtg agatggaaat   2820
tctaaaatag gtgatgttta tacatgtctg tgaatatact aaaaaccatt gaattgtaca   2880
cattaaatgg atgaattgta taggaattat attttaataa agctatttaa aaaaatccag   2940
acacttcacc caagaggaaa tctaagtggt ccataaacat gaaaaggtct ttaatcacca   3000
gtcagaaaaa tgaaaatgaa aaccatgcca ggccacctcc caccaccata gtgacaagca   3060
tttcaagtgt ggcagttcca gctgttgttg ag                                  3092
```

<210> SEQ ID NO 374
<211> LENGTH: 2985
<212> TYPE: DNA
<213> ORGANISM: Homo sapiens

<400> SEQUENCE: 374

```
ctctcaggtc aggcttctga caagccacaa tgtgggtgag cctttgtgca ctgcctgccc     60
acctctcacc aggagccctc tctccccatg cctcaaggt accagtgagg ctttttttctg    120
tctcagcctg gccataagca gccctctgca agagttccgt taccagtcat ttgcattgta    180
gtataagtgg aaaccacaga atcgccttcc tccccagtta tttatacttc aagtcatatt    240
gtagagagaa aatttctgtc agcaaaaatc tcaggaatcc tcctcatttc tatttgtatg    300
gctttcaatc gttgacatga ttttttcaca tatgtcatct tctggggatg gattcgtata    360
accctgcttc acttgcttcc ctgtgggagg ctcacttgct tctcgacagg ctctggaaga    420
actaggcagt ctggtacatg gttgtgcaag aacccttgag ggggccttgg agtgtgtgct    480
tgggccctgg aactcatgcc taggatggag ggctgagatt gccccttccc atccaccagg    540
gagttgacaa gggggagaag aaacttcttg tgagcttgcg atgacttgtg gcacttgcat    600
cagaccttgg agttccctgg ggagaggcac tcttgggtat gacactgtat agtgccacct    660
gattgccatt tgacccagtt tggccctgga tccttgagca agagggctgg aaagaaagac    720
aggcccactt tttgggacac tattagggtc tgtagcattg gtggggagag aattccccca    780
acccccaaaa gagctgaaaa tgagacacgc gtggaggggt gaaagtggag tgtggtcaac    840
agtgtggtta cagagatgtg tgtcggggcc actcccactc accagggaga ctcatgaagc    900
agaagggatg gggcacaatg tggcttccat aggcacacca agccacctgg agagcgcatc    960
agccctttgg gtacccccaa gcggaaggag gttgggtctt tgggtctggg aactttggtg   1020
cttgttctgg tgggaagggc agggagtcaa gaccagctgt gtcttccact gctcttcttg   1080
tccactttgg ttactggcct ctgttggcat gaactgggga ggcagaggct acctacagac   1140
gaggaactgt gtggagtgcg agtgtatgca gtaaagggtt agcttagctg acttgaggta   1200
ctcacaccca tattccgaag aaaagactgg ccctcagcct gagcctccga aataatctct   1260
aagcccttag aataccctgc tttgtattca aagagtatct ttgaatgctg aacttagaac   1320
cactctagaa aatgtatgct aacaatgcga tttatgatga acacttgtct ttgttcccct   1380
ggggccctgg gccacattgt atcagtttga gccctagagg gacagagaat gagaaactaa   1440
gatcagtcat gcaggtgctc caggcctatg tgaccaacca ccaataaaaa ccctgaacat   1500
caaggctcaa gtgagcaata cagctggtcc caacttacag tggttcaact tgtgagtttt   1560
gcactctaca atgggtttat tgggacataa cccagtggag gaggatctgt acttcattca   1620
catgtgttgt cacatcatta ctgggagaat taagcactgt ccacgtgaat ccactgggag   1680
aggataactg gaagcttgca cctggcttct cctggattct gctctgtacg ccttttttccc   1740
ttgttaattt taatctgtat tctttcactg tagtaatcta caactataag cagaatagct   1800
tttctgagtt ctgtgagtct ttctagtgaa tcattgaatc caaggtggtc ttggggacct   1860
ctaacaaaag atgtctggac ctgaacttcc tgttgtttca aagatcctat agcaggctgt   1920
cttaccaact ttcagcatca agaagctggt ggagagtggg ttagtttaaa aatgaaactg   1980
gggagagaga tgaagccggg ggaagatgcc gtgaaatctc accttatagg cagcctctga   2040
ttcacctgag ggtttttcct tgaatacttt ctgggtacaa gtatttgaga caggtgatgt   2100
gctggtcact ttattctcag ctgcttgtgg cctagcccta acatgggcac tggaaacaat   2160
gggggtaggg gttgatgatg gagaaatggg gagtaaaggg atttaaaact ttgaaaaact   2220
gagctgtttc catgatttgt ctcttttgat tctcacaaaa cctttatgaa atatgtgctg   2280
acattttaag ctctcactta tagtgagaaa agcaatcttc agcaaggtga tgacttgtcc   2340
```

aagggaagac atggtcgccc ttgttccttg ggagattttg tgctcccagg ggaaagcata 2400
agccctcagg agccatgatg agaacagctg tagaacagca agtgaacagg tgtgtatcag 2460
tcaggatagg caaggctaag ctgcagtaat aaataatccc cggatctcag tggcggaaca 2520
ttgaggaggt ttatttcttc tttatacaaa tatgctgtgg atcaggatga ctctccaggc 2580
aactgtctgt gggactgtcc aggtgggctt ggatcacctg gtgttgggcc ttgaagtcgg 2640
taatggagag gacatgttag aagagaagga acttacaagc agtgggagtg cagcgccctt 2700
ttgtggatag gggtcaaggc aatgctttcc aaggctatga cttggtgtgg tcgaaaaagt 2760
caagcagtct tcacttttg ctgtggtccc agcaaatctg cttccaatcc aggcttctcc 2820
catataaaaa gcctcctttg tgtacagtga gtgaactaga acagggagga gatgccagtg 2880
gagcttggct tgctccttct gtggccagct ggcttgtttt accactgcct ttggggtaca 2940
gtggcagctg tggcaaatct ctctggagtt tctctagcgg gagcg 2985

<210> SEQ ID NO 375
<211> LENGTH: 3068
<212> TYPE: DNA
<213> ORGANISM: Homo sapiens

<400> SEQUENCE: 375
agcgaagcac ctaaagcaca tgggtgcagg agcagccagg cctgcaccca tagacatggt 60
acagagagga gcagggaagc ccgctgcctg cagacttcag gaggagagag gtaggggtgg 120
tgcaggggag agggccttaa tgccttcagg gaaaggagtc aaagaggaat acccaggaga 180
caactagact ttagaattct tggggccaga aacttgattc cacctctagt gctttctttt 240
agatttcttt ctctctttac tttctttctt tctttctctt tctttctctc tctctctctc 300
tctccctccc tccctccctc cctccctctc tctctctctc tctctctctc tctctccctc 360
cctctctctc cctctctctc tctctctcct ttctctctct ctcttcttaa gactgggtct 420
cgcagttggg cacagtggct catacctgta atcccagcac tttaggaggc tgaggtgggt 480
acatcacatg aggccaggag ttcaagacca ggctgggcaa cactgtgaaa cccatctcta 540
ctaaaaacac aaaaatttgc caggcatggt ggcagatgcc tgtaatccca gctactcagg 600
aggctgaggc aggagaatcg cttgaacctg gcaggtggaa gttgcagtga gccgagattg 660
cactactgca ctctagcctg ggtaacagaa caagactcta tctcaaaaaa aaaataaata 720
aataaaataa aagggatacc gggtcttgct ctgtgtccta ggctggagta ccatggtgtg 780
atcatggctc actgcagcct ccacctcccg ggttcaagca attctcctgt ctcagcctcc 840
caagtgagta cctgggacca caggcatgtg ccaccatgcc tggctaattt ttaaattttt 900
tgtagagatg aggtcttgat acgttgtcca ggctggtctt gaactcctgg gcccaagcag 960
tcctcccact ttggcctcct gaagtgctgg gggtacaggc gtgagcctcc acctggccag 1020
cctccagtgc ttttgcatcc ttcctgttaa cttgtgtagg aataaaacat tgtcacaata 1080
agattttttt cctttttatt gttttgattt tttagccaat gagaaggaaa attccttatt 1140
agggagggcg agggtgagga tatgtggggt ggggagaagc gaacgttcca agtttcgaaa 1200
acagcgactc tctcttggac tctctagcca gtagaaacct ccctcccact ctcttgcccc 1260
aagatctggt gcttagaaga gaatcaaggg aagttggaac ccagaagacg gagacagatt 1320
gagggactgc tgtgaaatgt tggggtgttt ggtgaataat attagaagtt gggctggcag 1380
agaccctgtc acataaacat taaatcaaca ctggagactg agcatttgtt agaaatgtaa 1440

```
gcgggaatgg cagaaaactt gtttttaagg gaaagcatgt tacggcttat gttcagcctc   1500
catcctctga aggcaaaagt tagcaaagtt gatgtatggc gttgcttttt ctgggaactt   1560
tatctcgttt ggtggggttc ccatctctgt ctcccaggag ccaagacttt cccctccctc   1620
tgctccagca gaagccagtc tcaggcaagg ctccctgtac ctcatttaca ctttggtgtg   1680
aatatgttat tgtaacctct ctcctggagg tgtctgcatt ccaagactga acttttctgt   1740
gaaagttact gtcactgtga aaggcagttc agcccccagg gattgaaaaa ggaaatcatt   1800
ttgggtaagg ggacagttag tccagatttt ttcagttgca agtaaaccta actcagccag   1860
taggcaaagg gggaaattgc tggtttgaac tggtgggaag aaagctgagg aaactcctac   1920
acttggggga agaactgcag gtgcctggct gcagggaacg cagcgggggc tcaggaccag   1980
gcagatgccc tgcctctgct tcccttggca cagtggcctc cttctccctt caagtaggca   2040
gatgctgcct gtggcagagg acagcagctg attggcagcc cagcagggag gatgtggtag   2100
acaggcactg agcatctctt ctaccctcct tctagagggc tatcctgtac tgttgaggct   2160
aaaagactga aaaccacatt tcccagcctc tcttgcagct accaatctgg atgagagtta   2220
gattctacac attagatgca ctttagcaag attttcaaaa gcagattgga gaaggagccc   2280
atgcttctgc tggttttttt tgctggcaag tgaggggttc tgtttttcct ggagtgactt   2340
tatcatggtg gcatctgaaa aaggctattt cttgatcaga gagacagcaa ccctctcagt   2400
gacctagttc tgtgggtgtg tctctcctga gagttaatcc cagagctcaa actagagctc   2460
aaccctagag tctcttcagg cttcccaggg gtgggggtgc atttaacagt ccaagttaaa   2520
gagaaaataa aggccattaa agaccaaaca ttgagcactg agtgaaaaag ttttattgcc   2580
aaacaggaaa cctgattcag gccagggtct tggaaggttg ttcaggatga gatgggggag   2640
gtgaaatggg gtaggtcttt gaaaaccaac agattgcaaa ttctctgtcc catagcagga   2700
aaccacagtc tctgatgtca gctggctgcc aacacgtcag ttgtatcagc attagctggc   2760
tggaggtggc ctgctgtgtg cagatggtac ctggtgcagg attgtggtgt ccaggtgtct   2820
ctccttagca cataagaccc tgtccgagga ctgtggcatg acgtgctgga gtcacgattc   2880
tgtcacccag tcaggtcatc agtgtcagag agctaggtgg ccaggttgga gttgattgcc   2940
aatgataggt ctttttctgc ttaaatcagc tggactggat tctattgcat taacttgacc   3000
ctgactcatg ccgccaggcc taatttataa accaagacaa gaaagggcta ctccaccccc   3060
tccaattt                                                            3068
```

<210> SEQ ID NO 376
<211> LENGTH: 3117
<212> TYPE: DNA
<213> ORGANISM: Homo sapiens

<400> SEQUENCE: 376

```
gtcacccagt caggtcatca gtgtcagaga gctaggtggc caggttggag ttgattgcca     60
atgataggtc tttttctgct taaatcagct ggactggatt ctattgcatt aacttgaccc    120
tgactcatgc cgccaggcct aatttataaa ccaagacaag aaagggctac tccaccccct    180
ccaatttgtg taaggccagg ggacttcccc cccactcccc aacctgaggc atgcaccctc    240
ccttagatca atggctgttt ctctgagaat gcggaaccgt gattaatcca gccttgatgg    300
ggaggcagca ggaactgtag gcattctcac ttcacaccca tcccaatccc ctccccccttg    360
ctgtcctctt gtacagagga ctgaaagcac aacactctct ccctccctcc cttataggtg    420
gtgacgatca tgtgactctc ttctggtcaa tgagatgcag cagaaagtcc tagggaggtc    480
```

```
taggaaaagt cctgttggga gagagcattt tttaccttct ccctgctact tcttgctact    540
agtaacatgg atgtgagcct tggaggggta gctaccatct ggcacctggg gtggcaagcc    600
aacatggaaa ggatggcaga gcgggaagga ggagccagcc ttaccgatgg catcactgtc    660
actgcgctag ccccagacca cctgctccag agttctggtt atggtaatga aataaacctt    720
gatttttatt ccttaaaact acccttcaat gggttttctg ttcattacag ttgaatgctt    780
tcataactga tacaggaggg accctgtgat tggcagttcc actagactgc atggagatgg    840
gtggagttat ctaaaagaac agagatagtg tccctagaag aaggggacag gaaagcatcc    900
tgggtacaca aaagtcaagg ctccaggatc tgccctgggg gctatctcaa cacccctaca    960
ctctcaccgc acgtatttgg tcagctatga atatgaccaa ctctcgtcgt ttatctctat   1020
tcagtggaac acagcagcac tgtgacctgc ccacgagaag aaggattttt agaacttatc   1080
ttagggcaat tttaggtaga ggagcagaca agatggtgta caggagaaac aggtctatta   1140
accctggtat taatattaac tggctgccca gaataaatga agaatagctt attctttgcc   1200
aggttgaaga tagaaaagga atgaagggcc ggagaagtac agctgggtga agcacagagc   1260
agcctagtgc ttggcatggg actcagatct gaagcagcct ctccgggact tctctgagcc   1320
tgcccctggt ggtatgactg tgatatccct gcttctatag ttggcaacca acatgtccta   1380
gctcctagac catagagggc cagattcatg tctcattgac tgtgtaatct ctgtgtggcc   1440
cagtacagag catgcacacc gtaggttctc acatatgttt gttgagtgaa tgaatacaat   1500
accaaacgaa tggacaggac agagctgtgg gctagcagga aggatatctg gcttttgctt   1560
gaattagcta gtgaattgct gtgtggcctc cttactgagc ctcatttccc tctgtctgca   1620
gagtcaagca aatcttccat tttttgttcc cctgctgcca gagcatggca gagtaaatgt   1680
gtgagttgaa gggagcaacc tcatgaggtt ttgctttgtg tcttaattac agccatttgt   1740
ggaattaggc ttttaatata aatatttgtg tgcctgcgcc tgcatatatg tatttggacc   1800
aatgctctca tgtgtgcaaa tacatgtatt ctaaagaaat ctgtccagaa ccccagcatc   1860
tgtggtgtct gtggtgggag gggcttccat attacagaga gatgcccaca gtgcatgacg   1920
ttacccgcac aggtgtgaca tcacagggta accaaatgct tttgccctgg gggtgggaga   1980
gggatgggtg cacggtgaac agcaggtggg ggtctttcca taggggatga ggaagacaag   2040
gccacttgga ggcagaggag accacagtgg ggcatgatgg ttggggaagg ccttttactt   2100
ctgcccctta aggatgccct ggaattcagg ctttcggatc ccagagctct cattagagca   2160
gccctgcgtt gtagactttt ctgcagtgac agaaatgttc tatatctgtg ctatccaata   2220
tggtagccac aagttacatg tggctattga acacttgaaa tggggttagt gcaattgacg   2280
agctgaaaat gtagtttaaa ttcacttaca tttaaatagc tgtgtgtggc ttgtggctgc   2340
ctattggact gtgcagttct ggagaatggt actttacttg tccttgggga agcagaaaca   2400
aatgaaaacg aggatctgga gctcatgaag tttctcatgg ggtggggtat gtgtgttgaa   2460
gctgcacctt cagcaggaac ctggccagtc cttagtggag gacatttctt tccatcctgc   2520
atccagatgg ctggtcctgc tcctcccagt ccatggagaa aaaagaattg aacaaactgt   2580
ctaagctggg tcaggtactc tgcagatgtt tgctgagtat cgttcttgat ggaaatcccc   2640
gtggaactcc tacattttct cctctcttct ccttcctttc agaacctcag agtgacagag   2700
ccaaaagacc agtgcctcat tttgctgaca tggaaaagga aacttcgtgg gggaaagaga   2760
tctgcttgca gtcggccaga gagacagaac cagggcagtg gtgagctctc atgacctggt   2820
```

gtctgttgcc ttctggttaa gtttttcatt tgtaattcta caaacatccc ttctgtaaac 2880
atttccctca aaatggagca ggaagctctc aaaaatggac cagaaagggg tcaggaatat 2940
aactttctct gcccagattc caggacttac agtgagaaag cgccttctgg gaacttcaca 3000
atggctaaag tgtgctaatg ggatgatgtg cccttgtaca cccactgcct ctgaactctg 3060
ctctgcattg ctgagcaaac tacatttccc agaactcctt gttggattcc ttccaaa 3117

<210> SEQ ID NO 377
<211> LENGTH: 3117
<212> TYPE: DNA
<213> ORGANISM: Homo sapiens

<400> SEQUENCE: 377
tcccagaact ccttgttgga ttccttccaa acaggtttac cactgggaga gcctgttggt 60
tggggagggc aggaagaggg aggaaagagg aagggactca cttcctgttt ccagctgaag 120
tctaaatcaa tccactatca acaggtagct atcatactac cctcattgtc acccctcaga 180
ggtcccactg cagctgcata atgtcccctc agtggcctga acatgagatg aacaacactc 240
ttcttgggag taccagcctt gcttggttca tggccacttt tcctgattat cttgcagcta 300
tattaggtca tgtgacaaag ttctggccag tggcaaggga acacaagtga taggtacaga 360
tagaagtgtc tgatactaca tagattatgc ttgcactcac tcttaagaga gagacatgaa 420
cttttaccaa cggaagccag tattattttg aacctctgtt agagtggctt gaatctgtat 480
cctaacttgt atccctaatg tgtgacccat gaaaattagc caggcagcac cagttccaaa 540
gaagctcaca ctcccctgcg gctgcttctg ccaaggtcac tgatatttcc ctttgctaaa 600
tcttgtgggt gtttcttca gtccttgtct taatcactca gtggcacttg gcacttattc 660
cttcttgaaa cccttgtttc ccttggcttt gtggcatcct gtgctcttgg ttttctccca 720
tatctctgac cctctttcct tagtcttttt tcttcttcct cctgtccctt aaatgctggt 780
tgtgatcctc tttttatctc attctacaca ctcacagcct gagtaattca caccatcttg 840
atgctgagaa cttccaaaat gttggtctag cctgggtcat tgttatgagc tctagactca 900
caaggccaat tgcttggtgg gaacccctcc cccatggtta tctcatgggt ccctgaagtc 960
caacttctcc ttcattgaac tcatcacctc ttctgttcct cctcctgggt tcccaggctc 1020
agtggtggca ccactgtcta cctggctgct tagcctgaga cctggctccg tcccaattcc 1080
tctctctcag tcttatcatc cccatccagg caaatcattg attctgtgga cctactcttt 1140
cgggtgtccc tcaaatctct ccacgtctct gtgttctcac tagcactacc ttggtccacc 1200
ctgccatctg ctttcctcct ccactcctgc attctgagtc attttcggca gcacacgcat 1260
ccttaaaacc cctccactgg cttgccagtg tcctcaggat taggcgaaaa gtctttgctt 1320
tgttttacaa ggcccttcgc tatctggccc cctcattacc tcccttgctc tgcatgctcc 1380
agtcctgcag aactacacac agttccccca acaaggccct gctctgttct tcccacacac 1440
tgctcctctg cctgggccac tcttcctgct ccttgtcagc aggcttgctg ctctcaggct 1500
cagcatggac agctgcttct gagagccttc tctgcctacc caggctgggt ggctgcctct 1560
ctttggtgtg cccatggcag cccagaatgc ctggtggaca gggagccctc agcaggccgt 1620
actgcagcgc cctgcccccg tcagcctcca ggagcctgga gtccagggac atcaagggcg 1680
gtcctgtctt tctcaccctt gtctctccag cccctaacac aggggatgcc tgaccccaaa 1740
ctagacgagt tacttgacct ctctgaccca agacaaaatg ggaggaaagt gccaaatttc 1800
caagattggc caggggatta aataagataa atatgcaagt ctcttatctg gggtctggc 1860

```
ttggtaaata taaagttctt ttttcttttc ttccttttttc ttttttttt ttctttcttt   1920
ttgagacagg gtcttactct gtcaccaagg ctggagtgca gtggcatgat catggctcaa   1980
tgaaacatcg acttcctggg ctcaggcgat cctcccacct cagccccctg agtctcttgg   2040
actccaggcg tgcaccacca tgactggcta attttttgta tttttagtaa agacagggtt   2100
tcgacatgtt gcctaggctg gtctcgaact cctaggctaa agtgatccac ttgtctcagc   2160
ctcccaaagt gctgggatta tagacatgag ccaccatgcc cagctaaaag ttcctttttta   2220
aaatctgctt gttagataca ctcatagaaa ggtaactggc cacagaaggg agaggaatgg   2280
cagtccatcc agggatcact ggagtgtcat atgaaatgtt ataggaatca caggccttag   2340
aacttgaaag gaacccaagg atcatctagg ctactttatg caggtaaaac agccacctgt   2400
gcccatcaca tagctggggc acagctggag accccaacag agaggagagc tgatgggtga   2460
cgagaaatca ggcctctccg ccacggcagc ctagctaatg ggtcttggct ggaagctaac   2520
aggaaggcct ctttccagaa acactgtaag ccagtgtttc tcagattgct gggtgtaatt   2580
cataggcaga tcatgaaatc agtttaatag ctttgaccag cattaaccta tttatgccta   2640
gcgttccctt attggaacac taagtctgtg agagttattt acatcctact gcttaaggtc   2700
atcgccaaaa tctgattttt tacacaaaaa atttgcaacc tccagcataa atgggttaaa   2760
acaagacaaa acaaaacaat accagaatgg aaaatagtgc atgatctgta cagtatagtt   2820
gtagaaaact tcttgtttta tcatttgatg tcatgaaagt ccctgctgta gataaaagat   2880
ggagcttgtg cttctgagtg gtcatgctca acagggtggg gagcccaggg gagtggggag   2940
tgatcgtata gacagaggtg ggtggggcca gtgtgagcct gatggtcaat tacttctcat   3000
ttctagggaa aattgaagga aaagaaggag ggggatgtgg aggggagaga aggcctcagt   3060
agagtttgca ctattattag ggcaagtaag ctgcttctga aaagaagggg tttgcaa      3117
```

<210> SEQ ID NO 378
<211> LENGTH: 3192
<212> TYPE: DNA
<213> ORGANISM: Homo sapiens

<400> SEQUENCE: 378

```
ccccatgcag aagcaatagg gcagcctggt cccatatcct catgaaatgc ctcttataat     60
tgtgacatct tgcaattgtg gaggacttta cacttttcgg agttcctagc ccctcactta    120
tttctcgtaa gaccgctggg aggtgggggg atggtatcat catcccactt tagagatgag    180
gaaacaggat cagagtgagc taaatgactg ccagatccaa aactagaatt cagacctcct    240
agtttctaag tggacgctct ttctacacca ccataatgtg agtgttctgt gtttacaggg    300
tgtattcaag tccatgactg cccattagaa tccccccaaa aaattccagg actggcctga    360
gttgctcctt agaccaatga aatcagactc ctgggagtac ggcccgggcc tcgggatcct    420
ttaaagctcc atttggagag cctcgggcac agccaggttg gatccatctc ccagtccccc    480
agccttggct cagcctggcc aagctgccca ggaggtccct tggtgccctg ggctctgttt    540
cactgttgtt ttgtagagca acttcccagt gatgctgcca ctgggcccca tcctaacagt    600
gaagtccccc gggccctcct gagaggaggt gtgaactgga agatggggag gcaggcggct    660
ctgacagaca gaaagcaaac agctcagagg ggtggcaggc tgcattttat tcatcgttaa    720
tttaaacacc cttcaagtcc tctcttggaa tgctgctcag aaaaatagat gtattgtttg    780
agaaaccctg caggcttgtc ccgcatgctc tagccccctc ctgagagaac agatagcata    840
```

-continued

```
aaaaatgatt tgtaaagcaa gggggagctt ccttagggaa gaaggggaag gggaagaggg    900
tttggggcca ggtccgagtg cagaaatcct caatgcatga gactagcgtg gaaggtgtag    960
caattgtgct ctggggtgcc tgaaagtgcc agagctgctt caggggcaag agtccaggcc   1020
ccaagtccat gctgatgagc ccaccctggg ggtcaggaat ggcctcagca ggccctccct   1080
ccctccctct ccaccctaca aagtgaggag ccttgagtca ccaccagcac attatacaac   1140
aatacaagaa ccctgcaaca gataaagccc cagcgcctct tctggactca gatgccctag   1200
gctggctgtc tggctgtgct ttccagacag tgtgtatgtg gaattgtgct tttgtttttt   1260
taagaatgta aaaagttaca gtaagatcga accacagggc ccgtcgctcc tatggtctct   1320
gcctgactgg gctgccgtct gcctcagttc cccagaagct tctcctttgg ccatgagggc   1380
tcagtcatcc ctcaccccag agtccacagg aagagggggt ctgctgggag gcctgtctga   1440
aggacggagg atcctgggtc aatttagcag ctattttcca gggtttggct tgggtttgga   1500
tgctggcttc tgtgtgaaac ctgaatacat gcaaattgta cataaaactc cccaaggca   1560
gagagggatt ttccaggccc tggtacatct ctagagagtt aaaaatggga aatctttctt   1620
cttaaagtgg cccagactga gacttttcct tggggaaaag ggttagtagc tctttgtaag   1680
gctggtgtgt atgtgtgtgt gtatatatat atacatatat gcatgatgct gtgcaaatgc   1740
ccagggctgt ctggcatttt ccacaaaatg agagcctgag attgcctaag ccttctgatg   1800
ccttctccag gcctggaggc actgcttcat tcagaggaca caaaggcctg accacctggc   1860
tttagcaagc taggacaccc agggtggctt ctttaccttt ctcctcagct ctgagaaggc   1920
tgctagccaa gactctggat tctctgtggc cacagtcata tggtgagggc ctcttggagt   1980
tcattcaaac tttaagggag ccccacagca ccggcatgat gggtaagtcc aggcctaagg   2040
ttaggaagca aatcctggag catgaggaaa ttgtaggcta cagtgagcta ccagtggtgt   2100
gcaaactgga gacccccaag acagtgagag aggccacagc atctgaggga atggagctct   2160
ttcttggcct gaggttcaga agaacctgca ccaaagaaag gcatccctat caatgtcact   2220
gttcctgaaa tgatgggaga accacatccc tgcttcaggg aagcagtccc tgtcgtctgg   2280
ggcgctgagc cctttggcct gagatgaagg atgatggtgt gatgtatcat ggcagtgtga   2340
ctgagactgg attgggggat ggggacaggg gaacataggc aaaaatacac atgtgccact   2400
ggatcctgag ctgccattgt accttggagg actggcgttt ctctgggaag ttgggaggtg   2460
ggaagaggaa gggtctcatt ttcctgcccc ttgaaaccat gcttaccatt cctttagaag   2520
attgctcaag ctgcctccaa ttgcctcttt ccaaaaccaa agcataggaa aacaagtaaa   2580
aacagctgag gctgcagcat aagcaactta ggatagagtc taggaagcac cgccaacaga   2640
gaagactgcc aagaaacatt ttgagttttt cttctctgga ggtgggtcct ggttcctccc   2700
atggagacca cgattctgtg tagtcctgca cgctgggcgg gggattgcct ggaggtttct   2760
ttagacctgt ctagctcaca cagtcttgat gcctgggttt taggctgctg tactgttgct   2820
ggggctcact tcctgtgggt aggctgttat tttgcccgca gatcaagtcc tcactgtcta   2880
gatgcctcta tcatggggat ctcttcttcc ctctctggat ggctctgatc cccaagttat   2940
ttcctgttgc ctaggtaaca cctctaattg gatgcctttt aatcgttccc ttttttaaag   3000
ggataaatgt ggattttatt tccaggtcct gtcagagggc cctgccctag agaacacgtg   3060
cgcccctgcg tgggcaatcc cttcactgtg accgcaacca tgggttggat ggggggcact   3120
cactgggctg gcctgacagt cacagtgaat cctgaaagca tggttttcac aggaacccac   3180
cttcaggatt ta                                                       3192
```

<210> SEQ ID NO 379
<211> LENGTH: 1944
<212> TYPE: DNA
<213> ORGANISM: Homo sapiens

<400> SEQUENCE: 379

```
agtttcagcc atgttgcagc atgcatcagt acttcatttc tttttatagc tgaataatat     60
tccatagtat ttatatatca aaatttgttt atccattaac ctgtggaggg acatttaggc    120
tgtttccacc ttttggctat tgtgaatggt gctactataa acatgtgtac acatgcctgt    180
ttaagtatat gttttcagtt ctttggggta tatacctagg agtggaattg tagaatcatg    240
tggtaatttt gtttaacttt ttggaaaaat atcaagctgt acccaaagtg gttgcaccat    300
tttgcatttc caccagcaaa atgtgagagt tccagtttct ccatatcctt gccaatactt    360
atttttcttt ttaaaaaata gctatcctag tacatgggaa gtgacattca ttgtggtttt    420
aatttgcatt tccctaatga ttagtgatgt tgagcatctt ttcatgtgtt tattagtcat    480
ctggatatct ttggagaaat ggctattcaa gccctttgtc catttttaac tgggttgttc    540
ggttttgttg ttgagttgta ggagttcatt atgtattctg gatattaatc acttacctga    600
tacatgattt gcaaatattt tctcccattc tgtgggatgc cttttcattc tcttcatagt    660
gtcctttgat acacaaaagt tttcattttt gatgaagtcc aattcacctg ttttttttctt   720
gaccaaaaag tagaaacaac tgaaatgtcc accaactcat gaacagataa acaaaatgtg    780
tatataatgg gatatattca gccataaaat gaatgaagta caaacacata caacatggat    840
gaaccttgga aactttatgc taagtgaata cagtcagata caaaaaggga actattgtat    900
aattctatgc atgtgaggta cacagaatag tcattttcat aaggacagga aatggaatag    960
tggttagcag gggctgaaca gaggagaaga ttggcagtta ttatttaatg gacatagagt   1020
gtttttcttt gaatgattaa taagttatgg aactagatag tgataatcat gaatgtactt   1080
aataccactg aattgtacat tttaaaattg ttaaaatggg gctgggaaca gtggctcatg   1140
cctgtaatct aatcctagca ctttgggagg acaaggaggg aggatggcat gagccttgga   1200
gttcgaagtt acagtgaact ctgattgtaa ccacccaatg tgttcacctt gcccgctgcc   1260
tagacagagc cgatttatca agacaggata actgcaatgg agaaagagta attcacacag   1320
agctggctgt gcaggaaacc ggagttttat tattactcaa atcagtctcc ccaagcattc   1380
ggggatcagg gtttttaaag ataatttggc aggtaggagt ttgggaagtg gggagtgctg   1440
attggtcagg ttagagatgg aatcataggt ggttgaagtg agtttttctt gctgtcttct   1500
gttcttgggt gtgatggcag aactggttga gccagattcc tggtctgagt ggtgtcagct   1560
gatccattga gtgtagggtc tgcaaatatc tcaagcactg atcttaggtt ttacaatagt   1620
gatgttatcc ccagaagcaa ttaggggaag ttcagactct aggcgccaga ggtggcatga   1680
tccctaaact gtaatttcta atcttgtagc taatttgtta gttcgcaaag gcagactggt   1740
ccccaggcaa gaagggggtc ttttcaggaa agggctgtta ttaattttgt ttcagagtca   1800
aaccatgaac tgaattcctt cccaaggtta gtttggccta ctcgcaggaa tgaacaaaga   1860
cagcttaaag gttagaagca agatggagtt atttaggtct gattgctttc attgtcataa   1920
tttcctcagt cacaattttg ccaa                                          1944
```

<210> SEQ ID NO 380
<211> LENGTH: 2197
<212> TYPE: DNA

<213> ORGANISM: Homo sapiens

<400> SEQUENCE: 380

```
cagtcacaat tttgccaagg cggtttcatg atcatgcaac tgcactccag cctgggcaac     60
agagcaagac cttgcctcta aaaaaagtaa ataaaatggt taaaatggaa atttttatat    120
tatgtgtatt ttaccatgat aaaaaaaatg aaagaaaact ggtctagctt tattaatatg    180
agacaaaaca gaatttagga caaaaaaatt agagaggacc acttaattat gataaaagct    240
tcaagtcatc aggaataatt aacattggta caaaatatgt atgtaccaaa tattattgcc    300
ttgacatgta taaagcaaaa gctgtcagaa tcacagagaa actcacaatc cttgcgggag    360
atttgaacaa aattatctca gtaactgata gaacaagcag tcaaaaattt tctttcggcc    420
gggcgcggtg gctcacgcct gtaatcccag cactttggga ggccgaggcg ggcagttcac    480
gaagtcagga gttcgagacc agcctggcca acacagcgaa accctgtctc tactaaaaaa    540
tacaaaaaat tagctggtca tggtggcggg cacctgtaat cccagctact cgggaggctg    600
aggcaagaga attgcttgaa cccgggaggc agaggttgca aggagcctag atcacgccat    660
tacgctacag cccaggcgac agtgcgagac tctgtctcaa aaaaaaaaaa aattttcttt    720
cacatcaggg tgagaaaact catacaaaga tcttcctagc agcattattc atgacagcct    780
caaactggaa ccgacctatt aataaatatc tatcactagt agaagagata aacacattgt    840
attagattaa tccaatgtaa tactgaacag caatggaaat gaaatgaact gtaggtacat    900
ccaacaacat ggatgaattt caaaacataa tgctaagcaa ataaagccag actcaaaata    960
atatatgctg tattattcca tttacgtgaa gctcaaaaat aagcaaacta aattatatgt   1020
gtagagaagc atatttattt gataacatta tttttataaa gcaagaaagt tatttccata   1080
aaattcagaa ttgtagattt tttttttttt tttgaaacag agtctcattc tgtcgccagg   1140
ctggagtgca gtggcatgat ctcagctcac tgcaatctcc gcctccaggt tcgagtgatt   1200
accctgcctc agcctcccta gtagctggga ttacaggtgt gcaccaccac gcccagctaa   1260
tttttgtat tttagtagag acagggtttc accatgttgg ccaggatggt ctcgatctcc   1320
tgacctcgtg atccgcccac ctcggcctcc caaagtgctg ggattacagg catgagccac   1380
tgtggctggc ctcttttttt ttgagacaga gtctcgtaat tgtggatatt tctaagagga   1440
aagaggaaca ttggaattgg aaagagacca gtgggccaaa ggtggaaaat gttgatgtag   1500
acttctaaga ttttgacaaa attttgtttt atggcctggt ggttatataa atatttactg   1560
tataacaatt cattaagata cacatttgtg tttttgtat atatgtgttc tatttcacaa    1620
tcttaaatgt tccttaatta attaatggag cacaccttca gagttgggtg ggaaaataat   1680
tctgcctaga aatccaaact tagacaagct agctatcaag actgaggaca aactaaagcc   1740
attcttacac ctgtaaggat tcagggttta tctactattt atgctatctg aaggagacaa   1800
ttgaatatgt tggccaggaa accaagtgtg aggagtatgt agaaaacaga agatgatagt   1860
actaaccctg ttaatctaat aaaaagaaac cccaggatga ctgcttgcag tggggtttga   1920
aagaaatcta ttcaaattaa aacaggaggt ccatgtgctc caaaaagata ttcttttttt   1980
ttaaatatat atatatcttt tattatactt taagttctag ggtacatgta cacaacgtgc   2040
aggtttgtta catatgcata catgtgccat gttggtgtgc tgcacccatt aactcctcat   2100
ttacattagg tatgtctcct aatgctatcc ctcccccctc ccctacccca taacaggccc   2160
cagtgtgtga aaaaacgata gttagatgcc acgaact                            2197
```

<210> SEQ ID NO 381
<211> LENGTH: 3184
<212> TYPE: DNA
<213> ORGANISM: Homo sapiens

<400> SEQUENCE: 381
ggtccatgtg ctccaaaaag atattctttt tttttaaata tatatatatc ttttattata 60
ctttaagttc tagggtacat gtacacaacg tgcaggtttg ttacatatgc atacatgtgc 120
catgttggtg tgctgcaccc attaactcct catttacatt aggtatgtct cctaatgcta 180
tccctccccc ctcccctacc ccataacagg ccccagtgtg tgaaaaaacg atagttagat 240
gccacgaact aggtggcaat gccttaaccg tatgtgtgtt gtcaggcctg agggcctctt 300
ccatccttgt caaggggagt actaaccttc tccccttca tacaacacaa agatattctt 360
aagacttcta gaatagaccc tgaacaattt tagagtaagg aactaataga tatcagtgct 420
ttcatgaaga aggcttttgc ttctcctgat gagggaaaaa ttataaaaat tctaagacag 480
gaaagttatg atccaaactt gaaataaaca aatgtggtat gaatttgggc aactgtggtt 540
ctttaagaaa agagaatcca ccatgcaatt ttctttttct ttttttttt ttttttttt 600 tgagacaggg tctcactctg tcacccaggc tggagtgcag tggtgatctc agttcactgc 660
aacctctgct tcccggggtc aagtgattct catgcctcag cgtcccaagc agctgggatt 720
acaggtgccc gccacaacac ctggctaatt tttgtatttt ttagtagaga caggatttca 780
ccctgtttgt caggctggtc ttgaactccc gaactcaagt gatctgccaa cctcagcctc 840
ccaaagtgct gggattatag gcgtgagcca ccgcgcctgg cccatcatag aattttctag 900
gaatattgtc ctttgagagg tctagggtga tgacataatt atacaagaaa acataatgtc 960
ataacaattt aatattttta gtaattttaa atttgtgtca tcaacctaca gacaaaggat 1020
gggggttcag gtttctgaac agaatgtaaa ttttcaacct caacaatgta aatatcaaag 1080
tgaagctcac agaaaccaga aggtagaagt aggaaaagag atggaggcaa gggtagggga 1140
aaaaagtcaa gagacgttag tgaaaattga cagaattaaa aacaaatagt ttaagaacag 1200
aatctaaatg tataaaagta accaatggaa agaaaaccaa tgatacaaca aaagtcatgg 1260
taaaaagaag aaaaggagaa atggggtggt attaattagt taaatcctta ttaatcataa 1320
gcaataagta gacaatgcct acagttgata aattaagaat tagcaatata cagaaatata 1380
tatgaaacca aaataactaa tgaaagaaaa ggaggctggg cacggtggct caggcctgta 1440
atcccagcac tttgggaggc agaggcaggc agatcatttg agtcccggag tttgagacca 1500
gcctaagcaa cgtagtgaga cctcatcgct acaaaaaaac agaaaaatta gctgggtgtg 1560
gtggtgtatg cctgtattcc cagctacttc agaggctgag gcaggagaat cagttgagcc 1620
cagaaggtgg aagctacagt gagccaacag agtgagacca tctcaaaaaa aatttaaaaa 1680
aatgaagaag gaaggaagga agagagggag ggagggagcg tgggcggggg ggggggggtg 1740
gaggaggagg agagaaggag tgggaggagt ggagaaggag ggggaggagg agaaggataa 1800
aaggttacaa gtggttgtta ctaggaatgg gggagaagag aagtgggtaa tggcactgaa 1860
gctttttatt atgtctttca gcattctctg attgttctta aaccatcaac agatctcagt 1920
atgtagacta aaagggaata tttggtgaag agatcttctt tcactattgt acacttgcta 1980
tggacatgtc catgcctgct gcctggcagg caccattcat taagtaggcc cctgttgcca 2040
aggaaaccag ctcttcactg ataccaaaga taatgcagag gcctgccgct caccaagcaa 2100
ccttcctcat gagctatgcc cccaccttcc tgaactgtct cttgctcctg tttgatactg 2160

-continued

```
tcatgctgca cgaagcttac acttgctatc tctcacttcc ctcttagtca tctgtgatgc   2220

tggctaaggg agctaggcca gtcagcagtg acctgttgcc cttggtttat tataagcaaa   2280

ctgttcacaa gaaatgaact tctgttgttt tataaatgat atgcatcaca gaacacagaa   2340

taatatcaaa accacattag ttttttcata cttgcttcat tgaccccagg ggaagagggg   2400

agagcaggga gaggactttc tcttttttta aatactaatt atattgaggt ataaagaaca   2460

tatagtaagt tcacagacct taagtataca gtttgatgag ttttggcaaa tatgtatacc   2520

tgtggaacca acacctcagt caagatataa atacttacat cagccgggcg cagtggctca   2580

tgcccgtaat cctagcactt tgggaggcca aggcaggtgg atcatgaggt caggagatcg   2640

agaccatcct ggctgtccac taaaaataca aaaaattagc caggcatggt ggcacatgcc   2700

tgttgtccca gctactcagg aggttgaggc aggaaaatcg cttgaacccg ggaggcagag   2760

gttgcattga gccgagatag caccactgca ctccagcctg ggcaacagag agagactccg   2820

tctcaaaaaa acaaaaaaca acaaaaaaaa ccatacatcg acccagaaag ttccttctgt   2880

cagtagcagt tcaccccccc atgcccccaa cccttggcct ccctgccttc ccatctccac   2940

tcccaaccct cactgctctg attctatcac cattgttttg attcttctgc tgttgatctt   3000

cataaaacca gtatatttcc ttttgtgtct ggtttatttt cctcagaata atgtttttaa   3060

catttatcca tattgttatg tgtatcagtc gtttcttcca gattagtact ctattgtatg   3120

gatagagcct attttgttta cccatttcct gttgacagac atttggtttg ttcccagttt   3180

tgga                                                                3184
```

<210> SEQ ID NO 382
<211> LENGTH: 3103
<212> TYPE: DNA
<213> ORGANISM: Homo sapiens

<400> SEQUENCE: 382

```
tggtttgttc ccagttttgg attataatga ataaagctgc tatgaacatt cttgaacgat     60

gaacattttt gtggacatat gttttgattt ttttgtgtaa atacctagga gtgaaattat    120

tgaggtatgg tataggttta tgcttaattt tatagagtac ttaaacttga ttcttttatt    180

taaaattgtg ataaaataca cataacataa aatgaaccgt cttaactgtt tttaactgta    240

cagtgcagtg gtacgaagca cattcacatt gttgcacaac catcaccacc atccatctgc    300

agaattattt ttatcttgca aaactggaac tctgaaccag gtgcggtggc tcacgactgt    360

aatctcagca ctttgagagg ccgaagcagg aggatcgctt cagcccagga gtttgagacc    420

agctggggca atatagtgag acaccgtctc tataaaaaca aaataaaaat agaccaggcg    480

cgatggctca tgcctgtaat cccagcactt tgggaggcca tggtgggcag attgcctgag    540

ctcaggagtt caagaccagc ctgcccaaca tggtgaaacc ccatctgtac taaaaataca    600

aaaaattacc tgggcatggt ggcgcgcacc tgtagtcccg gttactctgg aggctgcagc    660

aggagaatcg tttgaacctg ggaggcggag gttgcagtga gccaagatcg tgccactgca    720

ctacagcctg ggcaacagag tgagactcta tctcagaaaa ataaaatagc tgggcgcggt    780

ggctcatgcc tgtaatccca gcactttggg aggctgaggc gggcggatca cgaggtcagg    840

agattgagac catcctggct aacacgtgaa accccgtctc tactaaaaat acaaaaaaat    900

tagctgggag tagtggcggg cgcctgtagt cccagctact caggaggctg aggcaggtga    960

atggcatgaa cccgtgaggt ggagcttgca gtgagccgag atcatgccac tgcactccag   1020

cctgggcgac agagcgagac tccatctcaa aataaataaa taaataaatg aaatgaaata   1080
```

aaataaaata aaataaaaat agccaagtat agtgatacac atctgtagtc ccagctactc 1140
aggaagctga ggtgggaggg tcacttgagc ccaggagttc aaggctgcag tgagctttga 1200
gcgtgccatt gtactctccc tgggtgacaa agcaaggccc tatctaaaac aaacaaacaa 1260
gcaaacaaaa aaccccaaaa ctggaactct gtatctatta aacagtaatc tctcattgag 1320
tggtgttaag agtaaaattt tttttaacaa aagaaaaaag taaaaagtaa attttgaaaa 1380
aagaattaaa aacaaaaaat ctccattacc ccctccccca gcccctggca accaccattc 1440
tactttctgt ctttctgaat ttgactactg cacataacct tatataggtg gaatcaaaca 1500
gtatttgtct ttttgtgact gacttatttc acttaggata gtgccctcag cttttaaaag 1560
gaaagacatt ttgatatatg ctacaacata atattccatt gtatgtacat accaaatttt 1620
attaacgatt tcatctgtca atgaacattt gggttgcttc caccttttgt ctattgtgaa 1680
taatgctgcc gcgaacatgt ttaagtcctt gctttcactt ttttgtgtat acacccagaa 1740
gttgaaatgc tggattatat gtaattctat ttttaatatg agtgactgcc atactgtttt 1800
ctatagtggc tgtaccgttt tacgttccca ctaagagaac atgagtgttc cagtttcacc 1860
atatcctcac caacacttat tttctgtttt gttggtggta gccatcctac tggatgtaaa 1920
ctttattcat ttttcgaacc tttttaatat ggaattttca aacacacaca aaagatgaga 1980
gatctccagg tacccaccac aagctttaat aatgattaac atttggtagc aggtggacaa 2040
agatatacct tctctatagc agctataaga tcagggacaa acaaagatct atttggaact 2100
ccaactaaga atggtgtttt gtaggctgcc tgatgaataa ggttagataa ctaatggcca 2160
gtctttcagc ctgtgctcaa gggataggat aacaataaag catagttggt gaaggagcag 2220
cagataaagg tcacaataga taggccataa gagaaccctc actatcactt accattcaga 2280
ccattcgctt catattctaa caagttattt tcctttcata aaaggaagct gaagctttta 2340
tttgtgtttg tggtgcatgt gatccatgag aggggactca accaggtgct atgtgtgagt 2400
agtacttaat ccgacagtat tagtgggctg gtgggctttc ctggttacat gggaacccta 2460
gaaacccaag ccaagcacaa aagccaagac tgaattctcc agtaagtcac ctggtagcct 2520
tgacatgctc atgcttaaaa aagagccagt gacctattaa taggaagctc ctgaaatgag 2580
tcctctgaac atctgcaagt atggtcagct acacctgagc tgagacttgc ctgtttccct 2640
gccaggaaat catgggctca gaaatggcag gtaccatgtg tattaactat atttccttac 2700
tttctgtctt cttgatgttc tagcatcagg tgcctctttg acctaagaga cttcccctcc 2760
taggactagc taattcctag aaatatcaaa ccactcccct gtaagcatgc cattcctatg 2820
caaaccaacc aatccagagc ccatactcga aaccacttcc tttacctggc tcttccacac 2880
cagagggcaa tgttcctctg tcctaatcat tctcagggct agatatcaga taactacaaa 2940
tgctccttga cttatggtgg ggttacatcc taataaaccc atcataagtt gaaaatatca 3000
taagtcaaaa gtacatttaa atcaggtgtg gtggcacatg cctgtagtcc cagctatctt 3060
gggaggctga gacaggagga tcacttgagg ctgtggtgca cta 3103

<210> SEQ ID NO 383
<211> LENGTH: 2997
<212> TYPE: DNA
<213> ORGANISM: Homo sapiens

<400> SEQUENCE: 383
ggatcacttg aggctgtggt gcactatgat catgcctgtg aatagccact gcaccccagc 60

-continued

```
ctgggcaaca gagtgagacc tcatacctta aaaaaaaatt aaaaaacaag ctctcaccag    120
tcgaagatga ggcaacataa gcaataagca ctaaaaagaa taatgactgc aaaccaaaat    180
aaataagaag ataaaagtcc acaagtttat aaataaaagg ttttatttaa aagcccacaa    240
gtaaaaaaga ggagagaaac gctaactcct aactctgaaa attagtaatt aaagggaaag    300
aagccttcaa caattttttt ttttctgaga cagagtcttg ctctgtcact caggctgaag    360
tacagtggca taatcacagc tcactgcacc ctcaaactcc tgggcttaag caattctcct    420
gcctcagcct cccaagtggc ttggactaca ggtgtgtgcc tccacactcg gctgatttta    480
aatgttttgt agagatgggg tctcactata ttgcccaggc tggtctccaa ctcctgagct    540
caagcaaaac tcccacctca gcctcccaag tagccagggc cataggtgtg caccaccatg    600
cccagctaat tttccttttt tccattttgt agagatgggc tctcgccatg ttgcccaagc    660
tgttctccaa ctcctgagct cagacaatcc tcccgcctcg gcctcccagg tgtgagccac    720
tatgcctggc caaaaatttt ttaatgaagt ccccctgggt ccaggcactg gtttgggcac    780
tgaagattca gcagtaaagt aaaataaatt tcctcattga tcttgtcagt gactcctttg    840
catgcttgct tcacactata tttcaaggta accaaatagt tgtagttaga aaaagttcca    900
tcttacagaa aactttcagc taataaatgt agagggaatg ataaagttag aaaaataact    960
atattttaag tcctaatgaa acaacagacc cacacaacaa tgaccaacgg atgaaaaata   1020
tcaggtgaaa cacttatacg gaacctgtca gtggcaagat tggggctgtaa ccacctgaaa  1080
ccactgacca atctcggcat tactaaaaca gggctgacca gatagtctgt gattctgatg   1140
taaagcaata aggagtacat agcaccacct tttcagtagc caaaacagtt aaacctgaat   1200
ctaatcaaga ctttagaatt acctttacga ttggatgaaa tatggagagc agaagaacaa   1260
attcaacagc acaaaaagga agaaaacaga taaatctaga gtgggccacg ttctacaaaa   1320
ctgagctggt ttcttggtca agacaatagc atggaaaaaa atgggaagta ggcaaagaga   1380
ctcctctgga ttgaatgaaa tttaagagac acaatagcca agtatgatgt gtggaccttg   1440
tttggatcta gatttgaaga aatcgattgt aaaaagtaat ttttgaaaac aaatagggaa   1500
atctgaatat gggctaggca ttagttttta ccaaagaatt attattaggt gtgataatgg   1560
tactgtaatt acgtaagatt gtaattattt atattgtttt tagagataaa aataagacct   1620
tcagtgctga agaagggcac agtggcacat ggcacagcac agcatctaca tcatcagtca   1680
aataagaatt tttttttttt tttttgagac agagtctcgc tctgtcggcc aggttggagt   1740
gcagtggcaa gatctcgact cactgcaacc cctgcctccc gggctcaagc aattctcctg   1800
cctcagcctc ccgagtagct gggattacag gggtgtgcca ccatgcccgg ctaatttttt   1860
ttgtgttttt agtagagacg gggtttcacc atgttggcca ggctggtctt gaactcctga   1920
cctcaggtaa tccacccgcc tcggcctccc aaagtgctgg gattataggc gtgagccacc   1980
gtgcccggcc cagtcaaata attcaaggca gctgtcaggc taaagttcgg cgagcgacac   2040
gcggctgggc ggcgggagga aacgcggggc cgggccgggc gctggagatg gtccccggcg   2100
ccgcgggctg gtgttgtctc gtgctctggc ttcccacggc ttccgtatcc atgattattt   2160
gtactttcaa gtgctgagtc ctggggacat tcgatacatc ttcacagcca cacctgccaa   2220
ggacttcggt ggtatctttc acacaaggta tgagcagatt caccttgtcc ctgctgaacc   2280
tccagaggcc tgcggggaac tcagcaggtt tcttcatcca ggaccagatc gctctggtgg   2340
agagtggggg ctgctccctc ctctccaaga ctcgggtggt ccaagagcat ggcgggcggg   2400
ccgtgatcat ctctgacaat gcggttgaca atgacagctt ctatgtggcg atgatccagg   2460
```

```
acagtaccca gcgcacagct gacatctccg ccctctttct tctcagccga gaggctacat   2520

gatccgccgc tccctggaac agcctgggct gccatgggcc atcatttcca tcccagtcaa   2580

tgtcaccagt atccccacct ttgagctgca gcaaccgtcc tggtccttct ggtagaagag   2640

tttgtcccac attccagcca taagtgactc tgagatggta aggggaaacc caggaatttt   2700

gctatttaga atttgggaat agcatttggg gacaagtgga gccaggtaga ggaaaaggat   2760

ttgggcgttg ctaggctgaa agagggaaac cacaccactg accttccctt ccccagggcc   2820

cccaagggtg tcccagaaga ggtaagagac aggccccagg gcttctggat agaacctgaa   2880

acaaaaggtg ctgaaggtag gtggcctgag agccatctgt gacctgtcac atctcacctg   2940

gctccagcct cccctaccca gggtctctgc acagtgacct tcacagcagt tgttgga      2997
```

<210> SEQ ID NO 384
<211> LENGTH: 2067
<212> TYPE: DNA
<213> ORGANISM: Homo sapiens

<400> SEQUENCE: 384

```
caccactgac cttcccttcc ccagggcccc caagggtgtc ccagaagagg taagagacag     60

gccccagggc ttctggatag aacctgaaac aaaaggtgct gaaggtaggt ggcctgagag    120

ccatctgtga cctgtcacat ctcacctggc tccagcctcc cctacccagg gtctctgcac    180

agtgaccttc acagcagttg ttggagtggt ttaaagagcc ggtgtttggg gactcaataa    240

accctcattg cctttttagc aattaaaaaa aaaaggcaat aaaaggcata atataggttt    300

tagaaattta tatttataat gggtttgatg tacaataaag atacattagt tattaaacaa    360

ggtataaaaa tactcaattc aaggatatgg aaaaataatg aaaaaaataa gaaaatagga    420

agaattaatt ttaaaaagca gaagtcaatg aaatagaaaa taataatact gatatatagg    480

ctgggtgtgg tggctcatgc ctgtaatccc agcaatttag gaggccaagg caggaggatt    540

gcttgagcct aggagttgga gaacagcctg ggcaatatag gaagacccca tctctacaaa    600

aaatttaaaa tcagccagac atggaggtgt gcgcctgtag acccagctgc aggggaggat    660

cacttgagcc caggatcctg aagctgcagt gtgccatgtt tgcaccactg cactccagcc    720

tgggtgacag agggagaccc tgtcaggaag gaaagaagag aggaaggaag gaaataataa    780

taataatata taaatgcagg aataaattct tttaaaaaga caaaaataat ctgtggtgag    840

cctaattaag aaaaagagaa agcccatgag agagggagca taacctgaga tacagagaaa    900

acaaaaatgc taaaaataac tcaataaatt tgaaaacctt aatgaaaaac tccctaggaa    960

aatttgttaa aattgaaatt aattcaatat gtgtaagata gaagaaatgg aaaagttgtc   1020

agagaactac ctaaagtgaa gctgggtgcg gtggctgaca cctgtaatcc cagcactttg   1080

ggaggttggg ggcgagagga tcatttgagc tcaggagttc aagaccagcc tgggcaacag   1140

ggcaaaaacc ccatctccac caaaaaaaaa cattaaaatt agccgggtgt ggtagagtgt   1200

gcctgtagtt ccagctacta aggaggctgt ggtgggagga tcacttgaac ctggaggtca   1260

aggctgcagt gagttgtgat tatcccaccg cacagcctgg gtgacagagt gagaccctgt   1320

ctcaaaaaaa ccaaaccaaa ataaaccgaa aaaaaaaaaa aacctaaagt gacaccatcc   1380

tcattctttc ttaaaaaatg aattattggc cgggtgcggt ggctcacgcc tgtaatccca   1440

gcactttggg aggccaagtc gggtggatca cgaggtcagg agatcgagac catcctggct   1500

aacacggtga aaccccatct ctactaaaaa tacaaaaaat tagctgggcg tggtggtgga   1560
```

-continued

```
cacctgtagt cccagatact cgggaggctg agacaggaga atggcgtgaa cccgggaggc   1620

ggagcttgca gtgagccaag atcatgccac tgcactccag cctgggcgac agagcaagac   1680

tccgtctcaa aaaaaaaaaa aaattatttt actgatgtat aataggtaca catagatttg   1740

gagtacatgg gattaataaa gttcaaattg gtgtacttgg gacatccatc accttaaata   1800

tttgtctttt ctttacactg gaaacatcca agctattctc ttctagctac tttgaaatgt   1860

acaagattac tgtaaactat caaacactag gtcatatttc ttctataaaa ccatatattt   1920

gtatcagttg atcaacttct cttcctcgtc tcctcctgat acctttcctg gcctctggta   1980

accataaatc tactctctat cttcatgaga tccaattttt tagtttccac atatgagtaa   2040

gagcatgtga tatttgtctt tctgtgc                                       2067
```

<210> SEQ ID NO 385
<211> LENGTH: 2054
<212> TYPE: DNA
<213> ORGANISM: Homo sapiens

<400> SEQUENCE: 385

```
ctcttcctcg tctcctcctg atacctttcc tggcctctgg taaccataaa tctactctct     60

atcttcatga gatccaattt tttagtttcc acatatgagt aagagcatgt gatatttgtc    120

tttctgtgct tgacttattt catttagcat gatgaccttt aattccatgt tgctacaaat    180

gacaggattt catttttatg gctgaataat attctatttt gtatatgtac cacatacaca    240

ttttcttttt ccttttcttt tttttttttt ttttttttga gatggagtct cgctctgttg    300

cccaggctgg agtgcagtgg ttccatctcg gctcactgca agctctgcct cctgggttca    360

tgccattctc ctgccttagc ctcccgagta gctgggacta caggcgcccg ccacaacgcc    420

cggctagttt tttttgtttt gtttttgttt tctgtatttt tagtagagat ggggtttcac    480

cgtgttagcc aggatggtct cgatctcctg accttgtgat ctgcccacct tggcctccca    540

aagtgctggg attacaggcg tgagccaccg tgcctggccc acatccacat tttctttacc    600

tattcatccg ttgatgagca ctttgattcc atatttgagc tattgtgagt agtgctgcaa    660

caaacatgag agtgcagata cctctttcgt atactgattt tctttctttt ggatatacac    720

tcagtagtgg aattgctgga tcatatggta gttctagatt tatgaagaaa cgccatactg    780

ttctccatag tgactgtact aatttacatt cccaccaaca gtgtacaagg gttccccttt    840

ctccacatcc tcaccagcat ccgttattgc ctgttgtttt gataaaagcc attttaactg    900

gggtaagctg acatctcatt gtagttttga tttgcattta tctaatgatt agtgatgttg    960

agcacttctt catgtacctg ttggccattt gtgtgtcttc ttttgagaac tgtctattca   1020

gatcttttgt ccatttttaa atcggatttt ttttctattt gtttgagctc cttgtatatt   1080

ctggtcacta actccttgtt agatgggtag tttgcaaata ttttctccta ttctgtgggt   1140

tgtctcttta gtctgctgat tgtttccttt actgtgccgc ttcttagctt gatgtaagct   1200

cacttgtcta ctttcgcttt ggttgcctgt gccgttgagg tcttacacaa aaaatttgcc   1260

cagatcactg tcctgaagaa gaaactgtct ccagtttctt ctaacagttt cacattagag   1320

ttaagtcttt ttttttttc tttaagacag aatctcgccc tgttgcccag gctggagtcc   1380

aatggtgcga tctcggctca ctgcaaccac agcctgtggg ttcacgccat tctcctgcct   1440

cagcctcccg agtagctggg actacaggtg tacgccatca tgcctggata attttttgta   1500

ttttcagtag agatgggttt tcaccatgct ggccaggctg gtctcgaact cctgacatcg   1560

tgatctgccc gcctccgcgt cccaaagtgc tgggattaca ggtgtgagcc accgcgccta   1620
```

```
gcccagactt aggtctttaa tcaattttga tgtgattttt ttttttgtat ggtgagagat   1680

agtttagttt atttcttctg catatagtta tccagttttc ccagtaacac ttactgaaga   1740

gactgtcttt ttcccattgt atattcttgg tacctttgtc aaagatgagt tggctgggtg   1800

gatttacatg agttctctat tctgttccat tggtctatgt ctctattttt atgccagtac   1860

catgctaatt tggttactac agctttgcag taaattttga agtcaggtag tgaaatgcct   1920

tcagctttat tctttttgct caggattgtt ttgtctatta ggggtctttt ctagttccac   1980

ataaatttaa ggattttttt tctatttctg tgaagaatgt cgttggtatt ttcacaggtt   2040

ttgcattgaa ttgg                                                     2054
```

```
<210> SEQ ID NO 386
<211> LENGTH: 3000
<212> TYPE: DNA
<213> ORGANISM: Homo sapiens

<400> SEQUENCE: 386

cgagcagctc tctcttcagg agtgaaggag gccacgggca agtcgccctg acgcagacgc     60

tccaccaggg ccgcgcgctc gccgtccgcc acataccgct cgtagtattc gtgctcagcc    120

tcgtagtggc gcctgacgtc gcgttcgcgg gtagctacga tgaggcggcg acagaccagg    180

cacagggccc catcgccctc cggaggctcc accaccaaat aacgctgggt ccactcgggc    240

cggaaaacta gagcctcgtc gacttccatc ttgcttcttt tgggcgtcat ccacattctg    300

cgggaggcca caagagcagg gccaacgtta gaaaggccgc aaggggagag gaggagcctg    360

agaagcgcca agcacctcct ccgctctgcg ccagatcacc tcagcagagg cacacaagcc    420

cggttccggc atctctgctc ctattggctg gatatttcgt attccccgag ctcctaaaaa    480

cgaaccaata ggaagagcgg acagcgatct ctaacgcgca agcgcatatc cttctaggta    540

gcgggcagta gccgcttcag ggagggacga agagacccag caacccacag agttgagaaa    600

tttgactggc attcaagctg tccaatcaat agctgccgct gaagggtggg gctggatggc    660

gtaagctaca gctgaaggaa gaacgtgagc acgaggcact gaggtgattg gctgaaggca    720

cttccgttga gcatctagac gtttccttgg ctcttctggc gccaaaatgt cgttcgtggc    780

aggggttatt cggcggctgg acgagacagt ggtgaaccgc atcgcggcgg gggaagttat    840

ccagcggcca gctaatgcta tcaaagagat gattgagaac tggtacggag ggagtcgagc    900

cgggctcact taagggctac gacttaacgg gccgcgtcac tcaatggcgc ggacacgcct    960

ctttgcccgg gcagaggcat gtacagcgca tgcccacaac ggcggaggcc gccgggttcc   1020

ctgacgtgcc agtcaggcct tctccttttc cgcagaccgt gtgtttcttt accgctctcc   1080

cccgagacct tttaagggtt gtttggagtg taagtggagg aatatacgta gtgttgtctt   1140

aatggtaccg ttaactaagt aaggaagcca cttaatttaa aattatgtat gcagaacatg   1200

cgaagttaaa agatgtataa aagcttaaga tggggagaaa aacctttttt cagagggtac   1260

tgtgttactg ttttcttgct tttcattcat tccagaaatc atctgttcac atccaaaggc   1320

acaattcatt ttgagtttct ttcaaaacaa atcgtttgta gttttaggac aggctgatgc   1380

actttgggct tgacttctga ttaccctatt gttaaattag tgacccctct tagtgttttc   1440

ctgtccttta tttcggagga cgcacttcga agataccaga ttttatgggt catccttgga   1500

ttttgaagct tataactgtg acaaaaaatg tgaagggaag agatttgaaa catgtggaag   1560

gaaaagtgag tgcagactat aaacttccaa aaagacaagc ccaaaataca cctaaacgtt   1620
```

-continued atgtcagatt attttgttaa aatcagttgt tagtgacgtc cgtacgttaa tagaaaaaag 1680
aatgcttcag tttggagtgg taggtttcta gagggattta ttgtgaaagt ataaactatt 1740
cagggcaatg ggactgagag aacagtgggt agaaaggacc actgaaggaa aggaagagaa 1800
ttggaaggta gatgaaagaa ggagcaagaa cctggggatg ttttttcctt ttcacttgta 1860
atagtagtaa cagaagcaat ggcagactgg cttttgtttc tactgtgtta gaatgaattg 1920
acaggacaac tgggcctatt attgtactgt gccagaatac tgtaaaacaa aactaaacat 1980
actagcttgg tggcttgtaa ttaattactt aagtggagat ttttattttt tttttatttt 2040
ttttttagac ggagtctcac tttgtcaccc aggctggagt gcagtggcgc gatctcagct 2100
gactgcaacc tcctcctcac aggttcaagg gagattctcc tgcctcagcc tcccgagtag 2160
ctaggactat aggcatgtgc caccacacct ggctaatttt gtatttttag tagagatggg 2220
atttctccat gttggtcagg ctggtgtcaa aactctcgat ctcaggtgaa ccgcctgcct 2280
cagccttcca aagtgctggg attacaggcg tgagccaccg cgccctgcag tttttttgtat 2340 ttttaataga gacagggttt caccatgtta gccaggatgg tctcgatttc ctgacctcag 2400
gtgatctgcc cgctttggcc tcccaaagtg ctgggattac aagcatgagc caccgcgccc 2460
ggctcaagtg gagattttta tatggagtcc agttatactc tttttaatat ataagttgag 2520
atgactaata caacttcaat acaggggctc atgagaaatg tctgtaatat ttaagtaact 2580
tattgtcttc tttctttttt ttttaagatg aagtcttact ctgttgccca ggcggaagtg 2640
cagtggcgtg atcttggctc agggcaacct ctgcctcctg gtttcaagcg atcttcctgc 2700
ctcagcctcc cgagtagctg ggagtacagg cgtgcatgac cacacccggc taattttttt 2760
atttttagta gagacggggt ttctccatgt tggccgggct ggtcttgaac tcctgacctc 2820
aggtgatccg cccacctcag cctccccaag tgttgggatt acaggtgtga gcccccgtgc 2880
ccagcctatt atcttatttc tgaataaaga attgtctgtg tggggaatag ataactcttt 2940
ctcatgcagc ccctgctaga aaatttgttt tctctagcag ttggtctgtg cttataggct 3000

<210> SEQ ID NO 387
<211> LENGTH: 1977
<212> TYPE: DNA
<213> ORGANISM: Homo sapiens

<400> SEQUENCE: 387
ttctctagca gttggtctgt gcttataggc tactctttga aagcacaaaa aatttattga 60
cttctttttt ttgggttttt tttttttttt gagacagagt tttgcccttg ttgcccaggt 120
tggagtgcaa tggcgcgatc tcagctcacc gcaacctcca cctcctgggt tcaagtgatt 180
ctcctgcctt agcctcctga gtagctggga ttacaggcat gcgtcaccat gcctggctaa 240
ttttgtattt ttagtacaaa tggggtttct ccatgttggt caggctggtc tcaaactcct 300
gacctcaggt gatccacccg ccttggcctc ccaaagtgct gggattatgg gtgtgagcca 360
ttgcgcctgg ccagaaaatt cattgacttc ctaaagattt attaactttc tgcattactt 420 tttttttttcc cctccatcgt aaatataaaa gggaatagta gagaaaatca ttcagaattt 480
tattttttag tgacattatt tagtgacatt ttattagagt cacttaggaa cctgaggctg 540
aataaagttc aggtaaaagt aaaattagtt gagaagagac atctgccaaa agaaatctat 600
ttttaacttc acttgctgtc tttcctagag gaacagaaat agtgctgaat gtcctattag 660
aaatgatggt tgctctgccc gtctcttccc tctctctcac acaatatgta aactcataca 720
gtgtatgagc ctgtaagaca aaggaaaaac acgttaatga ggcactattg tttgtatttg 780
gagtttgtta tcattgcttg gctcatatta aaatatgtac attagagtag ttgcagactg 840
ataaattatt ttctgtttga tttgccagtt tagatgcaaa atccacaagt attcaagtga 900
ttgttaaaga gggaggcctg aagttgattc agatccaaga caatggcacc gggatcaggg 960
taagtaaaac ctcaaagtag caggatgttt gtgcgcttca tggaagagtc aggacctttc 1020
tctgttctgg aaactaggct tttgcagatg ggatttttc actgaaaaat tcaacaccaa 1080
caataaatat ttattgagta cctattattt gctgggcact gttcagggga tgtgtcagtg 1140
aataaaatag attaaaatct attctcttct gatgcttaca ttatagtggt gggagacaaa 1200
atgggtataa taaatattat attagatagc attaagtgct gtggagaaaa ctaaagcagg 1260
gaggaagata ggagtgtgca agccagaaag gttgcaatta aattgagtag ttcaggaagg 1320
cttcaatatg gatgtgatat ttgagagacc ggtggaagtc aaggagcaag ttgtgaggct 1380
atttaaaggt attcttggct tacagaacaa tatacgcaaa gactattaaa tggaagcata 1440
cctgacatgt taaaggacta tcaaggaggc cagtttgtct agaggctgaa aaggaaagag 1500
taataggaga tgaggtctga gtgaaaacac gtaaatcctt gtgggccaag gtaaaatctt 1560
tagctttttt tctgaatatg gtgggatact gttagagggt tttaagcaga ggttacgtgg 1620
tgtggtgagt ttttttttt taatcctttg tctttctgtg tggaaaatag caggacaggg 1680
cagaagcagt ctgtcctgca gactgcttgg tcgcagtaga gatgtaagaa gcagtgagat 1740
tctgggttaa ttatggaggc aaagttctca gaatttgctg atatagggta tgagagaaag 1800
aggaatcagg aatgatttca aggttttggt ctgctaaatg gaaggagttg ccatttacta 1860
agatgggaaa gactatgaaa gaagcagatt ttcagagaga tcagaagttc attttggggc 1920
atgttcaatt taagatgcct gttagttgga tgtttatgtg agtttggaat gcagggt 1977

<210> SEQ ID NO 388
<211> LENGTH: 3091
<212> TYPE: DNA
<213> ORGANISM: Homo sapiens

<400> SEQUENCE: 388
gttcattttg gggcatgttc aatttaagat gcctgttagt tggatgttta tgtgagtttg 60
gaatgcaggg tagagattta gggatgaata tttggtagtt gtctgcattt taatggtatt 120
aaaagccacg agaaggatgg gcatggtggc tcacacctgt aatcccagca ctttgggagg 180
ccaaggcggg cagatcacct gaggtcggga gttcgagacc agcctgacca acatggagaa 240
accccatctc tactaaaaat atataattag ccgggcgtgg tggcacatgc ctgtaatccc 300
agctactcgg gaggctgagg caggagaatc gcttgaacct gggaggtgga ggttgcgatg 360
agccgagatc gcaccgttgc actccagctt gggcaacaag agcaaaactc catcaaaaaa 420
aaaaaaaaaa aaaaaaaaaa gccttgagac tcacctgaaa agatgctcaa cattattggt 480
cattaggaaa atgaatgaaa accacaatga gataccactt cacacctatt aggatggcta 540
ttatcaaaaa caaaaacaag tgtttgcaag gatgtagaga ttggaattct tgtgtattgc 600
tagagggaat gtaaaatagt gcagggtgct gtggaaaatg ctgtggtgat tcctcaaaaa 660
attaaacata attatataat ccagtaattc cacttctgag ttattcccaa aagaagggat 720
gcaagcagat atttgtacac tcatattcat ggcagcatta tttacagtag ccaaaaggtg 780
aaagcaacct aagtgtccgt cagtggatga atggataaac aaaatggaat aatttcagcc 840
ttaaatagaa ataaaatgtt gacacatgtt gcaacatata cgaaccttga agacatcatg 900
ttaagttaaa taagttggtc actaaaggac aaatattgta tgattcccct tatgaggttc 960
ctagagtagt cacattcata gagacagtag agtggtggtt gcccagggcc ggggggagcg 1020
aggagaatgg aaattattgt ttattgggta cagagtttct gtttggggaa gatgaaaaaa 1080
ttctggagat ggatcatgat gatagttaac acagcagtgt gaatatagtt aatggcacag 1140
aactgtacat ttaaaaatgg ttaagatgga aaattttctg ttacatatat tttactgcaa 1200 ttttttttaaa ttttattatt atactttaag ttttagggta catgtgcaca acatgcaggt 1260
ttgttacata tgtatacatg tgccatgttg gtgtgctgca cccattaagt catcatttag 1320
cattaggtat atctcctaat gctatccctc ccccctcccc caccccacaa cagtccccag 1380
tgtgtgatgt tccccttttct gtgtccatgt gttctcattg ttcaattccc acctatgagt 1440
gagcacatgc agtgtttggt tttttgtcct tgtgatagtt tgctgagaat gatggtttcc 1500
agcttcatcc atgtccctgc aaaggacatg aactcatcat tttttgtggc tgcatagtat 1560
tccatggtgt atatgtgcca ccttttctta atccagtcta tcattgttgg acatttgggt 1620
tggttccaag tctttgctgt tgcgaatagt gctgcagtaa acatacgtgt gcatgtgtct 1680
ttatagcagc atgatttata atcctttggg tatataccca gtaatgggat ggctgggtca 1740
aatggtattt ctagttctag atccctgagg aattgccaca ctgacttcca caatggttga 1800
actagtttac agtcccacca acagtgtaaa agtgttccta tttctccaca tcctctccag 1860
cacctgttgt ttcctgactt tttaagatcg ccattctaac tggtgtgaga tggtatctca 1920
ttgtggtttt gatttgcatt tctctgatgg ccagtgatga tgagcatttc ttcatgtgtt 1980
ttttggctgc ataaatgtct tctttcgaga agtgtctgtt catatccttc actcactttt 2040
tgatggggtt gtttgttttt ttcttgtaaa tttgagttca ttgaaaaatt agaatttttt 2100
tttttttccc ttttttagag gcaaggtctc actctgtcgc ccacactgga gtgcagtagt 2160
gtaagcatag ctcactgtaa ccttgaactc ctgggctcaa gcaattctgt catctcagcc 2220
agctgaagta gtaactgtag gttcacacca ccatgcctat ttttgttttt gtagaaatag 2280
ggccttgctt tgttgccaag gctggtcttg aactcctgac ctcaagcagt cctcctgtct 2340
cagcctccca aagtgctggg attataggtg tgagccactg cacccagcct tggagatttt 2400
taataaagaa gcttgtcaat taaacaaaca acaaaaagcc ctgagactga atgagataat 2460
caagagagta tgtgtagata gagaagaggt ccaaggaagg agtcttgggt gactctgatg 2520
tcaagtgagg acatgaggca gaaacagcag tgactgagaa ggagccacct agtaagaaag 2580
gaggaacacc aggacagtgt ggtattctgg attccaaaca aggaagttac tgctaatttt 2640
aaagctcttc tcaggctggg catggtggct cacacctgta gtcccagcac ttcgggaggc 2700
tgaggtaggt aaatcacttg agctcatgtg tttgagacca gcttgggcaa catggtgaaa 2760
cctcatctct actaaaaata taagaaatta aggccaggtg tggtagttca tgcctgtaat 2820
cccagtgctt tgggaggtca aggcagccag atcatttgag atcaggagtt cgagaccagc 2880
atggccagca tagtgaagcc ccatctctac taaaaataca agaaaaaatt aaccaagcat 2940
ggtggcgcat acctgtaatc ccagccactc tggaggctga gacatgaaaa ttgcttgaac 3000
ccgggaggcg gaggttgcag tgagctgaga tctcgccact gcacttcagc ctgggtgaca 3060
gagcaagact ctgtctcaaa ggaggttgca g 3091

<210> SEQ ID NO 389
<211> LENGTH: 2168
<212> TYPE: DNA
<213> ORGANISM: Homo sapiens

<400> SEQUENCE: 389

```
tgtctcaaag gaggttgcag tgagctgaga tctcgccact gcacttcagc ctgggtgaca     60
gagcaagact ctgtctcaaa aaaaaaaaaa acaaaaacca agaaaagaaa aaaaaactct    120
tctaagagga tttttttttc ctggattaaa tcaagaaaat gggaattcaa agagatttgg    180
aaaaatgagt aacatgatta tttactcatc tttttggtat ctaacagaaa gaagatctgg    240
atattgtatg tgaaaggttc actactagta aactgcagtc ctttgaggat ttagccagta    300
tttctaccta tggctttcga ggtgaggtaa gctaaagatt caagaaatgt gtaaaatatc    360
ctcctgtgat gacattgtct gtcatttgtt agtatgtatt tctcaacata gataaataag    420
gtttggtacc ttttacttgt taaatgtatg caaatctgag caaacttaat gaactttaac    480
tttcaaagac tgagaattgt tcataaataa actattttac ctgcagagac ctctgatata    540
tgtttcttga tggaagtacc cagtaccacc tatgaagttt tcttgtcaaa aaatcaaatg    600
tgaatctgat cattacttag atctaagtac caatatatga aaaatatagg agacaaggaa    660
gcatggtaaa tgatactgag attgggagac tacatggaaa aagacttgtt cccttcaaca    720
gatagacagc agggaaaaaa gaatagagaa aggagtaaag aacctgtaga ttaaaagaca    780
tttaagggac atatgaacca ggtccagtgt atagatctta cctaaatcct gatggagcaa    840
actataaaaa aatttttttg agacaaatgt ttgaatacag gttgactatt tgatggcatt    900
aaggagaaat tatgaattat cttggtataa gaatattgtc atgggttttt ttttttgagt    960
ccttacctgt taagatacat actaaaatat ttgtgggtaa aattatatga cgtataggag   1020
tatatgattt agaaaacgga ttaaaatata aaaggataaa ataggatctt atattttgtg   1080
actcacttcc tgttggatat ctttctaccc agtaaatata gtcctatcta ggttttaatg   1140
gctacatgta tgtactgtag tttgtttaaa tggtttccta ttgaacattt atgctctttg   1200
ccatttttttc ctgtttaacg ttctgttttt tttttttgttt ttttttttttt ttgagacagt   1260
cttgctctgt tatccagact ggagtgcagt gacatgatct cagctcactg caacctctgc   1320
cttctgggtt caagctattc tcctgcctca gcctcctgaa tagctgtgat tacaggcgtg   1380
caccactatg cccagctaat tttgtatttt tgggtagaga cagggtttgg ccatgttggc   1440
caggctggtc ttgaactcct gaccttgaat gatctgcccg ccttggcctt gcaaagtgct   1500
ggggttacag gcatgagcca ccacgtctgg ccttgtttaa ggtcctgatg agtattctta   1560
taggtacact gtgtttcgtt taattatttc cttaggataa atttatagaa ataacattcc   1620
ttggtaaaag aatacatatt ttaaaaactg tattagtttc ctgttgctgt caaaaaaattt   1680
ccagaaactt agtggcatta aacaatacaa attaattatt ctacagttct ggagatcaga   1740
agatacgggt cttactaggc ctcactaggc taaaatcaag gttttggcag ggctgtgttc   1800
ctctatggag gttccaaggg accagagaaa ctactttaca gtagttattt taagggaatg   1860
aaagtgaaga tggggttggg cagtcaaaga ggctgttact tttcattttt ggcctttcag   1920
tagtttgaat ttttttatca tatacatgta ttactttaat ttttaaaaag taaaaagcag   1980
ctgtgattca gtctctgtaa tttagatcaa tttacatcaa actagggtgg tctcatgtgt   2040
tgtcttgctc acagtgacca ctagattatt ccaagaaggg acaatttcca agacttggtt   2100
tacactgaga cggctcctga ttttaaggat accttagatc aaactctagg aaggcagttt   2160
cattttgg                                                            2168
```

<210> SEQ ID NO 390

<211> LENGTH: 2008
<212> TYPE: DNA
<213> ORGANISM: Homo sapiens

<400> SEQUENCE: 390
agttccctgg gtcattttcc aagcccatgg cctcctggag tcttcgccta gctgtaggtt 60
atctttgtgg ctattatttc actgtaatta tacaggaaga tttattgagg gatttctgtg 120
taccagccgt ggttctcagc actttgtata ctttgtatta actctgactc ctgacagtaa 180
ctctacagag gttctgctgt tacccagttt tacatagaaa catggccagc ggacgcagtt 240
agaaaatggc aaagtgggga ttagaaacta ggcagtttga ctccagagtc tgtgcccctg 300
tccacttggc tccactgctg gggaagaggc ctctgaagca gcaggaccat ctgctgtgcc 360
gtgtgtagtg gtactctatc ttcctggtgt gatgttgtgt tctactttgc attttcatgt 420
ctttccttat acaggtctca aaatcattta cttttttttt tttttttttg agacggagtc 480
tcactctgtt gcccaggcta gagtgtagtg gcatagtctc actcactgca acctccgcct 540
ccgaggttca agtaattctc ctgcctcagc ctcccaagta gctcggatta caggcacatg 600
ccaccacagc tagcaaattt ttgtattttt agtagagatt ggtgtttcac catgttggcc 660
aggctgttct tgaactcctg acctcaggtg atccacccac ctaggcctcc caaagtgctg 720
ggattacagg cgtgagccac cccacccagc cttatatttt ttaatgatgc acattagctc 780
aattacataa accagggaaa tccagctagg acctggtgat ttctgagcct gacccatgtg 840
actttcaatg aactgaactt gccacagctg tatttactgt ctactgagat gctgtcacac 900
agaccccgtc atagcacagt tcctgagtta catctttaca tactgtagta tccttcttgt 960
gaaaaaagat acagattcca aaggtctgag aaaccaatct tggttataaa ggggaaaaat 1020
ggtcatgggt ttttaaaatt tgttttgtct taattgcatt tcaaatttac atttctaaat 1080
gaataattgc ttatataaag cagttttgat taacaatata aaacactatc tatttggagt 1140
gattccttta cccatttctg aaggcaagtt ttaaaaatta ctagaagaca cttcattgag 1200
aatattatta aacatgccta tagttctacc acctcaacac aattgcttat taacacatta 1260
atgttttggt gtgttttgga ctttttaata tgtatttttc acttgttcta gtaattatgc 1320
tacagattga tcatttcttt ttcaacatgt catcaaagca agtgagcaaa gtgctcatcg 1380
ttgccacata ttaatacaaa atggaagcag cagttcagat aacctttccc tttggtgagg 1440
tgacagtggg tgacccagca gtgagttttt ctttcagtct attttctttt cttccttagg 1500
ctttggccag cataagccat gtggctcatg ttactattac aacgaaaaca gctgatggaa 1560
agtgtgcata caggtatagt gctgacttct tttactcata tatattcatt ctgaaatgta 1620
ttttttgcct aggtctcaga gtaatcctgt ctcaacacca gtgttatctt ttttggcaga 1680
gatcttgagt acgttttctt ttctccttat tgataaattg ataatcctca aggatgatta 1740
ttaggtgata ctcttacttc atggattctt aaaagatatg atttaacata ttacaagtgc 1800
ctagcaaggt gtctgttaca cgtaggtatt ttaagtaaat ggtagctgct gatgtaattt 1860
ctgccccttt gcccttcagt tggggtattg ctttggaccg attagagggc tgtggctggg 1920
atgctaaagg ttcatgtttc cttagctggc tcctgagcca ccagctccca ccacctgtgt 1980
atacctgtgc tagtttgcct tcccacaa 2008

<210> SEQ ID NO 391
<211> LENGTH: 3197
<212> TYPE: DNA
<213> ORGANISM: Homo sapiens

<400> SEQUENCE: 391
cctgtgctag tttgccttcc cacaagtagc tgctggctat ctgttatgct ggtacagttt 60
tcagaaactg atgaatggcc tttgaacaga acaaaaatga gattcagaat aacaaaattg 120
cacctttgtt tttataagca ctggccattc actagttgaa gactggtagg aatacctaat 180
tcatgccaaa agaaagataa tttttaaaaa tcacacaggt tgtttgtaga ttaaaaggga 240
aaataggcta ggtatagtgg ctttgcctgt gagtttggga ggctgaagtg ggaggattgc 300
ttgaagtcag gagtttgaga ccagcctggg aaacagagca agaccccgtc tctacagaaa 360
atttttaaaa aattagctgg gcatggtgat gcatatctgt agtcttagct actccggagg 420
tgggaagatt gcttgagccc agcagtttga ggctgcagtg agctgtgatt acaccactgt 480
actccaacct taaaataaat aaataaataa gggaaaatat cttcaacaaa ggatagttct 540
gtctgtttct cagtcttcct caacagataa atgtgtgaag taatggaagg tggagatttc 600
agattacaca acattaatgc taagggcgtt tgactctgtg tgaattctaa ttgccctaga 660
tctagacggg ctgatactat tagaatcccc tgtcactaac tgaagacaga gttgtaagtt 720
aatgccttcc tagatagcct agattgtggt atgctgctgc atgctaaaat ggctcccctt 780
ccatagcagg atgaaataga gtcattatct tggcaaccag cccctgccaa tgtgctctca 840
gtctgccttt ccagcccctt ctctctacct attcccagct gccatgtatt ctaaagcctc 900
tatgctttca tttttgtttt tgccttcctg gatggtcttt cctgctgtct ccacctgaaa 960
ctattcctct ctaaagaaca gatgaattgc catctctctg ggatgctttt acccaccctc 1020
actcccacct caggctgaat ggacccttct ctagatcgct tagcatattg ttctacagtt 1080
aggtaaaaag tctacctatc actagatcaa gagctttgtt ttttttttatt aatttaattt 1140
tctttttttt ttttcttttt tttttgagac agagtctcgc tctgtcgccc aggctggagt 1200
gcagtgcaca atcttggctc actgcaagct ccgcctccca ggttcacacc attctcctgc 1260
ctcagcctcc cgagtagccg ggactacagg cgcccaccac cacgcccagc taattttttg 1320
tatttttagt agagacgggg tttcaccatg ttagttagcc aggatggtct cgatctcctg 1380
acctcgtgat ccacccacct cggcctccca aagcactggg attacaggca tgagccaccg 1440
cgccgagccc caagaccttt ctttattacc agggcttcca cagacctgac acatggtagt 1500
tcctcaataa ataattgcag aattactgaa aaattttact gttaacttag gcagtggtaa 1560
aaccattgtt tggtagctca gaactcagca agtaaatagc aacatttgct ggaagaacag 1620
atagtttttc aaatccaatt caaggactgg gtatggtggc tcatgcctgt aatcccagca 1680
ctttgggagg ccgaggcagg cgtatccagg agttcgagac tagcctgacc aacatggtga 1740
aactccgtct ctactaaaaa tacaaaatta gccaggtgtg gtggtgggca cctgtaatct 1800
cagctacttg ggaggctgag gcaggagaat cgcttgaacc tggtaggcgg aggttgtagt 1860
gagctgagat tgtgccattg ctctccagcc tgggaaacaa gagcaaaact ccgtctcaaa 1920
aaaaaaaaaa atccaattca aatgattatg gaagtagtgg agaaataaac aggaaaatga 1980
taaataatta agataatata taatatggct atattttaat ctattgttga tatgattttc 2040
tcttttcccc ttgggattag tatctatctc tctactggat attaatttgt tatattttct 2100
cattagagca agttactcag atggaaaact gaaagcccct cctaaaccat gtgctggcaa 2160
tcaagggacc cagatcacgg taagaatggt acatgggaga gtaaattgtt gaagctttgt 2220
ttgtataaat attggaataa aaaataaaat tgcttctaag ttttcagggt aataataaaa 2280
tgaatttgca ctagttaatg gaggtcccaa gatatcctct aagcaagata aatgactatt 2340
ggcttttgtg gcatggcagc ctgccacgtc cttgtctttt ttaagggcta ggagattctt 2400
tattgggatg gcaaaagtca atggcagggt agttgtcatt gaaagaagat taagcttgac 2460
cccagaaggc atgggttaga gcccagcctt gtcactcaat ggttgtatgt ccagaggcaa 2520
gtcacttaac atcccttaac cccagttttc tcatctgtca aatgaagcaa agaatacttg 2580
ccctcttgac ttaaagggtg tctgatgaga catatgactg tatcattagc tgggagaaag 2640
tccatcgtgc tgcctatgta tagtgcctca agttggtctc tttcccttct atgattacac 2700
aaagcactcc gctgtcatgt tatccatccc gcccctccat tccaagtccc atctagagca 2760
catcttcttg aagtccactg taacctgcct aatcctggat gtgacgagcc aggcaggagg 2820
cagaaaagaa tgtgtgtttt gcaatacatg ttaagagaca tcttgggctg ggcacggtgg 2880
ctcacacctg taatctcagc actttgggag gctgaggagg gcggatcatc tgaggttggg 2940
agttcgagac cagcctgacc aacatggaga aaccccatct ctactaaaaa tacaaaatta 3000
gccaggcgtg atggcgcatg cctgtaatcc cagctactca ggaaggctga ggcaggagaa 3060
ttgcttgaac ccgggaggca gaggttgtgg tgagttgaga tcatgccact gcactccagc 3120
ctgggcaaca agagtgaaac agggtctcaa aaacaaaaac aaacaaacaa aaaaaatctt 3180
ttaccacggt gaccacc 3197

<210> SEQ ID NO 392
<211> LENGTH: 2964
<212> TYPE: DNA
<213> ORGANISM: Homo sapiens

<400> SEQUENCE: 392
gaccaccatg tgatttccaa gaacttcaaa tgatctaaga aattttgtga ttattactag 60
tttgaaaaat acttttttttt tttttgagac aaagtctcac tctgttgccc aggctgaagt 120
gcagtggtgt gatctcagct cactgcaatc actacctctt gagttcaagc agttgtcctg 180
cctcagcctc ttgagtacct gggattacag gcatgcgtca ccatgcccgg ctaatttttg 240
tatttttagt agagacaggg tttcaccatg ttggccaggc tggtctcgaa ctcctgacct 300
caggtgaccc acccaccttg gcctcccaaa gttctgggat tacagacgtg agccactgca 360
cccagcctga aaaatatctt tgaatgccat gtgatactat acttgtcagt ttacatgtgt 420
gtcccactaa atcatgtact ctcctgagca ggatcatgct ttgtcttcat attttctgta 480
caaagcaaag actctgacac aaagctagcc cccagtgcat agttgagaaa tcagtgaatg 540
aatgtgggag gcaggaaaaa tgtcctttaa ttcttctgtt aatgctgtct tatccctggc 600
cccagtcagt gcttagaact gtgctgttgg taaatataat tggattcact atcttaagac 660
ctcgcttttg ccaggacatc ttgggtttta ttttcaagta cttctatgaa tttacaagaa 720
aaatcaatct tctgttcagg tggaggacct tttttacaac atagccacga ggagaaaagc 780
tttaaaaaat ccaagtgaag aatatgggaa aattttggaa gttgttggca ggtacagtcc 840
aaaatctggg agtgggtctc tgagatttgt catcaaagta atgtgttcta gtgctcatac 900
attgaacagt tgctgagcta gatggtgaaa agtaaaacta gcttacagat agtttctggt 960
caaggtttag ccaccaattt tgcagtttct ctcatctccc caggaaagag cagttggtct 1020
ttagatcaat gagagctctt ttatggcaga caaaacaaag tgactctagc caacttgagc 1080
taaaaagaaa tttagtggaa ggctaggagt taccacatga agtgtgtgca gctgcccctt 1140
ggagagaata agaaccaggg tgcctctggg acttaacatc attactgtac tccagttgtt 1200
ttcattcttt tcctgacttt gctctagagt cagtttccta acagagtaca ttcgatgatc 1260
atgtgcccat atctgtgggg agaagatttc ttgattggca gtcttactaa gggtgcatat 1320
caagtagaat ggaatagagg tagtttccta aaggaagatg agaggctgtt accaggagga 1380
ggagaaggga ttcaggacag atgaaaacaa cgttatatcc atgatagact tacgctgctg 1440
gtacagatgg tacaggtggc ttcagtatag gctctccgaa cccacatatc attgattatg 1500
atagggatat gttaactatt tttcagtgta tatatgtata tgtgtgtgtg tatatatatg 1560
tatatgtata tatatatgta tgtgtatata tgtatatgta tatatttata tatgtatatg 1620
tatatattta tatatgtata tgtatatatt tatatatgta tatgtatata tatttatata 1680
tgtatatgtg tgtatatata tatttatata tatgtatatg tgtgtatata tatatatttt 1740
tttttgaaac ggaatttcgc tcttgttgcc caggctggag tgcaatggtg cgatctcagc 1800
tcactgcaac ctctgcctcc tgggttcaag cgattctcct gtctcagcct cccgagtagc 1860
tgggattaca ggcacttgcc accatgcccg gcaatttttt ttttgttttt ttttagtaga 1920 gaggggggttt aatcatttg gccaggctgg tcttgaactc ctgacctcag gtgatctgcc 1980
tgccttggcc tcctaaagtg ctgggattac aggcgtgagc caccatgcct ggccattttt 2040
cagtatttct ttttttttt ttttttttt tttttttgag acagagtttc actcttgttg 2100
cacaggctgg agtacaatgg tgtgatctcg gctcaccgca acctctactt cccaggttca 2160
agcaattcgc ctgcctcagc cttctcaagt agctgggatt acaggcatat gccaccatgc 2220
ccggctaatt ttgtgttttt agtagagatg ggtttctcc atgttggtca ggctagtctc 2280
aaactcccga cctcagatga tcctcccgcc ttggcctccc agagtgctgg gattactggc 2340
atgagccagc gctcctggcc catttttcag tatttctaaa aaaaatctaa agtgggtcaa 2400
acatttcacc ttaatagaat gacaggtttg tacatcaagt ttctttgctt tttcttggaa 2460
ttttatactt ttttttttt tttggagaca gagtcttgct gtgttaccca ggctggagtg 2520
cagtggtgcg atctcagctc accacaacct ccacctccag gttgaagcaa ttctcctacc 2580
tcagcctcct gagtagctgg gattacaggc acatgccacc acacccggct aattttttt 2640 ttttttttgt atttttagta gagacagggt ttcaccatgt tgtccaggct ggtctcgaac 2700
tcctgacctc aggtgatccg cccatctcgg cccaccaaag tgctgggatt acaggcgtga 2760
gccactgcac ccggcctttt tcttggaatt ttatcaatca gtgtcagaat attcattacc 2820
tcctaaaaat aaaggagttc tagttggctg ttttgattct aggtgtggta aagtgaaata 2880
ttgttactta ataaatgcat tttgctagac acaatccttc ggttcacgag ctctgtagag 2940
aaaagagaaa taaccgccaa ccaa 2964

<210> SEQ ID NO 393
<211> LENGTH: 2864
<212> TYPE: DNA
<213> ORGANISM: Homo sapiens

<400> SEQUENCE: 393
taaccgccaa ccaagaaaag attgggagat actagaataa gacccagggg caggaagaag 60
ccagtgagaa ggagggcatg ttgagagctc tgagagagaa taaaagcagg ggttgttgga 120
gctagcttct caagatgtcc ttgaggcaaa ccagaccttt gggacactct gaaaataaaa 180
ctgaaagtga agagattgtg ggccgaatgt ggtggctcac gcctgtaatc ccagcacttt 240
gggaggtcga ggcgggtgga tcacctgaga tcaggagttc gataccagcc tggccaacat 300

-continued

```
ggcgaaacgc catctctact aaaaatacaa aaaaaattag ctgggcctgg tggcaggcgc    360
ctataatccc agctactcgg gaggctgagg cgggagaatc gcttgagtcc aggaggcgga    420
ggttgcagtg agctgagatc gtgccattgc actccagcct gggcaacaag agcaaaactc    480
tgtctcaaaa ataaataaaa ataaataaaa aagagatagt ggcgtgatat ccttgattct    540
atcagcaacc tataaaagta gagaggagtc tgtgttttga ttcagtcacc tttagcattt    600
ttatttccat gaagtttctg ctggtttatt tttctgtggg taaaatatta ataggctgta    660
tggagatatt tttctttata tgtacctttg tttagattac tcaactccac taatttattt    720
aactaaaagg gggctctgac atctagtgtg tgtttttggc aactcttttc ttactctttt    780
gtttttcttt tccaggtatt cagtacacaa tgcaggcatt agtttctcag ttaaaaaagt    840
aagttcttgg tttatggggg atggttttgt tttatgaaaa gaaaaaaggg gatttttaat    900
agtttgctgg tggagataag gttatgatgt ttcagtctca gccatgagac aataaatcct    960
tgtgtcttct gctgtttgtt tatcagcaag gagagacagt agctgatgtt aggacactac   1020
ccaatgcctc aaccgtggac aatattcgct ccatctttgg aaatgctgtt agtcggtatg   1080
tcgataacct atataaaaaa atcttttaca tttattatct tggtttatca ttccatcaca   1140
ttattttgga acctttcaag atattatgtg tgttaagagt ttgctttagt caaatacaca   1200
ggcttgtttt atgcttcaga tttgttaatg gagttcttat ttcacgtaat caacactttc   1260
taggtgtatg taatctccta gattctgtgg cgtgaatcat gtgttctttc aaggtcttag   1320
tcttgaaaat atttatagtg tagtagaact attttatcct ccaatgctcc ttcttttcct   1380
tgtatttcca ttatcatcac tttaggattt cacttattta tcattcaaca tttattaatt   1440
gcctctcata ttccaggctt tgtgctagaa gttagggata taaagacaaa taagatattt   1500
cctgcccttta aagactagat tcgtgttgct aagtcttcat tatcaagaaa agcataagtg   1560
gggaaaagtg cttgcattat ggattcctca tagttgctcc cctctgcatg taaaaatcac   1620
catttccatc atagattcct agcggtctca ggactttata aagcccaaag tgcctatgtc   1680
ataatatgag gaaaaatact gagacccttc catatatggg aggtatatgg atgagacagc   1740
tcctgacttc acttttccca gaaatctgaa aagcagcagc agtcattcca gagcccagtt   1800
tctactttga agggcagatt atttattctt tgagctaacc tgactgagga acaattagtt   1860
tgcttttaat ttactatttt ctttttcttt tcttttcttt tttgagacag agtctcactc   1920
tgttgcctag gctggagtgc agtggctcaa acttggctca ctgcaagctc cgcctcccgg   1980
gttcacgcca ttctcctgcc tcagcctccc gagtagctgg gactacaggc gcctgtcacc   2040
acacccagct aattttttgt atttttagt agagacgggg tttcatcgtg ttagccagga    2100
tgatctcgat ctccagacct cgtgatccac ccacctcggc ctcccaaagt gctgggatta   2160
caggcgtgag ccaccgtgcc cagccactat tttctttcta attgttaatg aattaatttt   2220
ttaaaactgt gctcctagag cgaagggaga gctctgttta cagtgtaact tttcagagct   2280
tctttaacta gattttaaga tcagaattag ttgttgtgaa atcttaggga ctgtacaaga   2340
ttagaaatcc tctatagcag catttcccaa agcaggcttc cagaacacta gcctcatgag   2400
gcattttggg aaaaaagagt ttgctggttc agtgtgtatg ggcagtgcca caagccgtac   2460
cctccgttga agacactcat tccacacatt actgcataaa aagcttccac cagccattcg   2520
gcaaacttat tgagtgtctg ctatttcctg ggtattgtgc tatatggtag ggttatagta   2580
gtgaacaaag aagaaatgat gcctgctctc agctgacttt gcagttggaa agacacatga   2640
aataattacg ccattcatta gcagattgtg ctagatgcct cactggaaaa ataaaggaca   2700
```

tgatggaaaa ctctgtaggg tcagagaaag ggatcattag agaaggttct ttgaagaaat 2760 atttttgaa atatgaagga taaataggaa ttaactaggt accaataggt taggagtaga 2820
gctttccaga cagagggact agttcttggg aaggtctcca gaca 2864

<210> SEQ ID NO 394
<211> LENGTH: 3013
<212> TYPE: DNA
<213> ORGANISM: Homo sapiens

<400> SEQUENCE: 394
tgtgctagat gcctcactgg aaaaataaag gacatgatgg aaaactctgt agggtcagag 60
aaagggatca ttagagaagg ttctttgaag aaatattttt tgaaatatga aggataaata 120
ggaattaact aggtaccaat aggttaggag tagagctttc cagacagagg gactagttct 180
tgggaaggtc tccagacaga aataagtgtg gcttgtctga ggacctctta ttcgcctatt 240
aaccttccct ccccagtaaa cactcctggg aacaacacac attgtagaac cacgttgtgg 300
tgctgttcag tatagcaagt aattcagcag agataagttc ttggaatctc atctttggga 360
tttagttact aagatacatt caagtttgag caaaataagg tctcagagct tggattcatt 420
gttctgttcc agcaattaga gcagtacctg gcacatagca caagtgcttg aaaacactga 480
ctgagtaggg taggtgggtg agtgggtggg tgggtgggtg ggtggatgga tggatgggag 540
gatgggtggg tgaatgggtg aacagacaaa tggatggatg aatggacagg cacaggagga 600
cctcaaatgg accaagtctt cggggccctc atttcacaaa gttagtttat gggaaggaac 660
cttgtgtttt taaattctga ttcttttgta atgtttgagt tttgagtatt ttcaaaagct 720
tcagaatctc ttttctaata gagaactgat agaaattgga tgtgaggata aaccctagc 780 cttcaaaatg aatggttaca tatccaatgc aaactactca gtgaagaagt gcatcttctt 840
actcttcatc aaccgtaagt taaaaagaac cacatgggaa atccactcac aggaaacacc 900
cacagggaat tttatgggac catggaaaaa tttctgatcc ataggtttga ttaaacatgg 960
agaaacctca tggcaaagtt tggttttatt gggaagcatg tataattttt gtcctaagtc 1020
tgtgctcagc cctcccacat gtgctcattg ctggttgact gttggagtct ggttcttacc 1080
tctaagagga agcccaggag agggcataaa gccagcacac tgtcctcacc tgatggtgtc 1140
agagtcctta cgagtaagcc ctagccagaa cattgctgga agagatcaag ggccactgtt 1200
tgaaattgca cagcaggata cggaaaaggg gtaccttagg tataggcatt gtcattaaag 1260
aaattgctaa gatacttgag attttcctgt ttaaggaatg agctttatga tacaaagagc 1320
agttctaaaa attagggagg gaattaacta aattaattag gatatttctc aaattccttt 1380
acagtttttg tctctctgct gatatagtgt ttacatgatt gttatttact aaacaaatgc 1440
tattttgtat tgtgctcctt ataacttaat tgtttattac aaggttttga tggtgaccta 1500
ccaacaacaa gtaatcccaa acacagtctg aattttttgt tttccatcca gaaataagat 1560
gaatctttcc atttccgtgt tttcagtttt catcattttt atcctatagg ttacttatct 1620
ttattttaaa gcatttcata ataattttat agtttttgtt ttgtttgctt gtttgctgtt 1680
ggaaatggaa tattccctcc ttccatttag actgctaacc agctgtaaat gtttcaaaat 1740
atgcatgttt tacagcagtt gttcaaagca atacaggaac agtaaggaca gagccagtca 1800
ttttacaacc acattctgtt aaactgatgt ctattagcag ggtttttcct attttattag 1860
gaaggactta cacctgatat ataacaaagc ttgttttaat caaggctcag aaaatgtttt 1920

-continued

```
tcattagttt ttttcctaac catgaagaat aactgctttg taacacacat gctggctata   1980
aagcagacaa aaaattcact gtaggtgctg cctgactggc ctctgtccgt gtttctgttg   2040
gggctgctta ccacagcctc tgcattatca ttagctagtg tgttcacaat accaagttcc   2100
cagtagcaaa gaaaggtcaa gctcttacgc atgccattca tttatctaca ctgtgcaggc   2160
gcactcaggt ggcagggaca aagaccactc ctttggcgca tctcaagttc agaattctca   2220
gtagaggggc tccagctgtc cttttgtcag gtgcccatgc ctgctccagg cctgtgtggt   2280
caggacacgt gttacagagt acagtgacat taatgatggg gccatggata tggtcagcac   2340
tcagaggatg ttagtctctt cattgataaa gtcacaacca cttttcctgt tggaaataaa   2400
aagatttgac gtatccttgt ctacagcaac acaggacaac agataatcag caggtcatct   2460
aaatctgttc agagagaaag gagagctgtt tcctgaaaat acatcttccc ctgattttag   2520
tcttattttt ttctgccttt attgctttct accctcttca aaccagcctc atttcctaaa   2580
ttaccttgaa tatgcattga cacttgtact gcctgaaatt ctggaaaact cagtatggct   2640
actccaccgt cagaacttcc tgagcaaagt tagttgctct ctcggctcac tgttttgttt   2700
tgttttgttt tcctgcctca ggtttatttg tacaaatagc acaggaggac cagccccatg   2760
cagatggtag cccaggggcg ggggtagggg gtcacaccag tccttctgtc ctcatgttgg   2820
cagagatatc tactctgaag cctttgtagg ggcctgggca cctttgggag cctgagctgg   2880
aactgaaggt ggagctgcag cctgggcctt ggtttgatcc ttggccttgg cctttggccg   2940
gcacagcctg agccccttgg caatacgggc acgagcacgc ttcccaagct tgggatgggc   3000
aatgtaggca agt                                                      3013
```

<210> SEQ ID NO 395
<211> LENGTH: 2915
<212> TYPE: DNA
<213> ORGANISM: Homo sapiens

<400> SEQUENCE: 395

```
atgggcaatg taggcaagtc gatcgagctt gcggctgaca ccctttggga tcttgggctt     60
aacctccttg ggctttacga gggccttgat agcctcggca cgtgcactca tggccttggc    120
attgttggcc tgcatcttct ttaggccctt cttgttgtgc ttcttggcaa agtgcatgtt    180
cctcaggaac ttggggtcca ccccccttaag agattcgtat ctttgtgatc ggggtttctt    240
gataccattt ctgtgccatt ttcgggactg gttgtgtgtg gtgtggttct tggacttcgc    300
catgtctaca ccttaagccg cggctcccga agcacctaga accggaagag ttggctcact    360
atttagcaca cacacacgtc tataatagtg ctggccactt ggggttggaa ttagtttatt    420
tatcagcatg ttgtctccca gcacttggtg tgtgtgatat gcagtatgta tttgcagaat    480
gaaaagtctg agggctgaca tcatatttcc cactgtgccc agaaagagca cagttagtcc    540
acatgagcta atgggggcaa agggaagtga ggagggagaa tgtactgcct tatcatgttt    600
tctattactt ggctgaagta aaacagtccc aagccgatag taagatagtg ggctggaaag    660
tggcgacagg taaaggtgca cctttcttcc tggggatgtg atgtgcatat cactacagaa    720
atgtctttcc tgaggtgatt tcatgacttt gtgtgaatgt acacctgtga cctcacccct    780
caggacagtt ttgaactggt tgctttcttt ttattgttta gatcgtctgg tagaatcaac    840
ttccttgaga aaagccatag aaacagtgta tgcagcctat ttgcccaaaa acacacaccc    900
attcctgtac ctcaggtaat gtagcaccaa actcctcaac caagactcac aaggaacaga    960
tgttctatca ggctctcctc tttgaaagag atgagcatgc taatagtaca atcagagtga   1020
```

```
atcccataca ccactggcaa aaggatgttc tgtcccttct tacaggtaca aggcacagtt   1080
ttccttcatt tattcactaa tttagcagaa cctcactaag agcctcctat atgccaggct   1140
ctgcgttagc aataaaagga atgccatgcc tcaccccatc aggaggtgct gatagcttgt   1200
aggcggagtg gaaacagatg tgctctagag gctctaaata ttacttctgc tggggtcagt   1260
tgggaagcca caacagctac tgttcatctt ccataaaaga caatcagccg ggcacagtgg   1320
ctcacacctg taaatcccag cactttggga ggctgaggtg ggtggatcac aaggtcaggt   1380
gtttgagacc agcctggcca acgtggcgaa accctgtctc tactaaaaat acaaaaatta   1440
gccaggcatg gtggcgggcg cctgtagtcc cagctactcg ggaggctgag gcaggagaat   1500
cgcttgaacc taggaggtgg aggttgcagt gagctgagac tgtaccactg cactccagcc   1560
tgggcgacag agcgagactc catctcaaaa aaaaaaaaaa aaagactggg ttctgttctg   1620
tggaggttct tgtcttaaca tatccactgt tgattgccca gatgttgatg taattaattt   1680
agcagtcgta aatagtttag cacttgcatt aaatagacca aaccccatag taggtatttg   1740
aaatacagaa taaatgtgag gtacccctgc tctaaaggag tttatagtcc agagctgact   1800
tatggaggat ttctttctat tatttctggg tctgctacta atttgtctat ttcatatcct   1860
aattatcctt gttttcattt tgattgaaag ggggagagca tagaaattgt ggtaaaaggt   1920
agttttattt tttatttgag atggagtctt gctctgtcac ccaggctgga gtgcagtggc   1980
acaatctcat ctcattgcaa cctccacctc ccgcgttcaa gcaattctcc tgcctcagcc   2040
tcccgagtag ctgggattac aggtgtgcac caccacgccc agctaatttt tgtattttta   2100
gtagagatgg attttaccat gttggccagt ctggtcttga actcccgacc tcaggtgatc   2160
ctctcacttt ggcctcccaa agtgttagga ttacaggcct cagccactgc acccagccta   2220
aagttagttt tagattaagt gttttcatgt tttcccttgc aaagtaataa actggtcaag   2280
ttatcacctt gttccatctc catattaatc agggtccaaa caggagatag aaaccatgca   2340
acaatttgag tagttgaata aagaattata aacaggagat tagagtaata ggggattaga   2400
tagtaagagg tgaagagata ggaacagcag atataaagaa caaccatttc ctcctatggc   2460
tgagatacca tcccctcacc acactccccc acctactcac tgagatgcag accttattga   2520
agagaatgta actggcttgc tgcgaggtaa agtcaatgag gcgctcccca gtaccactct   2580
gaggggatgc tggggaaaac tgcccatgag aagagggcac atgctgctgg ccacttgtgc   2640
taaagaactt gaagtctgat aggagtgcac cctaacctgg catagaaacc ctttcttcct   2700
gctgagtccc tctagcacct tatactggca aagctttaca ttgcaaacct ccattatcac   2760
agagcaagca atgaaagatg gactcagagc tgaggcgata aattgatagc tagcatagcc   2820
tctaaactga cttttatgac tacattttat ggatagaaag tgttcttata tatattgttt   2880
ctttacataa taggggactt attcatggct gcaga                               2915
```

<210> SEQ ID NO 396
<211> LENGTH: 3033
<212> TYPE: DNA
<213> ORGANISM: Homo sapiens

<400> SEQUENCE: 396

```
cagagctgag gcgataaatt gatagctagc atagcctcta aactgacttt tatgactaca     60
ttttatggat agaaagtgtt cttatatata ttgtttcttt acataatagg ggacttattc    120
atggctgcag atgagaaaac agatcctaag aagttaagtg acttgcccaa ggtcacacaa    180
```

-continued

```
agaattccac tagttctaaa atgacagtaa ttacagttaa catacattgt atgtggcaga    240
tacatataaa gcacatggca ttaatttttt tttttgagat ggagtcttgc tctgtcgcca    300
agctggagtg cagtggcacg atctcggctt actgcaacct ctgactccct ggttgaaggg    360
attctcctcc ctcagcctcc cgagtacctg ggattacagg catgcgccac cacgcccagc    420
taatttttgt atttttagta gagacgtggt ttcatcatgt tggccaggat ggtctcgatc    480
tcctgacctt gtgatccacc cgcctcggcc tccccaaatg ctgggattac aggcgtgagc    540
caccacgccc ggccacttgg catgaattta attcccgcca taaacctgtg agataggtaa    600
ttctgttata tccactttac aaatgaagag actgaggcaa agaaagatga tgtaacttac    660
gcaaagctac acagctctta agtagcagtg ccaatatttg aacacactca gactcgatcc    720
tgaggttttg accactgtgt catctggcct caaatcttct ggccaccaca tacaccatat    780
gtgggctttt tctccccctc ccactatcta aggtaattgt tctctcttat tttcctgaca    840
gtttagaaat cagtccccag aatgtggatg ttaatgtgca ccccacaaag catgaagttc    900
acttcctgca cgaggagagc atcctggagc gggtgcagca gcacatcgag agcaagctcc    960
tgggctccaa ttcctccagg atgtacttca cccaggtcag ggcgcttctc atccagctac   1020
ttctctgggg cctttgaaat gtgcccggcc agacgtgaga gcccagattt ttgcctgtta   1080
tttaggaact ttctttgcaa gtattacctg gatagtttta acattttctt ctttgaacct   1140
agttataaag gtattgtgct gttgttccta ggcttagagt cataaggcct gagctcactt   1200
cctcactttg cctccatctg gaaccttaga ccaacttcct aggaaaacga gctgtctgaa   1260
aacagaatag ggtgcctctt caatgtgctc ttcactggag atgttcagga ggaggctact   1320
cccacctaca cagggtgcag tggagggtct gggccccagg gaggcagcag gaagagtgga   1380
aagagcggag gctctactgt tggacagacc tgggttacca gccgtgtgac tagccttccc   1440
tggcctccat atcccctca gtaatgaagg aatgtgtcat ccccaaatcc agggacagtt   1500
acaagcagtc agtgaacaga aagtgtctgg tacaggttct aagtgcttat tattctaagt   1560
cacttcactt acctgagttc tcagttttcc tatctataag ataagcaggt tggataaaat   1620
gttctccaat atactcctgg tcctgagatg atgtgattgt gggcagccct ttaatcatgg   1680
tgaagatgtt catcataagc acactgaaac tacaaaatag gaatataaat attttctcca   1740
ttaaattatg ctggatccta gaagcaaaaa ctggaactgt gaaaccctac ttcacagaaa   1800
acttaaaatt cccaagcaga tgaatgcttc tcggaaggac actgacagtt acctacctgg   1860
aaagaatcta gatggaggtg gcatgggcac taagcggtga gattaaaccc agttagggca   1920
gccccaccag ccttggaacc cacacatctg gagattgttg atgcagagag aaaggttcct   1980
actggtgaga cctgaaaggg atatgtggca ggtgggagga agaagttctg tctggaaacc   2040
aaccccttgtt cctccgttat tgattgactc ctggtaccaa catgagccct aggtcttata   2100
gaggccataa gtccctatgc cttatagtgc ccatggatga gatgaggcca cacatgcccc   2160
cagtgggtta acatgtctag cgtgggtaag gctcttggag cactatgata cacaggaaat   2220
gcccagtaac tcttagttgg tttgatatct gttcccattg ctcacttaag ctcagtgccc   2280
ctttactgat ccttttattc tgcctccctc tgcacatgtg cattgagact cctatctgag   2340
acacacactg tgttgggtgc ccagggatgc agcatagatg ttgctgcctt ccacagaagc   2400
gctcatggtc tgctagagaa tatatcccat gggagagaaa aacagactcg ggagaatata   2460
gcaggggccc ttgtcctgga ctttggcagt taggaaaggg agggaagaga catggaggct   2520
gggacccaaa ggctaaatag gaatttgctg ggccaaaggg gagggggaat gaaaagagtg   2580
```

```
tttctggcag aggaaatggc aaggataaag gcctggaggc gcaagagaat atgtgtttga   2640

ggatctgaaa gttgagtgca gtgggtccag tgttctctac cctggctgcc attagaatta   2700

cctgggaaac ttttagaaaa ttccagtgtc tgggccctcc ctaaaacaat aaatcattct   2760

tgggtggtgg ggtctgggca tcaggattgt ttaaaaccct ccccaggtac tgtcatgtgc   2820

agctggggtt aagctgtgct ggggtctgag tatggatctg ttagggcaag tggcggtgat   2880

ggagttgagg ctgcagaatt caggccaaat agagaggttt tcatcaggat attaaagagt   2940

ttagatttca atttggtggg aatggatggg atcttatttg cattttatga agagctccct   3000

ggttgcaata tcagaatgga ttggagagga gca                                3033
```

<210> SEQ ID NO 397
<211> LENGTH: 3024
<212> TYPE: DNA
<213> ORGANISM: Homo sapiens

<400> SEQUENCE: 397

```
atactttccc agcccaaacc ctggaatagg ccttttctcc gaggagctct agttcatttt     60

agtgggaaat ggtatttaga gactataatc tgggatctgg gagtcctcat tgctactgag    120

tagtcattac ttttaggctt ttccagtggt cagagctagg aaatatgtat atttaaaaat    180

ggacagttga atggttgttg ccaggagctg ggaggaaggg gaagtgagaa attgtttaat    240

gggcacagag tttcagtttg gggaagatga aaaagttcta gagatagctg gtggtgatgg    300

ttgcgcaaca atgtaaatgc cactgagctc tcatttaaaa atggttaaaa tggtaaattt    360

tatatatatt ttaccacaat aaaaaaaagt cttcttctgg gagcaccccc ccaagacaaa    420

aatatgaaaa ttttacactg atacttccat ttcaagataa ttttaagatt ataaggattt    480

tgcttaattc ttgaatttta tacctgtaaa ccttttatac ttcaaatttc gggcagaatt    540

gcttctataa caatgataat tatacctcat actagcttct ttcttagtac tgctccattt    600

ggggacctgt atatctatac ttcttattct gagtctctcc actatatata tatatatata    660

tatatatttt tttttttttt tttttttaat acagactttg ctaccaggac ttgctggccc    720

ctctggggag atggttaaat ccacaacaag tctgacctcg tcttctactt ctggaagtag    780

tgataaggtc tatgcccacc agatggttcg tacagattcc cgggaacaga agcttgatgc    840

atttctgcag cctctgagca aacccctgtc cagtcagccc caggccattg tcacagagga    900

taagacagat atttctagtg gcagggctag gcagcaagat gaggagatgc ttgaactccc    960

agcccctgct gaagtggctg ccaaaaatca gagcttggag gggatacaa caaaggggac   1020

ttcagaaatg tcagagaaga gaggacctac ttccagcaac cccaggtatg gccttttggg   1080

aaaagtacag cctacctcct ttattctgta ataaaactgc cttctaactt tggcttttca   1140

tgaatcactt gcatcttctc tctgcctgac ttgccctctg gaatggtgct ggaatggtcc   1200

tgtggccttg tccactgtct gcctttgacc ataacttgaa agtcacccac catagtgtcc   1260

tttgaaataa cttaaatgtc cacagttcca agcatgagtt aaaaacactt cagaatgtag   1320

agtagttgtt caattgaata aacacacaca ccagaaaaaa aagcaagttt atcttttatt   1380

tttagtaaag aattttgata gagcctcaac accagaaatg gctagagaga gaagcctaac   1440

atatctggag gattattttt catcctactt aaagctgctt tcactttttt caggaaaaaa   1500

cacacgttct gaatctaatt tataaaactc cctggccggg tgctgtggct cacacctata   1560

atcccagcac tttgggaggc tgaggcaggt ggatcacctg aaatcaagag ttcaagacca   1620
```

```
gcctgaccaa catggtgaaa ccccatctct actaaaaata caaaattagc cagacgtggt   1680
ggcgcatgcc tgtaatcccc gctactcggg aggctgagac aggagaatga cttgaacccg   1740
ggaggcggag gttgcagtga gccgagatcg cgccattgca ctccagcctg ggcaacaaga   1800
gcgaaactcc gtctcaaaac aaacgaacaa acaaaaaccc caaaaatccc tgaagtacgt   1860
gagctagtgg tgaaagaaag ctggagaaaa ggagcaggaa taataataat aataataata   1920
ataataaaga ttgtcattta attttgagta cttccagtgt acactttgca ggtactctaa   1980
gacattacct cactgaaatc tctaaggtag atattcttta tttaaagtgt acttgtatga   2040
aacctggagc tcaaggtgaa ggaatttgcc caaggctgca cttgcactat cgtggcacta   2100
attagccgtg tgaactggga cacgttactt cagtttgctc atttctgagt cagcctagca   2160
agatgacttc taagaatttt ttccagccgg gtacattggc ctgtaatccc agcacttcga   2220
gaggccaagg tggaagggtc acttgagtct aggagttaca cacaacacac acacacacac   2280
acacacacac actagccagg catggtggca aatgcctgta gtctcagcta ctccggaggc   2340
tcaggtggaa ggatcacttg agcccaggag gttggggctg cagtgagcca tgatcacgcc   2400
actgcactcc agcctggctg acagagtgag atcctctgtc tcaaaaaaag aaaaaaaaaa   2460
agattttttt ccagggaata ataaaggaag ctaatattta tggagcatct acggtgtgcc   2520
aaatactttg catacgttat ctcatttaat gctcttatcc ctgcagggaa agtattaaca   2580
tttgtttatc acttgcagaa ctaagtgata tttaccacag agtagacaaa tattttcaag   2640
cccaaaatca agtggtatca cttttctgct gagaatgttt cagtggtttc ctttgctctt   2700
gggataaaac ttaaatccct caccctaccc ttgctccaac cctccacttt ccttctccca   2760
tgtggtgatt tggccataca gctcttgtgg ctgatctgaa ctgactgagc tttttaccct   2820
tttgctcttg ctgttcttac agcctgggaa ccccctggtt acctcttggc ttggtgtggt   2880
ggcttacatc tgtaatccca gcactctggg aggccaaggc ggacggatca cctgaggttg   2940
ggagtatgag accagcaagt cacctcttgc cagtggcctt tgtccattga gtctgaagtt   3000
ctttctcctc tcatttcccc atca                                          3024
```

<210> SEQ ID NO 398
<211> LENGTH: 2157
<212> TYPE: DNA
<213> ORGANISM: Homo sapiens

<400> SEQUENCE: 398

```
agtggccttt gtccattgag tctgaagttc tttctcctct catttcccca tcattctatt     60
atgctacctt gttttatttt cttcattgtg tttattgata cttaaaatga tctcttttct    120
gttgctgttt gactctccca ctagaaagta agcattgtag atcgggcact gtggctcaca    180
cctgtaatcc cagcactttg tggggcagag gcgggtggat cacctgaggt caggagttcg    240
agaccagcct ggccaacacg gtgaaacccc atctctacta aaaatacaaa aaatagctgg    300
gtatggtggc tcgtacctgt aatcccagct actcaggagg ctgagacatg agactcactt    360
gaacctggga ggcagaggct gcagtgagct gagatcacac cacagcactc cagcctggaa    420
gacatagtga gactctctct caaaaaaaaa aaaaaaaaaa aaggaagtaa gcattgtgag    480
ggcaggtacc ttctctgttt tgttcattgc tggatgtagt tagtatacag cagtatctga    540
tggatggata gatggaggaa tgaatgaatg agacttcaca aattcagctc acttgctcaa    600
ggccctgcag ctctacggga tgaagctata ctccagagtc ctgctacatt ggctgtgtgg    660
ccagctgctg ggatctgagg gttgtcagat aagcagtcta ccagagaaca gactgatctt    720
```

gttggccttc tgccagcaca ggggttcatt cacagctctg tagaaccagc acagagaagt 780
tgcttgctcc tccaaaatgc aacccacaaa atttggctaa gtttaaaaac aagaataata 840
atgatctgca cttccttttc ttcattgcag aaagagacat cgggaagatt ctgatgtgga 900
aatggtggaa gatgattccc gaaaggaaat gactgcagct tgtacccccc ggagaaggat 960
cattaacctc actagtgttt tgagtctcca ggaagaaatt aatgagcagg gacatgaggg 1020
tacgtaaacg ctgtggcctg cctgggatgc atagggcctc aactgccaag gttttggaaa 1080
tggagaaagc agtcatgttg tcagagtggc cactacagtt ttgctgggca agctcctctt 1140
cctttactaa cccacaatag catcagctta aagacaattt ttgattggga gaaaagggag 1200
aaaaataatc tctgtttatt ttaattagca ttaattggta ttcttgttaa accataggag 1260
tcagagtaaa tcagccattt caccaatttt cagtttgttt ctgtcttagc taacagcagt 1320
gtaatggtca gcaaaattct tatcttgtgt actgaatggc atgtcctgtt gctgaaagtg 1380
cacaggcttg ggaggtagcc atgagctcaa atcctggcac taccacctct cttgtgtgac 1440
cttagactcc tgacctttct atgcctcagt tctttcttac ctataaaatg aaattaattt 1500
tacccttaaa gatcatcgtg ctgattagag ataaaatata aataataaca cttgttacag 1560
agcaaggagt tgacactttt atattctgaa gacaaagtgg taaatcatta tcatctatgt 1620
cagaaatagc ttttgagaat acctgagtat agaactatct tgatccctgt tacttcaaaa 1680
ctaaaataat ggttttagga attaaaaggt gaggctagtc acctccaagg gatgaactga 1740
ctcagggatt gaggtatata acagtgaact ggtccaaaca acagtcctga ccccacttta 1800
tgagtgagac tatgagtaat ggtctaagtg tagacatcat tgtccagggc tccagtaggc 1860
agctctgtac ttgagaattt agcagtgacc cttctatttt tcatctatta tacctttttt 1920
tttttttttt tttgacacag ggtctcactt tgtcacccag ctggagtgtg gtggtgcaat 1980
catggcccac tgcagcctca acctccctgg gcttaggtga tcctcccacc tcagcttcct 2040
gagtagctgt aattacaggc atgtgccatc atgcccagct aatttttctt ttcttagagg 2100
tggggttttg ccatgtttcc caggctggtc ttgaactcct aggctctcac ctctgtc 2157

<210> SEQ ID NO 399
<211> LENGTH: 3163
<212> TYPE: DNA
<213> ORGANISM: Homo sapiens

<400> SEQUENCE: 399
aatgtgttgg ggaagtggtc tcctattaga ctctccattt caaaccattc catgattttg 60
tcctcctttt gccaccttcc gagcctgtaa aaactaatgt ttgtgattcc tgaggtttct 120
ctaatgtctt ttaataaagt tgacctcaga gatctcgtta cctctctgag ttcctgcttt 180
gtcttagatt ttgatccttg agtgttcttt aatcttttag caattccttg ttgcatgtta 240
aaagattagt tatattttat tcctcatttg tgttcgtttt caccaggagg ctcaattcag 300
gcttctttgc ttacttggtg tctctagttc tggtgcctgg tgctttggtc aatgaagtgg 360
ggttggtagg attctattac ttacctgttt tttggtttta ttttttgttt tgcagttctc 420
cgggagatgt tgcataacca ctccttcgtg ggctgtgtga atcctcagtg ggccttggca 480
cagcatcaaa ccaagttata ccttctcaac accaccaagc ttaggtaaat cagctgagtg 540
tgtgaacaag cagagctact acaacaatgg tccagggagc acaggcacaa aagctaagga 600
gagcagcatg aggtagttgg gagggcacag gctttggagt cagacacatg tggtttcaaa 660

```
tccaagttcg accatttccc atttatttga ctgtagacaa gttacattcc taaactatgt    720
ctcagatttc tcatctgtaa gttgtggtat tactagttaa catgcagggg ttttgtttgt    780
ttgtttgttt gtttgtttgt gagggtaaga aataacccaa gaagcctagt ccttggtagt    840
tgctcagtgc cctataaatg ttgtgaacca ggtggtgagg gtttggtgct gctagagaat    900
tctggtatct gctctgtgca acagagtact gtaggtgatg caagagaaag aagacctgat    960
gccttctttc ctcccagctt tgagaatgga gcaaaggcct accccagcca ccaagtgagc   1020
cagtgggctt gatcagcaca ggaaaggtga ccccggcagt ttcatttgac tattgcatgg   1080
ctggcaacat ttctattgat tgtttccagg gaccttggcg gatgagctcc tgttgagtct   1140
agcatctctg ttaaatctgt tctcaaatag gtaatgcata tgggaggatg ctgccacctt   1200
gcatctacta gacatcacct atctactgtg agactctccc tctaagccct gctgtggcct   1260
cagagtgctt attggccctg tgagtggggc agccactata cattgcatgg agttggtaca   1320
tgagatagaa acctattcgc catcccttga aactgcccca gtccagaagc ttcctgttag   1380
cacatgtacc tccttgtatg tattcagaac tcattccatt taggcttgga aacccgtttg   1440
gtgcaactct gttcaagttc cattgtctgc tttgagaatg cttgggcttg tatagtgagc   1500
tgtcactttt taatttgtta ggaattctac tcgccttgct ttttcttttc cagcatgttt   1560
aagggaatga cctccaaggc cccaaatcac agttgtattc atgttctttc atttcacaga   1620
tacaatccag gccagtccca gatttgcagc tgttaataaa tgtgaatggt tttccagtaa   1680
gggggtagaa aaacataggg agagaaccgg gttcagagtt caatatctgg attcaagtcc   1740
ttcctttagc actttactaa ctgatgtaga ataagtcagc tactcaatag gtgcctcagt   1800
ttccccacca aaatgcagac atagaaggtg ctttgtctgc tttgatgaga agtctttaag   1860
caagtctatg ggttcaatg tgttttaaga actataaagt accatataaa tgtggccttt   1920
attcccattg tgttcttgga agtaattcaa tatagtgtgt acttcatagc tgcttttgga   1980
ctattgccag ccagtgtatc atcctaaact acatgtcagc atagtataat cctgccttag   2040
gtctactttt gattatttag gaagactccc tgcccttcct atacatttca cataattttt   2100
aataagttgt aaaaaagtga tttataggat tctttgtaag tgggggaagt taagcagaca   2160
aaaagttttt aaatcttact gcagagtgtc aggaaccttt tatagcacca gacaggtagg   2220
gacagaacat gagtggcagc aagccagact tggtcttagt gctctaacct gtctgttaga   2280
ggctggccag tcagacccct ggttgaagac gttgggaatc ccagctcttt ggaggggtaa   2340
gagattttgt tagactgtta accagattcc acagccaggc agaactattt ctgtctcatc   2400
catgtttcag ggattacttc tcccattttg tcccaactgg ttgtatctca agcatgaatt   2460
cagcttttcc ttaaagtcac ttcattttta ttttcagtga agaactgttc taccagatac   2520
tcatttatga ttttgccaat tttggtgttc tcaggttatc ggtaagttta gatccttttc   2580
acttctgaaa tttcaactga tcgtttctga aaatagtagc tctccactaa tatcttattt   2640
gtagtatgtt aaatttttct aaaacttcta aggatagttg ctgtattgta tgatttgcat   2700
atggaggtat ctataagaag ttttatactt tttagcaaaa tagtcatttg gtagccaact   2760
taaacaaatg tttattaata tagaagttaa taatatctac tgatactcgg ccgggtgcgg   2820
tggctcatgc ctgtaatccc accactttgg gaggctgagg cgggcagatc atttgaggtc   2880
aggagttcaa gaccagcctg accaatatga tgaaaccctg tctctactaa attacaaata   2940
ttagcagggt atggtggtgg gcgcctgtaa tcccagctac tcaggaggct aaggcaggag   3000
aatcatttga acccaggagg cagaggttgc aatgagctga gatcacgcca ctgcactcca   3060
```

gcctgggcaa cagagcaaga ttccctcaaa aaaataaata tctactgaca cttaatactt 3120
ggaaagggat aaaaataaac attgtctaaa gccgtggtcc aaa 3163

<210> SEQ ID NO 400
<211> LENGTH: 3066
<212> TYPE: DNA
<213> ORGANISM: Homo sapiens

<400> SEQUENCE: 400
aagctgaggt cacggatttg agacctttct tcttttctaa tacaggtgtt aagtgctaca 60
aatatccctt aagcactgct tcaacagcat cccacaaatt ttgatagttt gttttcattt 120
tcattcagtt caaaatacct tctaatttcc cttttgattt cgtctttgac ctacaggttt 180
tttagaactg tgttatttag tttccaatct cttgaggatt tttaaaacaa tatgttattg 240
atttctaatt tatttccatc tcagtcaaag aacatacttg cctttttta tacatttatt 300 gaaacttttt ttatggccca gaatatggtc tgtgttggta aatgttccat gtgtacttga 360
aaataatttg tattctgatc tcattgagtt gaatgttcta ggtatatcaa gttgatagtg 420
atgcccaagt ctcctgtatc tttactgatt ttctgcctgt tctgttattg agaaaggggt 480
attgaaactt ccaactataa ttatgatttg tctgttctct ttgcagttct cttagttttt 540
gccttcatat atatatacat atatatgtat atatatatat atttttttt ttttgagatg 600 gagtcttgct ctgttgccca ggctggagtg cagtggtgtg atcttggctc actgcaagct 660
ccgcctccca ggttcacgcc attctcctgc ctcagcctcc cgaatagctg ggactacagg 720
cgcccaccac cacgcccagc taattttttg tatttttagt agagacaggg tttcaccatg 780
ttagcaagga tggtctcgat ctgacctcgt gatccgccca gcttagcctc ccaaagtgct 840
gggattacag gcatgagcca ctgcacccag cccatatatt ttaaagctct gttattgggt 900
acataaacat ttaggattgt tatatccttt tgataatgga ctcttctatt atgaaaagat 960
aatatactgt gggtttataa catatgtaaa agtatgagta acatattatc agaaggggag 1020
aaatggaaga taacttaggc atcttatttt taagcatagt tttccctttg tttctgcatt 1080
agatgattta cctgaaatgt cattcaattt aacttactct ccatcctcac ccgcccagct 1140
ttggttatga ggcagtagaa agaaatgatc tgcctgtggt tttctagaaa tacgaaagtt 1200
gagtccttaa ggctacacag aaagaaagta cctccccagg gcttcaccct tcccatcctt 1260
tcagcaggct ttttgtctgt cgtatcttct ctgttgaaat ggccattgac aagaggagga 1320
aaggggtttt gttgtggatt gttcaggcac ttcctttggg gtatatgggg gatgagtgtt 1380
acatttatgg tttctcacct gccattctga tagtggattc ttgggaattc aggcttcatt 1440
tggatgctcc gttaaagctt gctccttcat gttcttgctt cttcctagga gccagcaccg 1500
ctctttgacc ttgccatgct tgccttagat agtccagaga gtggctggac agaggaagat 1560
ggtcccaaag aaggacttgc tgaatacatt gttgagtttc tgaagaagaa ggctgagatg 1620
cttgcagact atttctcttt ggaaattgat gaggtgtgac agccattctt atacttctgt 1680
tgtattcttc aaataaaatt tccagccggg tgcggtggct catggctgta atcccagcac 1740
tttgggaggc tgaggtgggc agataacttg gggtcaggag ttcaaaacca gctggccaac 1800
atgatgaaac cccgtctcta ctaaaaaaat agaaaaatta gccaggcgtg gtggcgggta 1860
cctgtaatcc aagctgctca ggaggctgag gcagaagaat cacttaaacc caagaggtag 1920
aagttgcagt gagccgagat tgcaccactg cactctagcc taggcgacag cgagactgcg 1980
tctcaaaaaa aaaaaaaaag aacgttccaa ggtcaggact aggcctcccc tcagaagcag 2040
caagtgacat atgtgacatc ctctccactc cctatttgca tttctaggtt atataactgt 2100
actactatcc atgcatgcct actcttgttc ccagggtgaa ggacccagac atggagagcc 2160
gaatccctgc aggccattat aaatgagatt atgccatttg ctcccatttc ttcttattct 2220
ttcatttttg gggctctcca tcttgatgtg ttctttggat cgtgaacaga tccaaagaaa 2280
aggttgttct gccgtgctgt ttgtcaggat gaaaaactct tttttaagtg tttaggtctg 2340
cccccagtgc ccagcccaat caagtaacgt ggtcacccag agtggcagat aggagcacaa 2400
ggcctgggaa agcactggag aaatgggatt tgtttaaact atgacagcat tatttcttgt 2460
tcccttgtcc tttttcctgc aagcaggaag ggaacctgat tggattaccc cttctgattg 2520
acaactatgt gccccctttg gagggactgc ctatcttcat tcttcgacta gccactgagg 2580
tcagtgatca agcagatact aagcatttcg gtacatgcat gtgtgctgga gggaaagggc 2640
aaatgaccac cctttgatct ggaatgataa agatgataag ggtgggatag ctgaaggcct 2700
gctctcatcc ccactaatat tcattcccag caatattcag cagtcccatt tacagtttta 2760
acgcctaaag tatcacattt cgtttttag ctttaagtag tctgtgatct ccgtttagaa 2820
tgagaatgtt taaattcgta cctattttga ggtattgaat ttctttggac caggtgaatt 2880
gggacgaaga aaaggaatgt tttgaaagcc tcagtaaaga atgcgctatg ttctattcca 2940
tccggaagca gtacatatct gaggagtcga ccctctcagg ccagcaggta cagtggtgat 3000
gcacactggc accccaggac taggacagga cctcatacaa tctttaggag atgaaacttg 3060
cccatc 3066

<210> SEQ ID NO 401
<211> LENGTH: 3065
<212> TYPE: DNA
<213> ORGANISM: Homo sapiens

<400> SEQUENCE: 401
tgggacgaag aaaaggaatg ttttgaaagc ctcagtaaag aatgcgctat gttctattcc 60
atccggaagc agtacatatc tgaggagtcg accctctcag gccagcaggt acagtggtga 120
tgcacactgg caccccagga ctaggacagg acctcataca atctttagga gatgaaactt 180
gcccatctct aaaatttcgg gatttctttg tacccaacaa ggttcaaaca caacagtcag 240
cttttattca tgatttttac ttccatctgc tgatgtagaa catacctcca gagtgacctc 300
agaaattgtc aaatgtgaaa acacaagcca tcacagtgag aaatgggagg ttgagttaga 360
ttgtctaagg ctggagagtc catatactcc cactgttagc tctgaagtgt gtagccagtc 420
ttcagattct gggtcagttg cctcagtctc tcttagcttt tgccttactc tttatccgac 480
cactgccctg ccaggaaaac aaggctctat aactcctctt acaggtcagc ttgacacaaa 540
aagggtgcct ggattcctaa tgtttcattg tcacttttcc cagtcagatg ataatgcttt 600
tcaaatcaac atatattttg ggggaggttg gaagggagag ttgaaatatt ctaagaatca 660
aagagtagcc cactttaatc agagtatgac ccctgattgc tcacagtcat ctcctgagca 720
gtgtgagcga gtttcagatg aggaggctga aggccagtca ggcatgctcg aggattccaa 780
gtctgtaggt gggagggcag agatttagtc ctgttggcca aagcctctag ggaatttctc 840
actccagtgg agaaggcaac acacttacca aactgtgtgg aaactatctc atttgattag 900
aaattttacc tcaagaagag gaaggacagt tgagaaagaa cattttctta cacatgagac 960
agctaaggct tacaagaagg agaggaataa tgaggcaaaa taatcctcat taatattttc 1020

-continued

```
attcctcccc tggggattag aactactttc agacccgatt ttaatggtaa gttaggtact   1080
tcctacagtt gccatccaaa tatcagtcag gatcagacat gatgttagct cctgctacaa   1140
taaaaccatt ttctccctga atgaaaacaa aggttccaca ggagacagtc ccacagagca   1200
gtggcttctt ttcctccctt taaaacctca tgttggctgg acacagtggc tcacacctgt   1260
aatcccagca ttttaggagg ctgaggtggg aagatggctt aagcccagga gtttgaggct   1320
gtagagctat gatcacacca ctgcccttca gcctgggtga cagagcaaga ccttgtctct   1380
aaataaacaa acaaacaaaa aatcctcttg tgttcaggcc tgtgggatcc cctgagaggc   1440
tagcccacaa gatccacttc aaaagcccta gataacacca agtctttcca gacccagtgc   1500
acatcccatc agccaggaca ccagtgtatg ttgggatgca aacagggagg cttatgacat   1560
ctaatgtgtt ttccagagtg aagtgcctgg ctccattcca aactcctgga agtggactgt   1620
ggaacacatt gtctataaag ccttgcgctc acacattctg cctcctaaac atttcacaga   1680
agatggaaat atcctgcagc ttgctaacct gcctgatcta tacaaagtct ttgagaggtg   1740
ttaaatatgg ttatttatgc actgtgggat gtgttcttct ttctctgtat tccgatacaa   1800
agtgttgtat caaagtgtga tatacaaagt gtaccaacat aagtgttggt agcacttaag   1860
acttatactt gccttctgat agtattcctt tatacacagt ggattgatta taaataaata   1920
gatgtgtctt aacataattt cttatttaat tttattatgt atatattgtg tcagttcaga   1980
tgccaaaaag aggtcttgaa catgtcacag gctctgatgg cactgaccat ggagaaagct   2040
tgatttgatc atctggtgtc tacaataacc aaagctaatt attaaggaaa aaaacttgaa   2100
gaaagaaaat agtccttact tcatctataa tgaggttttt gttttttgt tttgagacgg   2160
agtcttgctt tgttgcccag gccggagtgc agtggcgcga tattggctca ctgcaacctc   2220
cgcttaccgg gttcaagcaa ttctcctgcc tcagcttcct gagtagctgg gattacaggc   2280
acctgccacc acgcccggct aatttttgta tttttagtag agatgtggtt tcacgatgct   2340
ggccaagctg gtctcaaact cctgacctca ggtgatcctc ccacctcagc ctcccaaagt   2400
taagtgctgg gattacaggc atgagccact gcggccggca ttaagtatga gtttttaagt   2460
tagcccactt tgttaatgac tatgagtact aatagcttaa gataaagaag tttctaggta   2520
atcttgtttg aaggatgatg taaaaatata aatttaaact gtgagtgaca aaataaactt   2580
ccttaatatt tgcctacatt tagagaaatg gagcattcag ctcagaaagg aagaatgtct   2640
gtggttttaa ggtaaaatcc atattccaag actcagtgaa gaaagttcag tgataaagaa   2700
cagactactc tcatcttatg aagaaatgga gcaatttcac ttggaaagac taggaagaca   2760
aaatgttaca gacgtatttg ttgtgccaca aaataggcaa ggtcagtttt gaacaataag   2820
aactccataa agtagaccag ggcatctcag aagtgaggtt ccatgagccc aggtggggca   2880
caggctgggt gatcttgagt ggagaggaag aggggttttc tgagcttcaa gagctgggcc   2940
acacagtgtg ttggttttag ctgggatgga gttctagaac aaacctgcac tttagaacac   3000
ctttctaccc acccccaacc acacaacttg ctactattag taaatgtata ggctgaggca   3060
cggtg                                                               3065
```

<210> SEQ ID NO 402
<211> LENGTH: 3153
<212> TYPE: DNA
<213> ORGANISM: Homo sapiens

<400> SEQUENCE: 402

-continued

```
ggactaaccc acctcccttc caaggatctt gctatctatc ccttcttgcc ctcagctact     60
cactcccaca gtcatatacc agatctcatc attagacaat tgtaatccct acacaattta    120
gttccatgta tcctctctct aaccactatt cctcatcttt ccaggtcatt ctctctagac    180
ccgaattcca acaacccttc aaccacactg gtaccactaa tctacagatt acatcttctt    240
tctactatac cttgatgtgt tcctgaatat ctcccgaatc ctcttcatcc agtttaattt    300
caaggtccat cattataatc attttcttac atactccctc acctctcctg ccccattaat    360
actgtcctag taaaatctag ctctctaccc actccatgcc tgcccctatg ctgctgtaag    420
tagccagaga aacacatata ataaatgcat tcacacaaac cttctaacat atcatataat    480
attgtctgat gtcttcctac tagaatgcct ctcaggcagg aatttttttt ttctaaacta    540
atttattcac tgaaatatcc cagtgcctag aatagtgcat gttaaatagt agaatctcac    600
tcaacatttg ttgaatgact gaataggagt tccaaaatag agaacacagc atatgggagg    660
ggaaaaaaat cagtaacaaa atcattcaag aaattttccc agaactaaag gatgggagct    720
cctagaattg acaggggccc agcatcacac atgaaaactt caaatcacat gactatcttc    780
aaattacacc agaatgctag agagaaagag aataggatac aagcttccac aaagaggaga    840
aaaatagatc acaaatcaga aaagatcaga actcaaaatg ttcatgaaaa ctcaacagcc    900
atgctcgaag tcacagcaca atgaagaaat gtccttttaa aaaatcttaa ggagaaccat    960
ggcaactcag gattctctac ccagccaaac tattttaatc aagtgagagg gtagaatgaa   1020
gacatcttca ggcctgcaag gtcatgaaaa attaacaatc cacaaaccct cttctcagga   1080
agctactgga agatgtacca aaataagaga ataaataagg agaaaggcat gagacaccgg   1140
aaaaagggaa cccaacctaa atcacatgca aagaaaatct ccagatgcca atgaagggtg   1200
accacatcta tgtaccgaga gggcaagtca ctagtttaga aagggacaag tcagatgcac   1260
caagattcaa caaactggaa ctgaaataac accagatgca tctgaaaata ctgagtggga   1320
ttaatctact cttggagatt ctgtggctaa attgatgata gaaaaccaag caaatacaaa   1380
gaaaaaccat aacattaact ttagaggaaa ctaatagttc tgagggagat gatcctagaa   1440
tgcaacctgg ctccactgtg tgagtagtgt ttagagggtc ctaatgacac aagcaggctg   1500
gaattacact gttcctttat taggaggata taagagtgga aaataagtat gtgtgtggca   1560
gggacaaagg atgaaaaaca gctaaatcct catcttccat aaaaggatgt caatatagaa   1620
tgcctgaagc agaacaatca agatgcaaca taagtatgtt atacagagat acaaggacag   1680
tacacaagaa tcagctaaaa gtatttaaca gaaatggtca ggggcgaggt cagaggagcc   1740
agggcagggg actgctgtgt tcataacaag ctttgtaaaa aactatatga ctccttaaac   1800
tatgtgtcct taaaaaaatg ttttaagaac agaaaataac aaagaggtaa aatatgaatt   1860
atctatcctt catatctcac ttgagtactg atgtttgaaa gaagcatatt tttttaatga   1920
acatttcaat tagccagtat tttaccatgt aactttgtta aaattatatt acactccaat   1980
aagaatgcct ttacctgtga cagtagttct tccttctctc cagcaagttt tcgtagcctt   2040
acatctaaaa caaatgaaaa agatcataaa ctaaatatgt gatgatatag tacataaaca   2100
attaaaaatt tttcaaactc ataaacagct aatattatct gataaattac attacttaca   2160
gctctgaata tctaaagaaa taaaggtgtt aatagcatta cagaaaagtt cttaactatc   2220
taaaaagtat ttccacacaa ctgatattta tcagggcacc aaatccaaca tttgttcccc   2280
acagcagtga tttgccactt aaagacaaac agaagtacaa aggaggtcat ttccttgttt   2340
caagctttca ctagtagaca gacaactcaa atgtcaagtg tgttcctaaa ggctgagccc   2400
```

```
ttagcgggag agatccaaat atgtgaaaga agatggggta agagcaggac tgggcaaagg   2460
aagctagaga agagaaaaga gaggagcata atgctggaag aagcaaagtc cccaaaagct   2520
agtagggagg gaaggggacc cactccaaga tgtgggcagc caggccaggt gtggtggctc   2580
acgcctgtaa tcccagcact ttgggaggcc taggtgggtg gatcacttga ggtcaggagt   2640
tcaagaccag cctggccaaa atggtgaaac cacgtctcta ctaaacaaat acaaaaatta   2700
accaagcgtg gtggcaggcg cctgtaatcc cagctactcg ggaagccgtc tgaacctggg   2760
agatagaggt tgtatgttgc agtgaactga gatcgcgcca ctacaatcct gcctgggcga   2820
ccgagtgaga cttcgtctca aaaaaaaaaa aaaaaaagat gtgggcatcc atgggtagat   2880
ctgcggcttg gtggcagcac cattagggct cactcctagc ctgtggaggt ttgactcttc   2940
ccaagcctgc attaaaatag gccccttcag ctgaggagat accatggttc acttaaaaaa   3000
gcagctgata cctcgccaac cactaccctc tgtaaacagg gtcatagcca aataaagatt   3060
ttggtttctt ctgcaccttc caagcagatc tgcctgcttg gacctgcaga cgagggaaaa   3120
aacagcaggg aaacactctg ggctgcctat agc                                3153
```

<210> SEQ ID NO 403
<211> LENGTH: 3080
<212> TYPE: DNA
<213> ORGANISM: Homo sapiens

<400> SEQUENCE: 403

```
gccagactct cgttccattc tccagatctc tcttgctcac ccagcatcct gttttattca     60
aagtgcccta caatcacatt tctggaatgc acattagaga atgtgcttac taactttcaa    120
aatgtttttc agtttgcttc acacttgtat ctctcactcc tctaagaagc ttacacatat    180
atgaaaacaa gatgaaaaac aaaaaaattg ttttttttta aaataaaagt gagctaatga    240
tacagtatct atctgtgcca tttttcttcc tctagagtag atttctttgt ggggtcaatg    300
gatgggtgac tttgatttct cagacagagg tgtcagcaac tttgtggttt cctggagaga    360
ggtgtcagat tctcaaaggg ttaaatttaa gaggtttaga ctttaagagt ctgggaagcc    420
ctgctctgga agtcatactt ctctgatatc tttttggtca tctgtttctt ggcttaagaa    480
atgtggtgga aaagaggtac agaaccctgg ggtaagcagt ggaacataaa accagatgtt    540
ccaaggatga gaaacttata acacacttga gaagtctcct gctagcctac tgctccccta    600
gcacaggtat actagactat ctctttgcag aacagtttgt agttaagtaa aaaccgatgt    660
gtataggccc atagtacttc catccacagg ccttacagtt acacttattg ccttacagtg    720
acccagatgc tgatttccca aggtcaagga tgtctgaaga caatgtgcca atgtgcccag    780
attcttctag ttaaggatct acttgagtct cagcccttat gctgtttttg ttttccaagc    840
tgggatatga aaaagcagaa aacccaatag ggtaacatta atccaagtca acatagcaac    900
cagtatctta cctaatggcc cttctcctgc tgactccaag acctgagcag cttcctgaga    960
cacaacagtg atggctccag ccactggttc atgactgaca tcaccattgg gagtgccatc   1020
ggggattata actaagccat gtttctgcag gggggaaaaa cccaccatca caaaaggccc   1080
gtatggaagc tgtaagctct gtgaggtcac tctgcaacaa tacatgtttg ctacaggtaa   1140
aacctggtta gaatcagtta catgaaatat agctctgtgt aagaaatagc ttcaacctac   1200
caaatctgga ttagagaata aacactgtag tttgtattta ggctaggaaa gatggcagga   1260
tgaaaggaag gaagatagag agtaaaacag tgagggacct gaattccagg ctaatgctaa   1320
```

cataccctctc ccgtcttcac tgtctcctgc aggtcagcca gctcctctct gagcatatct 1380
cgctcattcc taaggcaggc aatgtattct ttctgtttct ctagggcctg gttttaggta 1440
aggtagcaag ggaaacaatg gcacagaaaa agagcaggtg aaaggtagca gagaagtacc 1500
taattcaaat aagcaaagat aaaggcataa aaagcaagaa agcagtcaaa agattggaaa 1560
caaacagtca gatatgggag gaaatacaga gttacatgga tatacatctc cagaagagac 1620
ttctcataga aactggttct catgcatcaa tttggcaaaa catgtttaat cacatcaagc 1680
agggaaataa atcttttcca gtcaatgaaa aaaataaaac aggaaaagga agataaagag 1740
agaagccaga gtaaaataaa gctttcctta ctgactgcct aagtgcattt ttatttggtg 1800
aacaaaaaaa accccacatt tcatgtttaa ctaaactagt ttattcaaga atacagttga 1860 tttttaaaa aatagttctg gaataaaaat aactattata cataggtatt ttaatttaat 1920
attggctgta gatttttctc caagtagtgt ggcaaaatac tcaaatacca cttaattcaa 1980
aatagttaac ctccaaaagg attcaaagat caacttctga caacttaatt aaatataact 2040
gagactcatt tggctttctg ttatactccc aaaatgtgaa aaacaaaaat aaacactgac 2100
aaaataaata cagccaagct atgaagagtt acagaatatg gatttcagaa tcaggctttt 2160
gggttctggc acatacttgt cctatgcctc agtttcctca ctggaaaaac agaagggata 2220
atagcaccca tcccaagggc agaggcataa atcaaggtaa agcattgcct gtaatgccta 2280
gatagcaggg acagttcagg agaatcaggt tggtgatttc atttgtaaat tccctgccat 2340
ttccttaatc tcacaactgt cagctgagga caatgcagaa gcaggaacat actttggtca 2400
tcaatgaaaa ataaaatcta ctatgaaaaa ataaaatcta ttgtaaaaga aaataaccca 2460
gaattaaaaa tacacccaag gtaagtagtc tatgcaggaa tctgattact ggcctatttg 2520
aaaaagcctt tccccaaata tttttgttca tatatttaat gtcttctgtt agcattccca 2580
ttaatccaag aagttaaact atatcaggta actttcctct cagttcactg ggtttggaag 2640
tgggacagcg aattgctgag aaattgatag ctgaatagct gggcaattca aaaaatcatt 2700
ataatcctgt tttgcaacca aatagggagc aagtaaataa gggatgatag caactacgat 2760
ttgtatagca caaattatat ggcaggcact attttatata atttctctct tatacattat 2820
tttacatttg aaacctctac atatcctgtg aggtacttgt attatcccca tttaacagat 2880
cagaaaattg aggctcacag tggttatatt ttttcgccca aagtcacagt aagtggcaaa 2940
accagaaaat gaatctggtt gtttttgttt ccaaagccct taaatagttt tttaaatatc 3000
acagctctat gaaggccaca ttatattccc ttattgttag cccagatgat gctaggaaag 3060
gagtccatac ggcaaatcct 3080

<210> SEQ ID NO 404
<211> LENGTH: 3074
<212> TYPE: DNA
<213> ORGANISM: Homo sapiens

<400> SEQUENCE: 404
tcgcccaaag tcacagtaag tggcaaaacc agaaaatgaa tctggttgtt tttgtttcca 60
aagcccttaa atagtttttt aaatatcaca gctctatgaa ggccacatta tattccctta 120
ttgttagccc agatgatgct aggaaaggag tccatacggc aaatcctact ctttacttat 180
ccaaactgca atgtcaatat ctgacttctt ttcaacaatt tacattcaca ctatatgatg 240
tgtctcaagt ctgcctgtga attaacaatg tgcatttcta gcaccatcta gctagtgtta 300
acactccatt atgttaataa ttaataataa ctgaaacatt gggaaaacaa agcacaacaa 360

-continued

```
tactttccca tgtgttgagt gtcactttat ggattaggta tttttggtta ctggtatctg    420
catgcatagt tatgtcatgt atcaccacat ataagtgggt aaatgatcac tgtcacaaca    480
tgctctacat aaacaacaac actgaataaa aaagacctct gaggaacagg ccaatttgaa    540
actaggaatt ctagcaaatg atatacatga catttgctct tcttccacat cgtattgcac    600
tgggttttat ttttaccttc ggacttttta atttcctctt cccataatta cagatgagaa    660
aataaaatac atcctgtaaa ttcacccact tcaccacaaa gtttgaagac tactaaaata    720
ccttataatt ggatcaaatg tattcaagct ggatctaaaa ccctctgtat tacctgacca    780
tataaccact acccttgtgt ttgtgtgcaa caatagctcc tacagtagat tttttttagg    840
gtaaaaagta cacgcttgta gagttcaaaa taactcttta tccctgacct aacctcaaat    900
cctaccaccc ggaagccaaa aggatgtgta taatgggctg aacttttggg caaggggtta    960
attctccaca taattgtact ggggaacaaa tatctttggt cagaatggaa gtgagtttat   1020
gctgggctat agagatacgc aagttcttca tacgcaccta ttctatacat gggctcctgg   1080
tgtttagaac cgcagtggag ctagaggcaa gaccactaat gaactgaact ttaacctggg   1140
aataatggac atatttcttc attaagttac taaatgtaaa tcttaaaaat gaagctagag   1200
acaagtagtt actgaccata ctgaaaatgt gtcttaaaag tcaagggagg accactgccc   1260
ttgtattata atgataacaa atgttggcaa ggacatggag aaattggaac ccttgttcac   1320
tagtggtggg aatgtaaaat ggtacatctg ctacagaaca cagtataact gttactcaaa   1380
aaaattaaac acagaattac catatgatcc agcaattcca cttctgggta cataccgaaa   1440
acaactgaag gcagagtctt gaagagttat ttgaataccc atgttcacag cagcattatt   1500
cacaatggcc aaaaggtaga tgtgttgata tatcaacaga agaatgtggt atatacatac   1560
aatggaatat gattcagcct taaaagggat ggacattctg acatatgctg caaaatgaac   1620
cttgagggca taatgccaag tgaaataaat cagatactgt atgattccac ttacatgaag   1680
tacctagagc agtcaaattc acagagacag aaggtggaat ggtagttgcc attccaccag   1740
gggtttggga gaagggactg aatggggagt tgtttaatgg gtacagattt cagctgggga   1800
agactaaaaa gttctatggt ggtgacagta gcacaacaac atgaatgtac tcaatgccac   1860
tgaactgtac acttaaaaat agttaaaatg gtaaatttta tgttatttgt actttagcac   1920
aatttttcaa attaaaaaag agtcaactcg tgattcaata acttggaaga atcttgaggg   1980
acttatacag agtgaaaagg gataattcca aaaggttaac atatactata taattccatt   2040
tttataacat tcttaaaaga gcaaaactac acaaatgaag aaaagattag tggttcttag   2100
ggcttgggag gggaagggga gattaaggct atgactataa aaaggcaaga ggaggagaaa   2160
tcccttatat tgatggaaat gttctgtatc ttcaccatat caagggcaat atcctggttg   2220
tgatattgta ctatagtttt gtaagatgtt acatttgggg aagattgagc aaagaatata   2280
taggatctct gttaaatttc ctcttttttt tttttttttt gaaacagggt tttggtctgt   2340
tgcccaggct ggactgcagt gacatgatct cagctcactg caaccttggc ctcccggatt   2400
caagtgattc tcatgcctca gcctcccaag tagctgggat tacaggtgtg caccaccatg   2460
cctggctaat tttgtatttt ttagtagaga cagcgtttta ccatgttggt caggctggtc   2520
tcgaactctt gacctcaagg gatccaccct ctttggcctc ccaaagtgct gggattaaag   2580
gcataagcca ccatgcccag ccctgtttaa tttcttacaa ctgcatgtaa atctaaaatt   2640
ctggccgggc acagtggctc atgcctgtag taccaccact ttggaaggcc gaggtgggtg   2700
```

-continued

```
gatcacttga ggtcaggagt tcgagaccag cctggccaac atggtgaaac cccatctcta   2760

ctaaaaatac aaaaattagc cggacgtggt ggtgcacacc tgtagtccca gctactcagg   2820

aggctgaggc aggagaattg cttgaaccca ggaggttgca gtgagctgag atcgtgccac   2880

tatactccag ccttggggag agagagagat tccatctcaa aaaaagaata ctaaaataaa   2940

atattttcca attaaaagcc aaataattta tattttaaac tgagacatct gaggggtttc   3000

tatggctggt ccaagattat cagtttaaaa tattaaggca ctcatacaag ctagaaatcc   3060

tgggcctaca gatc                                                     3074
```

```
<210> SEQ ID NO 405
<211> LENGTH: 2129
<212> TYPE: DNA
<213> ORGANISM: Homo sapiens

<400> SEQUENCE: 405
```

```
caagattatc agtttaaaat attaaggcac tcatacaagc tagaaatcct gggcctacag     60

atctgtgtta aagaaaatta tgtgaagtcc taaaagaagc ccattctaga cagtgaccag    120

attttaacta aaaattttaa attacctact ttgccccacg tttttcacc tcttatattt     180

cccaagcaaa aatttaaatc aaatcaatgg ttcaacaatc aaatttcact tttcaatttc    240

aaatttcaat tttaaaatca tagtttcaaa acacctaaca gaattattga tttattcccc    300

agaaggcttt tctaggttta gatggaattt ttaatactca gcaatttgaa agtcagagaa    360

ttatctataa agtagctttt gttctttaaa tttttggtct acaaactttt ttaaagaaag    420

ggtatcactc tattgcttag gctggagtgc catggcacga tcatagctca ctgcagcctc    480

catcgtgtgg gctccagtga tcctcccacc tcagcctcct aagtagctgg ggcaggtgca    540

tgctctgcaa attttaaaat tcttttgcag agacagggtg ggtctcacta tgttgcccaa    600

gctggtctca agctcctgac ctcaagcaat cctctggcct caagcgatcc tccgtgctag    660

gattccaggc atgagcctac aaactcttaa gaggtaatgt aatcttccca tgtgtatatt    720

aatgagagag gtccttgaag tgatgaaaaa gactggatcc tgctgactac tggttgggct    780

tcagaatgtt cctaacaaca ttctgagggt ataatccaca ggatttcata tccaggcctg    840

tctctcaaga gatgttctca gggatcttta acaactattc cctactcccc ctaaccttaa    900

gcagaacaag actttcttta catgttctat ttcctctgcc cttccctgac aaggtaagcc    960

tctggcaact atggctaagt ggttccccta ctgtagaaca gagagctcag ccaggtgatg   1020

ggactgccaa tcaaaggcca catgagatga actggaggga atttttcca gcttttggtg    1080

tacatggaat ctacctgcaa ggcttagcaa aacagcaatg aagacatttc gtttatctgg   1140

gcccttactt gggggagttc tgtggttata attacagaca gccaccctag aaagtcttac   1200

attcctatcc atttctgtaa ttgaattgat tttaatctct tcctatttta tacaccaagg   1260

atttatagga tgctaataac tttctcccca ccactaccct cttcttatcc aaattcctgt   1320

aacgtaagga tatcaagtta accacagagt ttgaattgaa tgcctgtggc tgtttctgga   1380

taagaatctg aagggaggcc aggcatggtg gctcacgcct ataatcctag cactttggga   1440

ggccaaggtg ggtggattac ctgaggtcag gagttggaga ccagcctggc taacatggtg   1500

aaaccccgtc tctaataaaa agacaaaaaa ttagctgggc atggttgtgt gtgcctgtaa   1560

tcccagctac tcgggaggct gaggcaggag aatcacttga acccaggagg cagaggttgt   1620

agtgagccga gatcatgcca ctgcactcca gcctgggcaa cagagtgaga ctccgtctca   1680

aaaaaaaaaa aaaaaaaaaa aaaagaatcc taagggaata cagagaaact tcctttaaaa   1740
```

gttcctactt atacatttta caagcctagt gtttgctgaa aagaagagtt cttccaggca 1800
caacgtcagg ttttcctatg gaagtctctg tctcctactg actcattttt catactgtgt 1860
aaatgctcaa gaagaatcaa aaggacaggt tttttcaatc tctaggttaa attctactgt 1920
agtcctcatc aatgagcttc taaccaaagc ccaatttcat ttcatacccc aattttttta 1980
tctttccaaa gaagtgtctc ctggaggtca aacacctctt ttgtcatggt gtctattttc 2040
tgctgcatgc gctgcttctc ctgcagagga agaggggaag agaagtaata aaagagcaga 2100
aagaaaaggg agaggaggtt tgagggagg 2129

<210> SEQ ID NO 406
<211> LENGTH: 3170
<212> TYPE: DNA
<213> ORGANISM: Homo sapiens

<400> SEQUENCE: 406
ttctcctgca gaggaagagg ggaagagaag taataaaaga gcagaaagaa aagggagagg 60
aggtttgagg gaggaaacaa aaataaagcc gataaagaaa cttaaccaaa agggaaagtc 120
tgtgatgaac aggaaaagca aaattggtct gccaaaagaa aagatgacat tcacagtctt 180
ggccacaaga ttcttattgg cttgccccta caaaagtaag caaaggaacc aggaataatt 240
gttccaacca cagctacgtg gcagcaagcc agctagaatt tctgtgtaca tacagctcca 300
tatgtatatt ctttctttga taactgcctt tttaccaaac aagaacttac attcctagag 360
agggaaattt aggtttgctt atgaacaaat gatctttcat cttagagaac aagcagtttt 420
gaattttatt ttttaagcag aactgatcat tttgaatttc tgttagcaaa atctatgaca 480
gcaagaacac catgaatttt gtattatttt aaaattatat tattttgaaa catttaaatt 540
tagcatttaa caatccttaa atgacctttc taattaggca atggtgctta acaggttttc 600
ttcttatgca ttattggtaa attattatgt cctcctttcc ctactcatac attaggtact 660
ttaccatgga attttcaatt ccaaagacca aaaaacatta tttgtaatat ttaaagtttt 720
tcagcataac catagatact aacatctaaa agatgttcat tctagatgta aaaaacatct 780
aaaactatag ttctcaaagt ttgtatacct agcaccctaa gcttttaaag aagccacagt 840
gatgaactat agaaatcaag cattatattc ttcttaaatg caattacaat taattactag 900
aacactttac cagtcctaac ttaagctatt gaatttgaga agcagccccc aaagcaggtt 960
tattatttta tgtggttggc attttggcac aaaaagataa aagaacaaaa agggaaagaa 1020
tttcacatta ttttaaaata ccagcaggat acagattctg gaaaatatgc ttcctacctt 1080
atatggagaa aaaccaagaa aattaacttc acatgtaatc tgatagatcc aaaaggttat 1140
ctgtatctgc acttgaaatc cacaaattct gagtatgttc aattattctt aatgatgaca 1200
aaaattaaca cgtcttcaaa tttaaagtca tttctttttc tctattaaat ggtttttaaa 1260
aatcatttgt agagagacat attaagaggt aggtccgagg ggaaagagag aaagagggag 1320
agaaaaagaa aggctaaggt ctgagtagcc aggaatgtgg acaagtgtgg ttgtgagatc 1380
tctctcctgg gatcattaac aatctatgct tcctgacatc tctggcgtgt caacactaac 1440
ttaacattag atgcctttga tagccacacc tagatagtgg gcaggatccc ccttcaaact 1500
tatttccata tttatctaaa aacatcgtct caggagggaa aaccacattt aaagaaaaaa 1560
gatgcatgca atgtagcagg cctgcaagga tgactaatgt tttcaaagag ttcttggtag 1620
actatgcttc attccattcc taagatgttg ccagcaatgt ggcagagtcc cttcgcttgc 1680

-continued

```
agaaacctga accttcagac taaccattct ttaccttttt gtacagaacg tatcttgatg   1740
tttcttcttt tttcatttag ccacctgaga aatgtattta cctgagtgaa aatcaaactt   1800
attccccaag aatcatgtcc caaaagatgg cattcactaa ttccaaagaa taatgttatt   1860
ctataatttt tccttttgcc catttcctaa gatatctgta ggaaacagtg tgcttaggaa   1920
taaaagacac aaaaatttct gctaccaaag tggggtaatg tttataggat ttatagtatt   1980
aatttttaag cataatctgg tttatgtttg aaaatttgta gtgtacagtc aaatataaag   2040
agacaaactc tgatgcatct taactctcct tccctcccaa cacatcctca tcccattcaa   2100
ctcatttttt ttcaaaatta agtattccca cagttcatgt acatacctca ataagctcat   2160
ctctttgccg caggccttct ttaagttctt ccatcttatg ctgcagcaca ctacacatat   2220
gtttctgcct ttctaactcc tgttattaaa caaataatat catttacaca ggtcatggca   2280
cacaagaaat ttgaacatac acaatacaac acagaggtta agtatgacct ccagaaacat   2340
gcccaaactc ctgattcata gtaacttaga aaaattgtgt attctataga aaagttaaga   2400
aaattttaaa attccatctt gtataattat caggaaaacc tgaactaatc aatggcaaaa   2460
ttattaaaaa caaaagataa tttagtaaag taacaggtta taaaatgaac atatacaatt   2520
caatgacatt catatacaaa taaaattcaa agaaggaata ataaatgcaa tatcaaaata   2580
aaatcaatat taaataaaaa acatacatgt aaacttacaa aatatatcaa aaacctatat   2640
gaggaaaatt atataaagca ttcccaaaag acagagaaat aggattgaat aaatggaaag   2700
gcataccgtc ttcttggatt aaaagtctca caacattata aaaatgccag ttctccctaa   2760
attaatctat acatttaatg tagtacaaat aaaaatacca tcaggttttt cttttatcat   2820
catcagagca agttgatttg aaagaaaaac acaagaaaaa gtagccagaa aaatacatac   2880
tgaaaaagaa gaaagccggc cttattaggt attaaaacat attataaagc ttctataatt   2940
aaaacaatgt tgttatggca catgaatata gaccaaggga gcagaataga gaattcagga   3000
aaaacccact taaatataca aatatattta aaaacaataa aaataagagc atctcaaatc   3060
aatgagaagg aaagactttt aaattagtaa tgttgggata actggatatc catttggaaa   3120
aagataaaat tggaactata cctcatacca cacaccagga caaattccaa              3170
```

```
<210> SEQ ID NO 407
<211> LENGTH: 3157
<212> TYPE: DNA
<213> ORGANISM: Homo sapiens

<400> SEQUENCE: 407

aaagccaggg agtgaatggg ggaagaggga agggaaggga gaacaaactg tacaggaata     60
aaagtaacca aggagtgggg caatctttac tgaaaaaatg actcaaaaat ccacaagcaa    120
tgaggtaatg gtacaataaa ttagactaca taaaaataaa aattttgggc tgggcatggt    180
agctcatgcc tgtaatccca gcactctggg aggctgaagc aggcagatcc cttgagccga    240
agaattcaag accctgcctg ggcaacatgg caaaaacccca tctctataaa aaaaattcaa    300
aaattagcca gggttggtgg cgtgtgcctg tagtcccagg tactctggag gctgaggtgg    360
gaggaccacc tgagcctggg gaggtcaagg ctatagtgag ccatgatggt gccattgcac    420
tccagcctga cgacggagtg agactctgtc tccaaaaaat aaatacataa ataaataaaa    480
cttttgaatg gcagagaatc tctaaaacta ggccaggcac ggtggctcac gcctgtaatc    540
ccagcacttt gggaggccga ggtgggcgga tcacctgagg tcgggagttc gagaccagcc    600
tgaccaacat agagaaaccc tgtctctact aaaaatacaa aattagtcag gcgtggtggt    660
```

-continued

```
gcatgcctgt aatcccagct actcgggagg ctgaggcagg agaattgctt gaacctggga    720
ggcggagatt gtggtgagcc gagattgcgc cattgcactc cagcctgggc aacaggagcg    780
aaactctgtc ttaaaaaaca aacaaacaaa aactagaaag aaagaaaaca ctaactgcat    840
agaataataa gctacggaaa cggacagttt acagaaaaag aaatagaaat agctctgaat    900
atgaaaagat actcatacta agagaaacgg aaacaaacaa aatactagca aaagttcaaa    960
aacttgacaa catattccag aacagaacta tggggaaaga aataggccct catacatttt   1020
ggtgagaatg caaatggtat aatgcttaca aaggagacta cagcagtatc tgcaaaacta   1080
catacctttc gacccagcaa tctcactctt catcatagat acattggcaa aaatacaaaa   1140
agacctatgc agtatgttat ttctacagga ctatttttaa cagcaaaaca tgacaaactt   1200
gaatgtctat taatataggg aactggtaga ataaagtgtg gtacatccat actgtggaat   1260
aattatgcag tggtgaaaaa gaatgagcaa gatatctcta tacaacattc ataaggtgat   1320
aaaatctaca tgcacgacag catttatatt aacaatatgc tactattttc taagaagagt   1380
aagaaataca tatatttgta catatatttt gaatgattat atatacatat atatcttttt   1440
agattaaaaa tggctaccta atttatcttc ttggatttaa aacatggaaa gataaaccat   1500
taaaatttaa aattccctaa aggaaggaga aaatagagac agagacaggg atagaagatt   1560
aacttcttca gatatattct ttgttaacgt gactccagat ctatgtaact attctagata   1620
gttacaaaat tgtaaaacaa aattaaattt aaaaagcaat tcctagtgga aacaattcaa   1680
gtggccattg atagatgaat gcataagcaa aatgtggtat atatacagtg gaatattatt   1740
cagctttaaa aaagaaactc ttgtcacacg ctacaacatg gatgagcctt aggacattat   1800
gctaaatgaa gtaaaccagt caagaaaaga tatattatta tatgattcta cttacttatg   1860
agtttggtac acagagtagc caaactcaca gagacagaaa gtaggatggt agttgccaag   1920
ggctggtggt agggagaaat gggtaattgt ttaatgggta cagagttcta gttttgaaag   1980
ataaaaaatt tctggagatc tgatgtacac taatgtgaat atgcttcaca ctactgaact   2040
ctacacttta aaatggttaa gataataaat ttatcatgtt ttttaatgat aattaaattt   2100
tttaaaataa aaataatttt aaaagtaatt ccaaatattg aaaataaaat gcagtgaacc   2160
taactataca tccagttaga agcgcagaaa gaaactattt caagtaactt ctaaaaacaa   2220
tagtttggcc acacacagac tagtggcaaa aataacagcc aagcaaaaca aacaaaataa   2280
aaatctttta actattttca gtaattaaat tgttggtgtt aatgttggta ttgctattct   2340
aggcaacttc ggataaagca aagagaacag aacgtaacat aattactatc atccctagaa   2400
actttgagaa ctaggaattg tagtgtaggg gaaacaaaca aagatacaga tgtaagacag   2460
aagaggttaa ataaccctag agtcctgcat gtgaactgga actatcagca agaactcata   2520
atgtattttg ttgttaaaaa caaaaaaaaa cttcacacac atatttccca aatttatcca   2580
ctgaaaagac ccataaacac tgacctactt ggtggcaatg agcatctcta gcactcatac   2640
taaaacagaa ctagggctcc ttggacaaat ggctgattcc aggtctgggg cagaaaatgt   2700
acaagatgag actgggacat cttctgccag aaagcaaaga agctatcaaa aacaattaga   2760
ctcaccagaa gtacttgaga atcaacctca agaggttcac attagccaaa gatgggacaa   2820
ttttatcatc aaaaagaata aaagctgcaa tgcaactgaa gatatcaaat gcttgaattt   2880
atgacttcat attgatattt taagagaaaa gtaattggtc acaaccaatt cctttttttg   2940
aaaactcata aagggagaaa atatttgcga ataatatatc tgataaaatt cttatatcta   3000
```

gaatatataa accttacaag tcaataataa taaggcaaaa tccaatttta aaatggacaa 3060
aggatctgaa tagacatttt gccaaggaag atatgcaaat agccaataag cccatgaaaa 3120
tatgttcaaa atcattagtc accagggaga tgcacat 3157

<210> SEQ ID NO 408
<211> LENGTH: 3166
<212> TYPE: DNA
<213> ORGANISM: Homo sapiens

<400> SEQUENCE: 408
tgtggggaaa tcaaaacctg catacattgc tggtgtgaga atataaaatg gtgcagccac 60
ttcggaaaac agtctggcac tgttcaaatg gttaaacaca gatttatcgt atgaatcagc 120
aattccactc ccaagtatat acttaagaaa aaggaaagca tatatccaga ccatgagcag 180
tggctcatgc ctgtaattcc aacactttgg gaggccaagg caggaagatt gcttgaggcc 240
aggagttacc agcctgggca acatagcaag gccccatctc ttagaataaa aaagaaaaag 300
aaaacttacg tccaaaaaac aacctgtata caaatgttta tggaagcatt attcttaaca 360
ggaaaaagta taaacaaccc aaatgtcaat caatgcacaa atgggtaaac aaaatgtagc 420
atacccaaaa aaatggaata ttaataggct ataaaaagga attaagtatt gatacatggt 480
ataacatgga tgaaccttga aaacatcacg ctaagcgaaa gaagccagtc acaaaagacc 540
atgtattata tgactccttt catatgagtc tagaataggg aactctatag atagaaagta 600
gatcagtggt tacttaagac tgaggggttt gggggaaagg aagatgatac taaagggtat 660
atggtttctt tctgaggtaa tgaaaacata ctaaaagtaa ctgtgatgaa ggttacacat 720
atatgtgaat atactaaaaa ccactgaatt gtacacttta aatggatgat ttgtatgtta 780
tttgaattat atctcaataa agctgcttaa aaataacatt aaataggcca ggcgcagtgg 840
ctcacacctg taatcccagc actttgggag gccgaggtgg gtggatcacc tgaggtcagt 900
tcgggaccag cctgaccaac aaagtgaaac cccatctcta ctaaaaatac aaaattagcc 960
aggcgtggtg gtccatgcct gtaatcccag ctactcagaa ggctgaggca ggagaatcac 1020
ttgaacccgg gaggcagagg ttgcagtgag ccgagattgc gccattgcac tccaccctgg 1080
gcaacaagag caaaactcgt ctaaaaaaat aaaataaata aaatttaaaa aaataaataa 1140
aataacataa aataaaataa attggtaatg ataaaatcag aacatcccat tttgcagccc 1200
ctagtcaatt aaaggatcta agcacacaca tacagcctaa cagtcagcca cacatctggg 1260
cctcctgaag gaagacaact gcatcatcta tgaagcagac tttcaaaaaa aactgaagtt 1320
atatttgatt aagcctctgt gcctaactac ctatttacag agaatacaga ggaaagggaa 1380
acatggtaaa gatactatgg ggacgaaaac ggaaaaactt gtaagactgg gaaatattaa 1440
gcaacccagt ttcttcaaca tatatattat aaggagaaaa aacatgaaag aggacctata 1500
catgaaaaga gacttaaaag atttatcaac tcattctaag gtgtgaaact tacctggatc 1560
ccgatttttt taagtgtaaa aaagaaaaat catttatgac attttgaaac tactgaaatt 1620
ttaacattga ttagatatat aatatgaatt attgttaatt ttacaggtgt gaaatggtct 1680
tttgattatg ctttaaaaga gaaacaatgg gctgggcaaa gtggctcatg cctgtaatcc 1740
caacactttg ggaggtcaaa gaaggaggat tgggcaatac agcaaggccc catctccaca 1800
aaaagatttt taaaaaacag ccaggcatgg tagcatgtgc ctacagttct agctactcca 1860
gattacttaa gcgtaggaga tcaaagttac agtgggctat gatcgtgcca ctgcactcca 1920
gcctggggag cagagcaaga ccctgtctgt aaaaacaata aaattaaatt aaattaaaat 1980

-continued

```
ataaaacaaa atagttattg taattccagg aggaggcacc aaagacattt tgaaaatttt   2040
tattaatact gtataattat tatggaatgg tccttctcta ctctcactac ctgcttctgt   2100
aatgaaatac accagaatgc ctgacctctt tgtgtatctc tgaatataaa cattctactt   2160
tataaagcaa tagttgttta gaacaagaga gctcggagta aaggtatgtt agaaagagat   2220
actgtcacaa agtgttctgc atcacagtac gtgaagcaaa tttccagggt attaaaaaaa   2280
acaatacatt ttaggtttga aaagtacaag acctgccacg gtggctcaca actgtaatct   2340
cagcactgtg ggaagctgag gtgggtggat tgcttgagcc caggagttcg agaccagcct   2400
gggcaacatg gtgaaaccgt ttctataaaa aaaaatttgt ctttaattag ccaggcgtgg   2460
tggtacgtgc ctgtagtccc agctactcag gaggctgagg tgggaggatc acttgagcct   2520
ggagacagag gctgcagtga gctatacttg cgctactcca ctccagcctg ggctacagag   2580
tgagaccttg tctccaaaag aaaaaaaaaa aaaaaaaaag gacaagatta agaaaacaac   2640
tctatgcata ctaaaataac tctattacct tctaaaatga tggagggaaa aactaagttg   2700
gttaaaatag ctaattataa gggttttctt tatttttaaa aatgctgaag gatatttgag   2760
acgatggaaa gataattcat tttagtaatg acccttaaat acttagcatg agatttttac   2820
tctagtctgc tagaagcaaa gagccaaaga cagataagaa aaaatgtgtg ggacagcaaa   2880
aaaaggagtc cagaggctct aggaaaagca tgatggctca gaatctccaa aaatggccta   2940
tgggatatat aagaagaatc aaagatatac atatctagca tatataatgc tcttcaatgg   3000
gccactgtca gtccaatatg aaaacaacta gaagcctctt tttcaccatc taaataccaa   3060
tcctaaataa acaattttag agcagtttaa gattcacagt aaaattatgt ttaaagtaca   3120
gagagttttc atatactccc tgtccccaca cacgcacagt ctaccc                  3166
```